US008408439B2

(12) United States Patent
Huang et al.

(10) Patent No.: US 8,408,439 B2
(45) Date of Patent: Apr. 2, 2013

(54) SURGICAL STAPLING INSTRUMENT WITH AN ARTICULATABLE END EFFECTOR

(75) Inventors: Zhifan F. Huang, Mason, OH (US); Chad P. Boudreaux, Cincinnati, OH (US); Joseph C. Huell, Loveland, OH (US); Dean B. Bruewer, Fairfield, OH (US); David B. Smith, Mason, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 349 days.

(21) Appl. No.: 12/765,337

(22) Filed: Apr. 22, 2010

(65) Prior Publication Data

US 2010/0264193 A1 Oct. 21, 2010

Related U.S. Application Data

(63) Continuation-in-part of application No. 12/008,266, filed on Jan. 10, 2008, now Pat. No. 7,954,684, which is a continuation-in-part of application No. 11/821, 277, filed on Jun. 22, 2007, now Pat. No. 7,753,245.

(51) Int. Cl.
*A61B 17/068* (2006.01)

(52) U.S. Cl. ............... 227/175.1; 227/176.1; 227/179.1; 227/180.1; 227/181.1; 227/19

(58) Field of Classification Search ............... 227/175.1, 227/176.1, 179.1, 180.1, 181.119
See application file for complete search history.

(56) References Cited

U.S. PATENT DOCUMENTS

| | | | |
|---|---|---|---|
| 2,853,074 | A | 9/1958 | Olson |
| 2,959,974 | A | 11/1960 | Emrick |
| 3,490,675 | A | 1/1970 | Green et al. |
| 3,551,987 | A | 1/1971 | Wilkinson |
| 3,643,851 | A | 2/1972 | Green et al. |
| 3,662,939 | A | 5/1972 | Bryan |
| 3,717,294 | A | 2/1973 | Green |
| 3,819,100 | A | 6/1974 | Noiles et al. |
| RE28,932 | E | 8/1976 | Noiles et al. |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Partial European Search Report, Application No. 08252151.9, dated Mar. 17, 2009 (4 pages).

(Continued)

*Primary Examiner* — Brian D Nash
*Assistant Examiner* — Michelle Lopez

(57) ABSTRACT

In various embodiments, a surgical instrument can comprise an end effector including a channel configured to support a staple cartridge and, in addition, an anvil pivotable between open and closed positions relative to the staple cartridge channel. The surgical instrument can further comprise a closure tube configured to at least partially surround the anvil and the staple cartridge channel to hold the anvil in a closed position. The closure tube can extend around the anvil a greater distance than the staple cartridge channel. The surgical instrument can further comprise a shaft and, in addition, an articulation joint pivotably connecting the end effector to the shaft. The articulation joint can further comprise a floating guide member which can guidably support a knife bar extending into the end effector and, at the same time, move independently of the end effector and the shaft to provide such support.

19 Claims, 140 Drawing Sheets

U.S. PATENT DOCUMENTS

| | | | |
|---|---|---|---|
| 4,331,277 | A | 5/1982 | Green |
| 4,383,634 | A | 5/1983 | Green |
| 4,396,139 | A | 8/1983 | Hall et al. |
| 4,402,445 | A | 9/1983 | Green |
| 4,415,112 | A | 11/1983 | Green |
| 4,429,695 | A | 2/1984 | Green |
| 4,475,679 | A | 10/1984 | Fleury, Jr. |
| 4,489,875 | A | 12/1984 | Crawford et al. |
| 4,500,024 | A | 2/1985 | DiGiovanni et al. |
| 4,505,273 | A | 3/1985 | Braun et al. |
| 4,505,414 | A | 3/1985 | Filipi |
| 4,506,671 | A | 3/1985 | Green |
| 4,522,327 | A | 6/1985 | Korthoff et al. |
| 4,530,453 | A | 7/1985 | Green |
| 4,565,109 | A | 1/1986 | Tsay |
| 4,566,620 | A | 1/1986 | Green et al. |
| 4,573,622 | A | 3/1986 | Green et al. |
| 4,580,712 | A | 4/1986 | Green |
| 4,610,383 | A | 9/1986 | Rothfuss et al. |
| 4,619,262 | A | 10/1986 | Taylor |
| 4,629,107 | A | 12/1986 | Fedotov et al. |
| 4,632,290 | A | 12/1986 | Green et al. |
| 4,655,222 | A | 4/1987 | Florez et al. |
| 4,664,305 | A | 5/1987 | Blake, III et al. |
| 4,671,445 | A | 6/1987 | Barker et al. |
| 4,715,520 | A | 12/1987 | Roehr, Jr. et al. |
| 4,728,020 | A | 3/1988 | Green et al. |
| 4,752,024 | A | 6/1988 | Green et al. |
| 4,754,909 | A | 7/1988 | Barker et al. |
| 4,767,044 | A | 8/1988 | Green |
| 4,805,823 | A | 2/1989 | Rothfuss |
| 4,809,695 | A | 3/1989 | Gwathmey et al. |
| 4,817,847 | A | 4/1989 | Redtenbacher et al. |
| 4,819,853 | A | 4/1989 | Green |
| 4,821,939 | A | 4/1989 | Green |
| 4,844,068 | A | 7/1989 | Arata et al. |
| 4,869,414 | A | 9/1989 | Green et al. |
| 4,869,415 | A | 9/1989 | Fox |
| 4,880,015 | A | 11/1989 | Nierman |
| 4,941,623 | A | 7/1990 | Pruitt |
| 4,944,443 | A | 7/1990 | Oddsen et al. |
| 4,973,274 | A | 11/1990 | Hirukawa |
| 5,065,929 | A | 11/1991 | Schulze et al. |
| 5,071,430 | A | 12/1991 | de Salis et al. |
| 5,074,454 | A | 12/1991 | Peters |
| 5,129,570 | A | 7/1992 | Schulze et al. |
| 5,137,198 | A | 8/1992 | Nobis et al. |
| 5,139,513 | A | 8/1992 | Segato |
| 5,141,144 | A | 8/1992 | Foslien et al. |
| 5,158,567 | A | 10/1992 | Green |
| 5,209,747 | A | 5/1993 | Knoepfler |
| 5,211,649 | A | 5/1993 | Kohler et al. |
| 5,221,036 | A | 6/1993 | Takase |
| 5,222,975 | A | 6/1993 | Crainich |
| 5,236,440 | A | 8/1993 | Hlavacek |
| 5,258,009 | A | 11/1993 | Conners |
| 5,271,543 | A | 12/1993 | Grant et al. |
| 5,282,806 | A | 2/1994 | Haber et al. |
| 5,282,829 | A | 2/1994 | Hermes |
| 5,304,204 | A | 4/1994 | Bregen |
| 5,307,976 | A | 5/1994 | Olson et al. |
| 5,312,024 | A | 5/1994 | Grant et al. |
| 5,318,221 | A | 6/1994 | Green et al. |
| 5,336,232 | A | 8/1994 | Green et al. |
| 5,342,395 | A | 8/1994 | Jarrett et al. |
| 5,342,396 | A | 8/1994 | Cook |
| 5,350,400 | A | 9/1994 | Esposito et al. |
| 5,366,479 | A | 11/1994 | McGarry et al. |
| 5,383,888 | A | 1/1995 | Zvenyatsky et al. |
| 5,397,324 | A | 3/1995 | Carroll et al. |
| 5,405,072 | A | 4/1995 | Zlock et al. |
| 5,413,268 | A | 5/1995 | Green et al. |
| 5,413,272 | A | 5/1995 | Green et al. |
| 5,417,203 | A | 5/1995 | Tovey et al. |
| 5,417,361 | A | 5/1995 | Williamson, IV |
| 5,425,745 | A | 6/1995 | Green et al. |
| 5,431,654 | A | 7/1995 | Nic |
| 5,437,681 | A | 8/1995 | Meade et al. |
| 5,452,837 | A | 9/1995 | Williamson, IV et al. |
| 5,456,401 | A | 10/1995 | Green et al. |
| 5,465,894 | A | 11/1995 | Clark et al. |
| 5,474,566 | A | 12/1995 | Alesi et al. |
| 5,478,354 | A | 12/1995 | Tovey et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,497,933 | A | 3/1996 | DeFonzo et al. |
| 5,503,320 | A | 4/1996 | Webster et al. |
| 5,505,363 | A | 4/1996 | Green et al. |
| 5,507,426 | A | 4/1996 | Young et al. |
| 5,509,596 | A | 4/1996 | Green et al. |
| 5,514,157 | A | 5/1996 | Nicholas et al. |
| 5,520,700 | A | 5/1996 | Beyar et al. |
| 5,529,235 | A | 6/1996 | Boiarski et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,547,117 | A | 8/1996 | Hamblin et al. |
| 5,553,765 | A | 9/1996 | Knodel et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,564,615 | A | 10/1996 | Bishop et al. |
| 5,571,116 | A | 11/1996 | Bolanos et al. |
| 5,575,799 | A | 11/1996 | Bolanos et al. |
| 5,577,654 | A | 11/1996 | Bishop |
| 5,579,978 | A | 12/1996 | Green et al. |
| 5,580,067 | A | 12/1996 | Hamblin et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,609,285 | A | 3/1997 | Grant et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |
| 5,632,432 | A | 5/1997 | Schulze et al. |
| 5,632,433 | A | 5/1997 | Grant et al. |
| 5,634,584 | A | 6/1997 | Okorocha et al. |
| 5,636,779 | A | 6/1997 | Palmer |
| 5,636,780 | A | 6/1997 | Green et al. |
| 5,639,008 | A | 6/1997 | Gallagher et al. |
| 5,645,209 | A | 7/1997 | Green et al. |
| 5,647,526 | A | 7/1997 | Green et al. |
| 5,649,937 | A | 7/1997 | Bito et al. |
| 5,651,491 | A | 7/1997 | Heaton et al. |
| 5,653,373 | A | 8/1997 | Green et al. |
| 5,653,374 | A | 8/1997 | Young et al. |
| 5,655,698 | A | 8/1997 | Yoon |
| 5,657,921 | A | 8/1997 | Young et al. |
| 5,662,258 | A | 9/1997 | Knodel et al. |
| 5,662,260 | A | 9/1997 | Yoon |
| 5,667,527 | A | 9/1997 | Cook |
| 5,669,544 | A | 9/1997 | Schulze et al. |
| 5,669,918 | A | 9/1997 | Balazs et al. |

| | | | |
|---|---|---|---|
| 5,673,840 | A | 10/1997 | Schulze et al. |
| 5,673,841 | A | 10/1997 | Schulze et al. |
| 5,673,842 | A | 10/1997 | Bittner et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,685,474 | A | 11/1997 | Seeber |
| 5,690,269 | A | 11/1997 | Bolanos et al. |
| 5,692,668 | A | 12/1997 | Schulze et al. |
| 5,695,524 | A | 12/1997 | Kelley et al. |
| 5,697,543 | A | 12/1997 | Burdorff |
| 5,702,408 | A | 12/1997 | Wales et al. |
| 5,704,534 | A | 1/1998 | Huitema et al. |
| 5,706,997 | A | 1/1998 | Green et al. |
| 5,706,998 | A | 1/1998 | Plyley et al. |
| 5,709,334 | A | 1/1998 | Sorrentino et al. |
| 5,711,472 | A | 1/1998 | Bryan |
| 5,713,505 | A | 2/1998 | Huitema |
| 5,715,987 | A | 2/1998 | Kelley et al. |
| 5,715,988 | A | 2/1998 | Palmer |
| 5,716,366 | A | 2/1998 | Yates |
| 5,718,359 | A | 2/1998 | Palmer et al. |
| 5,718,360 | A | 2/1998 | Green et al. |
| 5,725,536 | A | 3/1998 | Oberlin et al. |
| 5,725,554 | A | 3/1998 | Simon et al. |
| 5,730,758 | A | 3/1998 | Allgeyer |
| 5,732,821 | A | 3/1998 | Stone et al. |
| 5,732,871 | A | 3/1998 | Clark et al. |
| 5,732,872 | A | 3/1998 | Bolduc et al. |
| 5,735,445 | A | 4/1998 | Vidal et al. |
| 5,743,456 | A | 4/1998 | Jones et al. |
| 5,752,644 | A | 5/1998 | Bolanos et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,785,232 | A | 7/1998 | Vidal et al. |
| 5,794,834 | A | 8/1998 | Hamblin et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,799,857 | A | 9/1998 | Robertson et al. |
| 5,809,601 | A | 9/1998 | Rivera |
| 5,820,009 | A | 10/1998 | Melling et al. |
| 5,826,776 | A | 10/1998 | Schulze et al. |
| 5,829,662 | A | 11/1998 | Allen et al. |
| 5,833,695 | A | 11/1998 | Yoon |
| 5,836,503 | A | 11/1998 | Ehrenfels et al. |
| 5,836,960 | A | 11/1998 | Kolesa et al. |
| 5,839,639 | A | 11/1998 | Sauer et al. |
| 5,855,311 | A | 1/1999 | Hamblin et al. |
| 5,855,583 | A | 1/1999 | Wang et al. |
| 5,865,361 | A | 2/1999 | Milliman et al. |
| 5,868,760 | A | 2/1999 | McGuckin, Jr. |
| 5,871,135 | A | 2/1999 | Williamson IV et al. |
| 5,878,937 | A | 3/1999 | Green et al. |
| 5,878,938 | A | 3/1999 | Bittner et al. |
| 5,893,506 | A | 4/1999 | Powell |
| 5,894,979 | A | 4/1999 | Powell |
| 5,897,562 | A | 4/1999 | Bolanos et al. |
| 5,901,895 | A | 5/1999 | Heaton et al. |
| 5,904,693 | A | 5/1999 | Dicesare et al. |
| 5,908,427 | A | 6/1999 | McKean et al. |
| 5,911,353 | A | 6/1999 | Bolanos et al. |
| 5,915,616 | A | 6/1999 | Viola et al. |
| 5,918,791 | A | 7/1999 | Sorrentino et al. |
| 5,919,198 | A | 7/1999 | Graves, Jr. et al. |
| 5,937,951 | A | 8/1999 | Izuchukwu et al. |
| 5,941,442 | A | 8/1999 | Geiste et al. |
| 5,954,259 | A | 9/1999 | Viola et al. |
| 5,988,479 | A | 11/1999 | Palmer |
| 6,010,054 | A | 1/2000 | Johnson et al. |
| 6,032,849 | A | 3/2000 | Mastri et al. |
| 6,045,560 | A | 4/2000 | McKean et al. |
| 6,047,861 | A | 4/2000 | Vidal et al. |
| 6,050,472 | A | 4/2000 | Shibata |
| 6,053,390 | A | 4/2000 | Green et al. |
| 6,062,360 | A | 5/2000 | Shields |
| 6,079,606 | A | 6/2000 | Milliman et al. |
| 6,083,242 | A | 7/2000 | Cook |
| 6,086,600 | A | 7/2000 | Kortenbach |
| 6,099,551 | A | 8/2000 | Gabbay |
| 6,102,271 | A | 8/2000 | Longo et al. |
| 6,109,500 | A | 8/2000 | Alli et al. |
| 6,119,913 | A | 9/2000 | Adams et al. |
| 6,126,058 | A | 10/2000 | Adams et al. |
| 6,131,789 | A | 10/2000 | Schulze et al. |
| 6,155,473 | A | 12/2000 | Tompkins et al. |
| 6,171,330 | B1 | 1/2001 | Benchetrit |
| 6,193,129 | B1 | 2/2001 | Bittner et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,273,897 | B1 | 8/2001 | Dalessandro et al. |
| 6,302,311 | B1 | 10/2001 | Adams et al. |
| 6,315,184 | B1 | 11/2001 | Whitman |
| 6,330,965 | B1 | 12/2001 | Milliman et al. |
| 6,370,981 | B2 | 4/2002 | Watarai |
| 6,387,113 | B1 | 5/2002 | Hawkins et al. |
| RE37,814 | E | 8/2002 | Allgeyer |
| 6,436,107 | B1 | 8/2002 | Wang et al. |
| 6,439,439 | B1 | 8/2002 | Rickard et al. |
| 6,439,446 | B1 | 8/2002 | Perry et al. |
| 6,443,973 | B1 | 9/2002 | Whitman |
| 6,450,391 | B1 | 9/2002 | Kayan et al. |
| 6,488,196 | B1 | 12/2002 | Fenton, Jr. |
| 6,488,197 | B1 | 12/2002 | Whitman |
| 6,491,201 | B1 | 12/2002 | Whitman |
| 6,505,768 | B2 | 1/2003 | Whitman |
| 6,517,565 | B1 | 2/2003 | Whitman et al. |
| 6,517,566 | B1 | 2/2003 | Hovland et al. |
| 6,569,171 | B2 | 5/2003 | DeGuillebon et al. |
| 6,578,751 | B2 | 6/2003 | Hartwick |
| 6,588,643 | B2 | 7/2003 | Bolduc et al. |
| 6,601,749 | B2 | 8/2003 | Sullivan et al. |
| 6,616,686 | B2 | 9/2003 | Coleman et al. |
| 6,619,529 | B2 | 9/2003 | Green et al. |
| 6,629,630 | B2 | 10/2003 | Adams |
| 6,629,988 | B2 | 10/2003 | Weadock |
| 6,644,532 | B2 | 11/2003 | Green et al. |
| 6,669,073 | B2 | 12/2003 | Milliman et al. |
| 6,681,978 | B2 | 1/2004 | Geiste et al. |
| 6,681,979 | B2 | 1/2004 | Whitman |
| 6,695,199 | B2 | 2/2004 | Whitman |
| 6,698,643 | B2 | 3/2004 | Whitman |
| 6,716,233 | B1 | 4/2004 | Whitman |
| 6,722,552 | B2 | 4/2004 | Fenton, Jr. |
| 6,755,338 | B2 | 6/2004 | Hahnen et al. |
| 6,769,594 | B2 | 8/2004 | Orban, III |
| 6,773,438 | B1 | 8/2004 | Knodel et al. |
| 6,786,382 | B1 | 9/2004 | Hoffman |
| 6,805,273 | B2 | 10/2004 | Bilotti et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,830,174 | B2 | 12/2004 | Hillstead et al. |
| 6,843,403 | B2 | 1/2005 | Whitman |
| RE38,708 | E | 3/2005 | Bolanos et al. |
| 6,866,178 | B2 | 3/2005 | Adams et al. |
| 6,874,669 | B2 | 4/2005 | Adams et al. |
| 6,877,647 | B2 | 4/2005 | Green et al. |
| 6,905,057 | B2 | 6/2005 | Swayze et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,851 | B2 | 11/2005 | Heinrich |
| 6,959,852 | B2 | 11/2005 | Shelton, IV et al. |
| 6,960,107 | B1 | 11/2005 | Schaub et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |

| | | | |
|---|---|---|---|
| 6,981,628 | B2 | 1/2006 | Wales |
| 6,986,451 | B1 | 1/2006 | Mastri et al. |
| 6,988,649 | B2 | 1/2006 | Shelton, IV et al. |
| 6,988,650 | B2 | 1/2006 | Schwemberger et al. |
| 6,997,931 | B2 | 2/2006 | Sauer et al. |
| 7,000,818 | B2 | 2/2006 | Shelton, IV et al. |
| 7,000,819 | B2 | 2/2006 | Swayze et al. |
| 7,008,435 | B2 | 3/2006 | Cummins |
| 7,032,798 | B2 | 4/2006 | Whitman et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,056,330 | B2 | 6/2006 | Gayton |
| 7,059,508 | B2 | 6/2006 | Shelton, IV et al. |
| 7,070,083 | B2 | 7/2006 | Jankowski |
| 7,077,856 | B2 | 7/2006 | Whitman |
| 7,080,769 | B2 | 7/2006 | Vresh et al. |
| 7,083,075 | B2 | 8/2006 | Swayze et al. |
| 7,090,684 | B2 | 8/2006 | McGuckin, Jr. et al. |
| 7,097,089 | B2 | 8/2006 | Marczyk |
| 7,108,709 | B2 | 9/2006 | Cummins |
| 7,111,769 | B2 | 9/2006 | Wales et al. |
| 7,114,642 | B2 | 10/2006 | Whitman |
| 7,118,582 | B1 | 10/2006 | Wang et al. |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,147,139 | B2 | 12/2006 | Schwemberger et al. |
| 7,156,863 | B2 | 1/2007 | Sonnenschein et al. |
| 7,159,750 | B2 | 1/2007 | Racenet et al. |
| 7,168,604 | B2 | 1/2007 | Milliman et al. |
| 7,172,104 | B2 | 2/2007 | Scirica et al. |
| 7,182,239 | B1 | 2/2007 | Myers |
| 7,188,758 | B2 | 3/2007 | Viola et al. |
| 7,207,471 | B2 | 4/2007 | Heinrich et al. |
| 7,207,472 | B2 | 4/2007 | Wukusick et al. |
| 7,210,609 | B2 | 5/2007 | Leiboff et |
| 7,213,736 | B2 | 5/2007 | Wales et al. |
| 7,220,272 | B2 | 5/2007 | Weadock |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,237,708 | B1 | 7/2007 | Guy et al. |
| 7,238,195 | B2 | 7/2007 | Viola |
| 7,246,734 | B2 | 7/2007 | Shelton, IV |
| 7,258,262 | B2 | 8/2007 | Mastri et al. |
| 7,278,562 | B2 | 10/2007 | Mastri et al. |
| 7,278,563 | B1 | 10/2007 | Green |
| 7,296,724 | B2 | 11/2007 | Green et al. |
| 7,297,149 | B2 | 11/2007 | Vitali et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,308,998 | B2 | 12/2007 | Mastri et al. |
| 7,328,828 | B2 | 2/2008 | Ortiz et al. |
| 7,328,829 | B2 | 2/2008 | Arad et al. |
| 7,334,717 | B2 | 2/2008 | Rethy et al. |
| 7,343,920 | B2 | 3/2008 | Toby et al. |
| 7,354,447 | B2 | 4/2008 | Shelton, IV et al. |
| 7,357,287 | B2 | 4/2008 | Shelton, IV et al. |
| 7,364,060 | B2 | 4/2008 | Milliman |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,396,356 | B2 | 7/2008 | Mollenauer |
| 7,398,907 | B2 | 7/2008 | Racenet et al. |
| 7,398,908 | B2 | 7/2008 | Holsten et al. |
| 7,404,508 | B2 | 7/2008 | Smith et al. |
| 7,404,509 | B2 | 7/2008 | Ortiz et al. |
| 7,407,075 | B2 | 8/2008 | Holsten et al. |
| 7,407,078 | B2 | 8/2008 | Shelton, IV et al. |
| 7,410,086 | B2 | 8/2008 | Ortiz et al. |
| 7,416,101 | B2 | 8/2008 | Shelton, IV et al. |
| 7,419,080 | B2 | 9/2008 | Smith et al. |
| 7,422,136 | B1 | 9/2008 | Marczyk |
| 7,422,139 | B2 | 9/2008 | Shelton, IV et al. |
| 7,424,965 | B2 | 9/2008 | Racenet et al. |
| 7,431,188 | B1 | 10/2008 | Marczyk |
| 7,431,189 | B2 | 10/2008 | Shelton, IV et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,438,209 | B1 | 10/2008 | Hess et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,455,208 | B2 | 11/2008 | Wales et al. |
| 7,461,767 | B2 | 12/2008 | Viola et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,481,347 | B2 | 1/2009 | Roy |
| 7,481,349 | B2 | 1/2009 | Holsten et al. |
| 7,481,824 | B2 | 1/2009 | Boudreaux et al. |
| 7,490,749 | B2 | 2/2009 | Schall et al. |
| 7,494,039 | B2 | 2/2009 | Racenet et al. |
| 7,500,979 | B2 | 3/2009 | Hueil et al. |
| 7,506,790 | B2 | 3/2009 | Shelton, IV |
| 7,506,791 | B2 | 3/2009 | Omaits et al. |
| 7,510,107 | B2 | 3/2009 | Timm et al. |
| 7,546,940 | B2 | 6/2009 | Milliman et al. |
| 7,549,563 | B2 | 6/2009 | Mather et al. |
| 7,549,564 | B2 | 6/2009 | Boudreaux |
| 7,552,854 | B2 | 6/2009 | Wixey et al. |
| 7,556,185 | B2 | 7/2009 | Viola |
| 7,556,186 | B2 | 7/2009 | Milliman |
| 7,559,450 | B2 | 7/2009 | Wales et al. |
| 7,559,452 | B2 | 7/2009 | Wales et al. |
| 7,568,603 | B2 | 8/2009 | Shelton, IV et al. |
| 7,568,604 | B2 | 8/2009 | Ehrenfels et al. |
| 7,575,144 | B2 | 8/2009 | Ortiz et al. |
| 7,588,175 | B2 | 9/2009 | Timm et al. |
| 7,588,176 | B2 | 9/2009 | Timm et al. |
| 7,597,229 | B2 | 10/2009 | Boudreaux et al. |
| 7,600,663 | B2 | 10/2009 | Green |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,624,902 | B2 | 12/2009 | Marczyk et al. |
| 7,631,793 | B2 | 12/2009 | Rethy et al. |
| 7,637,409 | B2 | 12/2009 | Marczyk |
| 7,641,092 | B2 | 1/2010 | Kruszynski et al. |
| 7,641,093 | B2 | 1/2010 | Doll et al. |
| 7,644,848 | B2 | 1/2010 | Swayze et al. |
| 7,658,311 | B2 | 2/2010 | Boudreaux |
| 7,658,312 | B2 | 2/2010 | Vidal et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,699,204 | B2 | 4/2010 | Viola |
| 7,708,180 | B2 | 5/2010 | Murray et al. |
| 7,717,312 | B2 | 5/2010 | Beetel |
| 7,721,930 | B2 | 5/2010 | McKenna et al. |
| 7,721,931 | B2 | 5/2010 | Shelton, IV et al. |
| 7,721,934 | B2 | 5/2010 | Shelton, IV et al. |
| 7,721,936 | B2 | 5/2010 | Shalton, IV et al. |
| 7,726,537 | B2 | 6/2010 | Olson et al. |
| 7,726,538 | B2 | 6/2010 | Holsten et al. |
| 7,731,072 | B2 | 6/2010 | Timm et al. |

| | | | |
|---|---|---|---|
| 7,735,703 | B2 | 6/2010 | Morgan et al. |
| 7,738,971 | B2 | 6/2010 | Swayze et al. |
| 7,740,159 | B2 | 6/2010 | Shelton, IV et al. |
| 7,743,960 | B2 | 6/2010 | Whitman et al. |
| 7,753,245 | B2 | 7/2010 | Boudreaux et al. |
| 7,753,904 | B2 | 7/2010 | Shelton, IV et al. |
| 7,766,209 | B2 | 8/2010 | Baxter, III et al. |
| 7,766,210 | B2 | 8/2010 | Shelton, IV et al. |
| 7,770,775 | B2 | 8/2010 | Shelton, IV et al. |
| 7,780,054 | B2 | 8/2010 | Wales |
| 7,780,055 | B2 | 8/2010 | Scirica et al. |
| 7,784,662 | B2 | 8/2010 | Wales et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,810,692 | B2 | 10/2010 | Hall et al. |
| 7,810,693 | B2 | 10/2010 | Broehl et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,837,080 | B2 | 11/2010 | Schwemberger |
| 7,837,081 | B2 | 11/2010 | Holsten et al. |
| 7,845,533 | B2 | 12/2010 | Marczyk et al. |
| 7,845,534 | B2 | 12/2010 | Viola et al. |
| 7,845,537 | B2 | 12/2010 | Shelton, IV et al. |
| 7,857,185 | B2 | 12/2010 | Swayze et al. |
| 7,857,186 | B2 | 12/2010 | Baxter, III et al. |
| 7,861,906 | B2 | 1/2011 | Doll et al. |
| 7,866,527 | B2 | 1/2011 | Hall et al. |
| 7,870,989 | B2 | 1/2011 | Viola et al. |
| 7,909,221 | B2 | 3/2011 | Viola et al. |
| 7,922,063 | B2 | 4/2011 | Zemlok et al. |
| 7,938,307 | B2 | 5/2011 | Bettuchi |
| 7,942,303 | B2 | 5/2011 | Shah |
| 7,950,560 | B2 | 5/2011 | Zemlok et al. |
| 7,959,050 | B2 | 6/2011 | Smith et al. |
| 7,967,180 | B2 | 6/2011 | Scirica |
| 8,002,795 | B2 | 8/2011 | Beetel |
| 8,011,551 | B2 | 9/2011 | Marczyk et al. |
| 8,011,555 | B2 | 9/2011 | Tarinelli et al. |
| 8,028,883 | B2 | 10/2011 | Stopek |
| 8,034,077 | B2 | 10/2011 | Smith et al. |
| 8,038,045 | B2 | 10/2011 | Bettuchi et al. |
| 8,038,046 | B2 | 10/2011 | Smith et al. |
| D650,074 | S | 12/2011 | Hunt et al. |
| 8,091,756 | B2 | 1/2012 | Viola |
| 8,097,017 | B2 | 1/2012 | Viola |
| 8,123,103 | B2 | 2/2012 | Milliman |
| 8,152,041 | B2 | 4/2012 | Kostrzewski |
| 8,157,152 | B2 | 4/2012 | Holsten et al. |
| 8,167,895 | B2 | 5/2012 | D'Agostino et al. |
| 8,205,781 | B2 | 6/2012 | Baxter, III et al. |
| 8,245,898 | B2 | 8/2012 | Smith et al. |
| 8,245,901 | B2 | 8/2012 | Stopek |
| 8,256,654 | B2 | 9/2012 | Bettuchi et al. |
| 8,292,155 | B2 | 10/2012 | Shelton, IV et al. |
| 2002/0117534 | A1 | 8/2002 | Green et al. |
| 2004/0006372 | A1 | 1/2004 | Racenet et al. |
| 2004/0034369 | A1 | 2/2004 | Sauer et al. |
| 2004/0094597 | A1 | 5/2004 | Whitman et al. |
| 2004/0108357 | A1 | 6/2004 | Milliman et al. |
| 2004/0164123 | A1 | 8/2004 | Racenet et al. |
| 2004/0167572 | A1 | 8/2004 | Roth et al. |
| 2004/0173659 | A1 | 9/2004 | Green et al. |
| 2004/0222268 | A1 | 11/2004 | Bilotti et al. |
| 2004/0232201 | A1 | 11/2004 | Wenchell et al. |
| 2004/0243151 | A1 | 12/2004 | Demmy et al. |
| 2004/0243176 | A1 | 12/2004 | Hahnen et al. |
| 2004/0254608 | A1 | 12/2004 | Huitema et al. |
| 2004/0267310 | A1 | 12/2004 | Racenet et al. |
| 2005/0059997 | A1 | 3/2005 | Bauman et al. |
| 2005/0103819 | A1 | 5/2005 | Racenet et al. |
| 2005/0119669 | A1 | 6/2005 | Demmy |
| 2005/0125009 | A1 | 6/2005 | Perry et al. |
| 2005/0143759 | A1 | 6/2005 | Kelly |
| 2005/0145675 | A1 | 7/2005 | Hartwick et al. |
| 2005/0184121 | A1 | 8/2005 | Heinrich |
| 2005/0187576 | A1 | 8/2005 | Whitman et al. |
| 2005/0189397 | A1 | 9/2005 | Jankowski |
| 2005/0192628 | A1 | 9/2005 | Viola |
| 2005/0216055 | A1 | 9/2005 | Scirica et al. |
| 2005/0240222 | A1 | 10/2005 | Shipp |
| 2005/0263563 | A1 | 12/2005 | Racenet et al. |
| 2005/0274768 | A1 | 12/2005 | Cummins et al. |
| 2006/0011699 | A1 | 1/2006 | Olson et al. |
| 2006/0047307 | A1 | 3/2006 | Ortiz et al. |
| 2006/0049229 | A1 | 3/2006 | Milliman et al. |
| 2006/0052825 | A1 | 3/2006 | Ransick et al. |
| 2006/0060630 | A1 | 3/2006 | Shelton, IV et al. |
| 2006/0085033 | A1 | 4/2006 | Criscuolo et al. |
| 2006/0100643 | A1 | 5/2006 | Laufer et al. |
| 2006/0108393 | A1 | 5/2006 | Heinrich et al. |
| 2006/0167471 | A1 | 7/2006 | Phillips |
| 2006/0180634 | A1 | 8/2006 | Shelton, IV et al. |
| 2006/0226196 | A1 | 10/2006 | Hueil et al. |
| 2006/0235469 | A1 | 10/2006 | Viola |
| 2006/0241692 | A1 | 10/2006 | McGuckin, Jr. et al. |
| 2006/0278680 | A1 | 12/2006 | Viola et al. |
| 2006/0278681 | A1 | 12/2006 | Viola et al. |
| 2006/0289602 | A1 | 12/2006 | Wales et al. |
| 2007/0023476 | A1 | 2/2007 | Whitman et al. |
| 2007/0023477 | A1 | 2/2007 | Whitman et al. |
| 2007/0027469 | A1 | 2/2007 | Smith et al. |
| 2007/0034668 | A1 | 2/2007 | Holsten et al. |
| 2007/0073341 | A1 | 3/2007 | Smith et al. |
| 2007/0084897 | A1 | 4/2007 | Shelton, IV et al. |
| 2007/0102472 | A1 | 5/2007 | Shelton, IV |
| 2007/0106317 | A1 | 5/2007 | Shelton, IV et al. |
| 2007/0114261 | A1 | 5/2007 | Ortiz et al. |
| 2007/0170225 | A1 | 7/2007 | Shelton, IV et al. |
| 2007/0175949 | A1 | 8/2007 | Shelton, IV et al. |
| 2007/0175950 | A1 | 8/2007 | Shelton, IV et al. |
| 2007/0175951 | A1 | 8/2007 | Shelton, IV et al. |
| 2007/0175953 | A1 | 8/2007 | Shelton, IV et al. |
| 2007/0175955 | A1 | 8/2007 | Shelton, IV et al. |
| 2007/0181632 | A1 | 8/2007 | Milliman |
| 2007/0194079 | A1 | 8/2007 | Hueil et al. |
| 2007/0194081 | A1 | 8/2007 | Hueil et al. |
| 2007/0194082 | A1 | 8/2007 | Morgan et al. |
| 2007/0221700 | A1 | 9/2007 | Ortiz et al. |
| 2007/0221701 | A1 | 9/2007 | Ortiz et al. |
| 2007/0225562 | A1 | 9/2007 | Spivey et al. |
| 2007/0239028 | A1 | 10/2007 | Houser et al. |
| 2007/0246505 | A1 | 10/2007 | Pace-Floridia et al. |
| 2007/0270884 | A1 | 11/2007 | Smith et al. |
| 2007/0288044 | A1 | 12/2007 | Jinno et al. |
| 2007/0295780 | A1 | 12/2007 | Shelton et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0035701 | A1 | 2/2008 | Racenet et al. |
| 2008/0041916 | A1 | 2/2008 | Milliman et al. |
| 2008/0041917 | A1 | 2/2008 | Racenet et al. |
| 2008/0078800 | A1 | 4/2008 | Hess et al. |
| 2008/0078802 | A1 | 4/2008 | Hess et al. |
| 2008/0078803 | A1 | 4/2008 | Shelton et al. |
| 2008/0078804 | A1 | 4/2008 | Shelton et al. |
| 2008/0078806 | A1 | 4/2008 | Omaits et al. |
| 2008/0078807 | A1 | 4/2008 | Hess et al. |
| 2008/0078808 | A1 | 4/2008 | Hess et al. |
| 2008/0082115 | A1 | 4/2008 | Morgan et al. |
| 2008/0082125 | A1 | 4/2008 | Murray et al. |
| 2008/0082126 | A1 | 4/2008 | Murray et al. |
| 2008/0083813 | A1 | 4/2008 | Zemlok et al. |
| 2008/0140115 | A1 | 6/2008 | Stopek |
| 2008/0167522 | A1 | 7/2008 | Giordano et al. |
| 2008/0167644 | A1 | 7/2008 | Shelton et al. |
| 2008/0167671 | A1 | 7/2008 | Giordano et al. |
| 2008/0167672 | A1 | 7/2008 | Giordano et al. |
| 2008/0169328 | A1 | 7/2008 | Shelton |
| 2008/0169329 | A1 | 7/2008 | Shelton et al. |
| 2008/0169330 | A1 | 7/2008 | Shelton et al. |

| | | | |
|---|---|---|---|
| 2008/0169331 | A1 | 7/2008 | Shelton et al. |
| 2008/0169332 | A1 | 7/2008 | Shelton et al. |
| 2008/0169333 | A1 | 7/2008 | Shelton et al. |
| 2008/0172088 | A1 | 7/2008 | Smith et al. |
| 2008/0183193 | A1 | 7/2008 | Omori et al. |
| 2008/0185419 | A1 | 8/2008 | Smith et al. |
| 2008/0197167 | A1 | 8/2008 | Viola et al. |
| 2008/0210738 | A1 | 9/2008 | Shelton et al. |
| 2008/0237296 | A1 | 10/2008 | Boudreaux et al. |
| 2008/0245841 | A1 | 10/2008 | Smith et al. |
| 2008/0251568 | A1 | 10/2008 | Zemlok et al. |
| 2008/0251569 | A1 | 10/2008 | Smith et al. |
| 2008/0283570 | A1 | 11/2008 | Boyden et al. |
| 2008/0290134 | A1 | 11/2008 | Bettuchi et al. |
| 2008/0296346 | A1 | 12/2008 | Shelton, IV et al. |
| 2008/0300580 | A1 | 12/2008 | Shelton, IV et al. |
| 2008/0300613 | A1 | 12/2008 | Shelton, IV et al. |
| 2008/0308602 | A1 | 12/2008 | Timm et al. |
| 2008/0308603 | A1 | 12/2008 | Shelton, IV et al. |
| 2008/0308608 | A1 | 12/2008 | Prommersberger |
| 2008/0314957 | A1 | 12/2008 | Boudreaux |
| 2008/0314960 | A1 | 12/2008 | Marczyk et al. |
| 2009/0001121 | A1 | 1/2009 | Hess et al. |
| 2009/0001122 | A1 | 1/2009 | Prommersberger et al. |
| 2009/0001124 | A1 | 1/2009 | Hess et al. |
| 2009/0001130 | A1 | 1/2009 | Hess et al. |
| 2009/0005807 | A1 | 1/2009 | Hess et al. |
| 2009/0005808 | A1 | 1/2009 | Hess et al. |
| 2009/0005809 | A1 | 1/2009 | Hess et al. |
| 2009/0012556 | A1 | 1/2009 | Boudreaux et al. |
| 2009/0057369 | A1 | 3/2009 | Smith et al. |
| 2009/0076534 | A1 | 3/2009 | Shelton, IV et al. |
| 2009/0090763 | A1 | 4/2009 | Zemlok et al. |
| 2009/0108048 | A1 | 4/2009 | Zemlok et al. |
| 2009/0114701 | A1 | 5/2009 | Zemlok et al. |
| 2009/0149871 | A9 | 6/2009 | Kagan et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh, II et al. |
| 2009/0206132 | A1 | 8/2009 | Hueil et al. |
| 2009/0206133 | A1 | 8/2009 | Morgan et al. |
| 2009/0206137 | A1 | 8/2009 | Hall et al. |
| 2009/0206138 | A1 | 8/2009 | Smith et al. |
| 2009/0206139 | A1 | 8/2009 | Hall et al. |
| 2009/0206140 | A1 | 8/2009 | Scheib et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0206144 | A1 | 8/2009 | Doll et al. |
| 2009/0209946 | A1 | 8/2009 | Swayze et al. |
| 2009/0218384 | A1 | 9/2009 | Aranyi |
| 2009/0242610 | A1 | 10/2009 | Shelton, IV et al. |
| 2009/0255974 | A1 | 10/2009 | Viola |
| 2009/0255975 | A1 | 10/2009 | Zemlok et al. |
| 2009/0255976 | A1 | 10/2009 | Marczyk et al. |
| 2009/0255977 | A1 | 10/2009 | Zemlok |
| 2009/0255978 | A1 | 10/2009 | Viola et al. |
| 2009/0289096 | A1 | 11/2009 | Shelton, IV et al. |
| 2009/0308907 | A1 | 12/2009 | Nalagatla et al. |
| 2010/0001036 | A1 | 1/2010 | Marczyk et al. |
| 2010/0012704 | A1 | 1/2010 | Tarinelli Racenet et al. |
| 2010/0032470 | A1 | 2/2010 | Hess et al. |
| 2010/0065605 | A1 | 3/2010 | Shelton, VI et al. |
| 2010/0069942 | A1 | 3/2010 | Shelton, IV |
| 2010/0072252 | A1 | 3/2010 | Baxter, III et al. |
| 2010/0072254 | A1 | 3/2010 | Aranyi et al. |
| 2010/0072256 | A1 | 3/2010 | Baxter, III et al. |
| 2010/0076474 | A1 | 3/2010 | Yates et al. |
| 2010/0076475 | A1 | 3/2010 | Yates et al. |
| 2010/0089970 | A1 | 4/2010 | Smith et al. |
| 2010/0089972 | A1 | 4/2010 | Marczyk |
| 2010/0089974 | A1 | 4/2010 | Shelton, IV |
| 2010/0096431 | A1 | 4/2010 | Smith et al. |
| 2010/0096435 | A1 | 4/2010 | Fuchs et al. |
| 2010/0108740 | A1 | 5/2010 | Pastorelli et al. |
| 2010/0108741 | A1 | 5/2010 | Hessler et al. |
| 2010/0127042 | A1 | 5/2010 | Shelton, IV |
| 2010/0133317 | A1 | 6/2010 | Shelton, IV et al. |
| 2010/0133318 | A1 | 6/2010 | Boudreaux |

| | | | |
|---|---|---|---|
| 2010/0163598 | A1 | 7/2010 | Belzer |
| 2010/0179382 | A1 | 7/2010 | Shelton, IV et al. |
| 2010/0181364 | A1 | 7/2010 | Shelton, IV et al. |
| 2010/0193566 | A1 | 8/2010 | Scheib et al. |
| 2010/0193567 | A1 | 8/2010 | Scheib et al. |
| 2010/0193568 | A1 | 8/2010 | Scheib et al. |
| 2010/0193569 | A1 | 8/2010 | Yates et al. |
| 2010/0198220 | A1 | 8/2010 | Boudreaux et al. |
| 2010/0200637 | A1 | 8/2010 | Beetel |
| 2010/0213241 | A1 | 8/2010 | Bedi et al. |
| 2010/0222901 | A1 | 9/2010 | Swayze et al. |
| 2010/0224669 | A1 | 9/2010 | Shelton, IV et al. |
| 2010/0230465 | A1 | 9/2010 | Smith et al. |
| 2010/0237132 | A1 | 9/2010 | Measamer et al. |
| 2010/0243707 | A1 | 9/2010 | Olson et al. |
| 2010/0243708 | A1 | 9/2010 | Aranyi et al. |
| 2010/0243709 | A1 | 9/2010 | Hess et al. |
| 2010/0258611 | A1 | 10/2010 | Smith et al. |
| 2010/0264194 | A1 | 10/2010 | Huang et al. |
| 2010/0276471 | A1 | 11/2010 | Whitman |
| 2010/0294827 | A1 | 11/2010 | Boyden et al. |
| 2010/0294829 | A1 | 11/2010 | Giordano et al. |
| 2010/0301095 | A1 | 12/2010 | Shelton, IV et al. |
| 2010/0301096 | A1 | 12/2010 | Moore et al. |
| 2010/0305552 | A1 | 12/2010 | Shelton, IV et al. |
| 2010/0308100 | A1 | 12/2010 | Boudreaux |
| 2011/0006099 | A1 | 1/2011 | Hall et al. |
| 2011/0006101 | A1 | 1/2011 | Hall et al. |
| 2011/0006103 | A1 | 1/2011 | Laurent et al. |
| 2011/0011914 | A1 | 1/2011 | Baxter, III et al. |
| 2011/0011915 | A1 | 1/2011 | Shelton, IV |
| 2011/0017801 | A1 | 1/2011 | Zemlok et al. |
| 2011/0024477 | A1 | 2/2011 | Hall |
| 2011/0024478 | A1 | 2/2011 | Shelton, IV |
| 2011/0024479 | A1 | 2/2011 | Swensgard et al. |
| 2011/0036887 | A1 | 2/2011 | Zemlok et al. |
| 2011/0042441 | A1 | 2/2011 | Shelton, IV et al. |
| 2011/0060363 | A1 | 3/2011 | Hess et al. |
| 2011/0062212 | A1 | 3/2011 | Shelton, IV et al. |
| 2011/0068145 | A1 | 3/2011 | Bedi et al. |
| 2011/0068148 | A1 | 3/2011 | Hall et al. |
| 2011/0084112 | A1 | 4/2011 | Kostrzewski |
| 2011/0084113 | A1 | 4/2011 | Bedi et al. |
| 2011/0084115 | A1 | 4/2011 | Bedi et al. |
| 2011/0087276 | A1 | 4/2011 | Bedi et al. |
| 2011/0087279 | A1 | 4/2011 | Shah et al. |
| 2011/0095068 | A1 | 4/2011 | Patel |
| 2011/0101065 | A1 | 5/2011 | Milliman |
| 2011/0114697 | A1 | 5/2011 | Baxter, III et al. |
| 2011/0114698 | A1 | 5/2011 | Baxter, III et al. |
| 2011/0114699 | A1 | 5/2011 | Baxter, III et al. |
| 2011/0114700 | A1 | 5/2011 | Baxter, III et al. |
| 2011/0118761 | A1 | 5/2011 | Baxter, III et al. |
| 2011/0121051 | A1 | 5/2011 | Shelton, IV et al. |
| 2011/0121052 | A1 | 5/2011 | Shelton, IV et al. |
| 2011/0125176 | A1 | 5/2011 | Yates et al. |
| 2011/0125177 | A1 | 5/2011 | Yates et al. |
| 2011/0132962 | A1 | 6/2011 | Hall et al. |
| 2011/0132963 | A1 | 6/2011 | Giordano et al. |
| 2011/0132964 | A1 | 6/2011 | Weisenburgh, II et al. |
| 2011/0132965 | A1 | 6/2011 | Moore et al. |
| 2011/0139852 | A1 | 6/2011 | Zingman |
| 2011/0144430 | A1 | 6/2011 | Spivey et al. |
| 2011/0147433 | A1 | 6/2011 | Shelton, IV et al. |
| 2011/0147434 | A1 | 6/2011 | Hueil et al. |
| 2011/0155780 | A1 | 6/2011 | Boudreaux |
| 2011/0155781 | A1 | 6/2011 | Swensgard et al. |
| 2011/0155785 | A1 | 6/2011 | Laurent et al. |
| 2011/0155787 | A1 | 6/2011 | Baxter, III et al. |
| 2011/0163147 | A1 | 7/2011 | Laurent et al. |
| 2011/0174860 | A1 | 7/2011 | Shelton, IV et al. |
| 2011/0174863 | A1 | 7/2011 | Shelton, IV et al. |
| 2011/0192882 | A1 | 8/2011 | Hess et al. |
| 2011/0210156 | A1 | 9/2011 | Smith et al. |
| 2011/0226837 | A1 | 9/2011 | Baxter, III et al. |
| 2011/0233258 | A1 | 9/2011 | Boudreaux |
| 2011/0275901 | A1 | 11/2011 | Shelton, IV |
| 2011/0276083 | A1 | 11/2011 | Shelton, IV et al. |
| 2011/0288573 | A1 | 11/2011 | Yates et al. |

| | | | |
|---|---|---|---|
| 2011/0290851 | A1 | 12/2011 | Shelton, IV |
| 2011/0290853 | A1 | 12/2011 | Shelton, IV et al. |
| 2011/0290854 | A1 | 12/2011 | Timm et al. |
| 2011/0290855 | A1 | 12/2011 | Moore et al. |
| 2011/0290856 | A1 | 12/2011 | Shelton, IV et al. |
| 2011/0295242 | A1 | 12/2011 | Spivey et al. |
| 2011/0295269 | A1 | 12/2011 | Swensgard et al. |
| 2011/0295270 | A1 | 12/2011 | Giordano et al. |
| 2011/0295295 | A1 | 12/2011 | Shelton, IV et al. |
| 2012/0024934 | A1 | 2/2012 | Shelton, IV et al. |
| 2012/0024935 | A1 | 2/2012 | Shelton, IV et al. |
| 2012/0024936 | A1 | 2/2012 | Baxter, III et al. |
| 2012/0029272 | A1 | 2/2012 | Shelton, IV et al. |
| 2012/0029544 | A1 | 2/2012 | Shelton, Iv et al. |
| 2012/0029547 | A1 | 2/2012 | Shelton, IV et al. |
| 2012/0046692 | A1 | 2/2012 | Smith et al. |
| 2012/0061448 | A1 | 3/2012 | Zingman |
| 2012/0071711 | A1 | 3/2012 | Shelton, IV et al. |
| 2012/0071866 | A1 | 3/2012 | Kerr et al. |
| 2012/0074196 | A1 | 3/2012 | Shelton, IV et al. |
| 2012/0074198 | A1 | 3/2012 | Huitema et al. |
| 2012/0074200 | A1 | 3/2012 | Schmid et al. |
| 2012/0074201 | A1 | 3/2012 | Baxter, III et al. |
| 2012/0080332 | A1 | 4/2012 | Shelton, IV et al. |
| 2012/0080333 | A1 | 4/2012 | Woodard, Jr. et al. |
| 2012/0080334 | A1 | 4/2012 | Shelton, IV et al. |
| 2012/0080335 | A1 | 4/2012 | Shelton, IV et al. |
| 2012/0080336 | A1 | 4/2012 | Shelton, IV et al. |
| 2012/0080337 | A1 | 4/2012 | Shelton, IV et al. |
| 2012/0080338 | A1 | 4/2012 | Shelton, IV et al. |
| 2012/0080339 | A1 | 4/2012 | Shelton, IV et al. |
| 2012/0080340 | A1 | 4/2012 | Shelton, IV et al. |
| 2012/0080344 | A1 | 4/2012 | Shelton, IV |
| 2012/0080345 | A1 | 4/2012 | Morgan et al. |
| 2012/0080475 | A1 | 4/2012 | Smith et al. |
| 2012/0080477 | A1 | 4/2012 | Leimbach et al. |
| 2012/0080478 | A1 | 4/2012 | Morgan et al. |
| 2012/0080479 | A1 | 4/2012 | Shelton, IV |
| 2012/0080480 | A1 | 4/2012 | Woodard, Jr. et al. |
| 2012/0080481 | A1 | 4/2012 | Widenhouse et al. |
| 2012/0080482 | A1 | 4/2012 | Schall et al. |
| 2012/0080483 | A1 | 4/2012 | Riestenberg et al. |
| 2012/0080484 | A1 | 4/2012 | Morgan et al. |
| 2012/0080485 | A1 | 4/2012 | Woodard, Jr. et al. |
| 2012/0080486 | A1 | 4/2012 | Woodard, Jr. et al. |
| 2012/0080487 | A1 | 4/2012 | Woodard, Jr. et al. |
| 2012/0080488 | A1 | 4/2012 | Shelton, IV et al. |
| 2012/0080489 | A1 | 4/2012 | Shelton, IV et al. |
| 2012/0080490 | A1 | 4/2012 | Shelton, IV et al. |
| 2012/0080491 | A1 | 4/2012 | Shelton, IV et al. |
| 2012/0080493 | A1 | 4/2012 | Shelton, IV et al. |
| 2012/0080496 | A1 | 4/2012 | Schall et al. |
| 2012/0080498 | A1 | 4/2012 | Shelton, IV et al. |
| 2012/0080499 | A1 | 4/2012 | Schall et al. |
| 2012/0080500 | A1 | 4/2012 | Morgan et al. |
| 2012/0080501 | A1 | 4/2012 | Morgan et al. |
| 2012/0080502 | A1 | 4/2012 | Morgan et al. |
| 2012/0080503 | A1 | 4/2012 | Woodard, Jr. et al. |
| 2012/0083833 | A1 | 4/2012 | Shelton, IV et al. |
| 2012/0083834 | A1 | 4/2012 | Shelton, IV et al. |
| 2012/0083835 | A1 | 4/2012 | Shelton, IV et al. |
| 2012/0083836 | A1 | 4/2012 | Shelton, IV et al. |
| 2012/0132450 | A1 | 5/2012 | Timm et al. |
| 2012/0138660 | A1 | 6/2012 | Shelton, IV |
| 2012/0160721 | A1 | 6/2012 | Shelton, IV et al. |
| 2012/0175399 | A1 | 7/2012 | Shelton et al. |
| 2012/0187179 | A1 | 7/2012 | Gleiman |
| 2012/0199630 | A1 | 8/2012 | Shelton, IV |
| 2012/0199631 | A1 | 8/2012 | Shelton, IV et al. |
| 2012/0199632 | A1 | 8/2012 | Spivey et al. |
| 2012/0199633 | A1 | 8/2012 | Shelton, IV et al. |
| 2012/0203247 | A1 | 8/2012 | Shelton, IV et al. |
| 2012/0205421 | A1 | 8/2012 | Shelton, IV |
| 2012/0211546 | A1 | 8/2012 | Shelton, IV |
| 2012/0234890 | A1 | 9/2012 | Aronhalt et al. |
| 2012/0234891 | A1 | 9/2012 | Aronhalt et al. |
| 2012/0234892 | A1 | 9/2012 | Aronhalt et al. |
| 2012/0234893 | A1 | 9/2012 | Schuckmann et al. |
| 2012/0234895 | A1 | 9/2012 | O'Connor et al. |
| 2012/0234896 | A1 | 9/2012 | Ellerhorst et al. |
| 2012/0234897 | A1 | 9/2012 | Shelton, IV et al. |
| 2012/0234898 | A1 | 9/2012 | Shelton, IV et al. |
| 2012/0234899 | A1 | 9/2012 | Scheib et al. |
| 2012/0234900 | A1 | 9/2012 | Swayze |
| 2012/0238823 | A1 | 9/2012 | Hagerty et al. |
| 2012/0238824 | A1 | 9/2012 | Widenhouse et al. |
| 2012/0238826 | A1 | 9/2012 | Yoo et al. |
| 2012/0238829 | A1 | 9/2012 | Shelton, IV et al. |
| 2012/0239009 | A1 | 9/2012 | Mollere et al. |
| 2012/0239010 | A1 | 9/2012 | Shelton, IV et al. |
| 2012/0239012 | A1 | 9/2012 | Laurent et al. |
| 2012/0239075 | A1 | 9/2012 | Widenhouse et al. |
| 2012/0239082 | A1 | 9/2012 | Shelton, IV et al. |
| 2012/0241491 | A1 | 9/2012 | Aldridge et al. |
| 2012/0241492 | A1 | 9/2012 | Shelton, IV et al. |
| 2012/0241493 | A1 | 9/2012 | Baxter, III et al. |
| 2012/0241496 | A1 | 9/2012 | Vasudevan et al. |
| 2012/0241497 | A1 | 9/2012 | Vasudevan et al. |
| 2012/0241498 | A1 | 9/2012 | Gonzalez et al. |
| 2012/0241499 | A1 | 9/2012 | Baxter, III et al. |
| 2012/0241500 | A1 | 9/2012 | Timmer et al. |
| 2012/0241501 | A1 | 9/2012 | Swayze et al. |
| 2012/0241502 | A1 | 9/2012 | Aldridge et al. |
| 2012/0241503 | A1 | 9/2012 | Baxter, III et al. |
| 2012/0241505 | A1 | 9/2012 | Alexander, III et al. |
| 2012/0248169 | A1 | 10/2012 | Widenhouse et al. |
| 2012/0253298 | A1 | 10/2012 | Henderson et al. |
| 2012/0265230 | A1 | 10/2012 | Yates et al. |
| 2012/0273551 | A1 | 11/2012 | Shelton, IV et al. |
| 2012/0286019 | A1 | 11/2012 | Hueil et al. |

FOREIGN PATENT DOCUMENTS

| | | | |
|---|---|---|---|
| CA | 2514274 | A1 | 1/2006 |
| CN | 1634601 | A | 7/2005 |
| CN | 1868411 | A | 11/2006 |
| CN | 1915180 | A | 2/2007 |
| CN | 101095621 | A | 1/2008 |
| DE | 273689 | C | 5/1914 |
| DE | 1775926 | A | 1/1972 |
| DE | 3036217 | A1 | 1/1982 |
| DE | 3210466 | A1 | 9/1983 |
| DE | 9412228 | | 9/1994 |
| DE | 19509116 | A1 | 9/1996 |
| DE | 19851291 | A1 | 1/2000 |
| DE | 19924311 | A1 | 11/2000 |
| DE | 69328576 | T2 | 1/2001 |
| DE | 10052679 | A1 | 5/2001 |
| DE | 20112837 | U1 | 10/2001 |
| DE | 20121753 | U1 | 4/2003 |
| DE | 10314072 | A1 | 10/2004 |
| DE | 202007003114 | U1 | 6/2007 |
| EP | 0122046 | A1 | 10/1984 |
| EP | 0070230 | B1 | 10/1985 |
| EP | 0387980 | B1 | 10/1985 |
| EP | 0033548 | B1 | 5/1986 |
| EP | 0276104 | A2 | 7/1988 |
| EP | 0248844 | B1 | 1/1993 |
| EP | 0545029 | A1 | 6/1993 |
| EP | 0277959 | B1 | 10/1993 |
| EP | 0233940 | B1 | 11/1993 |
| EP | 0261230 | B1 | 11/1993 |
| EP | 0639349 | A2 | 2/1994 |
| EP | 0324636 | B1 | 3/1994 |
| EP | 0593920 | A1 | 4/1994 |
| EP | 0594148 | A1 | 4/1994 |
| EP | 0427949 | B1 | 6/1994 |
| EP | 0523174 | B1 | 6/1994 |
| EP | 0600182 | A2 | 6/1994 |
| EP | 0310431 | B1 | 11/1994 |
| EP | 0375302 | B1 | 11/1994 |
| EP | 0376562 | B1 | 11/1994 |
| EP | 0630612 | A1 | 12/1994 |
| EP | 0634144 | A1 | 1/1995 |
| EP | 0646356 | A2 | 4/1995 |
| EP | 0646357 | A1 | 4/1995 |
| EP | 0653189 | A2 | 5/1995 |
| EP | 0669104 | A1 | 8/1995 |
| EP | 0511470 | B1 | 10/1995 |

| | | | |
|---|---|---|---|
| EP | 0679367 | A2 | 11/1995 |
| EP | 0392547 | B1 | 12/1995 |
| EP | 0685204 | A1 | 12/1995 |
| EP | 0364216 | B1 | 1/1996 |
| EP | 0699418 | A1 | 3/1996 |
| EP | 0702937 | A1 | 3/1996 |
| EP | 0705571 | A1 | 4/1996 |
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0843906 | B1 | 3/2000 |
| EP | 0552050 | B1 | 5/2000 |
| EP | 0833592 | B1 | 5/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1156917 | B1 | 11/2005 |
| EP | 1344498 | B1 | 11/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1632191 | A2 | 3/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813201 | A1 | 8/2007 |
| EP | 1813203 | A2 | 8/2007 |
| EP | 1813207 | A1 | 8/2007 |
| EP | 1813209 | A1 | 8/2007 |
| EP | 1487359 | B1 | 10/2007 |
| EP | 1599146 | B1 | 10/2007 |
| EP | 1839596 | A1 | 10/2007 |

| | | | |
|---|---|---|---|
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1897502 | A1 | 3/2008 |
| EP | 1330201 | B1 | 6/2008 |
| EP | 1702568 | B1 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1693008 | B1 | 12/2008 |
| EP | 1759640 | B1 | 12/2008 |
| EP | 2000102 | A2 | 12/2008 |
| EP | 2008595 | A2 | 12/2008 |
| EP | 1736104 | B1 | 3/2009 |
| EP | 1749486 | B1 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550413 | B1 | 6/2009 |
| EP | 1745748 | B1 | 8/2009 |
| EP | 2090237 | A1 | 8/2009 |
| EP | 2090256 | A2 | 8/2009 |
| EP | 2095777 | A2 | 9/2009 |
| EP | 2110082 | A1 | 10/2009 |
| EP | 1813208 | B1 | 11/2009 |
| EP | 2116195 | A1 | 11/2009 |
| EP | 1607050 | B1 | 12/2009 |
| EP | 1815804 | B1 | 12/2009 |
| EP | 1566150 | B1 | 4/2010 |
| EP | 1813206 | B1 | 4/2010 |
| EP | 1769754 | B1 | 6/2010 |
| EP | 1535565 | B1 | 10/2010 |
| EP | 1702570 | B1 | 10/2010 |
| EP | 1785098 | B1 | 10/2010 |
| EP | 1627605 | B1 | 12/2010 |
| EP | 1813205 | B1 | 6/2011 |
| EP | 1785102 | B1 | 1/2012 |
| FR | 999646 | A | 2/1952 |
| FR | 1112936 | A | 3/1956 |
| FR | 2598905 | A1 | 11/1987 |
| FR | 2765794 | A | 1/1999 |
| GB | 939929 | A | 10/1963 |
| GB | 1210522 | A | 10/1970 |
| GB | 1217159 | A | 12/1970 |
| GB | 1339394 | A | 12/1973 |
| GB | 2109241 | A | 6/1983 |
| GB | 2272159 | A | 5/1994 |
| GB | 2284242 | A | 5/1995 |
| GB | 2336214 | A | 10/1999 |
| GB | 2425903 | A | 11/2006 |
| JP | 58500053 | A | 1/1983 |
| JP | 61-98249 | A | 5/1986 |
| JP | 63-203149 | | 8/1988 |
| JP | 3-12126 | A | 1/1991 |
| JP | 5-212039 | A | 8/1993 |
| JP | 6007357 | A | 1/1994 |
| JP | 7051273 | A | 2/1995 |
| JP | 8033641 | A | 2/1996 |
| JP | 8229050 | A | 9/1996 |
| JP | 2000033071 | A | 2/2000 |
| JP | 2000171730 | A | 6/2000 |
| JP | 2000287987 | A | 10/2000 |
| JP | 2000325303 | A | 11/2000 |
| JP | 2001-514541 | A | 9/2001 |
| JP | 2001286477 | A | 10/2001 |
| JP | 2002143078 | A | 5/2002 |
| JP | 2002369820 | A | 12/2002 |
| JP | 2004-344663 | | 12/2004 |
| JP | 2005-028149 | A | 2/2005 |
| JP | 2005505322 | T | 2/2005 |
| JP | 2005103293 | A | 4/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005152416 | A | 6/2005 |
| JP | 2005-523105 | A | 8/2005 |
| JP | 2005524474 | A | 8/2005 |
| JP | 2006-281405 | A | 10/2006 |
| RU | 2008830 | C1 | 3/1994 |
| RU | 2187249 | C2 | 8/2002 |
| RU | 2225170 | C2 | 3/2004 |
| SU | 169517 | A | 1/1967 |
| SU | 328636 | A | 9/1972 |
| SU | 886900 | A1 | 12/1981 |
| SU | 1009439 | A | 4/1983 |
| SU | 1333319 | A2 | 8/1987 |
| SU | 1377053 | A1 | 2/1988 |
| SU | 1561964 | A1 | 5/1990 |
| SU | 1722476 | A1 | 3/1992 |
| WO | WO 82/02824 | A1 | 9/1982 |
| WO | WO 91/15157 | A1 | 10/1991 |
| WO | WO 92/20295 | A1 | 11/1992 |
| WO | WO 92/21300 | A1 | 12/1992 |
| WO | WO 93/08755 | A1 | 5/1993 |
| WO | WO 93/13718 | A1 | 7/1993 |
| WO | WO 93/14690 | A1 | 8/1993 |
| WO | WO 93/15648 | A1 | 8/1993 |
| WO | WO 93/15850 | A1 | 8/1993 |
| WO | WO 93/19681 | A1 | 10/1993 |
| WO | WO 94/00060 | A1 | 1/1994 |
| WO | WO 94/11057 | A1 | 5/1994 |
| WO | WO 94/12108 | A1 | 6/1994 |
| WO | WO 94/18893 | A1 | 9/1994 |
| WO | WO 94/22378 | A1 | 10/1994 |
| WO | WO 94/23659 | A1 | 10/1994 |
| WO | WO 95/02369 | A1 | 1/1995 |
| WO | WO 95/03743 | A1 | 2/1995 |
| WO | WO 95/06817 | A1 | 3/1995 |
| WO | WO 95/09576 | A1 | 4/1995 |
| WO | WO 95/09577 | A1 | 4/1995 |
| WO | WO 95/14436 | A1 | 6/1995 |
| WO | WO 95/17855 | A1 | 7/1995 |
| WO | WO 95/18383 | A1 | 7/1995 |
| WO | WO 95/18572 | A1 | 7/1995 |
| WO | WO 95/19739 | A1 | 7/1995 |
| WO | WO 95/20360 | A1 | 8/1995 |
| WO | WO 95/23557 | A1 | 9/1995 |
| WO | WO 95/24865 | A1 | 9/1995 |
| WO | WO 95/25471 | A3 | 9/1995 |
| WO | WO 95/26562 | A1 | 10/1995 |
| WO | WO 95/29639 | A1 | 11/1995 |
| WO | WO 96/04858 | A1 | 2/1996 |
| WO | WO 96/19151 | A1 | 6/1996 |
| WO | WO 96/19152 | A1 | 6/1996 |
| WO | WO 96/20652 | A1 | 7/1996 |
| WO | WO 96/21119 | A1 | 7/1996 |
| WO | WO 96/22055 | A1 | 7/1996 |
| WO | WO 96/23448 | A1 | 8/1996 |
| WO | WO 96/24301 | A1 | 8/1996 |
| WO | WO 96/27337 | A1 | 9/1996 |
| WO | WO 96/31155 | A1 | 10/1996 |
| WO | WO 96/35464 | A1 | 11/1996 |
| WO | WO 96/39085 | A1 | 12/1996 |
| WO | WO 96/39086 | A1 | 12/1996 |
| WO | WO 96/39087 | A1 | 12/1996 |
| WO | WO 96/39088 | A1 | 12/1996 |
| WO | WO 96/39089 | A1 | 12/1996 |
| WO | WO 97/00646 | A1 | 1/1997 |
| WO | WO 97/00647 | A1 | 1/1997 |
| WO | WO 97/06582 | A1 | 2/1997 |
| WO | WO 97/10763 | A1 | 3/1997 |
| WO | WO 97/10764 | A1 | 3/1997 |
| WO | WO 97/11648 | A2 | 4/1997 |
| WO | WO 97/11649 | A1 | 4/1997 |
| WO | WO 97/15237 | A1 | 5/1997 |
| WO | WO 97/24073 | A1 | 7/1997 |
| WO | WO 97/24993 | A1 | 7/1997 |
| WO | WO 97/30644 | A1 | 8/1997 |

| | | | |
|---|---|---|---|
| WO | WO 97/34533 | A1 | 9/1997 |
| WO | WO 97/37598 | A1 | 10/1997 |
| WO | WO 97/39688 | A2 | 10/1997 |
| WO | WO 98/17180 | A1 | 4/1998 |
| WO | WO 98/27880 | A1 | 7/1998 |
| WO | WO 98/30153 | A1 | 7/1998 |
| WO | WO 98/47436 | A1 | 10/1998 |
| WO | WO 99/03407 | A1 | 1/1999 |
| WO | WO 99/03408 | A1 | 1/1999 |
| WO | WO 99/03409 | A1 | 1/1999 |
| WO | WO 99/12483 | A1 | 3/1999 |
| WO | WO 99/12487 | A1 | 3/1999 |
| WO | WO 99/12488 | A1 | 3/1999 |
| WO | WO 99/15086 | A1 | 4/1999 |
| WO | WO 99/15091 | A1 | 4/1999 |
| WO | WO 99/23933 | A2 | 5/1999 |
| WO | WO 99/23959 | A1 | 5/1999 |
| WO | WO 99/25261 | A1 | 5/1999 |
| WO | WO 99/29244 | A1 | 6/1999 |
| WO | WO 99/34744 | A1 | 7/1999 |
| WO | WO 99/45849 | A1 | 9/1999 |
| WO | WO 99/48430 | A1 | 9/1999 |
| WO | WO 99/51158 | A1 | 10/1999 |
| WO | WO 00/24322 | A1 | 5/2000 |
| WO | WO 00/24330 | A1 | 5/2000 |
| WO | WO 00/41638 | A1 | 7/2000 |
| WO | WO 00/48506 | A1 | 8/2000 |
| WO | WO 00/53112 | A2 | 9/2000 |
| WO | WO 00/54653 | A1 | 9/2000 |
| WO | WO 00/057796 | A1 | 10/2000 |
| WO | WO 00/64365 | A1 | 11/2000 |
| WO | WO 00/72762 | A1 | 12/2000 |
| WO | WO 00/72765 | A1 | 12/2000 |
| WO | WO 01/03587 | A1 | 1/2001 |
| WO | WO 01/05702 | A1 | 1/2001 |
| WO | WO 01/10482 | A1 | 2/2001 |
| WO | WO 01/35845 | A1 | 5/2001 |
| WO | WO 01/54594 | A1 | 8/2001 |
| WO | WO 01/58371 | A1 | 8/2001 |
| WO | WO 01/62158 | A2 | 8/2001 |
| WO | WO 01/62161 | A1 | 8/2001 |
| WO | WO 01/62162 | A1 | 8/2001 |
| WO | WO 01/62164 | A2 | 8/2001 |
| WO | WO 01/62169 | A2 | 8/2001 |
| WO | WO 01/78605 | A2 | 10/2001 |
| WO | WO 01/91646 | A1 | 12/2001 |
| WO | WO 02/07608 | A2 | 1/2002 |
| WO | WO 02/07618 | A1 | 1/2002 |
| WO | WO 02/17799 | A1 | 3/2002 |
| WO | WO 02/19920 | A1 | 3/2002 |
| WO | WO 02/19932 | A2 | 3/2002 |
| WO | WO 02/30297 | A2 | 4/2002 |
| WO | WO 02/32322 | A2 | 4/2002 |
| WO | WO 02/36028 | A1 | 5/2002 |
| WO | WO 02/43571 | A2 | 6/2002 |
| WO | WO 02/058568 | A1 | 8/2002 |
| WO | WO 02/060328 | A1 | 8/2002 |
| WO | WO 02/067785 | A2 | 9/2002 |
| WO | WO 02/098302 | A1 | 12/2002 |
| WO | WO 03/000138 | A2 | 1/2003 |
| WO | WO 03/001329 | A2 | 1/2003 |
| WO | WO 03/013363 | A1 | 2/2003 |
| WO | WO 03/015604 | A2 | 2/2003 |
| WO | WO 03/020106 | A2 | 3/2003 |
| WO | WO 03/020139 | A2 | 3/2003 |
| WO | WO 03/024339 | A1 | 3/2003 |
| WO | WO 03/079909 | A3 | 3/2003 |
| WO | WO 03/030743 | A2 | 4/2003 |
| WO | WO 03/037193 | A1 | 5/2003 |
| WO | WO 03/047436 | A3 | 6/2003 |
| WO | WO 03/055402 | A1 | 7/2003 |
| WO | WO 03/057048 | A1 | 7/2003 |
| WO | WO 03/057058 | A1 | 7/2003 |
| WO | WO 03/063694 | A1 | 8/2003 |
| WO | WO 03/077769 | A1 | 9/2003 |
| WO | WO 03/079911 | A1 | 10/2003 |
| WO | WO 03/082126 | A1 | 10/2003 |
| WO | WO 03/088845 | A2 | 10/2003 |
| WO | WO 03/090630 | A2 | 11/2003 |

| | | | |
|---|---|---|---|
| WO | WO 03/094743 | A1 | 11/2003 |
| WO | WO 03/094745 | A1 | 11/2003 |
| WO | WO 03/094746 | A1 | 11/2003 |
| WO | WO 03/094747 | A1 | 11/2003 |
| WO | WO 03/101313 | A1 | 12/2003 |
| WO | WO 03/105698 | A2 | 12/2003 |
| WO | WO 03/105702 | A2 | 12/2003 |
| WO | WO 2004/006980 | A2 | 1/2004 |
| WO | WO 2004/011037 | A2 | 2/2004 |
| WO | WO 2004/019769 | A1 | 3/2004 |
| WO | WO 2004/021868 | A2 | 3/2004 |
| WO | WO 2004/028585 | A2 | 4/2004 |
| WO | WO 2004/032754 | A2 | 4/2004 |
| WO | WO 2004/032760 | A2 | 4/2004 |
| WO | WO 2004/032762 | A1 | 4/2004 |
| WO | WO 2004/032763 | A2 | 4/2004 |
| WO | WO 2004/034875 | A2 | 4/2004 |
| WO | WO 2004/047626 | A1 | 6/2004 |
| WO | WO 2004/047653 | A2 | 6/2004 |
| WO | WO 2004/049956 | A2 | 6/2004 |
| WO | WO 2004/052426 | A2 | 6/2004 |
| WO | WO 2004/056276 | A1 | 7/2004 |
| WO | WO 2004/056277 | A1 | 7/2004 |
| WO | WO 2004/062516 | A1 | 7/2004 |
| WO | WO 2004/078050 | A2 | 9/2004 |
| WO | WO 2004/078051 | A2 | 9/2004 |
| WO | WO 2004/086987 | A1 | 10/2004 |
| WO | WO 2004/096015 | A2 | 11/2004 |
| WO | WO 2004/096057 | A2 | 11/2004 |
| WO | WO 2004/103157 | A2 | 12/2004 |
| WO | WO 2004/105593 | A1 | 12/2004 |
| WO | WO 2004/105621 | A1 | 12/2004 |
| WO | WO 2004/112618 | A2 | 12/2004 |
| WO | WO 2004/112652 | A2 | 12/2004 |
| WO | WO 2005/027983 | A2 | 3/2005 |
| WO | WO 2005/037329 | A2 | 4/2005 |
| WO | WO 2005/044078 | A2 | 5/2005 |
| WO | WO 2005/055846 | A1 | 6/2005 |
| WO | WO 2005/072634 | A2 | 8/2005 |
| WO | WO 2005/078892 | A1 | 8/2005 |
| WO | WO 2005/079675 | A2 | 9/2005 |
| WO | WO 2005/096954 | A2 | 10/2005 |
| WO | WO 2005/112806 | A2 | 12/2005 |
| WO | WO 2005/112808 | A1 | 12/2005 |
| WO | WO 2005/115251 | A2 | 12/2005 |
| WO | WO 2005/115253 | A2 | 12/2005 |
| WO | WO 2005/117735 | A1 | 12/2005 |
| WO | WO 2005/122936 | A1 | 12/2005 |
| WO | WO 2006/027014 | A1 | 3/2006 |
| WO | WO 2006/044490 | A2 | 4/2006 |
| WO | WO 2006/044581 | A2 | 4/2006 |
| WO | WO 2006/044810 | A2 | 4/2006 |
| WO | WO 2006/051252 | A1 | 5/2006 |
| WO | WO 2006/059067 | A1 | 6/2006 |
| WO | WO 2006/083748 | A1 | 8/2006 |
| WO | WO 2006/092563 | A1 | 9/2006 |
| WO | WO 2006/092565 | A1 | 9/2006 |
| WO | WO 2006/115958 | A1 | 11/2006 |
| WO | WO 2006/125940 | A1 | 11/2006 |
| WO | WO 2006/132992 | A1 | 12/2006 |
| WO | WO 2007/002180 | A2 | 1/2007 |
| WO | WO 2007/016290 | A2 | 2/2007 |
| WO | WO 2007/018898 | A2 | 2/2007 |
| WO | WO 2007/098220 | A2 | 8/2007 |
| WO | WO 2007/121579 | A1 | 11/2007 |
| WO | WO 2007/131110 | A2 | 11/2007 |
| WO | WO 2007/137304 | A2 | 11/2007 |
| WO | WO 2007/139734 | A2 | 12/2007 |
| WO | WO 2007/142625 | A2 | 12/2007 |
| WO | WO 2007/147439 | | 12/2007 |
| WO | WO 2008/021969 | A2 | 2/2008 |
| WO | WO 2008/039249 | A1 | 4/2008 |
| WO | WO 2008/039270 | A1 | 4/2008 |
| WO | WO 2008/045383 | A2 | 4/2008 |
| WO | WO 2008/070763 | A1 | 6/2008 |
| WO | WO 2008/089404 | A2 | 7/2008 |
| WO | WO 2008/109125 | A1 | 9/2008 |
| WO | WO 2010/063795 | A1 | 6/2010 |
| WO | WO 2012/044844 | A2 | 4/2012 |

OTHER PUBLICATIONS

European Search Report, Application No. 09250057.8, dated May 8, 2009 (7 pages).
European Search Report, Application No. 09250061.0, dated May 7, 2009 (7 pages).
Partial European Search Report, Application 11163532.2, dated Aug. 4, 2011 (5 pages).
Partial European Search Report, Application 11163523.1, dated Aug. 4, 2011 (2 pages).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown On Ultracapacitors," Nov. 15, 2007: [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
European Search Report, Application No. 08252151.9, dated Jun. 17, 2009 (12 pages).
European Examination Report, Application No. 08252151.9, dated Jan. 18, 2010 (8 pages).
European Examination Report, Application No. 09250057.8, dated Jan. 22, 2010 (5 pages).
European Examination Report, Application No. 09250061.0, dated Jan. 22, 2010 (5 pages).
European Search Report, Application 11163532.2, dated Dec. 1, 2011 (8 pages).
European Search Report, Application 11163523.1, dated Dec. 2, 2011 (8 pages).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).

SURGICAL STAPLING INSTRUMENT WITH AN ARTICULATABLE END EFFECTOR

CROSS REFERENCE TO RELATED APPLICATION

The present application is a continuation-in-part application claiming the benefit under 35 U.S.C. §120 of co-pending U.S. patent application Ser. No. 12/008,266, entitled SURGICAL STAPLING INSTRUMENT WITH A FIRING RETURN MECHANISM, filed on Jan. 10, 2008, now U.S. Pat. No. 7,954,684 which is a continuation-in-part application of U.S. patent application Ser. No. 11/821,277, entitled SURGICAL STAPLING INSTRUMENTS, filed on Jun. 22, 2007, now U.S. Pat. No. 7,753,245, the entire disclosures of which are hereby incorporated by reference herein.

BACKGROUND

1. Field of the Invention

The present invention generally relates to surgical stapling instruments and, more particularly, to surgical staplers having a closing system for closing an end effector and a firing system for deploying staples.

2. Description of the Related Art

As known in the art, surgical staplers are often used to deploy staples into soft tissue in order to reduce or eliminate bleeding from the soft tissue, especially as the tissue is being transected, for example. Surgical staplers, such as an endocutter, for example, can comprise an end effector which can be moved, or articulated, with respect to an elongate shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge. These closing systems, however, do not prevent the end effector from being articulated relative to the shaft assembly after the jaw members have been closed. As a result, when the end effector is articulated, the end effector may apply a shear force to the soft tissue captured between the jaw members.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

SUMMARY

In at least one form, a surgical stapler can comprise a channel configured to receive a staple cartridge comprising staples removably stored therein, wherein the channel comprises a distal end, a proximal portion, and a stop. The surgical stapler can further comprise an anvil configured to deform staples ejected from the staple cartridge, wherein the anvil comprises a distal end and a proximal portion, wherein the proximal portion of the anvil is pivotably coupled to the proximal portion of the channel, and wherein the anvil is rotatable between an open position and a closed position. The surgical stapler can further comprise a closure member movable between a first position and a second position, wherein the closure member is configured to move the anvil between the open position and the closed position when the closure member is moved between the first position and the second position, and wherein the closure member comprises a body, a first camming portion extending from the body a first distance toward the distal end of the channel, wherein the first camming portion is configured to be at least partially positioned around the anvil when the closure member is in the second position, and a second camming portion extending from the body a second distance toward the distal end of the channel, wherein the first distance is larger than the second distance, wherein the second camming portion is configured to be at least partially positioned around the channel and adjacent to the stop when said closure member is in the second position.

In at least one form, a surgical instrument can comprise a shaft comprising a drive bar and a first guide slot, wherein the first guide slot is configured to receive at least a portion of the drive bar, and an end effector pivotably coupled to the shaft about a pivot joint, the end effector being rotatable about the pivot joint in a first direction and a second direction. The end effector can further comprise a staple cartridge attachment portion configured to receive a staple cartridge, a second guide slot configured to receive at least a portion of the drive bar, a first recess positioned on a first side of the second guide slot, and a second recess positioned on a second side of said second guide slot. The surgical stapler can further comprise a guide member configured to move independently of the shaft and the end effector, the guide member comprising a third guide slot configured to receive at least a portion of the drive bar, a first catch positioned on a first side of the third guide slot, wherein the first catch is configured to be received in the first recess of the end effector when the end effector is rotated in the first direction, and a second catch positioned on a second side of the third guide slot, wherein the second catch is configured to be received in the second recess of the end effector when the end effector is rotated in the second direction.

In at least one form, a surgical instrument can comprise a shaft comprising a drive bar and a first guide slot, wherein the first guide slot is configured to receive at least a portion of the drive bar, and an end effector pivotably coupled to the shaft about a pivot joint. The end effector can be rotatable about the pivot joint in a first direction and a second direction, the end effector comprising a staple cartridge attachment portion configured to receive a staple cartridge. The surgical instrument can further comprise a guide member configured to move independently of the shaft and the end effector, wherein the guide member can comprise a second guide slot configured to receive at least a portion of the drive bar, and a projection, wherein the shaft comprises a recess configured to receive the projection, wherein the end effector is configured to push the guide member toward the shaft and position the projection in the recess when the end effector is moved in the first direction or the second direction, and wherein the recess comprises a sidewall configured to limit the movement of the projection relative to the recess and the shaft.

In at least one form, a surgical instrument can comprise a shaft comprising a housing, a first guide slot in the housing, and a drive bar movable between a first position and a second position, wherein the first guide slot is configured to receive at least a portion of the drive bar. The surgical instrument can further comprise an end effector pivotably coupled to the shaft about a pivot joint, wherein the end effector is rotatable about the pivot joint, and wherein the end effector comprises a staple cartridge attachment portion configured to receive a staple cartridge. The surgical instrument can further comprise a guide member configured to move relative to the shaft and the end effector, the guide member comprising a second guide slot configured to receive at least a portion of the drive bar, an end portion configured to be contacted by the end effector, and a datum portion. The drive bar can further comprises a shaft, a drive portion configured to be operably engaged with a cutting member and move the cutting member within the end effector when the driver bar is moved between the first position and the second position, and a stop configured to be engaged with the datum portion of the guide member to limit the movement of the drive bar relative to the end effector.

In at least one form, a surgical instrument can comprise a handle, a shaft extending from the handle, wherein the shaft comprises a housing, a firing member movable relative to the housing, a cutting member operably coupled to the firing member, and an end effector pivotably coupled to the shaft about a pivot joint, wherein the end effector is rotatable about the pivot joint. The end effector can further comprise a staple cartridge attachment portion configured to receive a staple cartridge, and a retraction stop. The surgical instrument can further comprise retraction means for moving the firing member and the cutting member relative to the staple cartridge attachment portion in a first direction and for positioning the cutting member against the retraction stop, and, in addition, drive means for moving the firing member and the cutting member relative to the staple cartridge attachment portion in a direction opposite the first direction a predetermined distance from the retraction stop.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 113 is a cross-sectional view of the indexing element of FIG. 112;

FIG. 114 is a perspective view of an indexing element in accordance with another alternative embodiment of the present invention;

FIG. 115 is a partial perspective view of a surgical instrument including an anti-backup mechanism in accordance with an alternative embodiment of the present invention with some components of the surgical instrument removed;

FIG. 116 is a cross-sectional view of the anti-backup mechanism of FIG. 115;

FIG. 117 is a perspective view of the surgical instrument of FIG. 115 illustrating a return carriage of a reversing mechanism in an actuated position;

FIG. 118 is a cross-sectional view of the anti-backup mechanism of FIG. 115 when the return carriage of FIG. 117 is in its actuated position;

FIG. 119 is a perspective view of a surgical instrument in accordance with an alternative embodiment of the present invention with some components of the surgical instrument removed to illustrate a switch for actuating a reversing drive of the surgical instrument;

FIG. 120 is a partial elevational view of a surgical instrument in accordance with another alternative embodiment of the present invention with some components of the surgical instrument removed to illustrate a switch for actuating a reversing drive of the surgical instrument;

FIG. 121 is a partial elevational view of the surgical instrument of FIG. 120 illustrating a first portion of the switch in an actuated position;

FIG. 122 is a partial elevational view of the surgical instrument of FIG. 120 illustrating a second portion of the switch utilized to position the first portion of the switch in its actuated position; and FIG. 123 is a perspective view of an articulation joint rotatably connecting an end effector a shaft of a surgical instrument;

FIG. 124 is an elevational view of an end effector of a surgical stapling instrument illustrating an anvil in an open position;

FIG. 125 is a detail view of a closure tube of the end effector of FIG. 124 holding the anvil of the end effector in a closed position;

Figure 123:
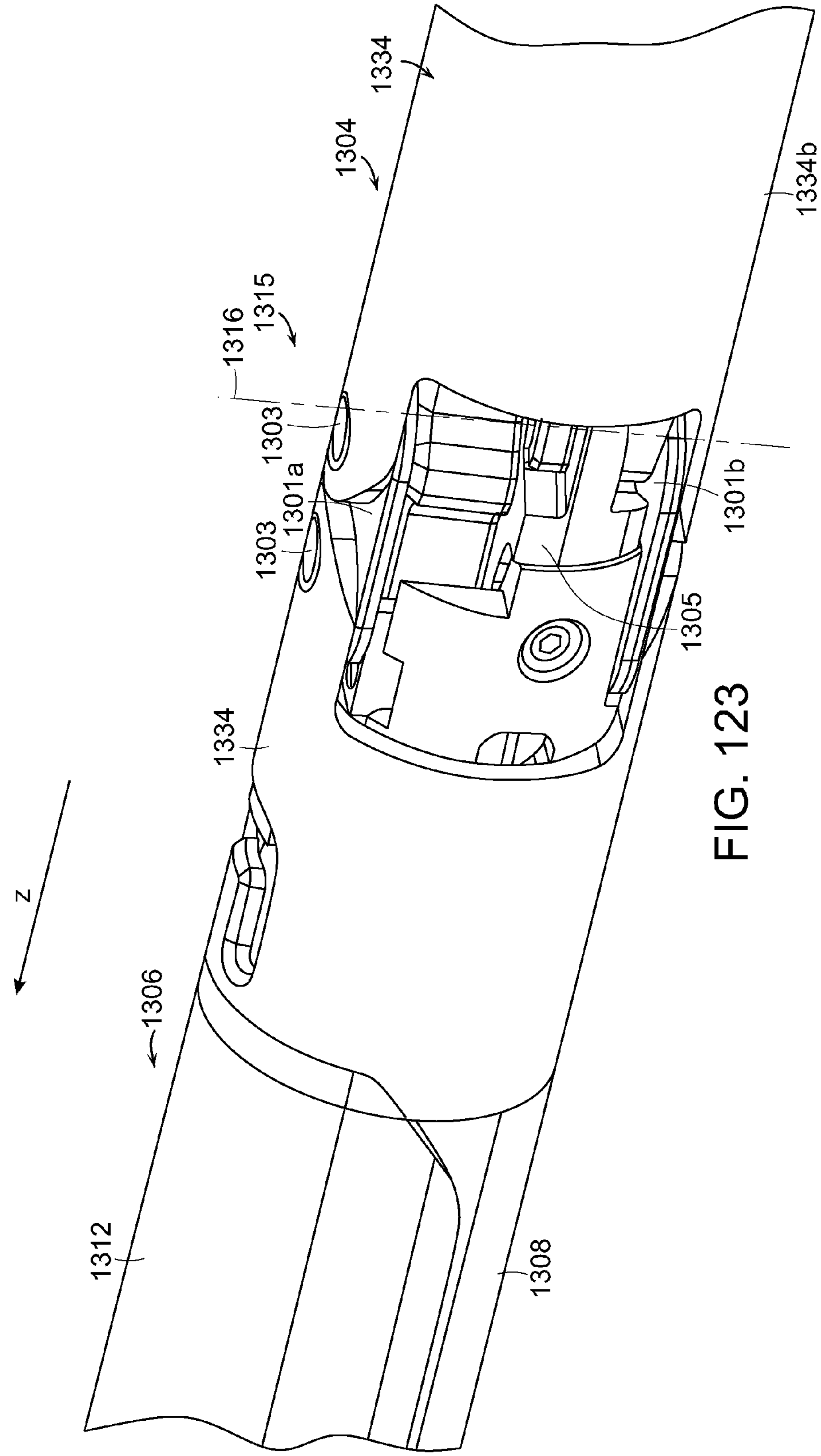
Figure 124:
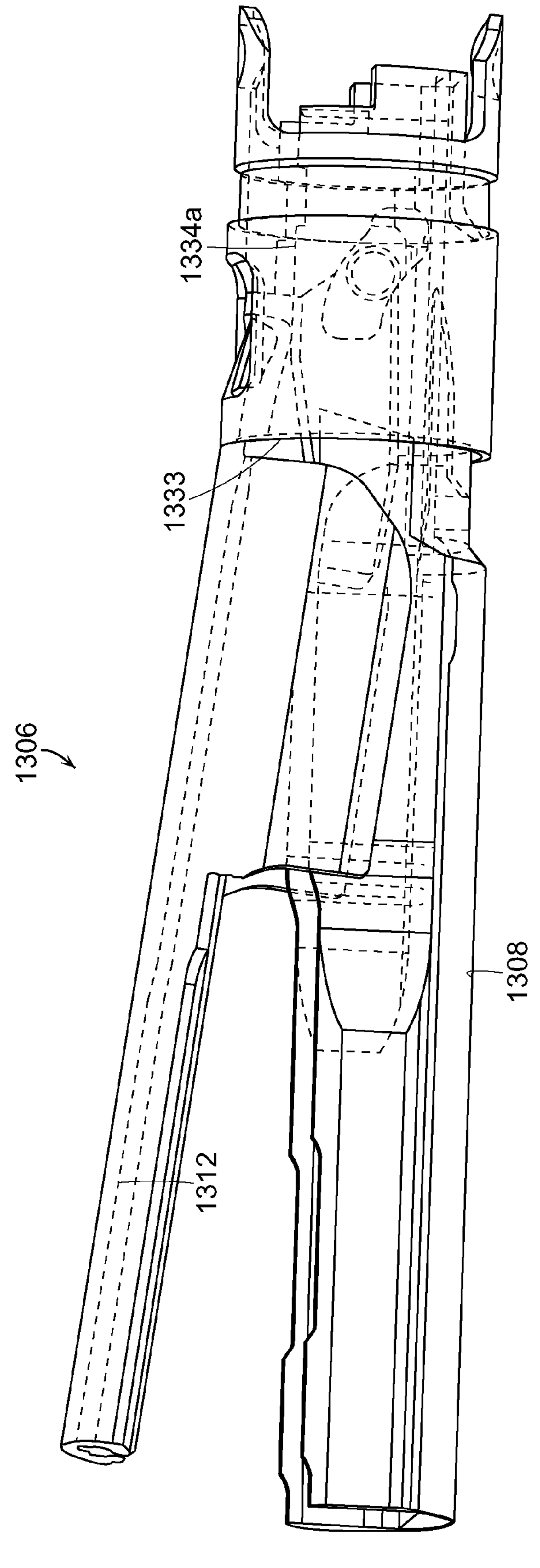
Figure 126:
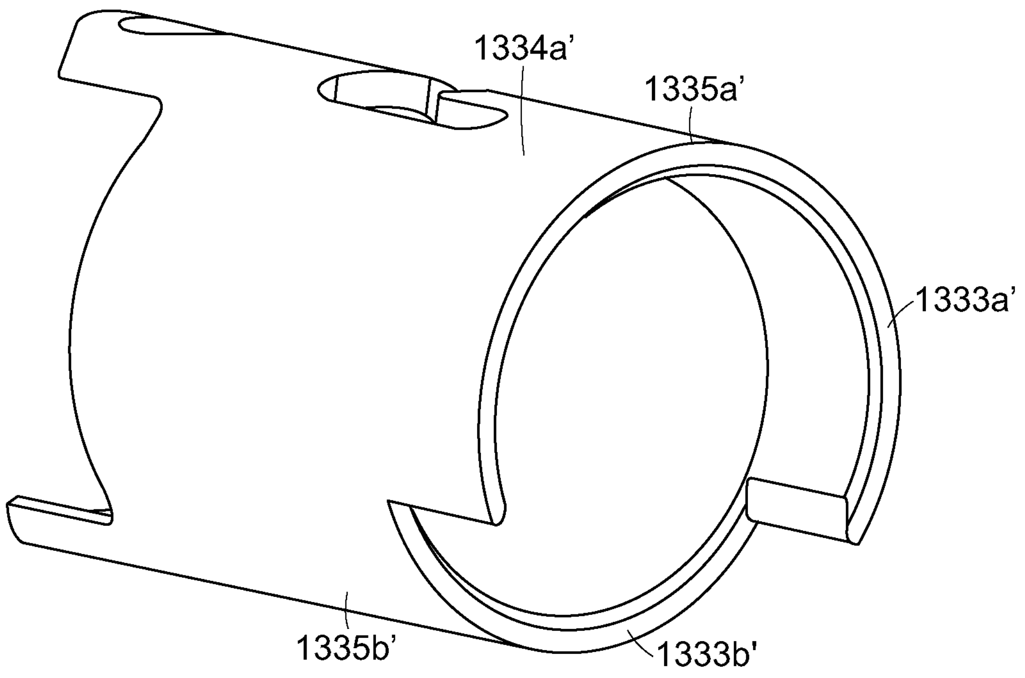
Figure 127:
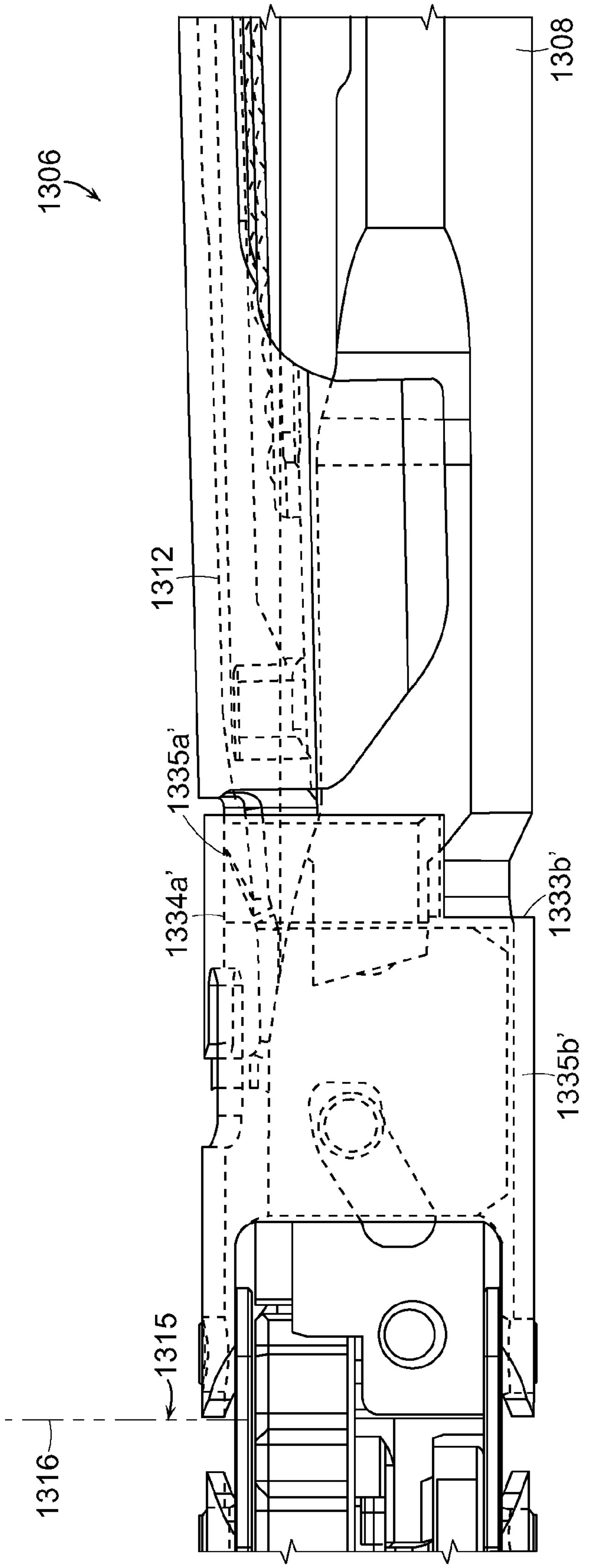
Figure 128:
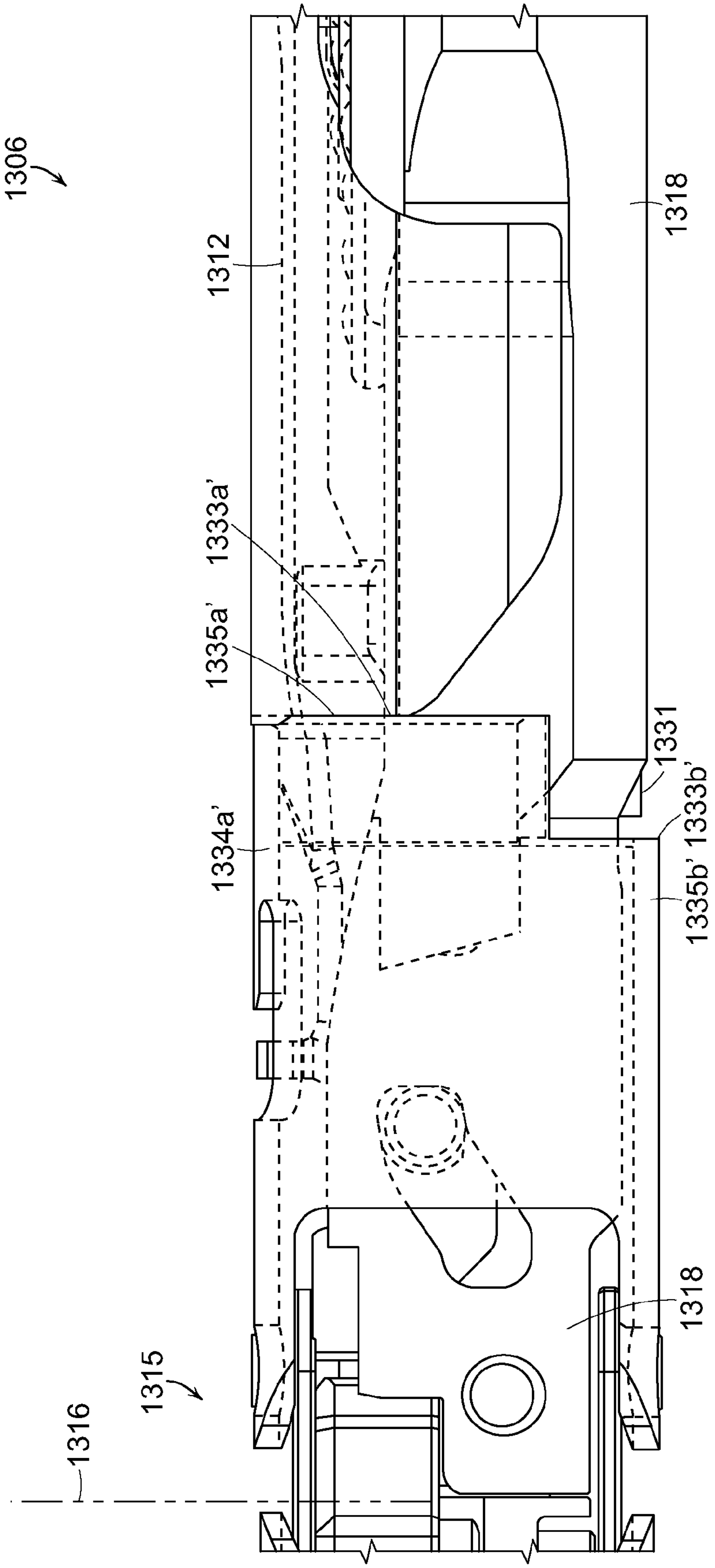
Figure 129:
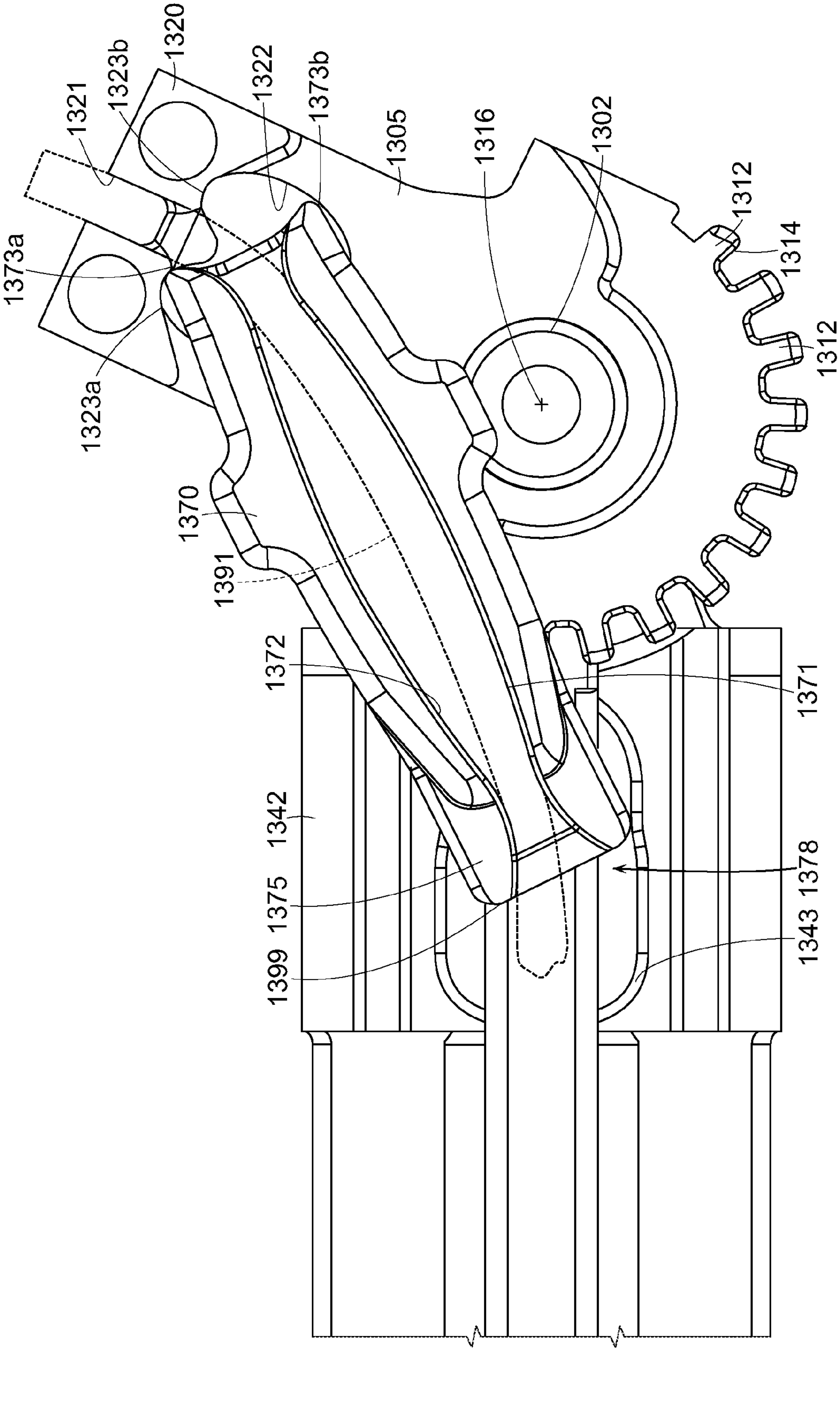
Figure 130:
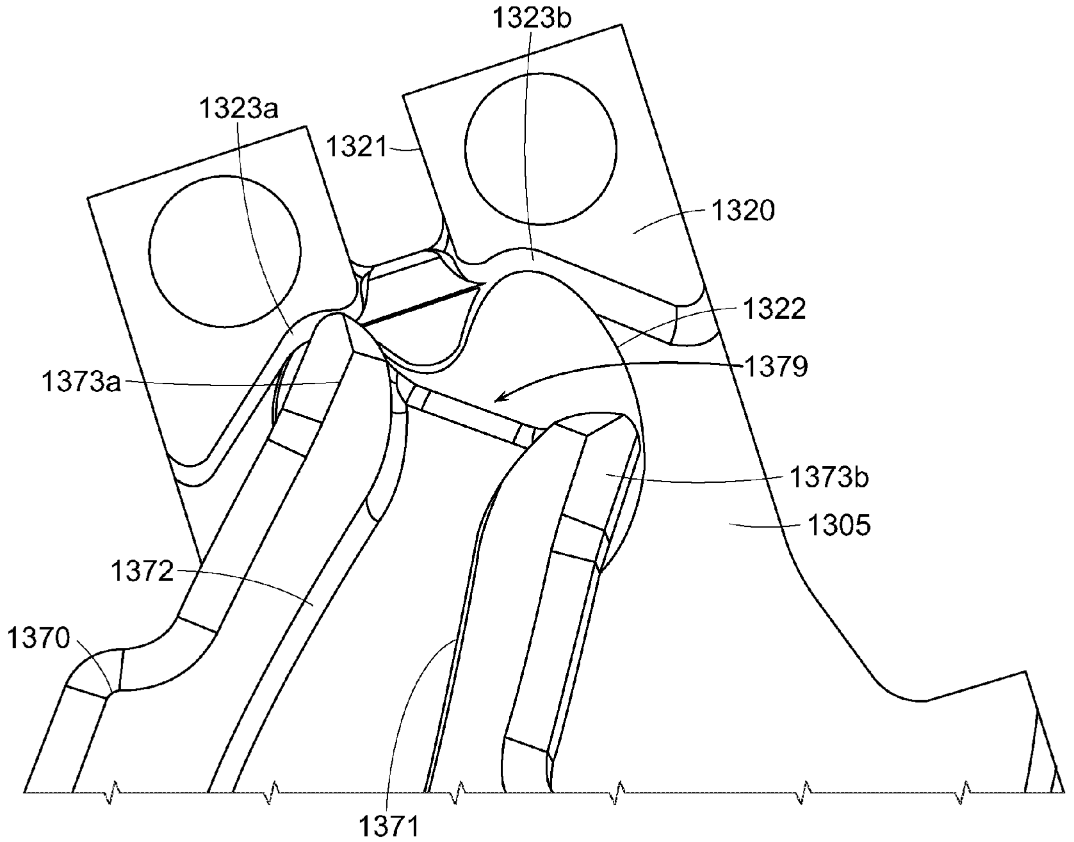
Figure 131:
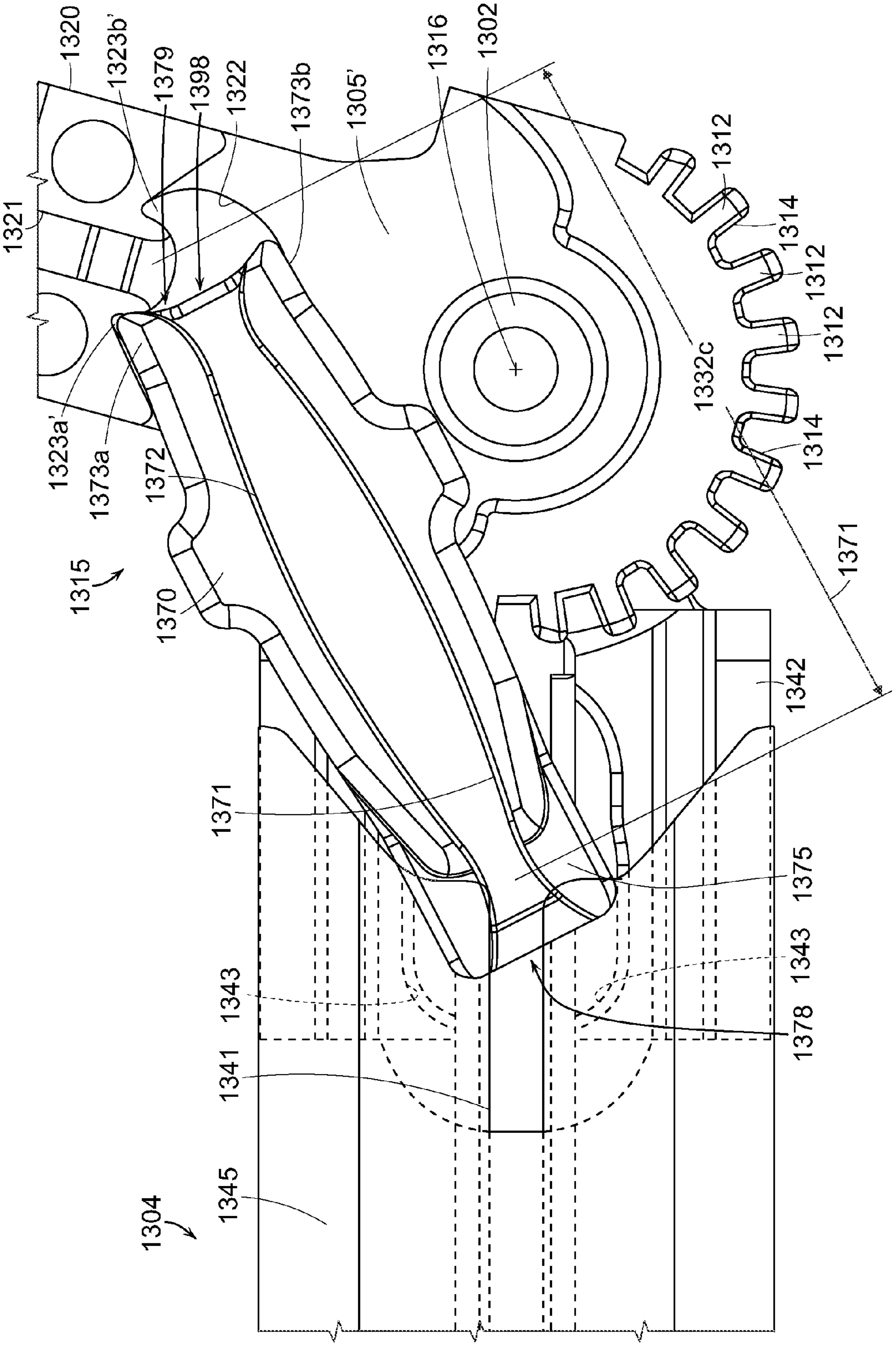
Figure 132:
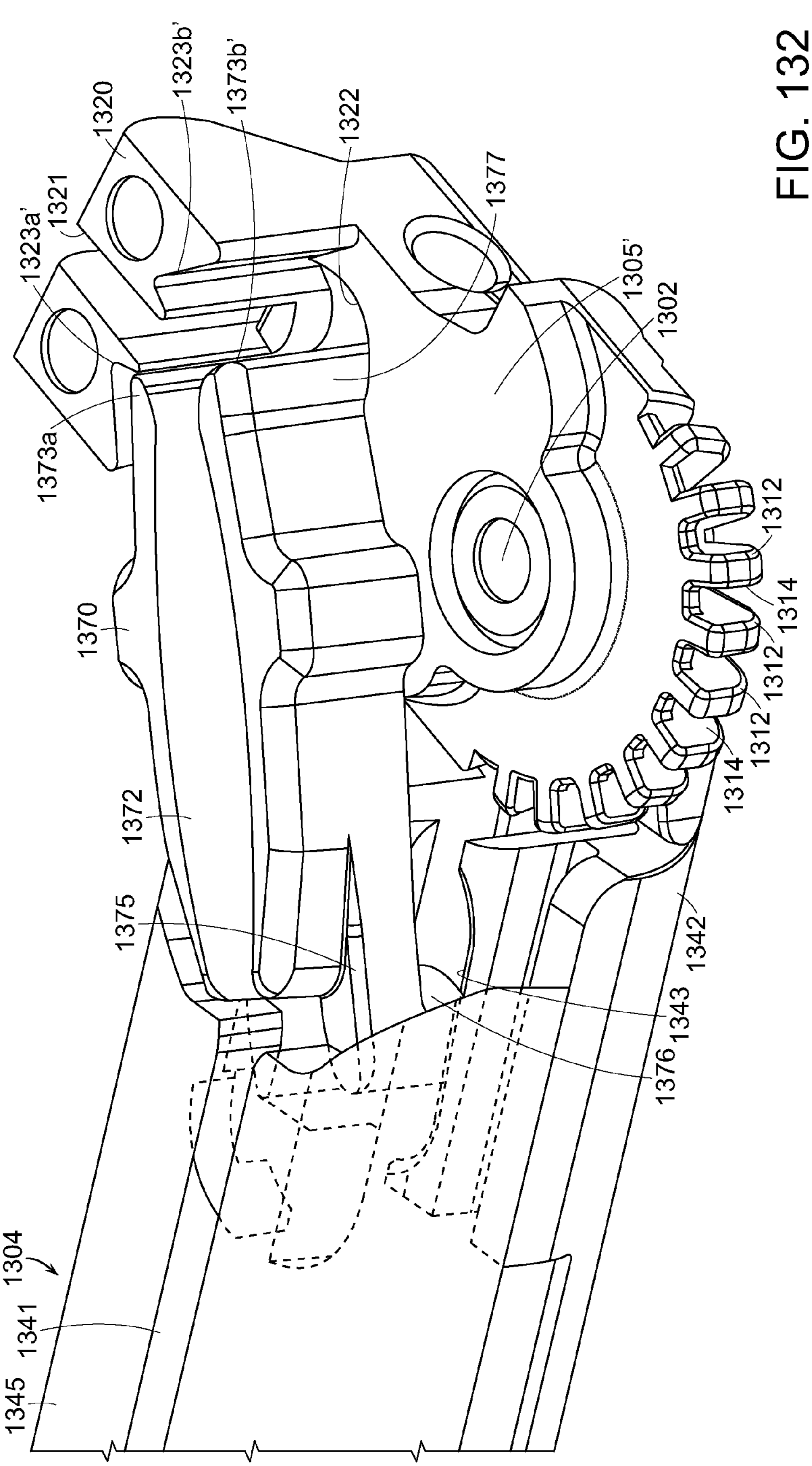
Figure 133:
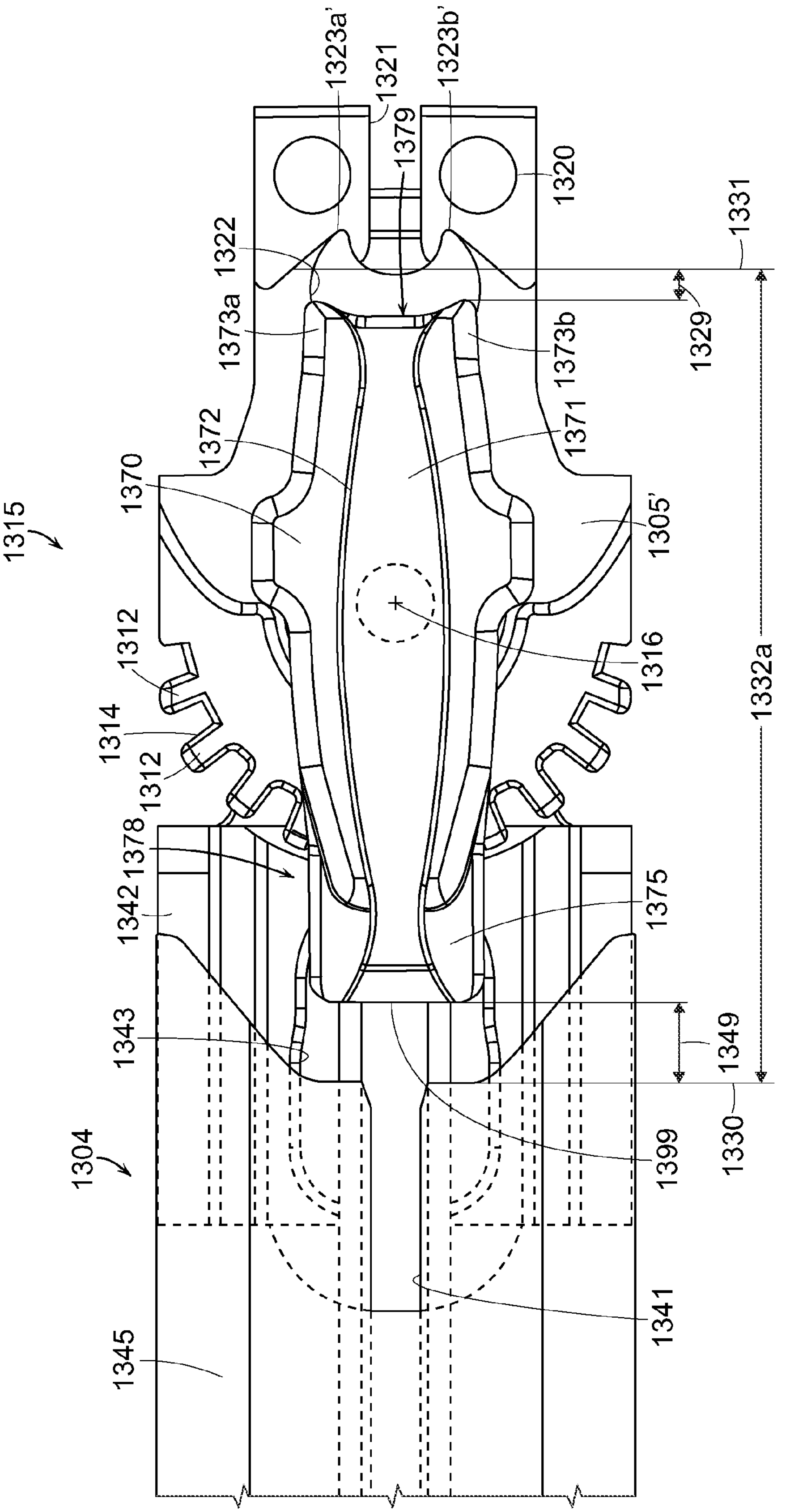
Figure 134:
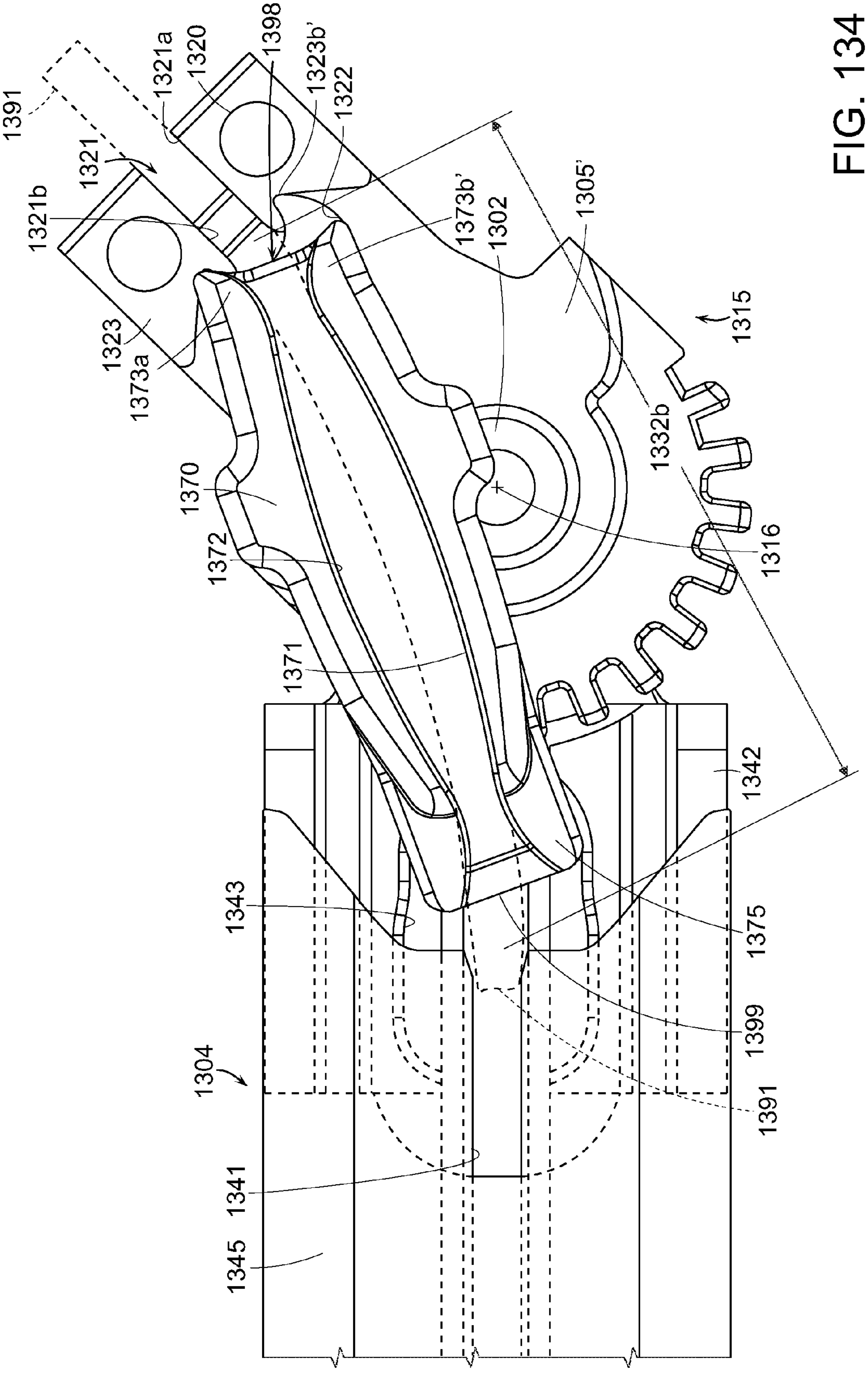
Figure 135:
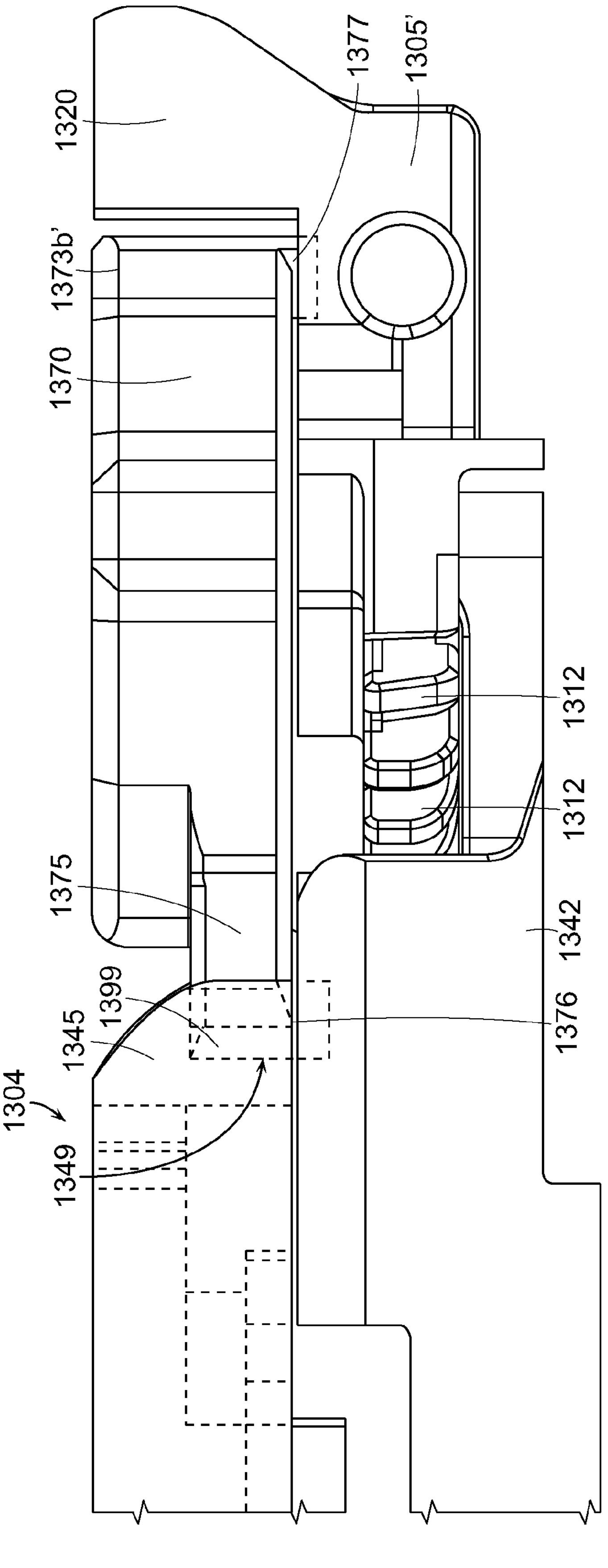
Figure 136:
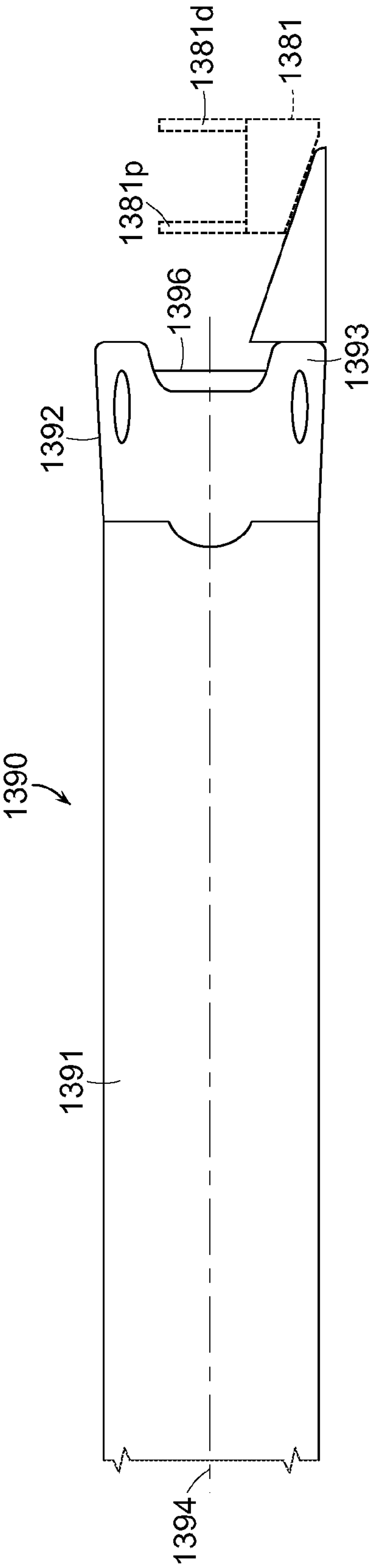
Figure 137:
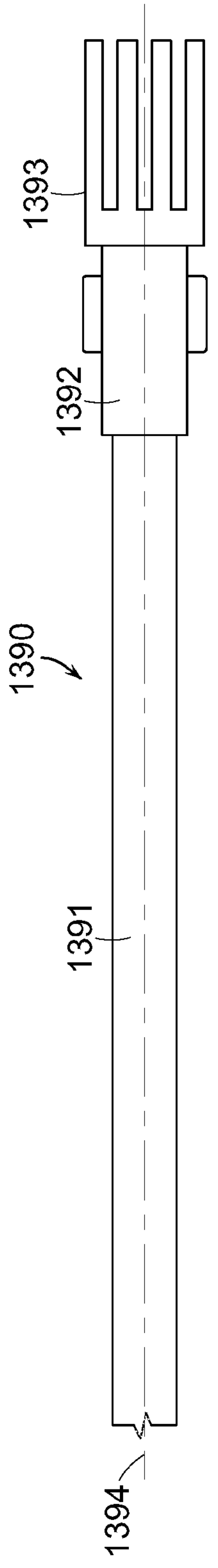
Figure 138:
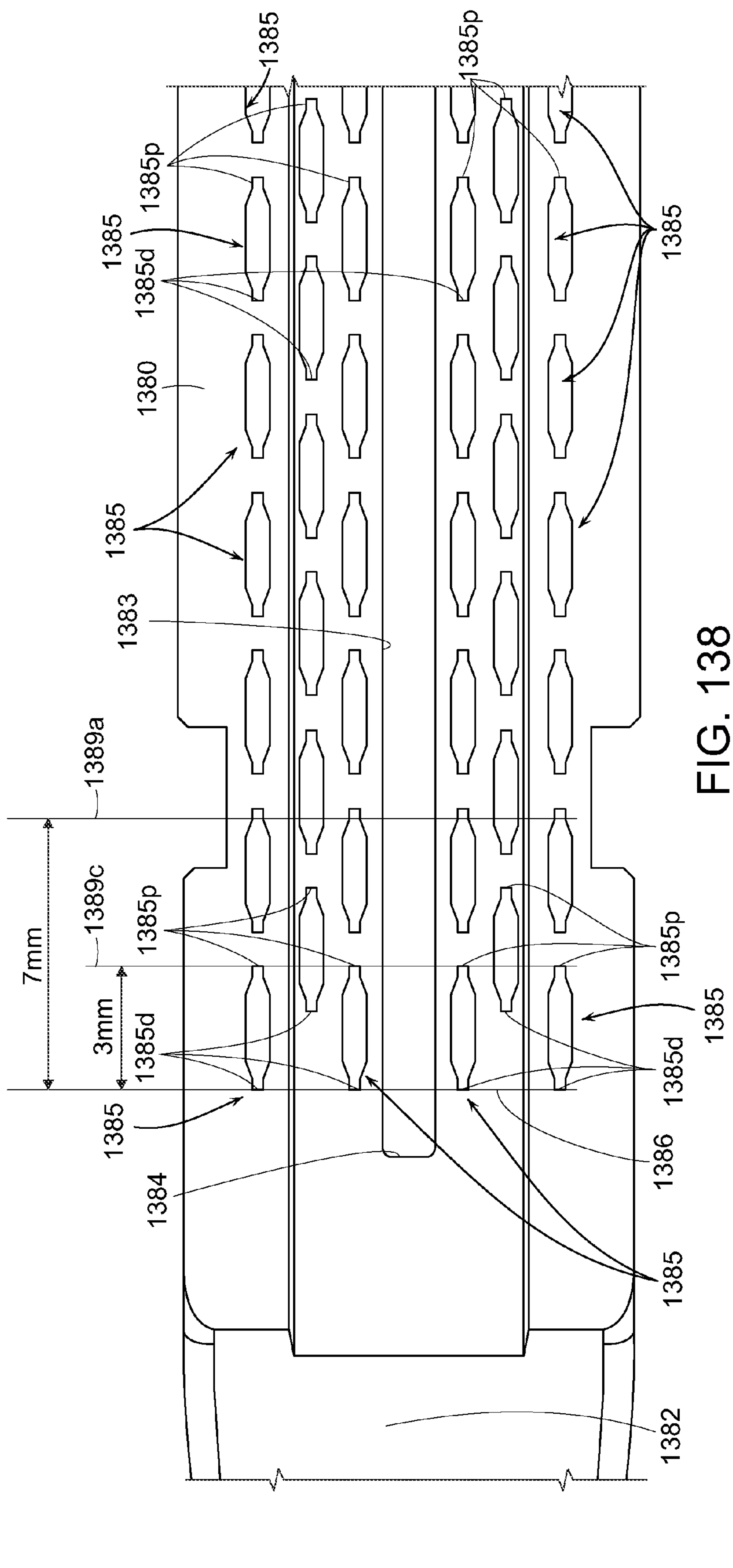
Figure 139:
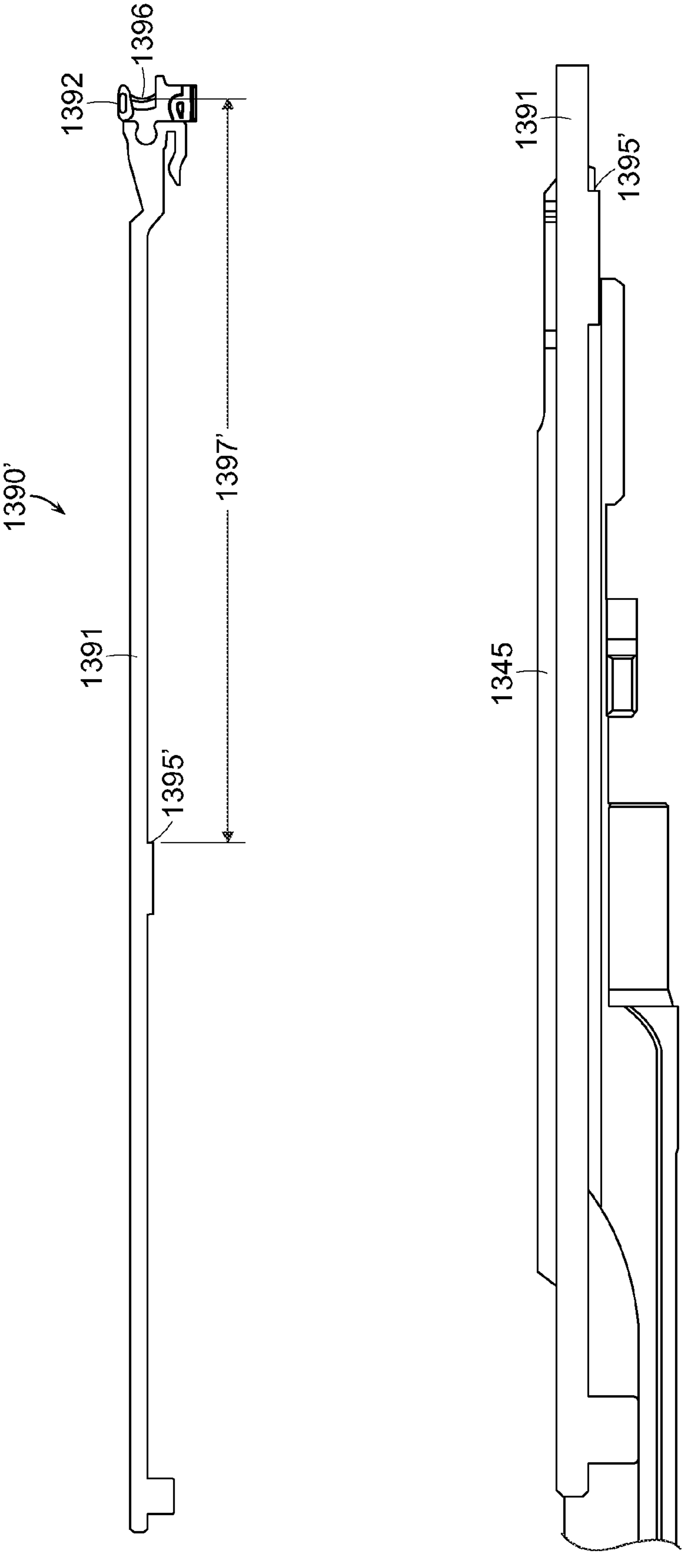
Figure 140:
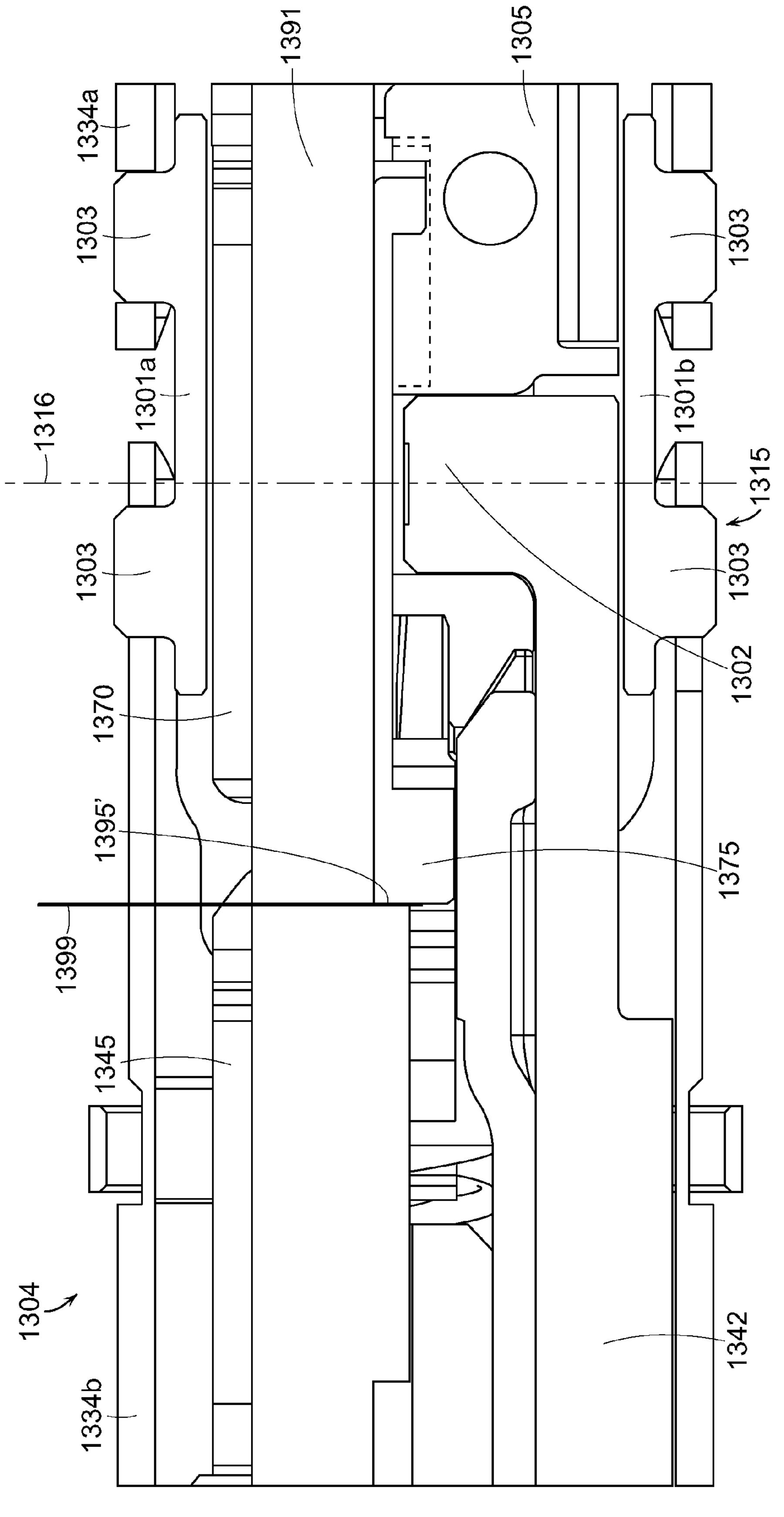
Figure 141:
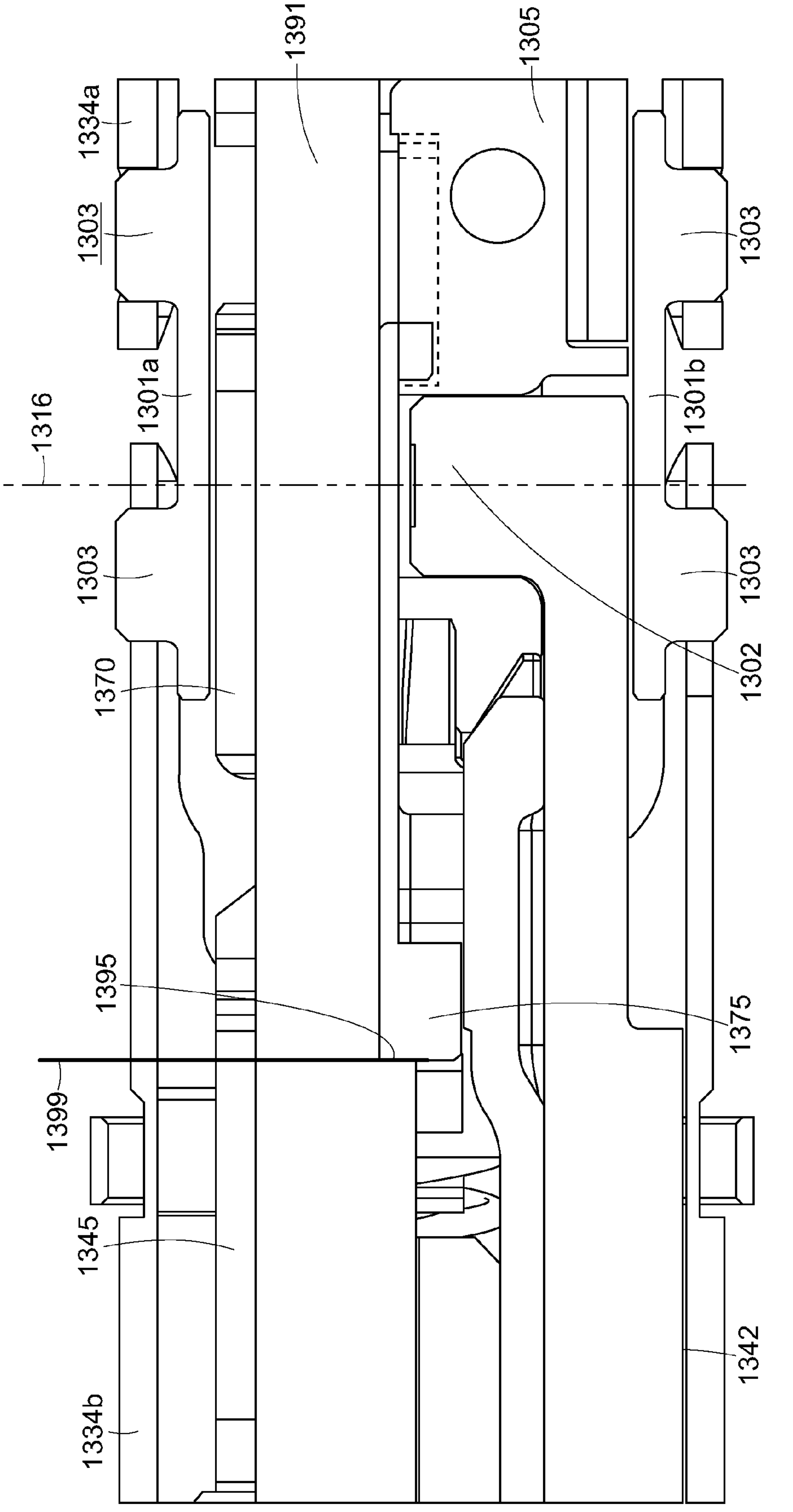
Figure 142:
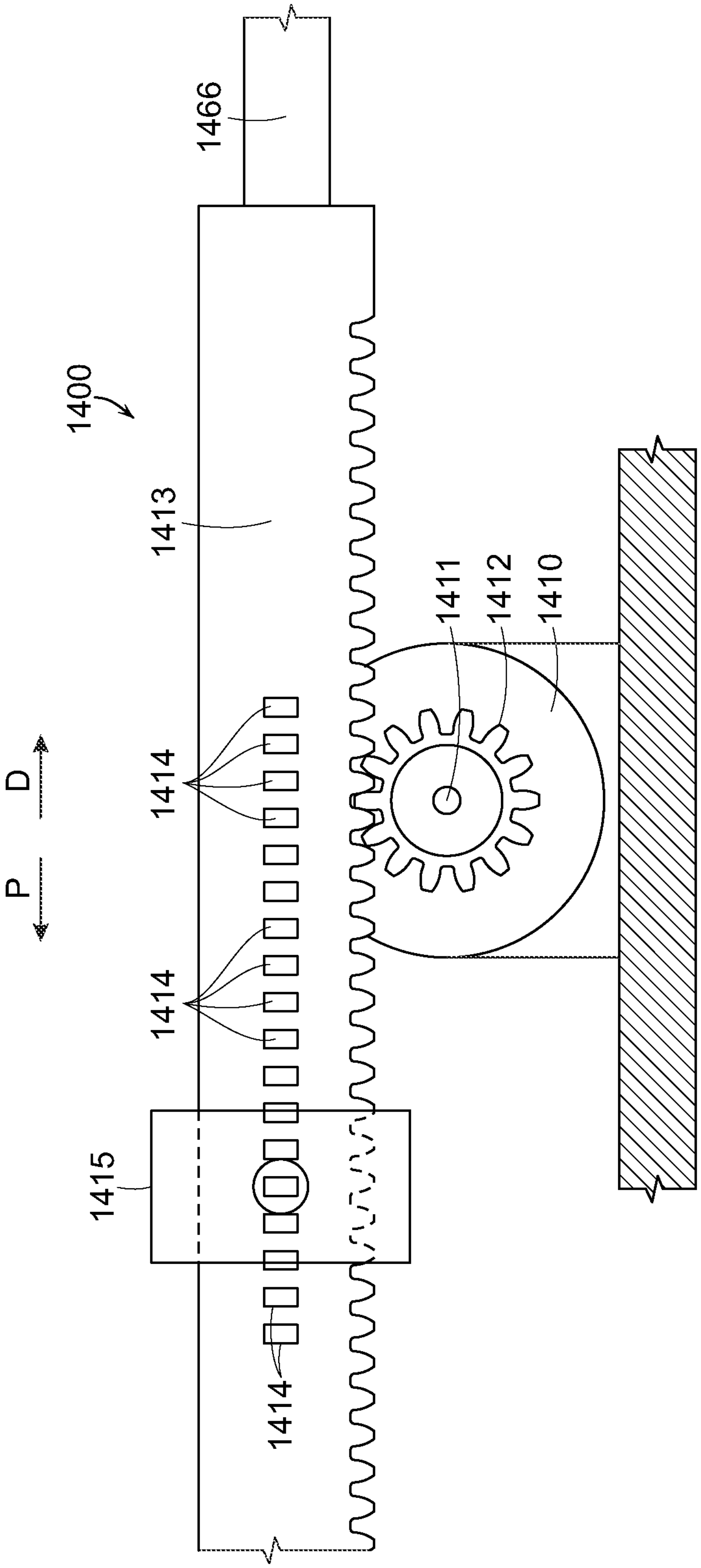
Figure 143:
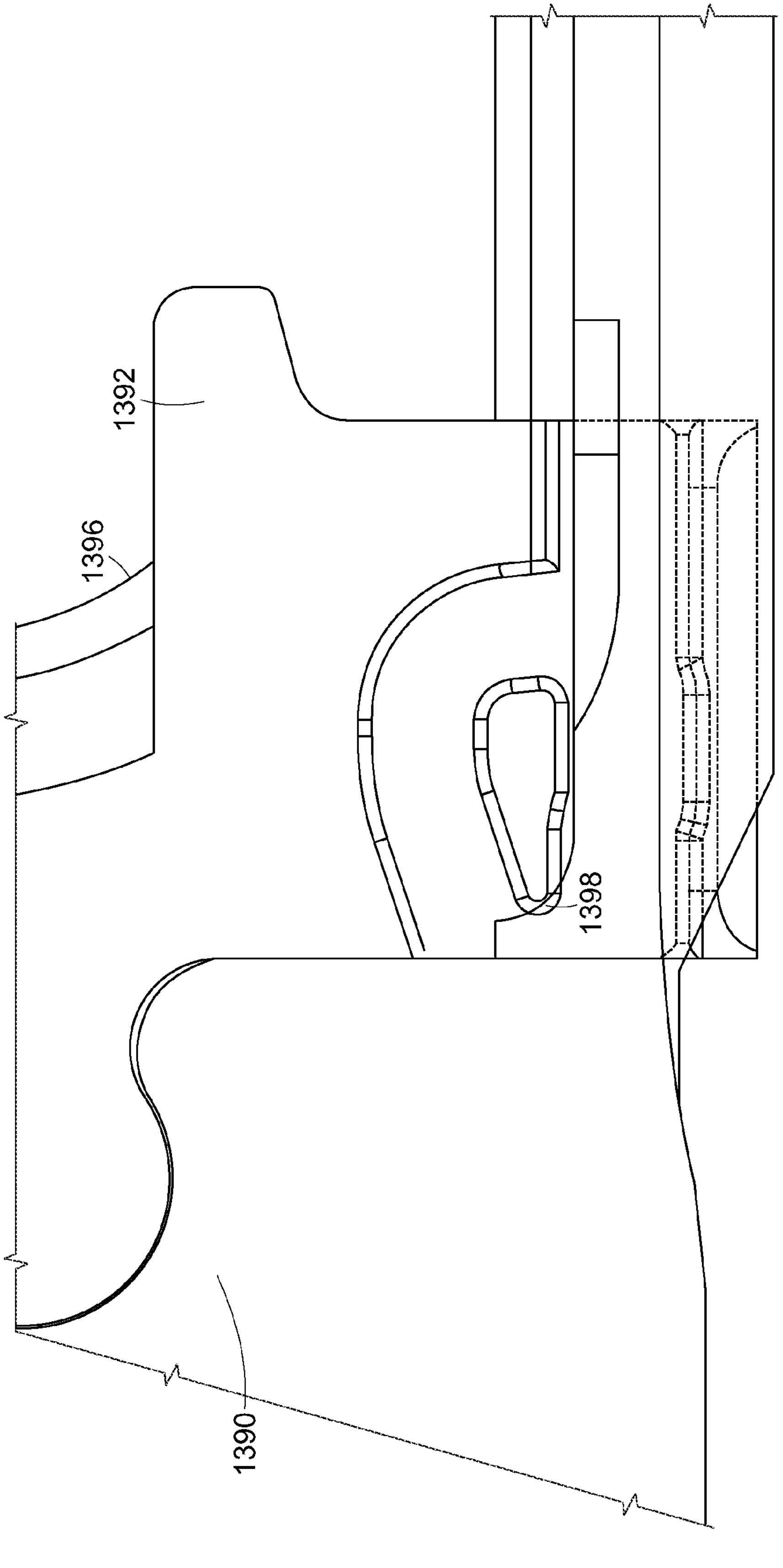
Figure 144:
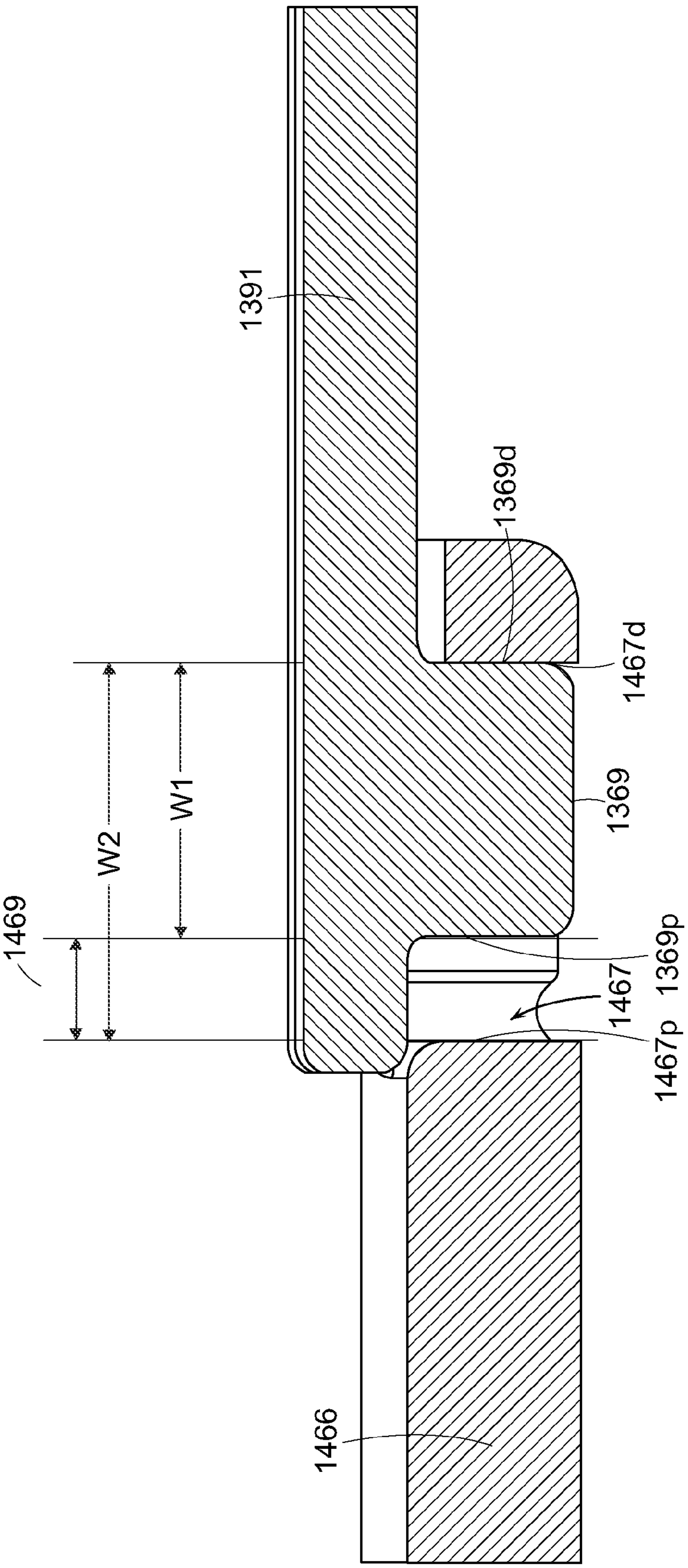
Figure 145:
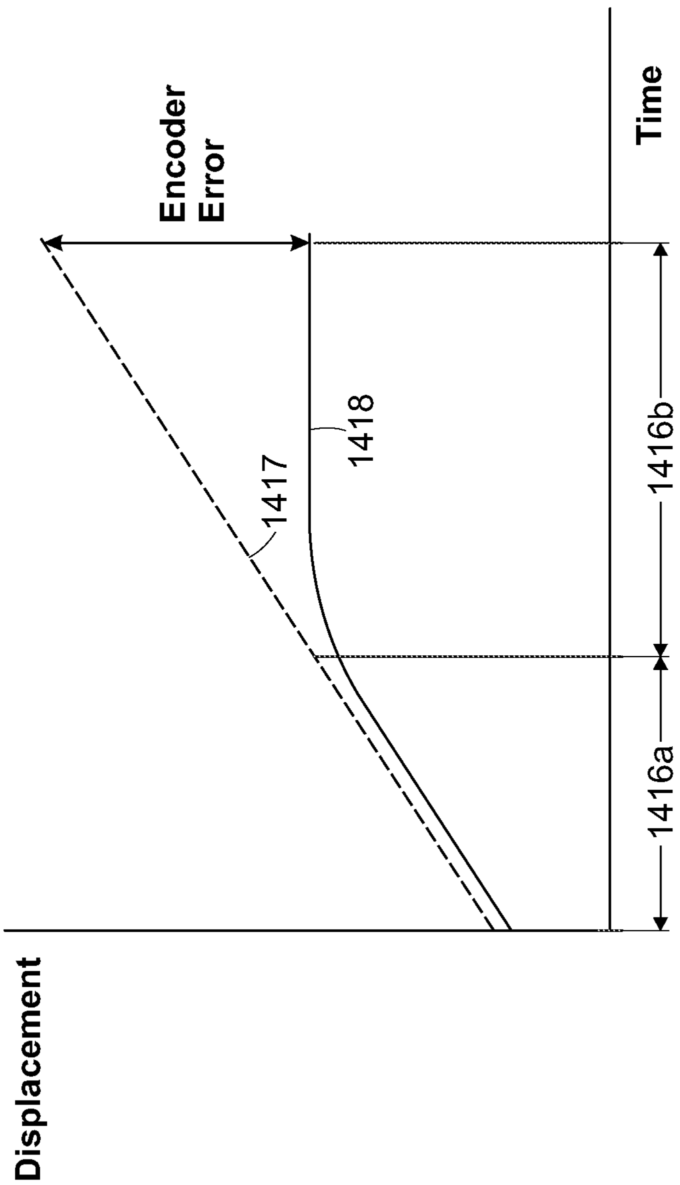
Figure 146A:
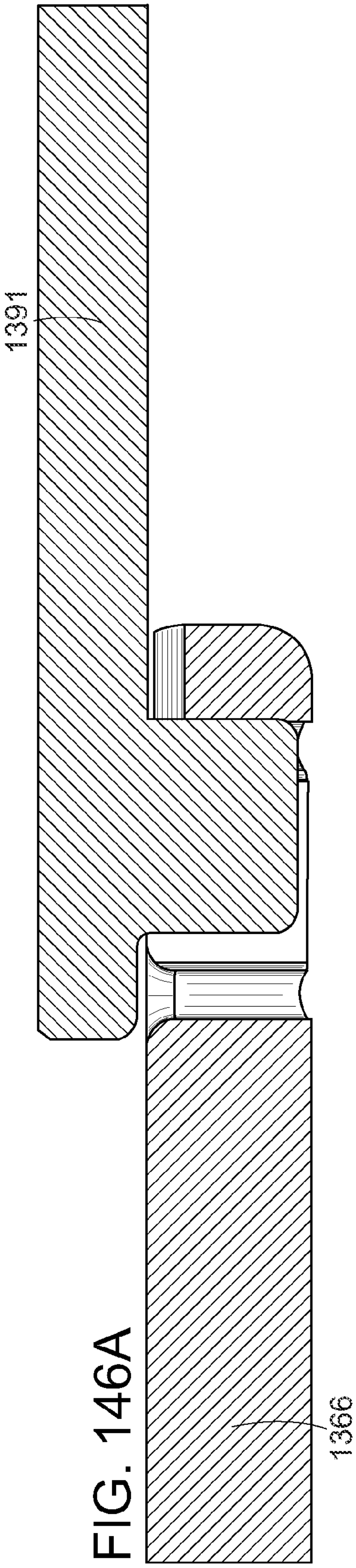
Figure 146B:
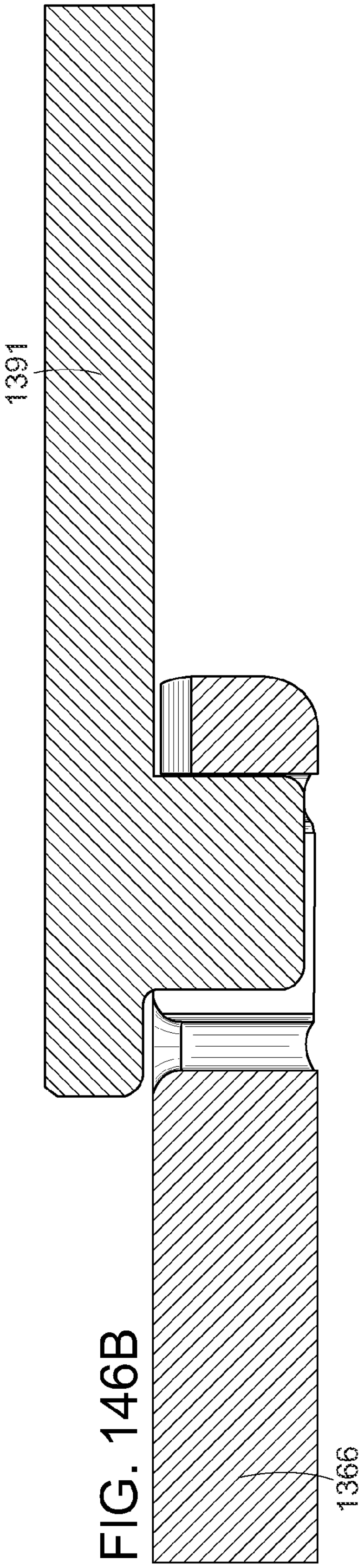
Figure 147:
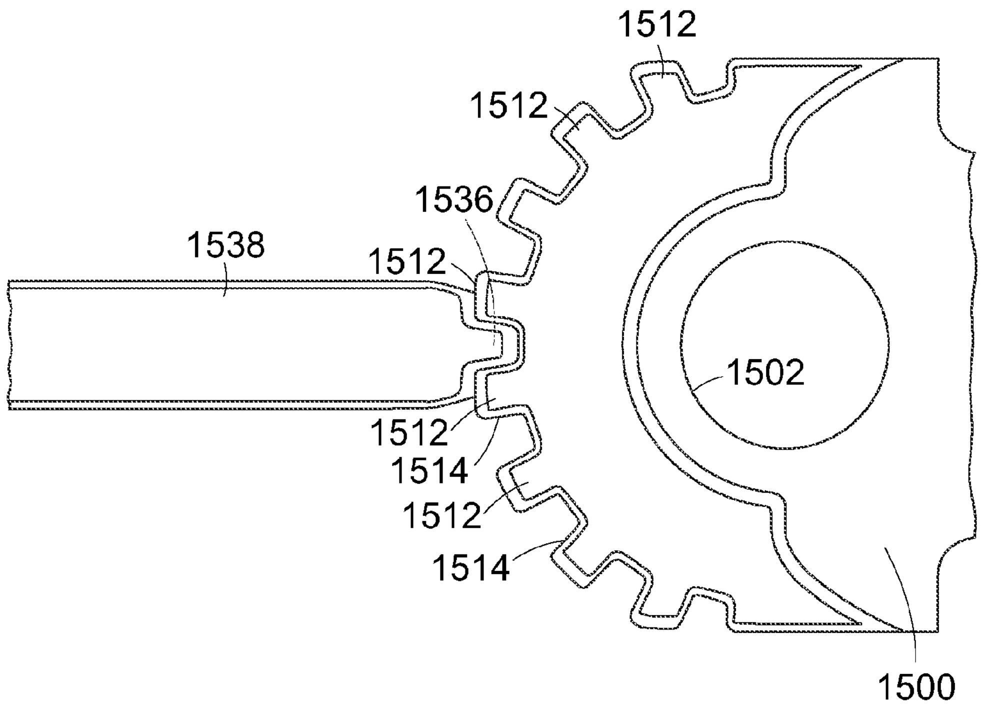
Figure 148:
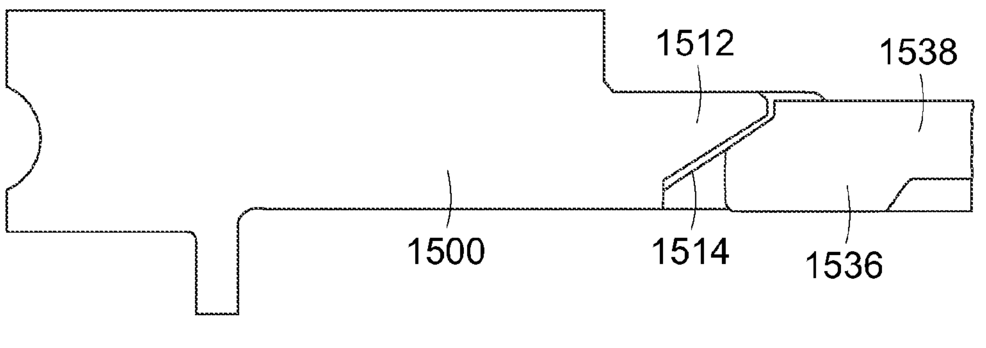

FIG. 126 is a perspective view of a closure tube in accordance with an alternative embodiment;

FIG. 127 is an elevational view of the closure tube of FIG. 126 engaged with the anvil of FIG. 123 to position the anvil in a partially-closed position;

FIG. 128 is an elevational view of the closure tube of FIG. 124 holding the anvil of FIG. 124 in a fully-closed position;

FIG. 129 is a top view of an articulation joint between a shaft and an end effector of a surgical stapling instrument illustrated with some components removed, the articulation joint further comprising a guide member which is movable relative to the shaft and the end effector;

FIG. 130 is a top view of a distal portion of the articulation joint of FIG. 129;

FIG. 131 is a top view of an articulation joint between a shaft and an end effector of an alternative embodiment of a surgical stapling instrument with some components removed, the articulation joint further comprising a guide member which is movable relative to the shaft and the end effector;

FIG. 132 is a perspective view of the articulation joint of FIG. 131 with some components removed;

FIG. 133 is a top view of the articulation joint of FIG. 131 with some components removed illustrating the end effector in a straight, or centered, position;

FIG. 134 is a top view of the articulation joint of FIG. 131 illustrating the end effector in an articulated position;

FIG. 135 is an elevational view of the articulation joint of FIG. 131 in the orientation illustrated in FIG. 133;

FIG. 136 is an elevational view of a drive bar comprising a cutting member configured to cut tissue and a driver configured to deploy staples from a staple cartridge;

FIG. 137 is a plan view of the drive bar of FIG. 136;

FIG. 138 is a partial plan view of a staple cartridge of a surgical stapler;

FIG. 139 is an elevational view of a cutting member and a knife bar attached to the knife bar, the knife bar including a stop surface configured to limit the advancement of the cutting member within an end effector of a surgical instrument;

FIG. 140 is a cross-sectional view of the articulation joint of FIG. 131 illustrated with the knife bar of FIG. 139, the end effector being arranged in a straight, or centered, configuration and the stop surface being engaged with the guide member of FIG. 131;

FIG. 141 is a cross-sectional view of the articulation joint of FIG. 131 illustrated with the knife bar of FIG. 139, the end effector being arranged in an articulated configuration and the stop surface being engaged with the guide member of FIG. 131;

FIG. 142 is a schematic of a firing drive of a surgical stapling instrument, wherein the firing drive comprises a motor, a rack and pinion system drivable by the motor, and a firing rod operably engaged with the rack, wherein the operation of the motor advances and/or retracts the firing rod FIG. 143 is an elevational view of a cutting member within the staple cartridge of FIG. 138 positioned against a retraction stop;

FIG. 144 is a detail view of a connection between a firing rod and a knife bar configured to move the cutting member of FIG. 142 within the staple cartridge of FIG. 138;

FIG. 145 is a graph depicting an encoder error that can be generated within an encoder when the cutting member is retracted against the retraction stop as illustrated in FIG. 143;

FIG. 146*a* is a detail view of the connection of FIG. 144 after the cutting member has been positioned against the retraction stop when the end effector is in a straight, or centered, configuration;

FIG. 146*b* is a detail view of the connection of FIG. 144 after the cutting member has been positioned against the retraction stop when the end effector is in an articulated configuration;

FIG. 147 is a top view of a lock engaged with a lock member of an end effector; and FIG. 148 is a cross-sectional view of the lock and lock member of FIG. 147.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims.

The features illustrated or described in connection with one exemplary embodiment may be combined with the features of other embodiments. Such modifications and variations are intended to be included within the scope of the present invention.

Figure 3:
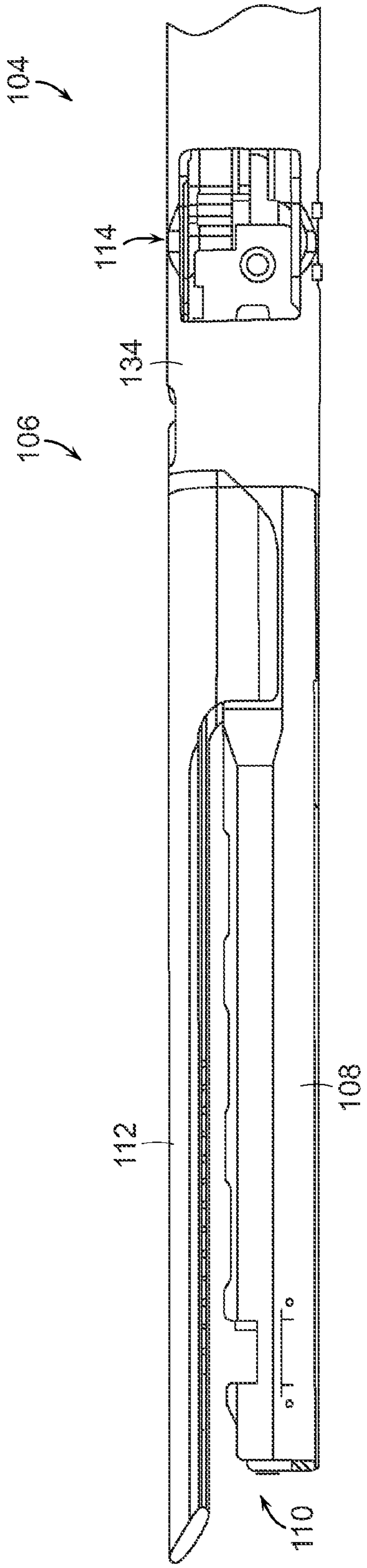
FIG. 3 is an elevational view of an end effector of the surgical instrument of FIG. 1.
Figure 4:
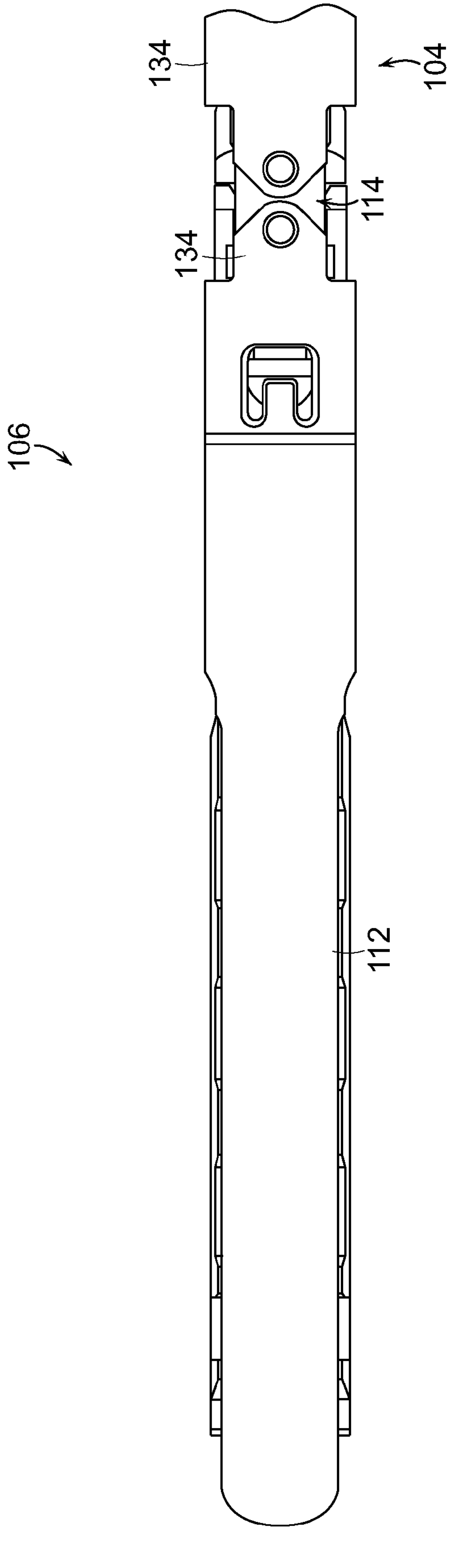
FIG. 4 is a top view of the end effector of FIG. 3.

In various embodiments, a surgical instrument in accordance with the present invention can be configured to insert surgical staples into soft tissue, for example. In at least one embodiment, referring to FIGS. 1-4, surgical instrument 100 can include handle portion 102, elongate shaft assembly 104, and end effector 106. In various embodiments, referring to FIGS. 3 and 4, end effector 106 can include staple cartridge channel 108 and staple cartridge 110, where staple cartridge 110 can be configured to removably store staples therein. In at least one embodiment, end effector 106 can further include anvil 112 which can be pivotably connected to staple cartridge channel 108 and can be pivoted between open and closed positions by an end effector closure system. In order to deploy the staples from staple cartridge 110, surgical instrument 100 can further include a staple driver configured to traverse staple cartridge 110 and a firing drive configured to advance the staple driver within the staple cartridge. In various embodiments, anvil 112 can be configured to deform at least a portion of the staples as they are deployed from the staple cartridge. Although various embodiments of an end effector closure system and a firing drive are described in further detail below, several embodiments of end effector closure systems and firing drives are disclosed in U.S. Pat. No. 6,905,057, entitled SURGICAL STAPLING INSTRUMENT INCORPORATING A FIRING MECHANISM HAVING A LINKED RACK TRANSMISSION, which issued on Jun. 14, 2005, and U.S. Pat. No. 7,044,352, entitled SURGICAL STAPLING INSTRUMENT HAVING A SINGLE LOCKOUT MECHANISM FOR PREVENTION OF FIRING, which issued on May 16, 2006, the entire disclosures of which are hereby incorporated by reference herein. Also incorporated by reference in its entirety is the disclosure of the commonly-owned, contemporaneously-filed U.S. patent application Ser. No. 12/765,330, now U.S.Pat. No. 8,308,040, entitled SURGICAL STAPLING INSTRUMENT WITH AN ARTICULATABLE END EFFECTOR.

In various embodiments, a surgical instrument in accordance with the present invention can include a system for moving, or articulating, an end effector relative to an elongate shaft assembly of the surgical instrument. In at least one embodiment, referring to FIGS. 3-7, surgical instrument 100 can include articulation joint 114 which can movably connect end effector 106 and elongate shaft assembly 104. In various embodiments, articulation joint 114 can permit end effector 106 to be moved relative to shaft assembly 104 in a single plane or, alternatively, multiple planes. In either event, articulation joint 114 can include one or more pivot axes 116 (FIG. 5) about which end effector 106 can be articulated. In various embodiments, referring to FIGS. 5 and 6, surgical instrument 100 can further include locking mechanism 118 which can fix, or lock, the relative relationship between end effector 106 and elongate shaft assembly 104. In at least one embodiment, locking mechanism 118 can include lock member 120 which can be slid relative to end effector 106 and engage end effector 106 in order to prevent, or at least partially inhibit, relative movement between end effector 106 and shaft assembly 104. In at least one embodiment, lock member 120 can be configured to engage at least one of teeth 312 (FIGS. 5 and 6) of end effector 106 such that the interaction between lock member 120 and teeth 312 can prevent, or at least partially inhibit, end effector 106 from rotating about axis 116 as described in greater detail further below.

Figure 6:
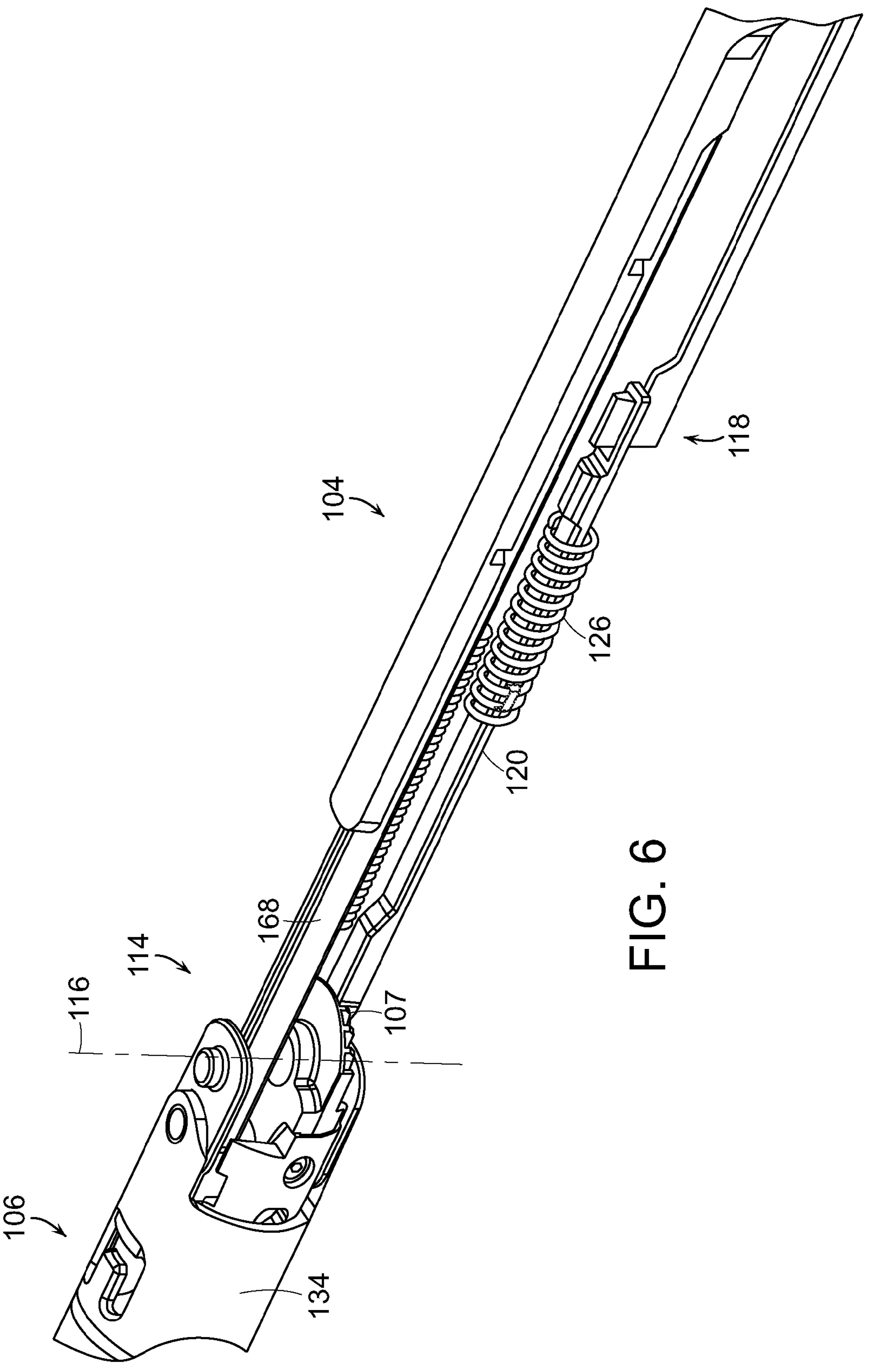
FIG. 6 is a perspective view of an elongate shaft assembly and the articulation joint of the surgical instrument of FIG. 1 with some components of the surgical instrument removed.
Figure 7:
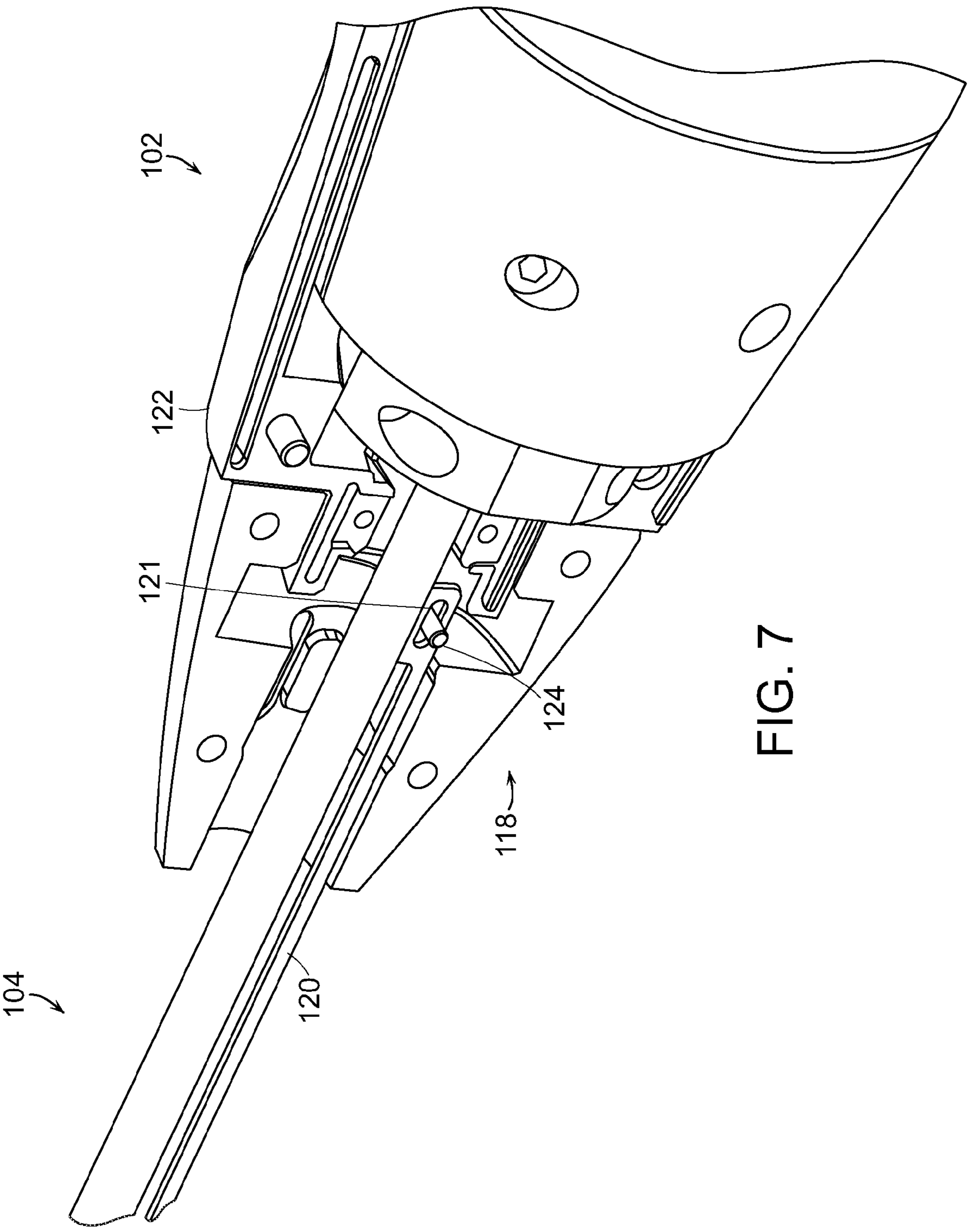
FIG. 7 is a partial perspective view of the handle portion and the elongate shaft assembly of the surgical instrument of FIG. 1 with some components of the surgical instrument removed.
Figure 8:
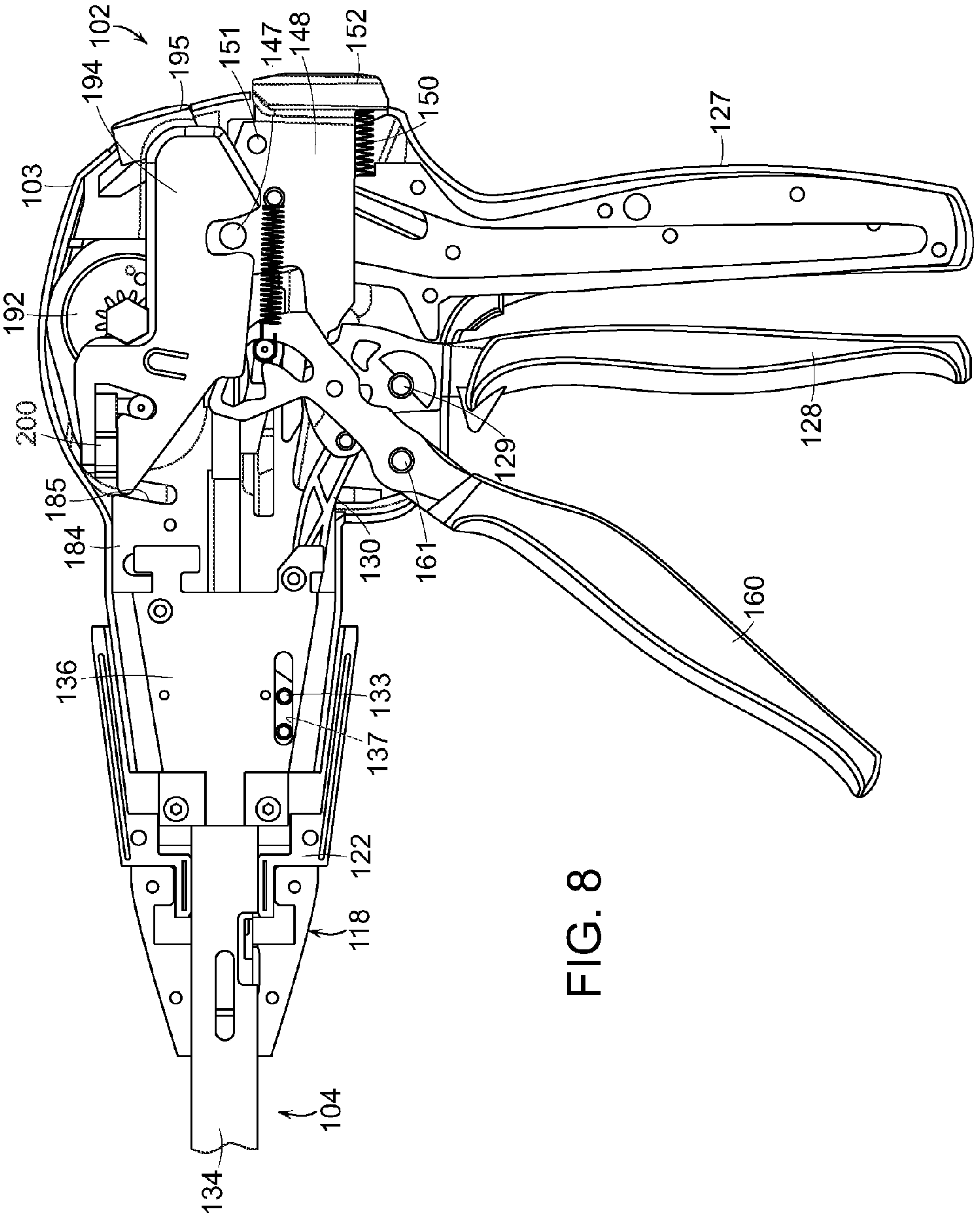
FIG. 8 is an elevational view of the handle portion of FIG. 2 with some components of the surgical instrument removed.
Figure 9:
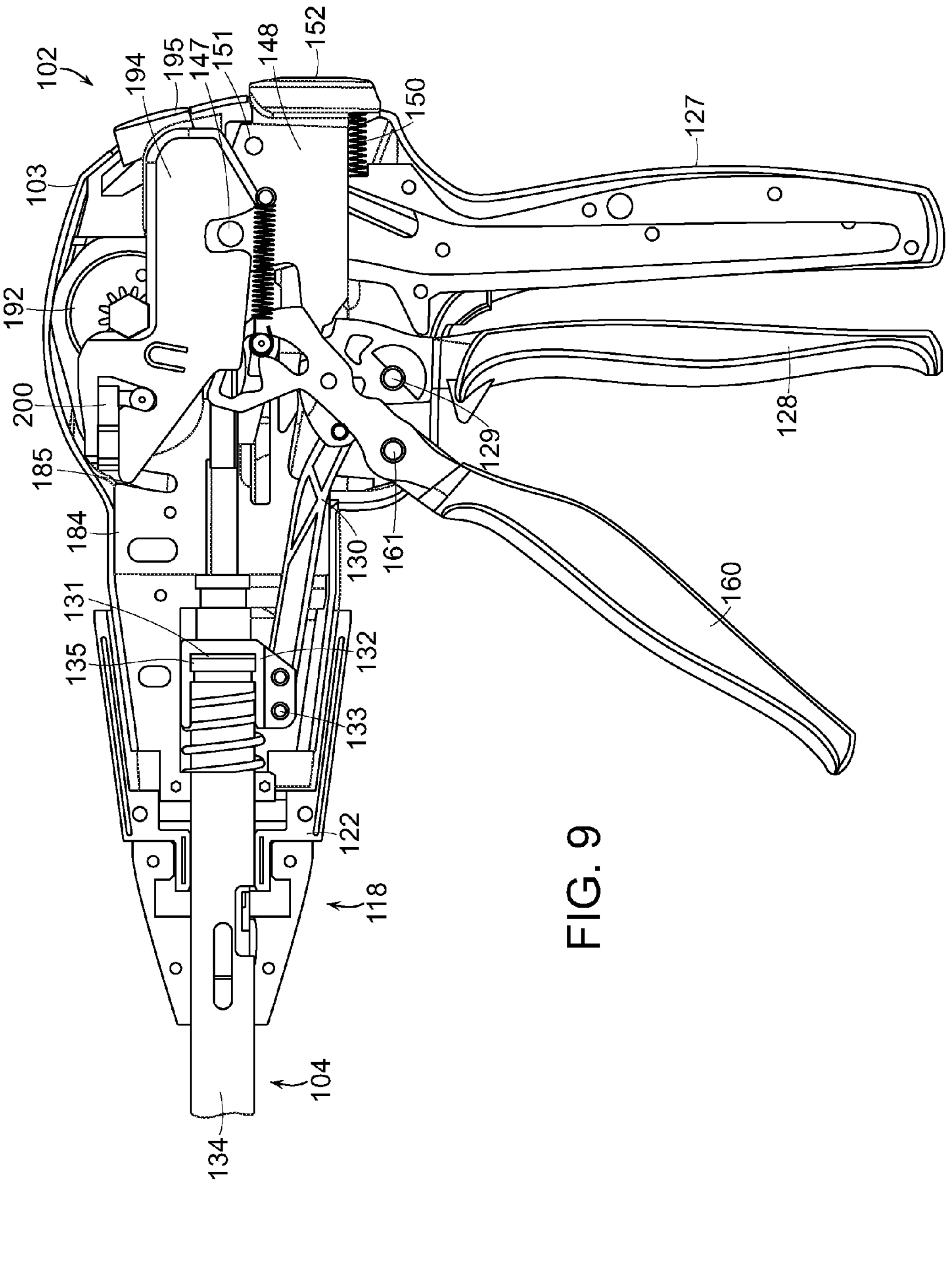
FIG. 9 is an elevational view of the handle portion of FIG. 2 with additional components of the surgical instrument removed.

In various embodiments, referring to FIGS. 7-9, locking mechanism 118 can further include actuator 122 which can be operably connected to lock member 120. In at least one embodiment, actuator 122 can include pin 124 which can be received within slot 121 in lock member 120 such that, when actuator 122 is slid relative to handle portion 102, pin 124 can abut a side wall of slot 121 and motivate lock member 120 relative to end effector 106. In at least one embodiment, actuator 122 can be pulled away from end effector 106, i.e., proximally, to disengage lock member 120 from end effector 106. Although not illustrated, other embodiments are envisioned where actuator 122 can be moved distally, or even rotated, in order to disengage lock member 120 from end effector 106. In either event, locking mechanism 118 can further include return spring 126 (FIG. 6) which can be configured to move lock member 120 toward end effector 106, i.e., distally, to engage lock member 120 with end effector 106 after actuator 122 has been released. Other locking mechanisms are disclosed in U.S. patent application Ser. No. 11/100,772, entitled SURGICAL INSTRUMENT WITH ARTICULATING SHAFT WITH SINGLE PIVOT CLOSURE AND DOUBLE PIVOT FRAME GROUND, which was filed on Apr. 7, 2005, U.S. patent application Ser. No. 11/238,358, entitled SURGICAL INSTRUMENT WITH ARTICULATING SHAFT WITH RIGID FIRING BAR SUPPORTS, which was filed on Sep. 29, 2005, and U.S. patent application Ser. No. 11/491,626, entitled SURGICAL STAPLING AND CUTTING DEVICE AND METHOD FOR USING THE DEVICE, which was filed on Jul. 24, 2006, the entire disclosures of which are hereby incorporated by reference herein.

Figure 1:
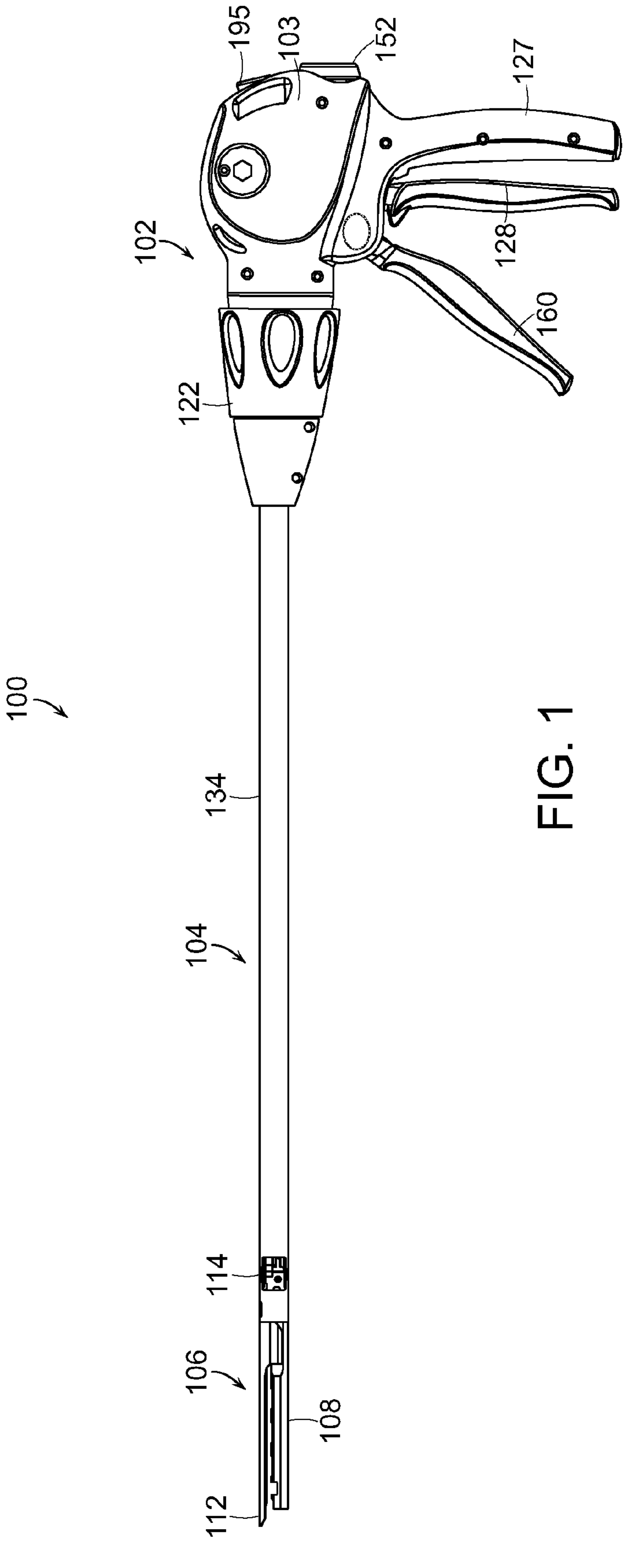
FIG. 1 is an elevational view of a surgical instrument in accordance with an embodiment of the present invention.
Figure 2:
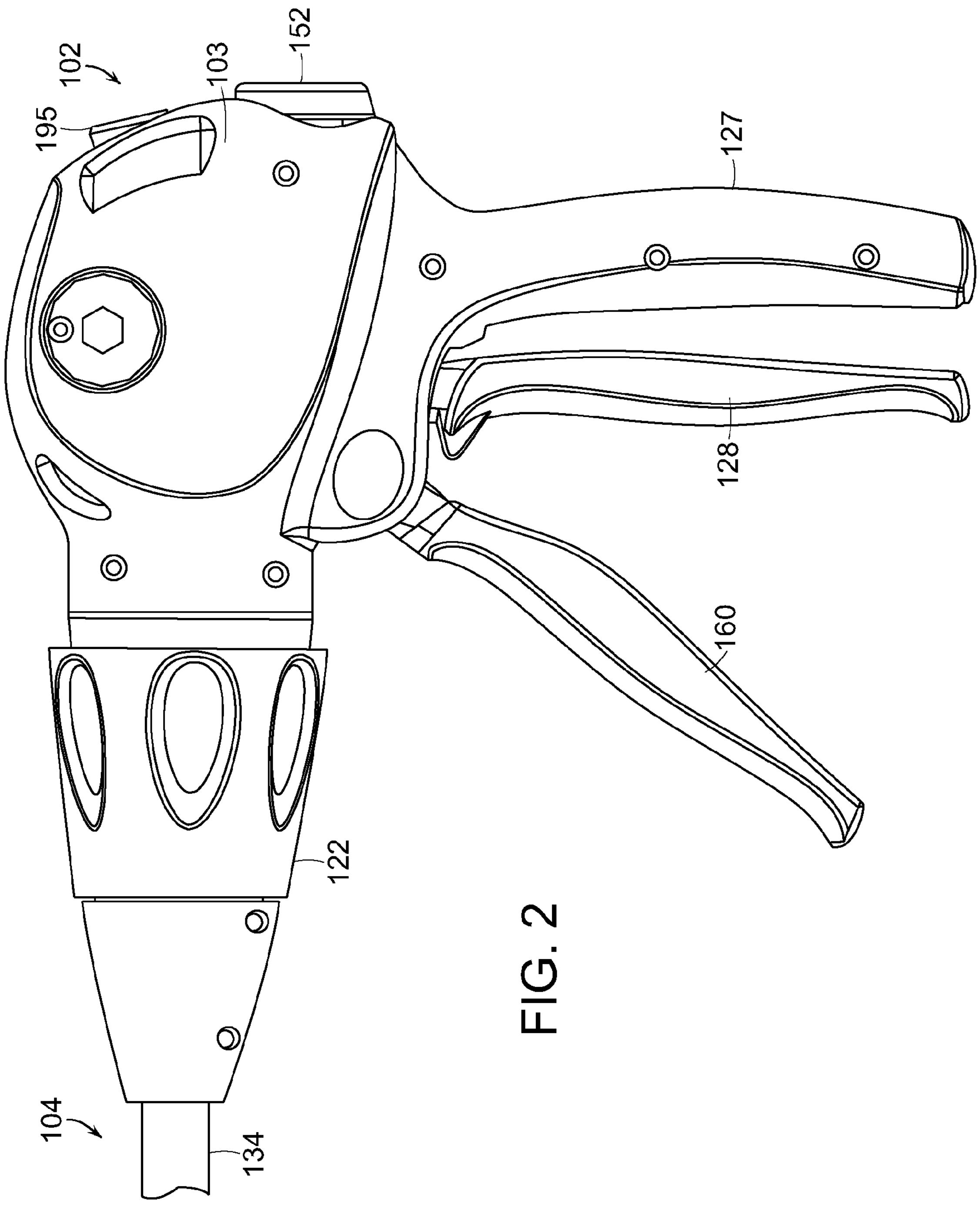
FIG. 2 is an elevational view of a handle portion of the surgical instrument of FIG. 1.

In various embodiments, referring to FIGS. 1 and 2, actuator 122 can be contoured such that a surgeon can grasp the outer surface of actuator 122 and pull actuator 122 proximally as described above. To move actuator 122, in at least one embodiment, a surgeon may place one hand on handle grip 127, for example, and place their other hand on actuator 122 so that the surgeon can move actuator 122 relative to handle grip 127. In other various embodiments, referring to FIGS. 10-13, actuator 122' can be configured such that a surgeon may only need one hand to operate the surgical instrument. More particularly, in at least one embodiment, actuator 122' can include hooks, or projections, 115 extending therefrom which can allow the surgeon to hold handle grip 127 with one hand and extend at least one finger from that hand distally to grip at least one projection 115 and pull actuator 122' proximally as described above. While actuator 122' is described herein as having projections 115, actuator 122, or any other suitable actuator, can also include projections 115 and/or any other suitable features that can assist a surgeon in operating surgical instrument 100 with one hand. In at least one embodiment, projections 115 can be at least partially comprised of and/or coated with an elastic or 'soft-touch' material which can improve the surgeon's grip on projections 115 and can provide other ergonomic benefits to the surgeon. In various embodiments, actuator 122', for example, can be operably engaged with shaft assembly 104 such that end effector 106 and shaft assembly 104 can be rotated about a longitudinal axis by actuator 122'. In such embodiments, a surgeon can orient end effector 106 in a surgical site by articulating end effector 106 as described above and/or rotating end effector 106 into position. In at least one embodiment, the surgeon can rotate actuator 122' by positioning a finger against one of projections 115 and applying a force thereto. In various embodiments, the surgeon can hold actuator 122' in position by placing a finger against a projection 115 and resisting any undesired motion of actuator 122' and, correspondingly, end effector 106.

Figure 5:
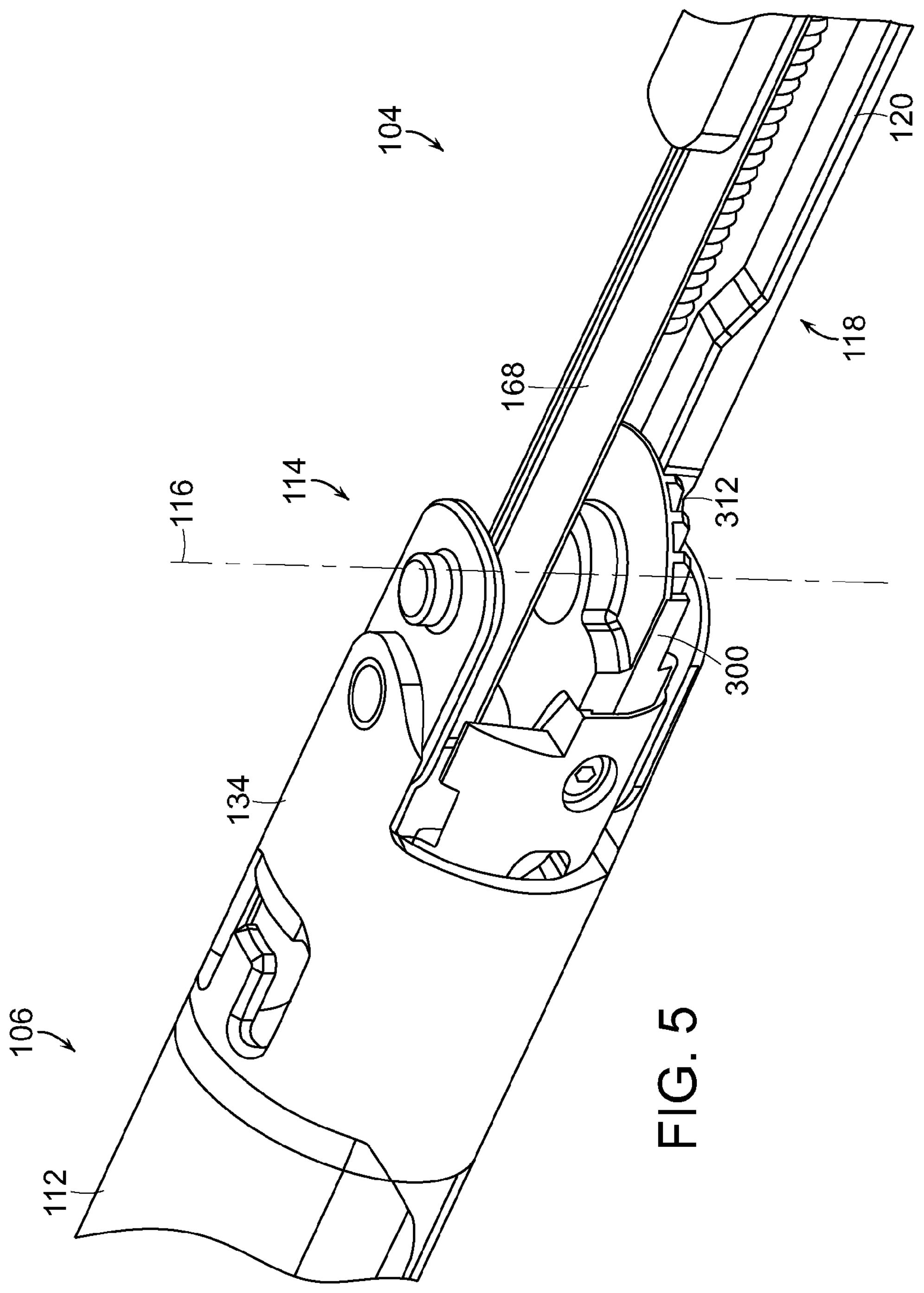
FIG. 5 is a perspective view of an articulation joint of the surgical instrument of FIG. 1 with some components of the surgical instrument removed.

In various embodiments, a surgical instrument in accordance with the present invention can include a system for closing, or clamping, an end effector onto soft tissue, for example. In at least one embodiment, referring to FIGS. 2, 5, 8 and 9, surgical instrument 100 can include closure trigger 128, drive link 130, driver 132, and closure tube 134. In various embodiments, upon an actuation of closure trigger 128, closure trigger 128 can be configured to displace drive link 130, driver 132, and closure tube 134 distally. More particularly, in at least one embodiment, drive link 130 can include a first end pivotably connected to trigger 128 and a second end pivotably connected to driver 132 such that the rotation of trigger 128 toward handle grip 127 can drive link 130 forward and slide driver 132 along an axis defined by driver guide 136 (FIG. 8). In various embodiments, driver 132 can include projections 133 extending therefrom which can be slidably received within slots 135 in driver guide 136 such that slots 135 can define a path for driver 132 as it is moved. In various embodiments, closure tube 134 can be operably engaged with driver 132 such that, when driver 132 is moved distally as described above, closure tube 134 can engage anvil 112 and pivot anvil 112 downwardly. Referring primarily to FIG. 5, closure tube 134 can be configured to slide over articulation joint 114 and pivot anvil 112 relative to staple cartridge 110. In at least one embodiment, as illustrated in FIG. 9, closure tube 134 can include a proximal end having projection 135 extending therefrom which can be received in slot 131 in driver 132 such that the displacement of driver 132 is transmitted to closure tube 134.

Figure 10:
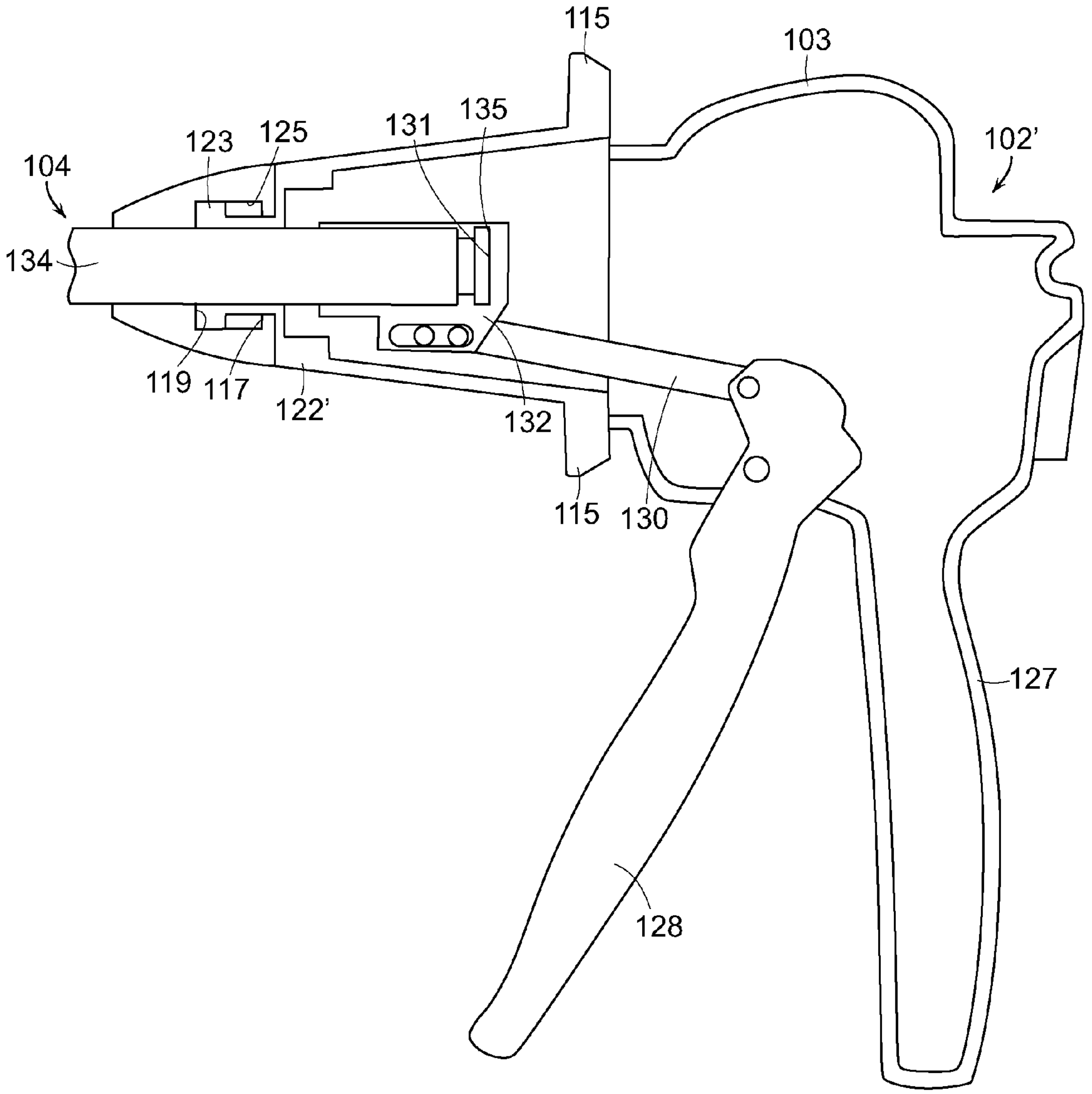
FIG. 10 is an elevational view of an actuator of an articulation locking mechanism and an end effector closure system of a surgical instrument in accordance with an alternative embodiment of the present invention with some components of the surgical instrument removed.
Figure 11:
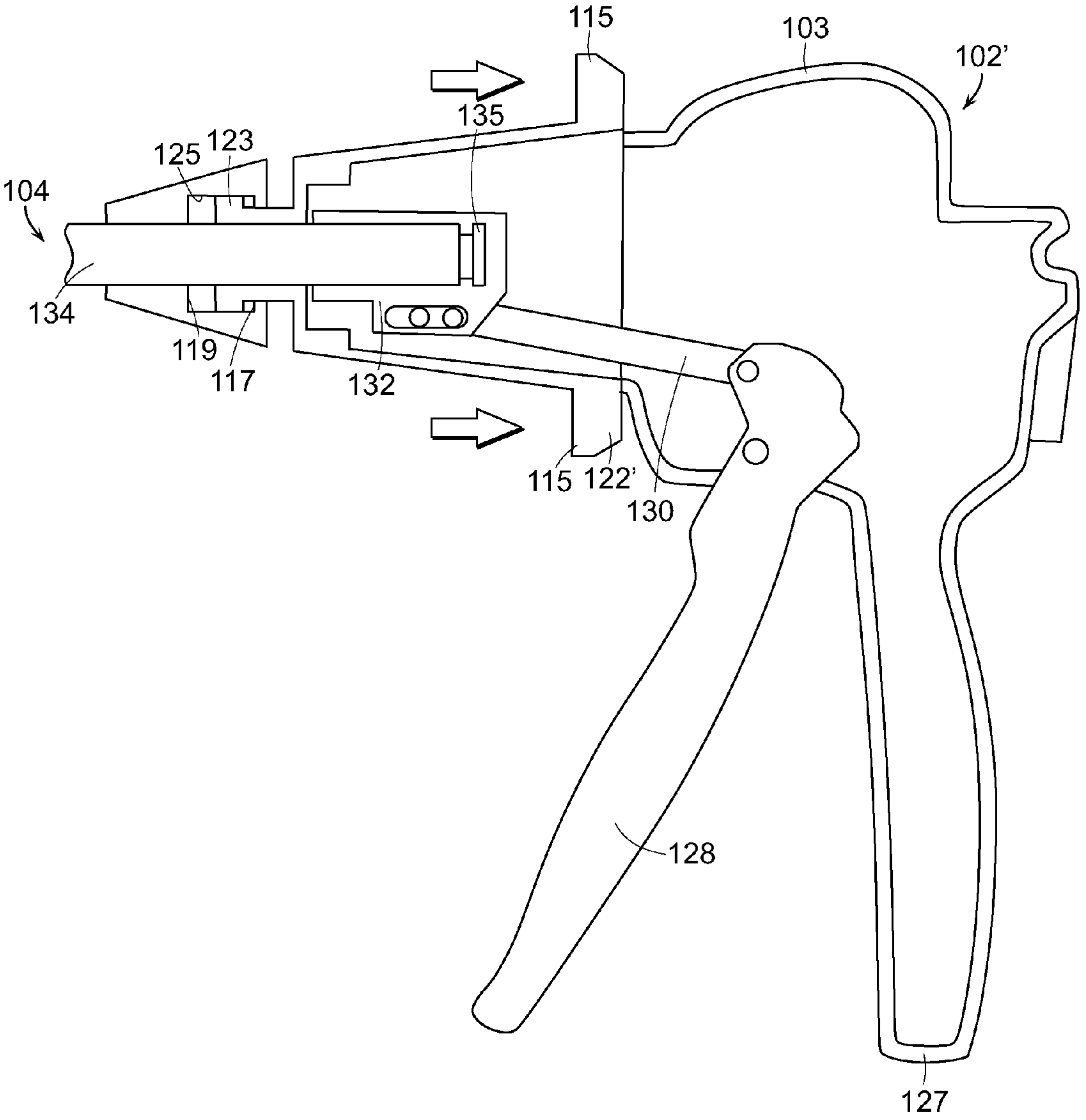
FIG. 11 is an elevational view of the surgical instrument of FIG. 10 illustrating the articulation locking mechanism actuator in an unlocked position and the end effector closure system in an open configuration.
Figure 12:
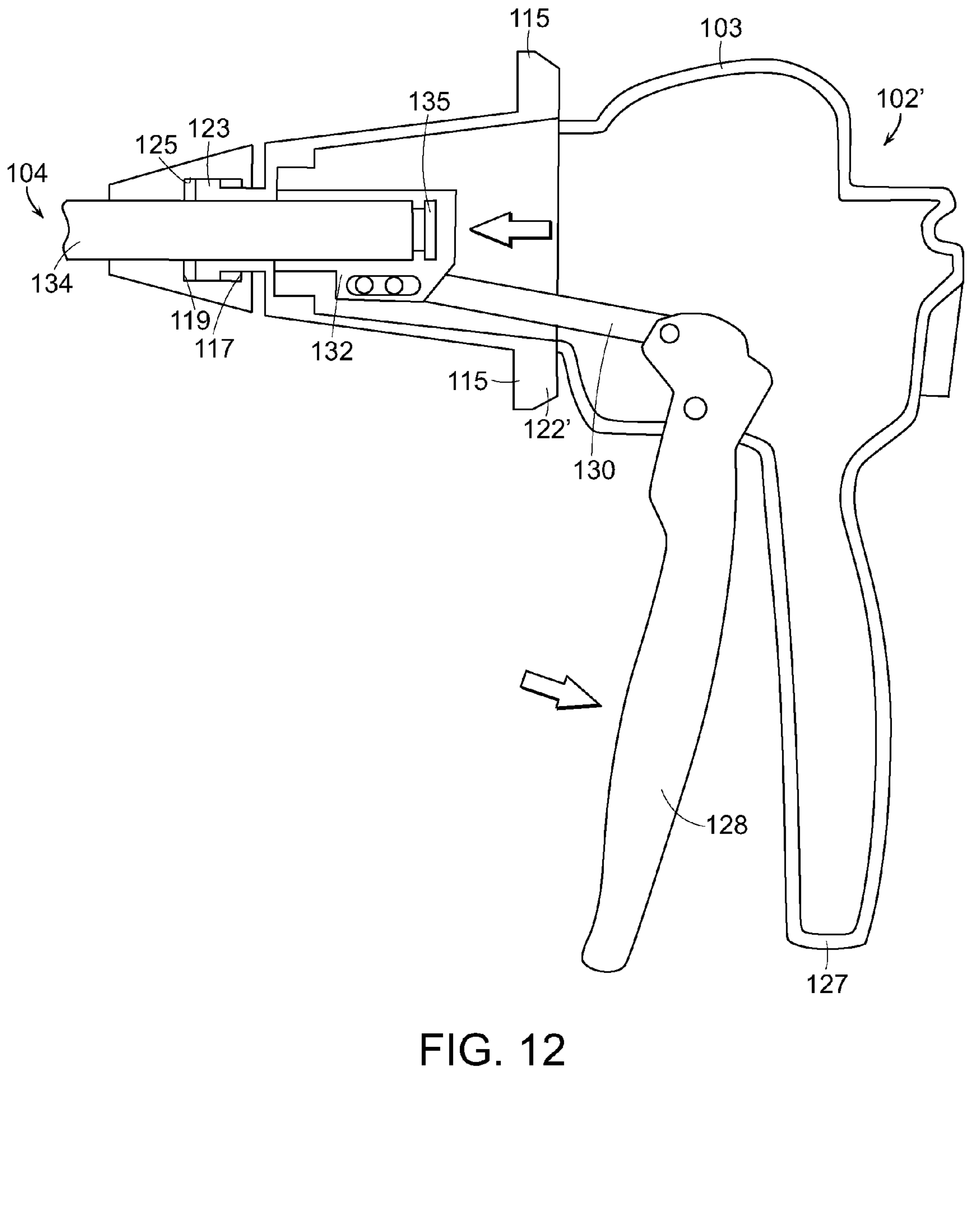
FIG. 12 is an elevational view of the surgical instrument of FIG. 10 illustrating the articulation locking mechanism actuator in an unlocked position and the end effector closure system in a partially closed configuration.

In various embodiments, as described above, locking mechanism 118 can prevent, or at least partially inhibit, relative movement between end effector 106 and shaft assembly 104. In circumstances where soft tissue is clamped between anvil 112 and staple cartridge 110, for example, relative movement between end effector 106 and shaft assembly 104 can apply a shear force to the soft tissue clamped therebetween which may damage it. In various embodiments, referring to FIGS. 10-13, in order to prevent, or at least reduce, relative movement between end effector 106 and shaft assembly 104 when end effector 106 is closed, the end effector closure system can be configured to engage locking mechanism 118 to prevent actuator 122' from being moved into its unlocked position. In effect, in at least one embodiment, the actuation of closure trigger 128 can not only close end effector 106, but it can also prevent locking mechanism 118 from being unlocked. In various embodiments, referring to FIGS. 10-13, surgical instrument 100' can include driver 132 which can be configured to abut, or be positioned closely adjacent to, actuator 122' when driver 132 is moved distally by trigger 128 and thereby prevent actuator 122' from being moved proximally as described above with respect to actuator 122. More particularly, before trigger 132 is actuated, as illustrated in FIGS. 10 and 11, actuator 122' can be slid proximally in order to slide lock member 120 relative to end effector 106 and unlock articulation joint 114. Upon an actuation of trigger of 132, however, referring to FIG. 13, driver 132 can be configured to abut, or be positioned adjacent to, actuator 122' such that actuator 122' cannot be moved proximally to disengage lock member 120 from end effector 106. As a result, the end effector closure system can prevent end effector 106 from being articulated after it has been closed, thereby reducing the possibility that a shear force will be transmitted to the soft tissue clamped therein.

Further to the above, the end effector closure system can provide feedback to the surgeon that the end effector has been closed and, in order for the surgeon to unlock and articulate the end effector, the surgeon must first at least partially re-open the end effector before the end effector can be articulated. More particularly, owing to the interaction between driver 132 and actuator 122' when end effector 106 is closed, when a surgeon attempts to pull actuator 122' proximally to unlock articulation joint 114, driver 132 can substantially prevent actuator 122' from moving thereby signaling to the surgeon that end effector 106 is closed and end effector 106 must first be opened before actuator 122' can be moved and the articulation joint can be unlocked. In various embodiments, such an end effector closure system can prevent the surgeon from damaging the surgical instrument and/or tissue captured within, or surrounding, the end effector. More particularly, in at least one embodiment, when closure tube 134 has been advanced to close anvil 112 as described above, closure tube 134 may apply a force to anvil 112 to maintain anvil 112 in a closed position and, in various circumstances, this force can create friction forces within articulation joint 114 which can inhibit, if not prevent, end effector 106 from rotating about articulation joint 114. In embodiments without the end effector closure system described above, if a surgeon attempts to overcome these friction forces without first at least partially opening the end effector, the surgeon may bend or break one or more components of the surgical instrument, for example. In various embodiments of the present invention, however, driver 132, for example, may prevent the surgeon from releasing articulation lock 120 as described above and, as a result, the surgeon may not be afforded the opportunity to unlock articulation joint 114 let alone articulate end effector 106.

In various embodiments, a surgical instrument in accordance with the present invention can include an end effector closure system which can position anvil 112, for example, in an open position, a closed position, and a partially closed position. In at least one embodiment, a surgeon can move an anvil 112 into a partially closed position and evaluate whether the end effector should be repositioned or articulated before anvil 112 is moved into its closed position. In such embodiments, anvil 112 can be moved relative to soft tissue positioned intermediate anvil 112 and staple cartridge 110 without applying a shear force, or at least a substantial shear force, to the soft tissue before anvil 112 is completely closed. In at least one embodiment, anvil 112 can be configured such that it does not clamp the soft tissue positioned between anvil 112 and staple cartridge 110 when it is in its partially closed position. Alternatively, anvil 112 can be configured to apply a light clamping force to the soft tissue when anvil 112 is in its partially closed position before applying a larger clamping force when it is moved into its closed position. In at least one such embodiment, the surgical instrument can include a trigger which can be moved between a first position (FIG. 11) which corresponds to the open position of anvil 112, a second position (FIG. 12) which corresponds with its partially closed position, and a third position (FIG. 13) which corresponds with its closed position. In various embodiments, referring to FIGS. 8 and 9, trigger 128 can be pivotably mounted to housing 103 of handle portion 102 such that trigger 128 can be rotated about pin 129 between its first, second, and third positions. In various embodiments, referring to FIGS. 8, 9, 17 and 18, surgical instrument 100 can further include trigger lock 148 which can be configured to engage trigger 128 and selectively lock trigger 128 in at least one of its first, second, and third positions described above. In at least one embodiment, trigger 128 can include pivot end 138 comprising cam surface 140, first notch 142, and second notch 144 where trigger lock 148 can be configured to engage first notch 142 and second notch 144. More particularly, surgical instrument 100 can further include, referring to FIGS. 8 and 9, trigger lock spring 150 which can be configured to bias follower portion 149 of trigger lock 148 against cam surface 140 such that when either first notch 142 or second notch 144 is aligned with follower portion 149, trigger lock spring 150 can push follower portion 149 into first notch 142 or second notch 144, respectively. In at least one embodiment, referring primarily to FIGS. 8 and 9, trigger lock 148 can be pivotably mounted to housing 103 of handle portion 102 via pin 151. In various embodiments, trigger lock spring 150 can be compressed intermediate button portion 152 of trigger lock 148 and housing 103 such that trigger lock spring 150 can rotate trigger lock 148 about pin 151 and bias trigger lock 148 downwardly against cam surface 140 of trigger 128.

Further to the above, in at least one embodiment, first notch 142 can be aligned with follower portion 149 when trigger 132 is moved into its second position and anvil 112 is moved into its partially closed position. In various embodiments, follower portion 149 can be securely retained within first notch 142 such that trigger lock 148 may need to be manually disengaged from trigger 132 before trigger 132 can be moved into its third position and/or returned to its first position. In at least one embodiment, referring to FIGS. 8 and 9, a surgeon can depress button portion 152 of lock member 148 such that lock member 148 is rotated about pin 151 and follower portion 149 is lifted upwardly and out of engagement with trigger 128. In other various embodiments, first notch 142 can be configured such that follower portion 149 can slide out of first notch 142 upon an application of force to trigger 132. In either event, after follower portion 149 has been disengaged from first notch 142, a surgeon can selectively move trigger 132 into its third position or release trigger 132 and allow a trigger spring, for example, to return trigger 132 to its first position. In at least one alternative embodiment, first notch 142 and follower portion 149 can be configured such that, after trigger 132 has been moved into its second position, trigger 132 must be moved into its third position before it can be returned into its first position. In either event, in at least one embodiment, second notch 144 of trigger 132 can be aligned with follower portion 149 when trigger 132 is moved into its third position and anvil 112 is moved into its closed position. Similar to first notch 142, second notch 144 can be configured to retain follower portion 149 therein until lock member 148 is disengaged from trigger 132 and/or a sufficient force is applied to trigger 132 to dislodge follower portion 149 from second notch 144. Thereafter, in various embodiments, a trigger spring can move trigger 132 from its third position into its second position where the surgeon may be required to, similar to the above, disengage follower portion 149 from first notch 142. In at least one alternative embodiment, first notch 142 can be configured such that follower portion 149 can slide past first notch 142 and allow trigger 132 to be moved from its third position to its first position without requiring the surgeon to dislodge follower portion 149 from first notch 142.

Further to the above, although not illustrated, button portion 152 of lock member 148 can be recessed, for example, within surgical instrument housing 103 when closure trigger 128 is in its first position. In alternative embodiments, button portion 152 can be positioned flushly with housing 103 or it can extend slightly from housing 103. In either event, in at least one embodiment, button portion 152 can move outwardly relative to housing 103 when closure trigger 128 is moved into its second position. Such movement can provide visual feedback to the surgeon that the anvil of the surgical instrument is in its partially closed position. In addition, the movement of button portion 152 can also be accompanied by audio and/or tactile feedback. In either event, a surgeon can access button portion 152 after it has been moved outwardly such that lock member 148 can be disengaged from trigger 128 as described above. In various embodiments, button portion 152 can move outwardly even further when trigger 128 is moved from its second position to its third position. Similar to the above, such movement can provide a visual cue to the surgeon that the anvil is now in its closed position and can be accompanied by audio and/or tactile feedback, as described above. Although button 152 is described above as moving outwardly as trigger 128 is progressed between its first and third positions, the invention is not so limited. On the contrary, button 152, or any other suitable indicator, can be provide feedback to the surgeon in any suitable manner.

In alternative embodiments, although not illustrated, anvil 112 can be held, or retained, in more than the three positions described above, i.e., its open, closed, and partially-closed positions. In at least one embodiment, anvil 112 can be retained in open, closed, and two or more intermediate positions. In such embodiments, anvil 112 could be progressed through these intermediate positions and apply an increasingly greater force to the soft tissue captured in end effector 106 as anvil 112 is moved toward its closed position. In at least one embodiment, similar to the above, trigger 132 could include a plurality of notches which could correspond with the various intermediate positions of anvil 112. In various alternative embodiments, although not illustrated, the end effector closure system could include a ratchet assembly which could allow trigger 132 and, correspondingly, anvil 112 to be held in a plurality of positions. In such embodiments, anvil 112 and trigger 132 could be held in place by a pawl pivotably engaged with a ratchet wheel operably engaged with trigger 132.

Figure 13:
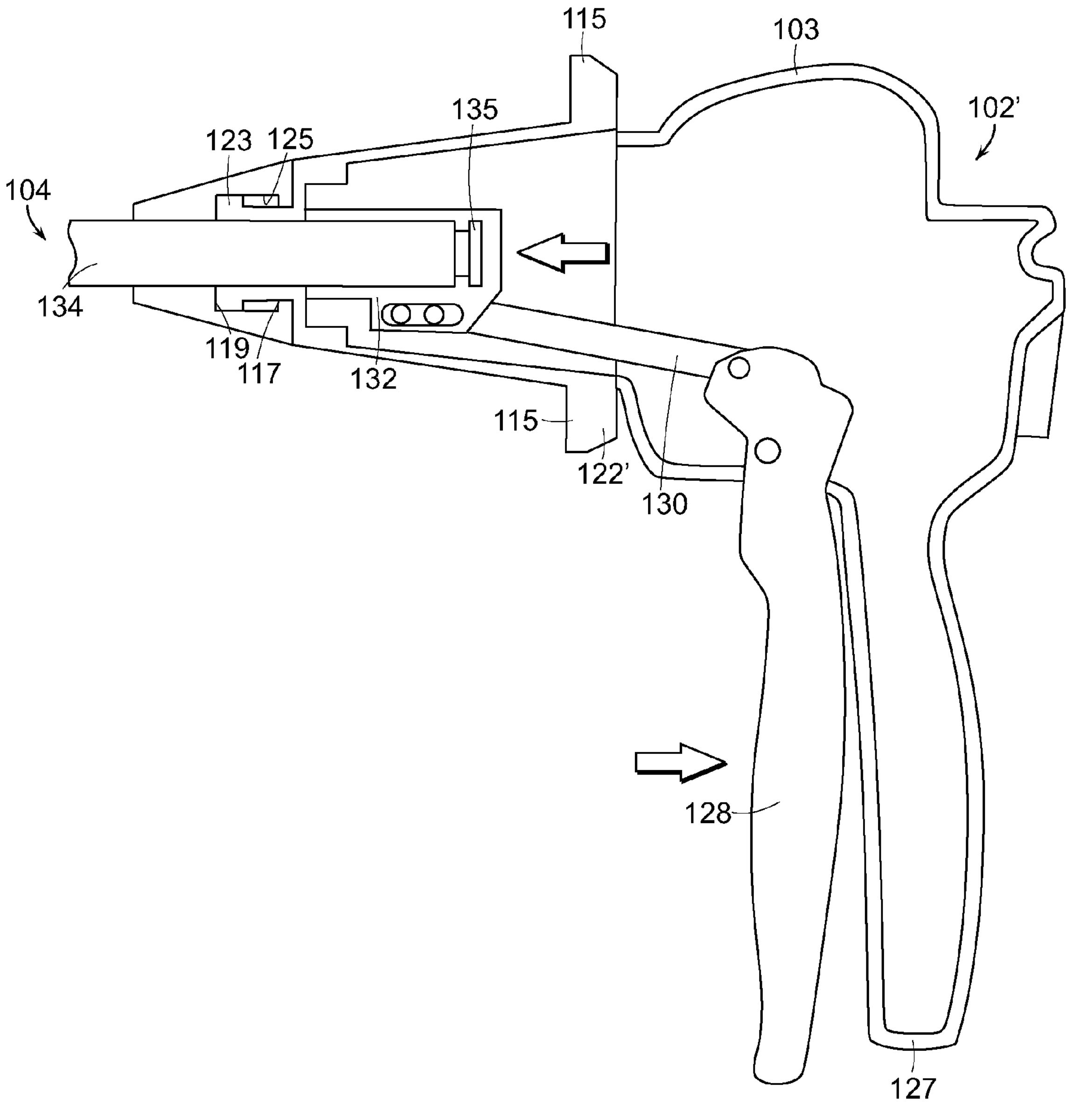
FIG. 13 is an elevational view of the surgical instrument of FIG. 10 illustrating the articulation locking mechanism actuator in a locked position and the end effector closure system in a closed configuration.
Figure 14:
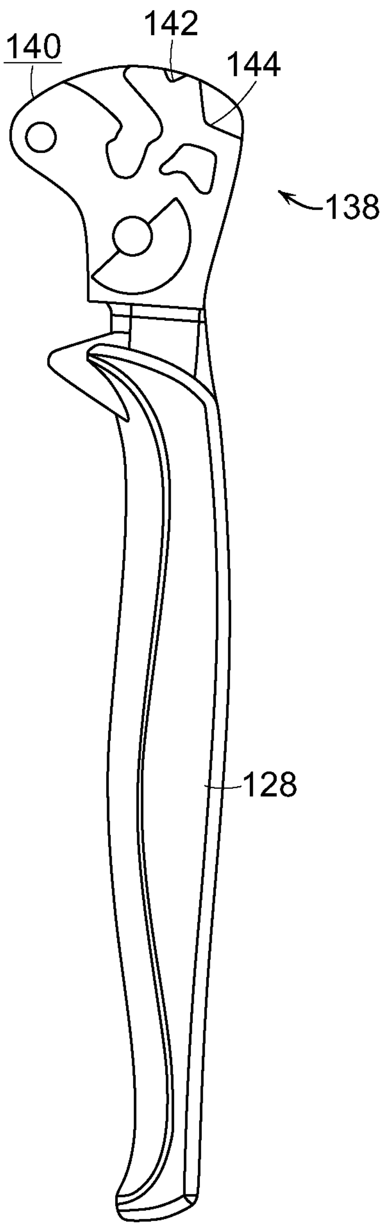
FIG. 14 is an elevational view of a closure trigger of an end effector closure system of the surgical instrument of FIG. 1.
Figure 15:
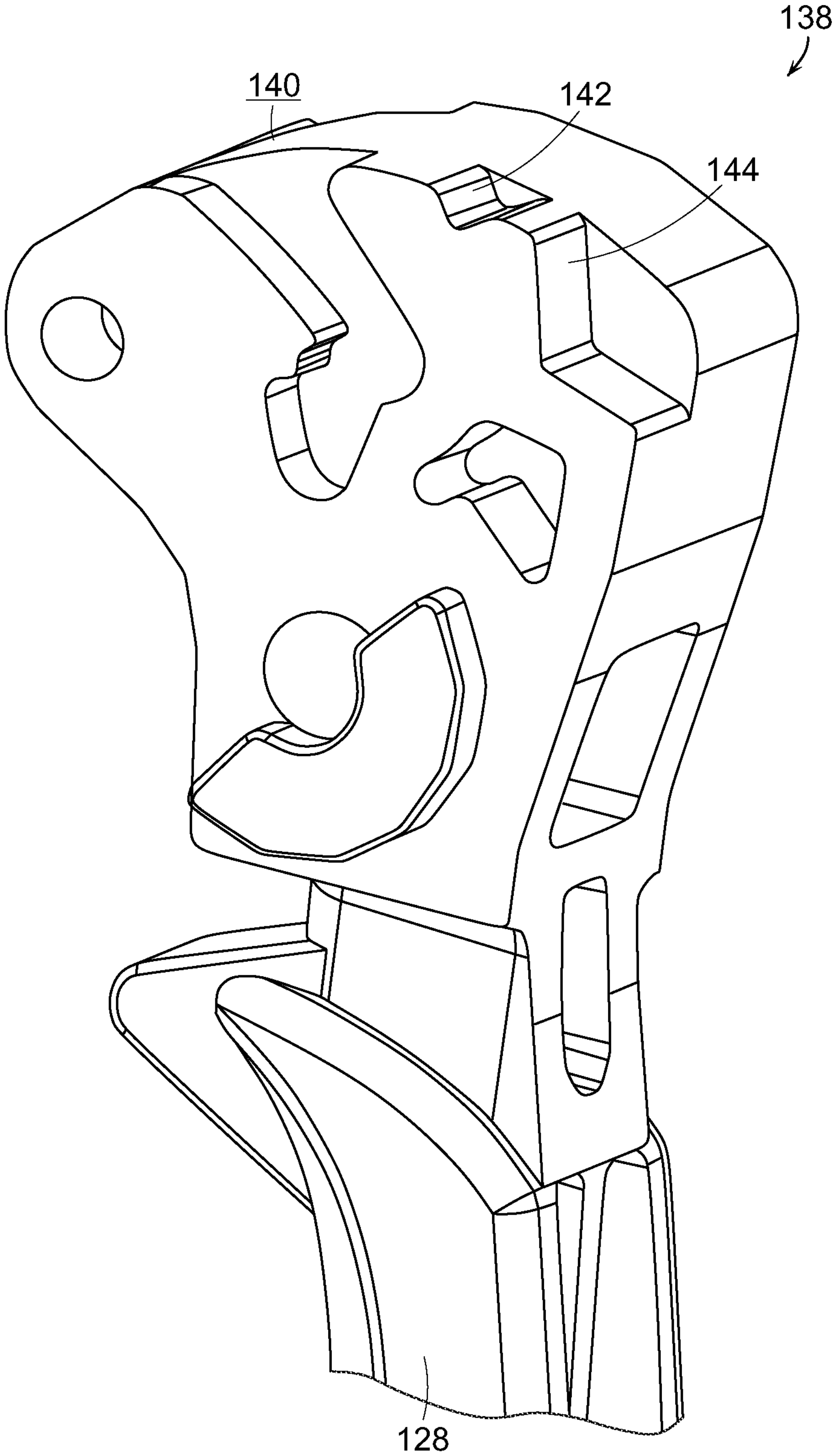
FIG. 15 is a partial perspective view of the closure trigger of FIG. 15.
Figure 16:
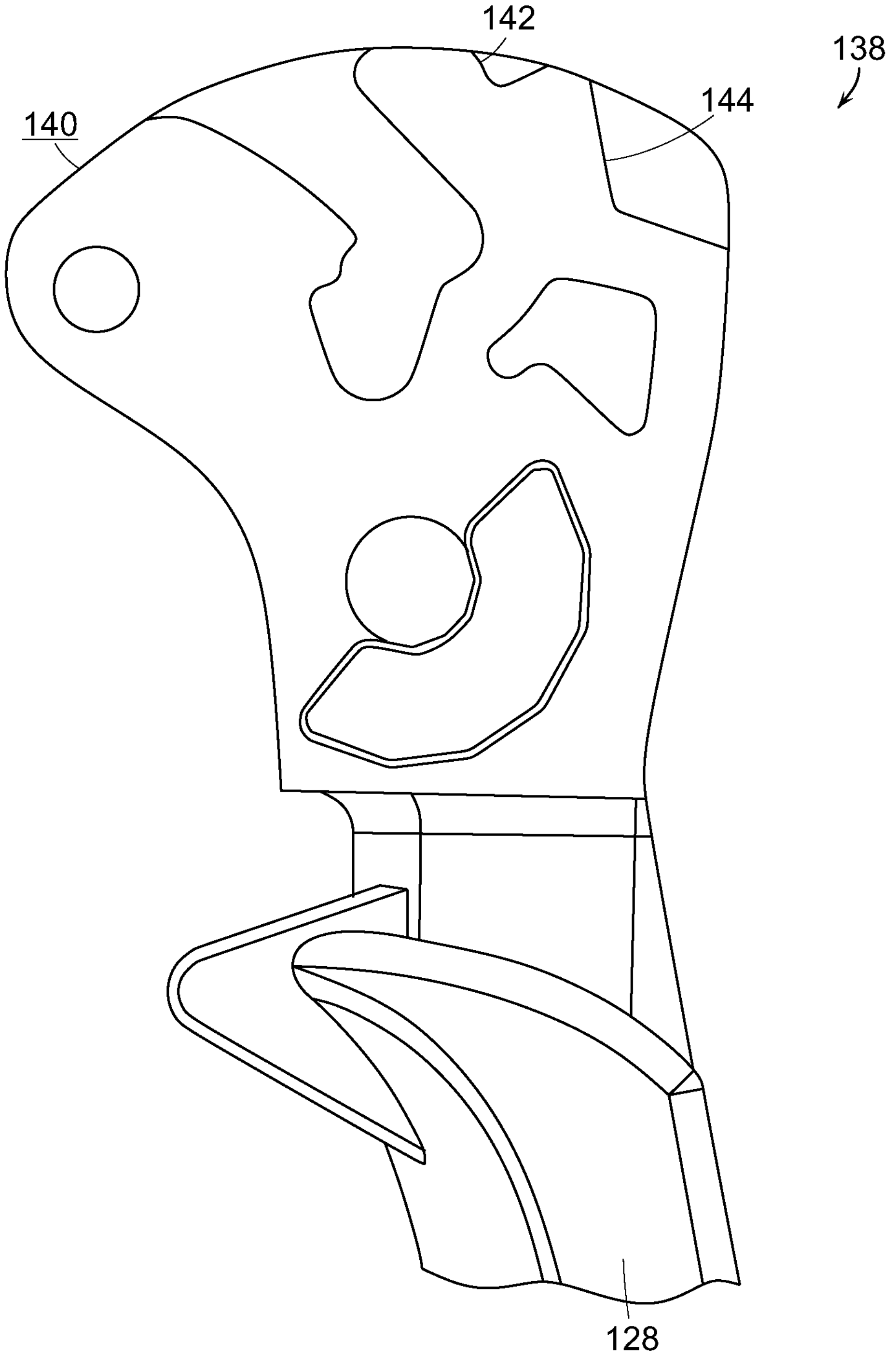
FIG. 16 is a partial elevational view of the closure trigger of FIG. 15.
Figure 17:
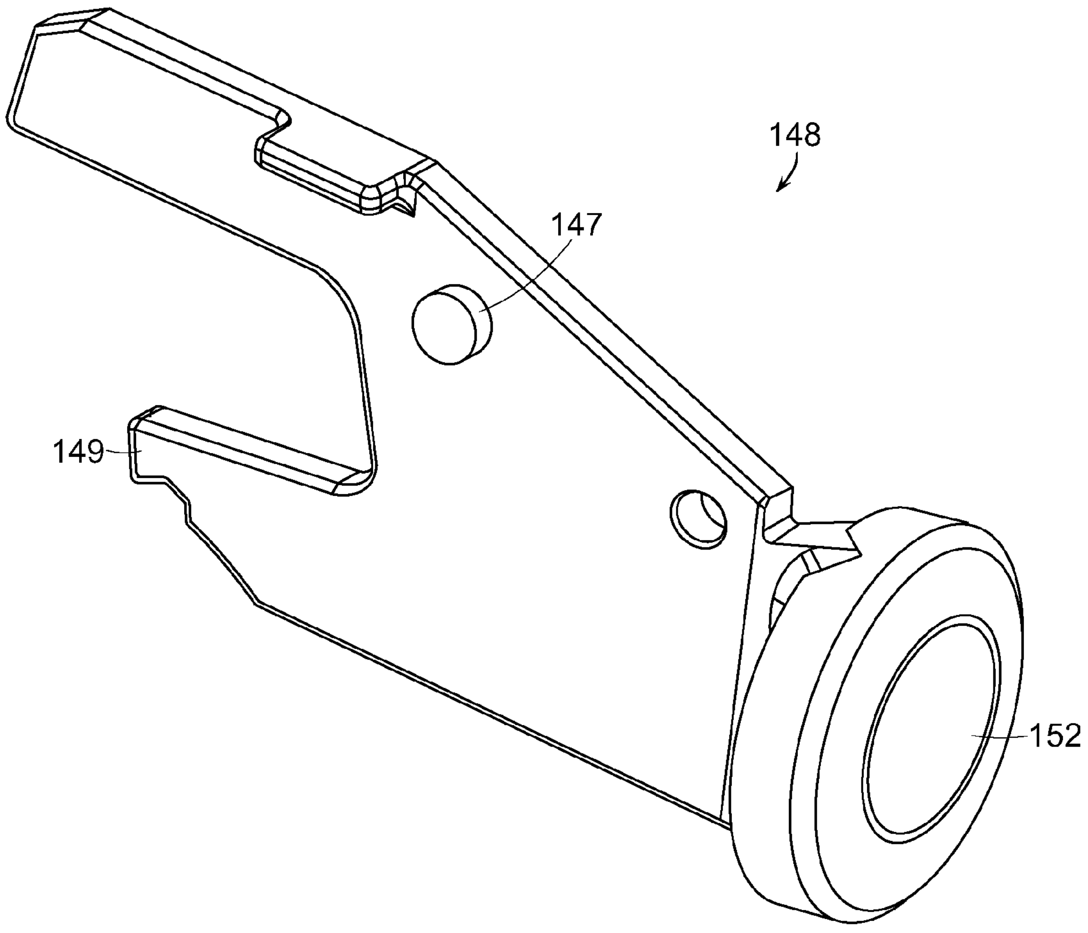
FIG. 17 is a perspective view of a trigger lock of the surgical instrument of FIG. 1.
Figure 18:
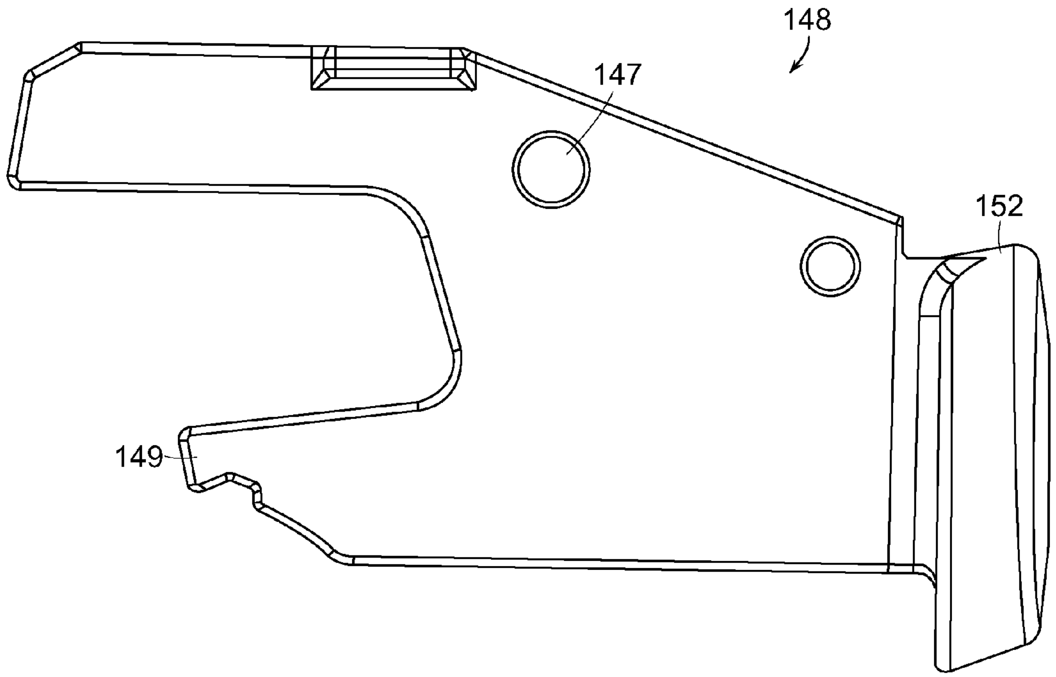
FIG. 18 is an elevational view of the trigger lock of FIG. 17.

In various embodiments, referring to FIGS. 10-13, the relative movement between actuator 122' and handle portion 102', as described above, can be limited in order to control the range through which lock member 120 can be displaced. More particularly, referring to FIGS. 10 and 11, the distal portion of actuator 122' can include projection 123 extending therefrom which can be received in cavity 125 where the displacement of actuator 122' can be limited by proximal wall 117 and distal wall 119 of cavity 125. In at least one embodiment, when trigger 128 is in its first position, as illustrated in FIGS. 10 and 11, actuator 122 can be moved from a distal position in which projection 123 can abut distal wall 119, as illustrated in FIG. 10, into a more proximal position in which projection 123 does not abut distal wall 119, as illustrated in FIG. 11. In this more distal position, as described above, lock member 120 can be disengaged from end effector 106 and end effector 106 can be rotated relative to shaft assembly 104. When trigger 128 is in its second position, referring to FIG. 12, driver 132 can limit the range of motion of actuator 122' such that projection 123 cannot be positioned against proximal wall 117. In at least one embodiment, however, actuator 122' can be moved proximally a sufficient distance to disengage lock member 120 from end effector 106. In these circumstances, a surgeon can reposition end effector 106 although anvil 112 may be partially closed onto the soft tissue, for example. When trigger 128 is in its third position, as illustrated in FIG. 13, driver 132 can force actuator 122' distally such that projection 132 abuts, or is positioned adjacent to, distal wall 119 and actuator 122' cannot be moved sufficiently to unlock articulation joint 114.

In various embodiments, a surgical instrument in accordance with the present invention can include a firing drive configured to advance a cutting member and/or staple driver within an end effector as described above. In at least one embodiment, referring to FIGS. 8, 9 and 19-25, the firing drive of surgical instrument 100 can include firing trigger 160, first firing link 162, second firing link 164, and firing member 166. In various embodiments, firing trigger 160 can be operably engaged with at least one of firing member 166 and firing links 162 and 164 in order to advance knife bar 168 within elongate shaft assembly 104. In at least one embodiment, knife bar 168 can be operably engaged with a cutting member (not illustrated) and a staple driver (not illustrated) in end effector 106 where the cutting member can be configured to incise tissue, for example, and the staple driver can be configured to deploy staples from staple cartridge 110. Cutting members and staple drivers are well disclosed in U.S. Pat. Nos. 6,905,057 and 7,044,352, which have been previously incorporated by reference into the present application, and, as a result, these devices are not described in greater detail herein. Other cutting members and staple drivers are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, which was filed on Sep. 29, 2006, and U.S. patent application Ser. No. 11/652,169, entitled SURGICAL STAPLING DEVICE WITH A CURVED CUTTING MEMBER, which was filed on Jan. 11, 2007, the entire disclosures of which are hereby incorporated by reference herein.

Figure 19:
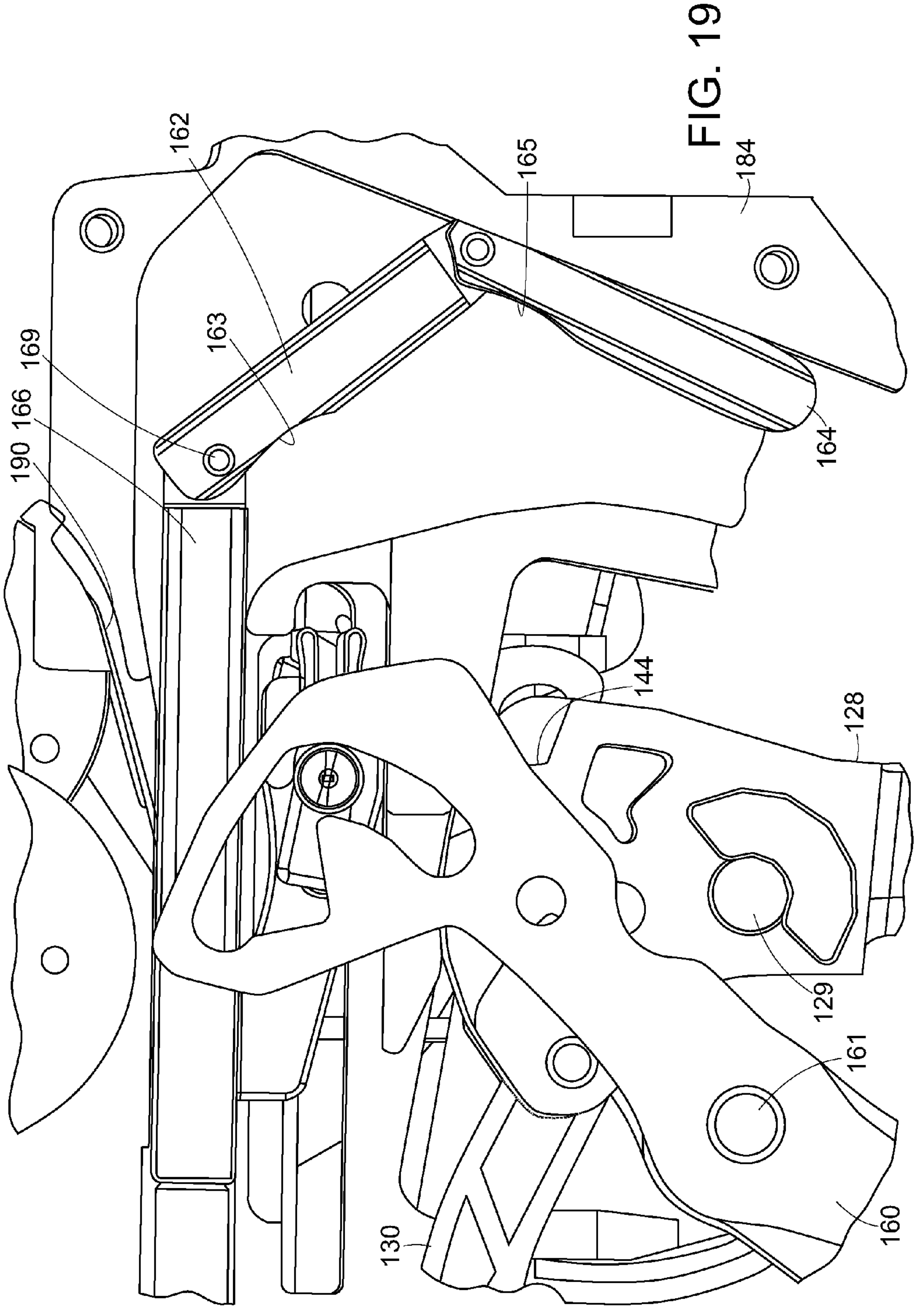
FIG. 19 is a detail view of a firing drive of the surgical instrument of FIG. 1 with some components of the surgical instrument removed.
Figure 20:
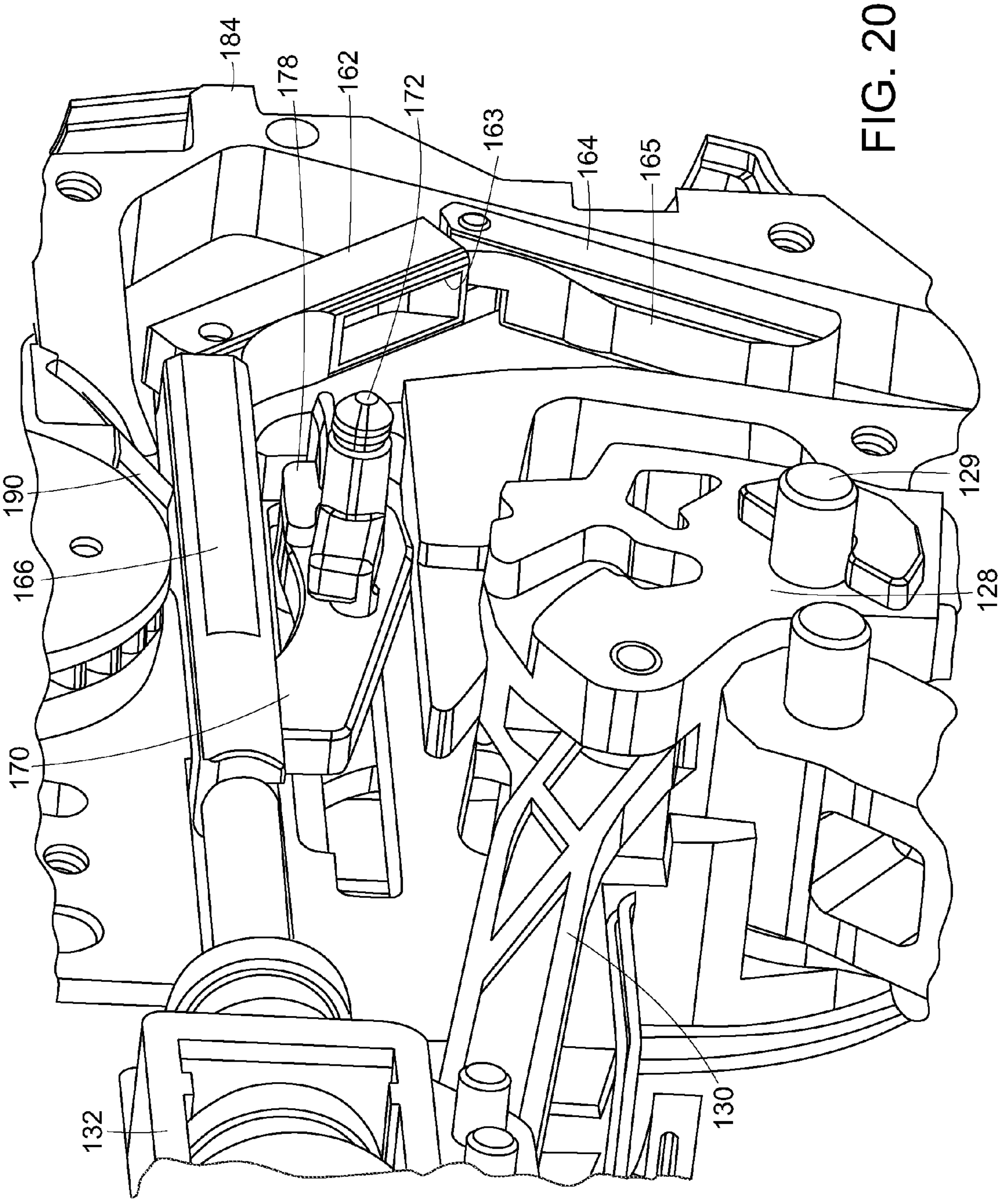
FIG. 20 is a perspective view of the firing drive of FIG. 19.
Figure 21:
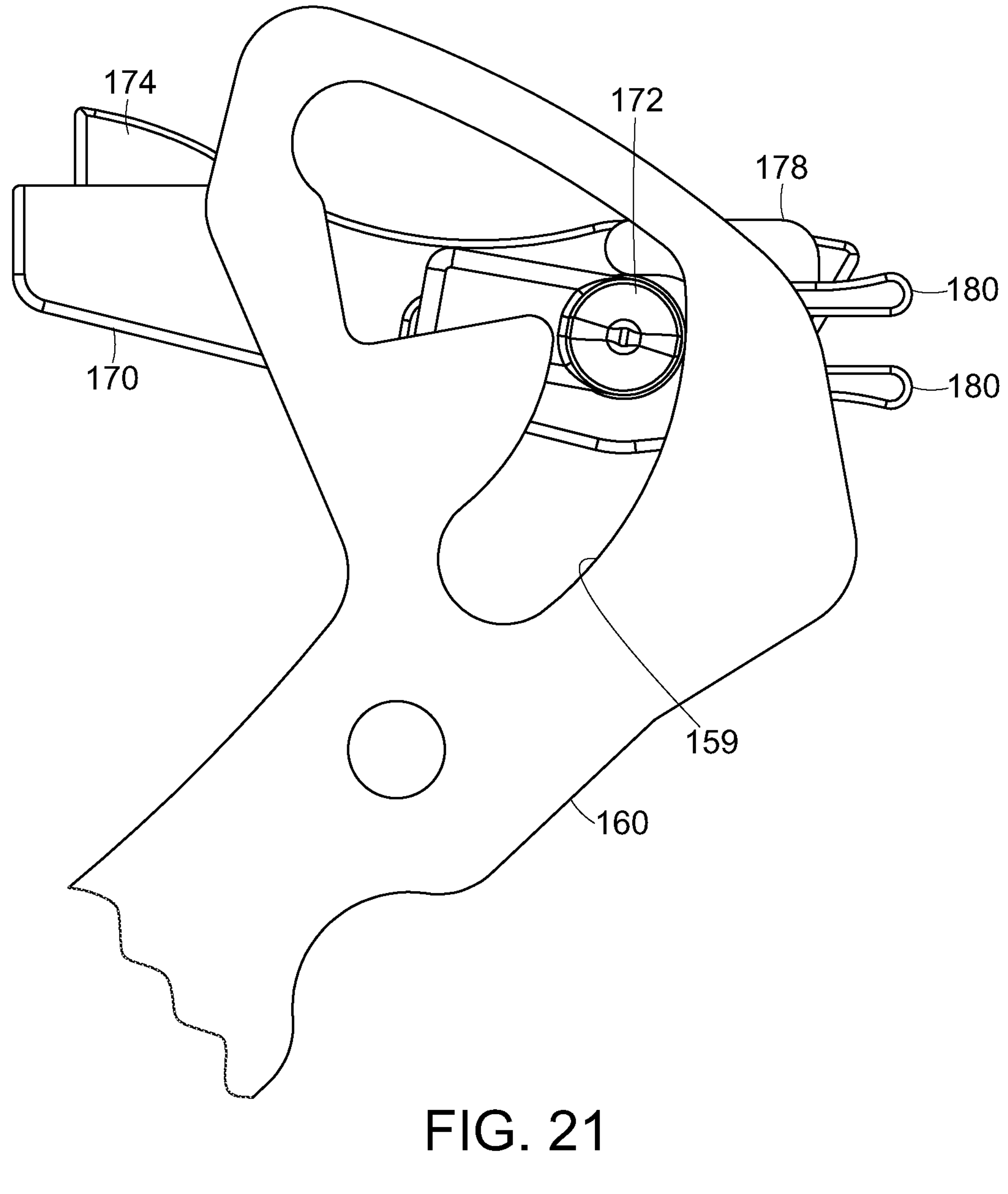
FIG. 21 is a partial detail view of a firing trigger, pawl, and tilter mechanism of the firing drive of FIG. 19.
Figure 22:
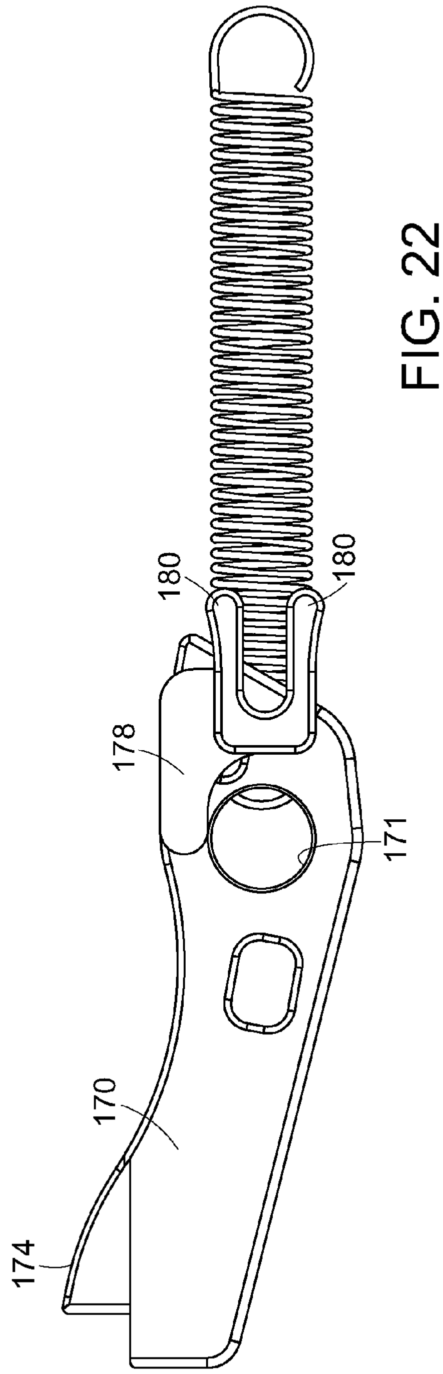
FIG. 22 is an elevational view of the pawl, tilter mechanism, and a pawl return spring of the firing drive of FIG. 19.
Figure 23:
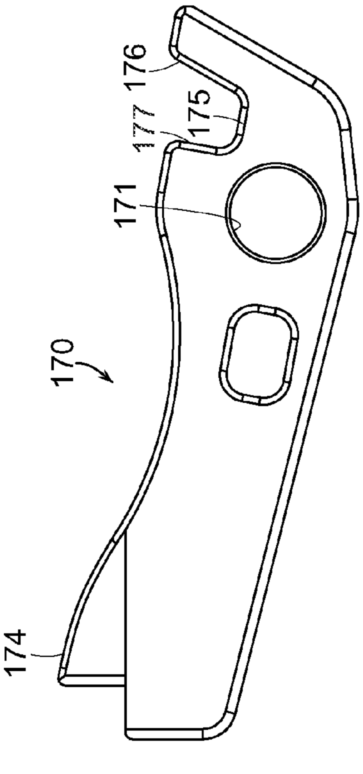
FIG. 23 is an elevational view of the pawl of FIG. 22.

In various embodiments, referring primarily to FIGS. 19 and 20, firing trigger 160 can be pivotably connected to surgical instrument housing 103 (FIGS. 8 and 9) by pin 161. In use, in at least one embodiment, firing trigger 160 can be pivoted about pin 161 in order to advance firing member 166 and firing links 162 and 164 distally. In various embodiments, firing trigger 160 can include slots 159, where slots 159 can be configured to receive firing pin 172. In various embodiments, when firing trigger 160 is actuated, or rotated, from its position illustrated in FIG. 2 to a position adjacent handle grip 127, the side walls of slots 159 can be configured to engage and advance firing pin 172 distally. In at least one embodiment, referring to FIG. 23, the firing drive can further include pawl 170, where pawl 170 can include aperture 171. In various embodiments, aperture 171 can be configured to receive at least a portion of firing pin 172 such that, when firing pin 172 is advanced distally by trigger 160, firing pin 172 can advance pawl 170 distally as well. In various embodiments, referring to FIG. 24, pawl 170 can include tooth 174 and firing member 166 can include recess 167, where recess 167 can be configured to receive tooth 174. In use, when pawl 170 is advanced distally by firing pin 172 and tooth 174 is engaged with a side wall of recess 167, pawl 170 can advance firing member 166 distally as well. In various embodiments, pawl 170 can be advanced distally by firing pin 172 along a substantially linear path. In such embodiments, slots 159 can include arcuate profiles which can, in cooperation with firing pin 172, convert the rotational motion of firing trigger 160 into translational motion of pawl 170. In at least one embodiment, the force applied to pawl 170 can be substantially, if not entirely, directed in the distal direction. In such embodiments, as a result, the possibility of pawl 170 becoming bound or stuck against stapler frame 184 can be reduced.

In various embodiments, pawl 170 can be pivoted between a first position in which pawl 170 is operably disengaged from firing member 166 and a second position, referring to FIGS. 19 and 20, in which pawl 170 is operably engaged with firing member 166. Referring primarily to FIGS. 21-25, the firing drive can further include tilter mechanism 178 which can be configured to pivot pawl 170 between its first and second positions. In use, when firing trigger 160 is actuated, pawl 170 can be moved, at least initially, relative to tilter mechanism 178 such that at least a portion of pawl 170 can abut tilter mechanism 178 and pivot pawl 170 upwardly and into operative engagement with firing member 166. In at least one embodiment, pawl 170 can include, referring primarily to FIG. 23, groove 175 which can be configured to receive projection 179 (FIG. 25) extending from the center portion of tilter mechanism 178. In at least one embodiment, as pawl 170 is advanced distally, proximal wall 176 of groove 175 can contact a cam surface on projection 179 and, owing to the force applied to pawl 170 by pivot pin 172, pawl 170 can be pivoted, or rotated, upwardly such that tooth 174 can be positioned in recess 167 of firing member 166 as described above. After pawl 170 has been pivoted, pawl 170 can drag tilter mechanism 178 distally as pawl 170 is advanced toward end effector 106. More particularly, in at least one embodiment, tilter mechanism 178 can include deformable members 180 which can be received within slots 182 in stapler frame 184 such that the interaction between deformable members 180 and stapler frame 184 at least partially inhibits the movement of tilter mechanism 178 relative to stapler frame 184. Stated another way, owing to static friction forces between deformable members 180 and the side walls of slots 182, a force sufficient to overcome these friction forces must be applied to tilter mechanism 178 before tilter mechanism 178 can be 'dragged' relative to stapler frame 184.

Figure 24:
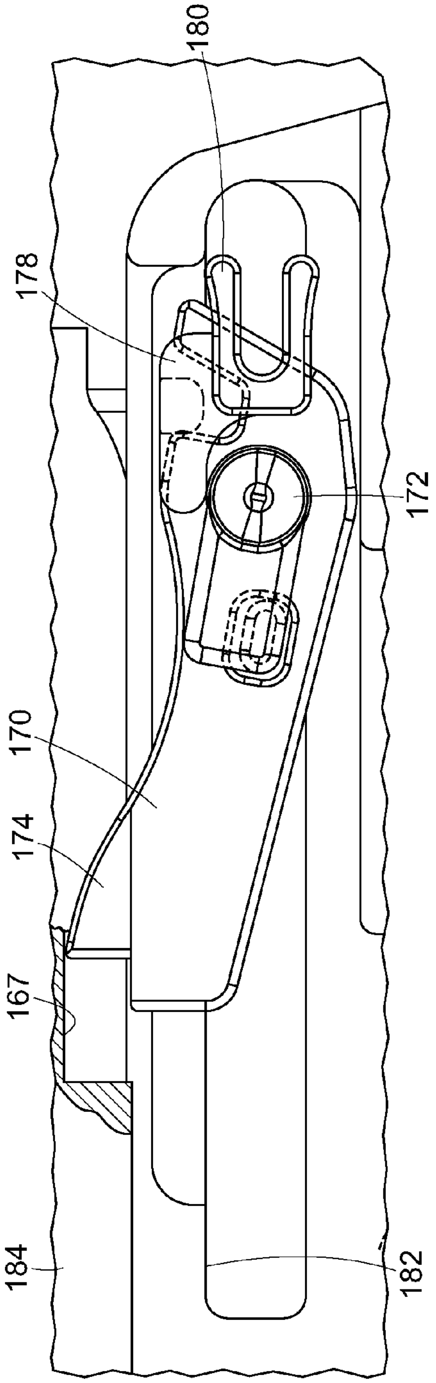
FIG. 24 is a detail view of the firing drive of FIG. 19 illustrating the pawl pivoted into a position to engage a firing link of the firing drive.
Figure 25:
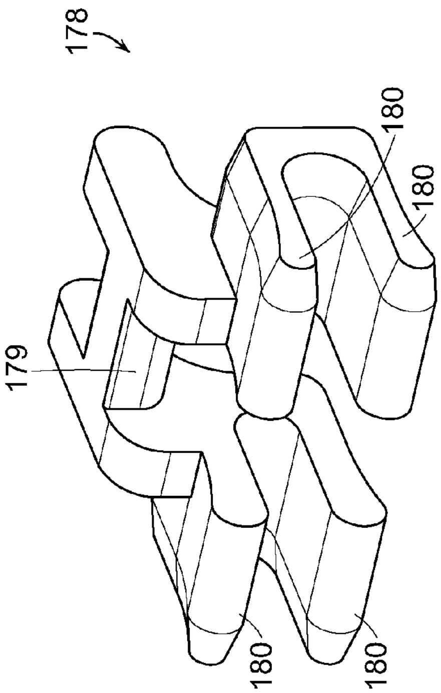
FIG. 25 is a perspective view of the tilter mechanism of FIG. 22.
Figure 26:
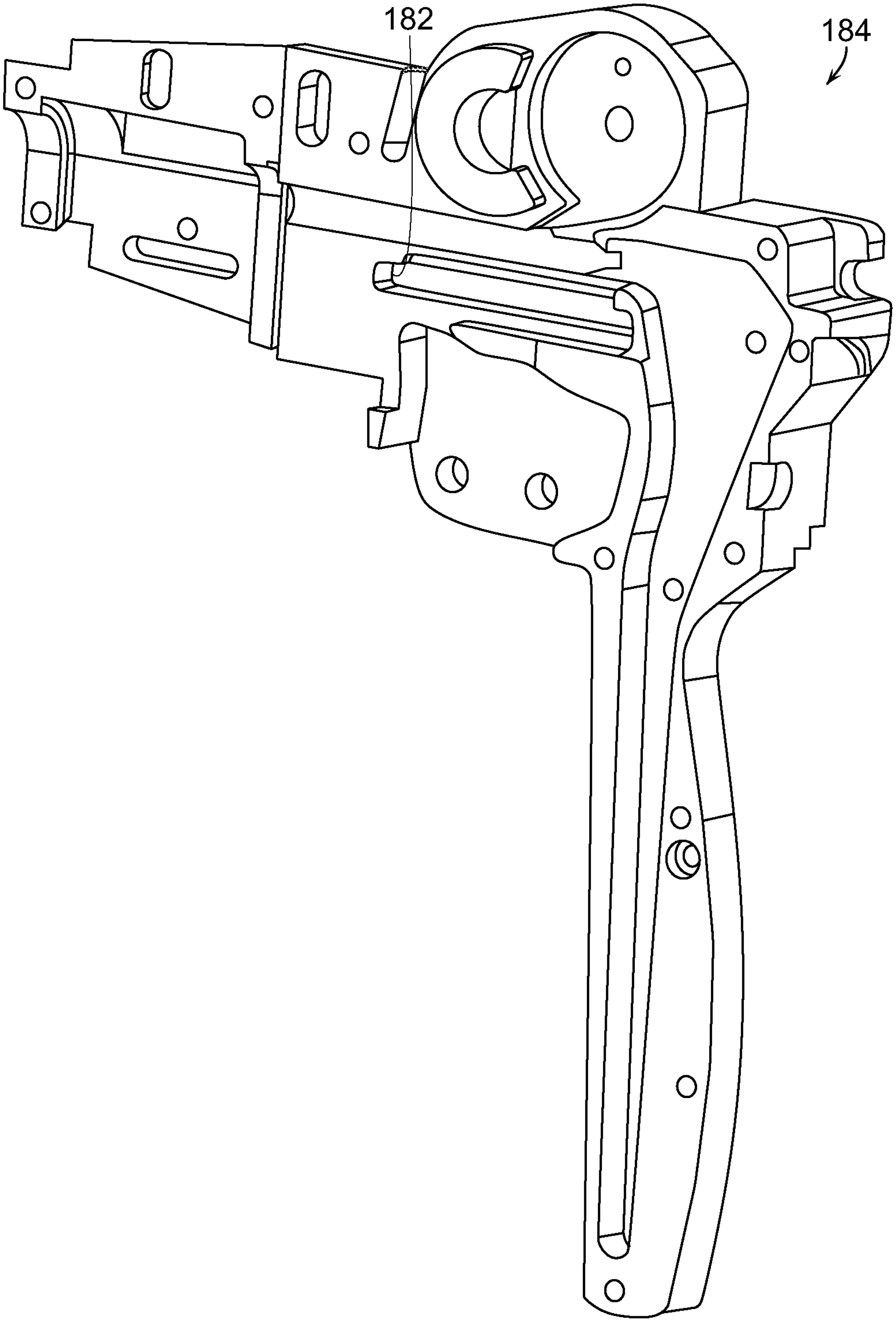
FIG. 26 is a perspective view of a frame of the surgical instrument of FIG. 1.

After firing trigger 160 has been actuated and firing member 166 has been advanced, trigger 160 can be released and returned to its unactuated position illustrated in FIG. 2 and pawl 170 can be disengaged from firing member 166 and retracted to its starting position illustrated in FIG. 19. More particularly, in at least one embodiment, surgical instrument 100 can further include a trigger spring (not illustrated) operably engaged with trigger 160 and housing 103, for example, where the trigger spring can be configured to rotate trigger 160 about pin 161 and drive firing pin 172 proximally after pawl 170 has been disengaged from firing member 166. In various embodiments, pawl 170 can be disengaged from firing member 166 when it is pivoted from its second position, as illustrated in FIG. 24, into its first position, as described above, by tilter mechanism 178. In such embodiments, pawl 170 can be moved, at least initially, relative to tilter mechanism 178 such that distal wall 177 of groove 175 can contact a second cam surface on projection 179 and can, owing to a force applied to firing pin 172 by trigger 160 or return spring 186, rotate pawl 170 downwardly such that tooth 174 of pawl 170 can be disengaged from recess 167 in firing member 166. Thereafter, trigger 160 and/or return spring 186 can pull, or retract, pawl 170 relative to firing member 166. In various embodiments, similar to the above, pawl 170 can be configured to drag tilter mechanism 178 proximally within slot 182. As a result of the above, pawl 170 does not need to be biased into its first or second positions. In various circumstances, pawl 170 can be rotated freely between its first and second positions without having to overcome a force applied thereto by a biasing spring. In effect, in various embodiments, the force to move pawl 170 between its first and second positions need only overcome the gravitational weight of pawl 170 and any frictional forces between pawl 170 and the surrounding components of the surgical instrument.

Once pawl 170 has been returned to its original position, in at least one embodiment, tooth 174 of pawl 170 may no longer be aligned with recess 167 in firing member 166. On the contrary, referring generally to FIGS. 19 and 20, tooth 174 of pawl 170 can be aligned with recess 163 in first firing link 162. More particularly, first firing link 162 can be pivotably connected to firing member 166 such that, when firing member 166 is advanced distally, as described above, firing member 166 can pull first firing link 162 into the position that firing member 166 previously occupied. As a result, upon a second actuation firing trigger 160, pawl 170 can be pivoted from its first position into its second position such that tooth 174 is operably engaged with recess 163 and pawl 170 can advance firing link 162 distally. In at least one embodiment, firing link 162 can push firing member 166 and knife bar 168 distally and, correspondingly, advance the cutting member and the staple driver distally within end effector 106. Thereafter, pawl 170 can once again be pivoted from its second position to its first position and can be retracted relative to first firing link 162. Once pawl 170 is returned to its original position for the second time, tooth 174 of pawl 170 may no longer be aligned with recess 163 of first firing link 162. On the contrary, similar to the above, tooth 174 can be aligned with recess 165 in second firing link 164 and the process described above can be repeated.

Although not illustrated, a surgical instrument in accordance with the present invention can include more than two, or less than two, firing links in order to advance the cutting member and staple driver to their desired positions within end effector 106. In various embodiments, as described in greater detail below, firing member 166 can include more than one recess 167 such that pawl 170 can directly advance firing member 166 toward end effector 106 more than once. In at least one such embodiment, pawl 170 can be retracted after advancing firing member 166 distally, as described above, such that, when pawl 170 is once again tilted upwardly, pawl 170 can engage another recess 167 in firing member 166 and advance firing member 166 toward end effector 106 once again. As a result, in at least one embodiment, firing links 162 and 164 may not be required.

Figure 27:
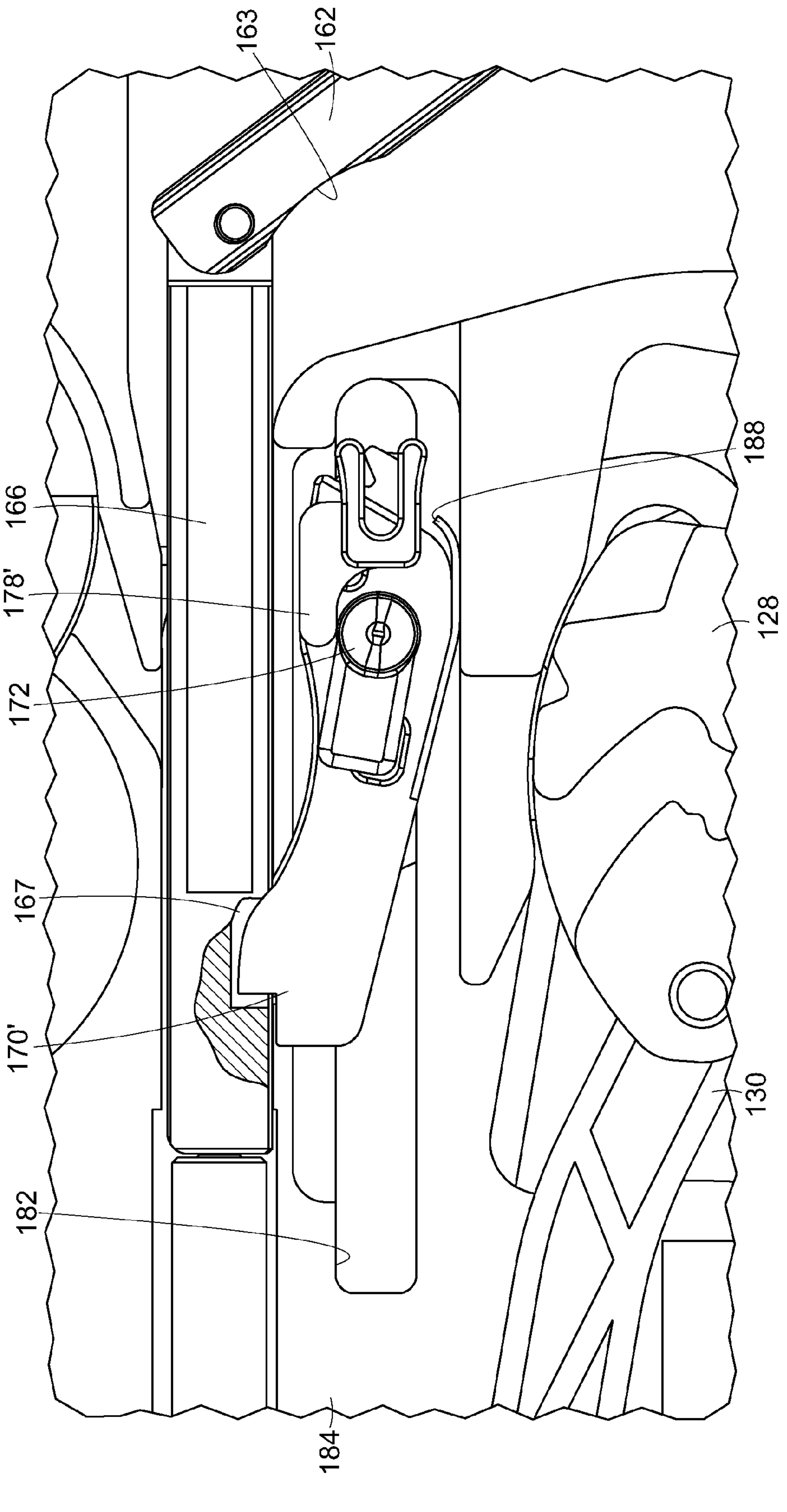
FIG. 27 is a detail view of a firing drive of a surgical instrument in accordance with an alternative embodiment of the present invention with some components of the surgical instrument removed.
Figure 28:
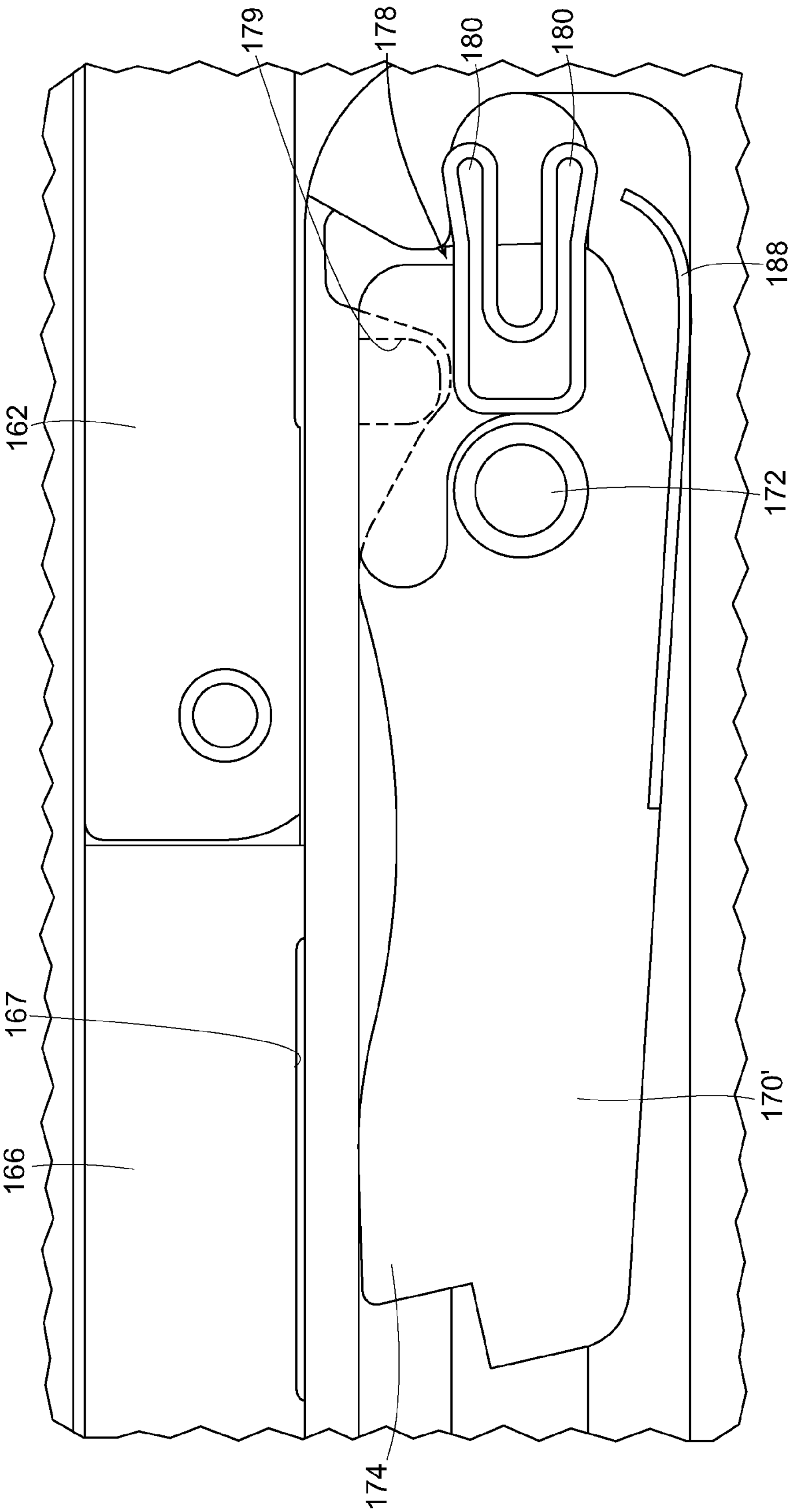
FIG. 28 is a detail view of the firing drive of FIG. 27 illustrating a pawl of the firing drive disengaged from a firing link.

In various embodiments, a surgical instrument can include one or more spring members configured to move pawl 170 into at least one of its first and second positions. In at least one embodiment, referring to FIGS. 27 and 28, the firing drive can include pawl 170', firing pin 172, and tilter mechanism 178' where, similar to the above, tilter mechanism 178' can be configured to pivot pawl 170' upwardly when pawl 170' is advanced distally. The firing drive can further include pivot spring 188 which can be operably connected to pawl 170' such that, when pawl 170' is pivoted upwardly into its second position as illustrated in FIG. 27, pawl 170' can flex, or resiliently bend, pivot spring 188. After pawl 170' has been advanced, pawl 170' can be pivoted downwardly into its first position by pivot spring 188 as illustrated in FIG. 28. More particularly, owing to potential energy stored in pivot spring 188 when it is flexed, spring 188 can move pawl 170' downwardly once pawl 170' is no longer held in its second position by tilter mechanism 178' and firing pin 172. Thereafter, as described above, pawl 170' can be retracted relative to firing member 166 and/or firing links 162 and 164. In various embodiments, tilter mechanism 178' may not include a second cam surface for pivoting pawl 170 into its first position. In such embodiments, pawl 170' can be retracted by a force applied to firing pin 172 as described above. In various alternative embodiments, although not illustrated, tilter mechanism 178' and pawl 170' can also include co-operating features for pivoting pawl 170' downwardly into its first position.

In various embodiments, referring to FIGS. 19 and 20, surgical instrument 100 can further include band 190 which can be configured to move firing member 166 and firing links 162 and 164 relative to end effector 106. In at least one embodiment, a first end of band 190 can be connected to firing member 166, for example, such that, when firing member 166 is advanced distally, band 190 can be pulled distally as well. In various alternative embodiments, band 190 can be connected to first firing link 162 and/or second firing link 164. In at least one embodiment, band 190 can be positioned around at least a portion of reel, or spool, 192 such that when band 190 is pulled by firing member 166, band 190 can be deployed, or unwound, from reel 192. In at least one embodiment, a second end of band 190 can be connected to reel 192 such that band 190 cannot be readily disengaged from reel 192 under the normal operating conditions of surgical instrument 100. In either event, when band 190 is pulled by firing member 166, reel 192 can be rotated in one of a clockwise or counter-clockwise direction, depending on the manner in which band 190 is positioned around reel 192. In order to retract firing member 166, reel 192 can be rotated in an opposite direction to move firing member 166, and firing links 162 and 164, proximally and wind band 190 around reel 192.

In various embodiments, band 190 can be wound around reel 192 such that band 190 is wrapped around a substantially cylindrical surface on reel 192. In at least one embodiment, the distance between an axis of rotation of reel 192 and the cylindrical surface can be substantially equidistant around the perimeter of reel 192. In these embodiments, the mechanical advantage of reel 192 can remain substantially constant as band 190 is pulled proximally as described above and the capacity for reel 192 to apply a pulling force to band 190 can remain substantially the same. In alternative embodiments, however, reel 192 can be configured to provide a variable mechanical advantage. In at least one embodiment, reel 192 can include a non-cylindrical surface on which band 190 can be wrapped such that the distance between the axis of rotation of reel 192 and the non-cylindrical surface is not equidistant around the perimeter of reel 192. In these embodiments, as a result, the capacity for reel 192 to apply a pulling force to band 190 can change as band 190 is wound around reel 192. In at least one embodiment, reel 192 can act as a cam and can include a shape which can be optimized to provide additional force to band 190 when it is initially retracted, i.e., when the force to retract the cutting member, for example, can be at its highest.

Figure 29:
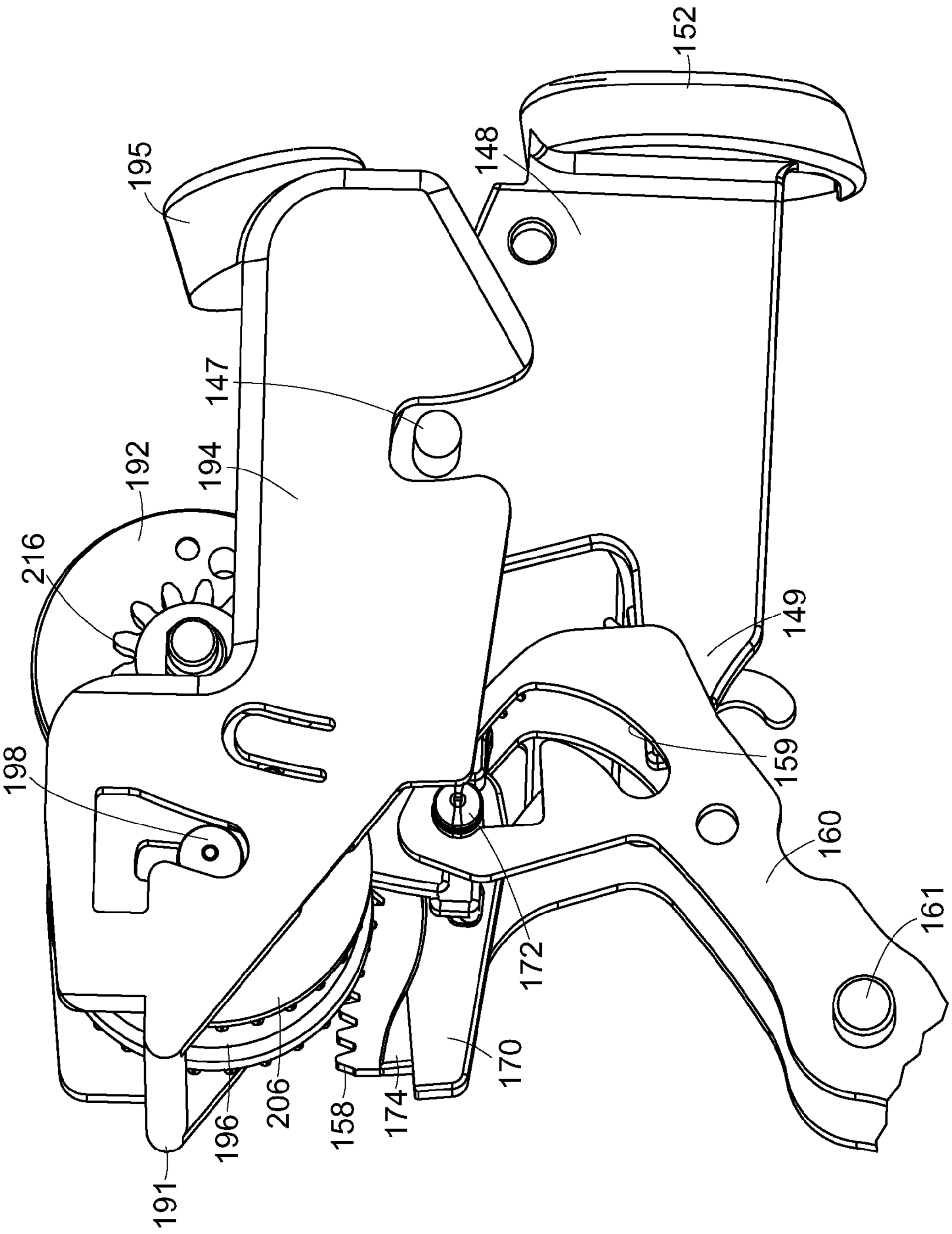
FIG. 29 is a perspective view of a return mechanism of the surgical instrument of claim 1 illustrating the firing trigger in an unactuated position with some components of the surgical instrument removed.

In various embodiments, referring to FIGS. 29-42, firing trigger 160 can be selectively engaged with a return mechanism of surgical instrument 100. In at least one embodiment, when firing trigger 160 is operably engaged with firing member 166 via pawl 170, as described above, an actuation of firing trigger 160 can advance firing member 166 distally and, when firing trigger 160 is operably engaged with firing member 166 via band 190, an actuation of firing trigger 160 can retract firing member 166 proximally. In various embodiments, the return mechanism can be manually actuated to disengage firing trigger 160 from firing member 166 and to operably engage firing trigger 160 with reel 192. In at least one embodiment, the return mechanism can include return carriage 194 which can be pivotably mounted in surgical instrument housing 103 such that return carriage 194 can be pivoted between a first, or unactuated, position as illustrated in FIG. 29 and a second, or actuated, position as illustrated in FIG. 32. In at least one such embodiment, return carriage 194 can include push button portion 195 which, when a force is applied thereto, can be configured to move return carriage 194 from its unactuated position to its actuated position.

Figure 30:
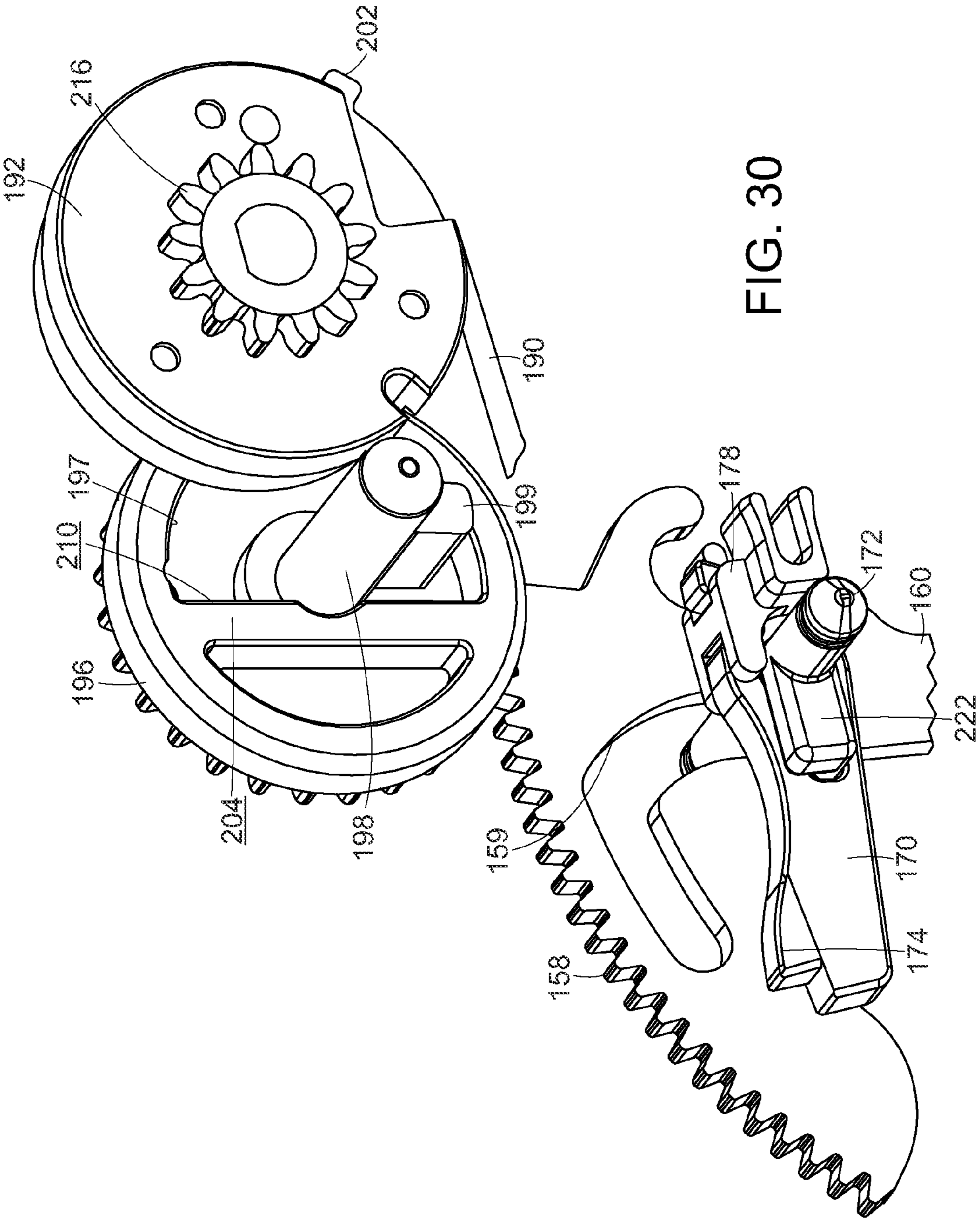
FIG. 30 is a partial perspective view of the return mechanism of FIG. 29 illustrating the firing trigger in an actuated position with some components of the return mechanism removed.
Figure 31:
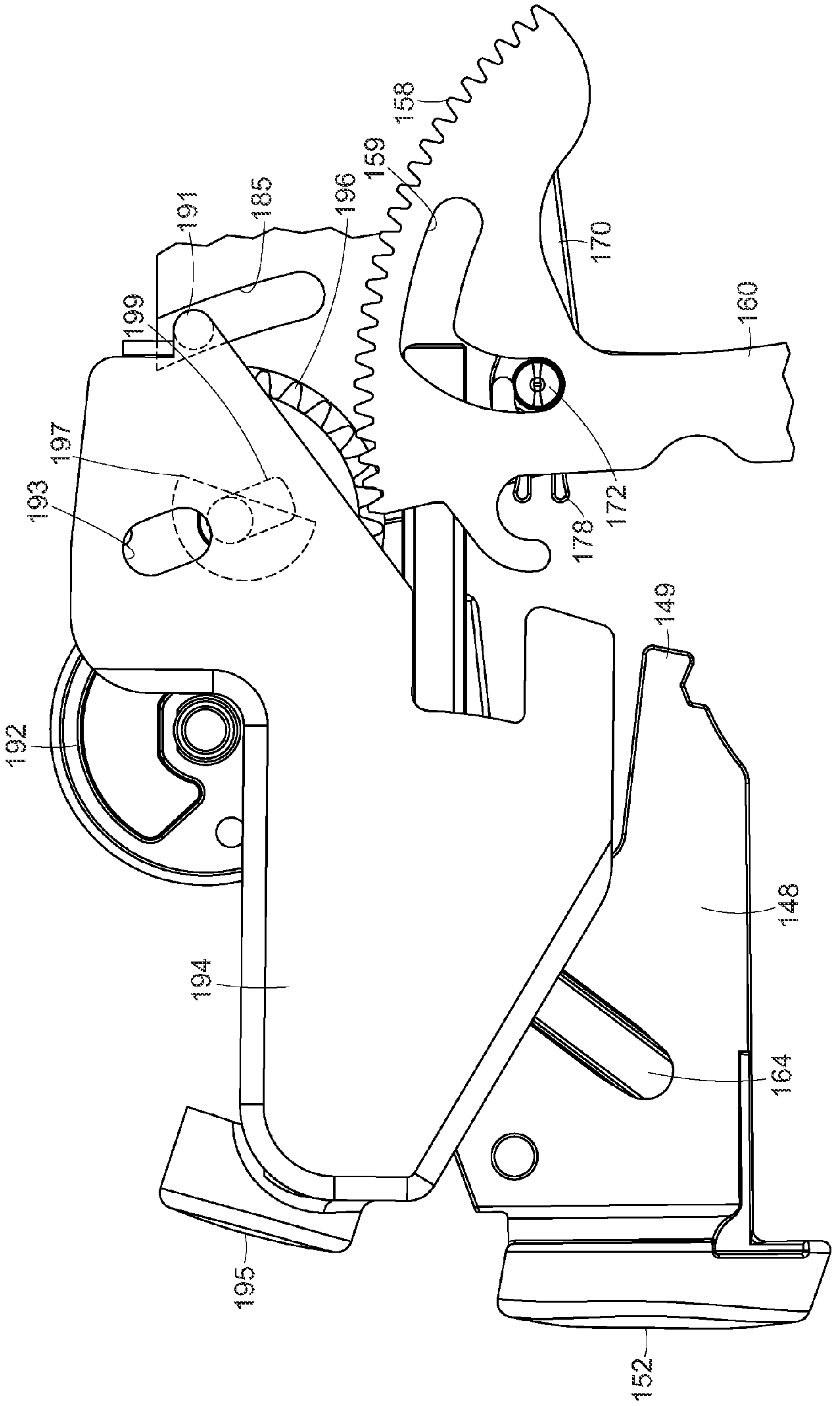
FIG. 31 is an elevational view of the return mechanism of FIG. 29 arranged in the configuration illustrated in FIG. 30.
Figure 32:
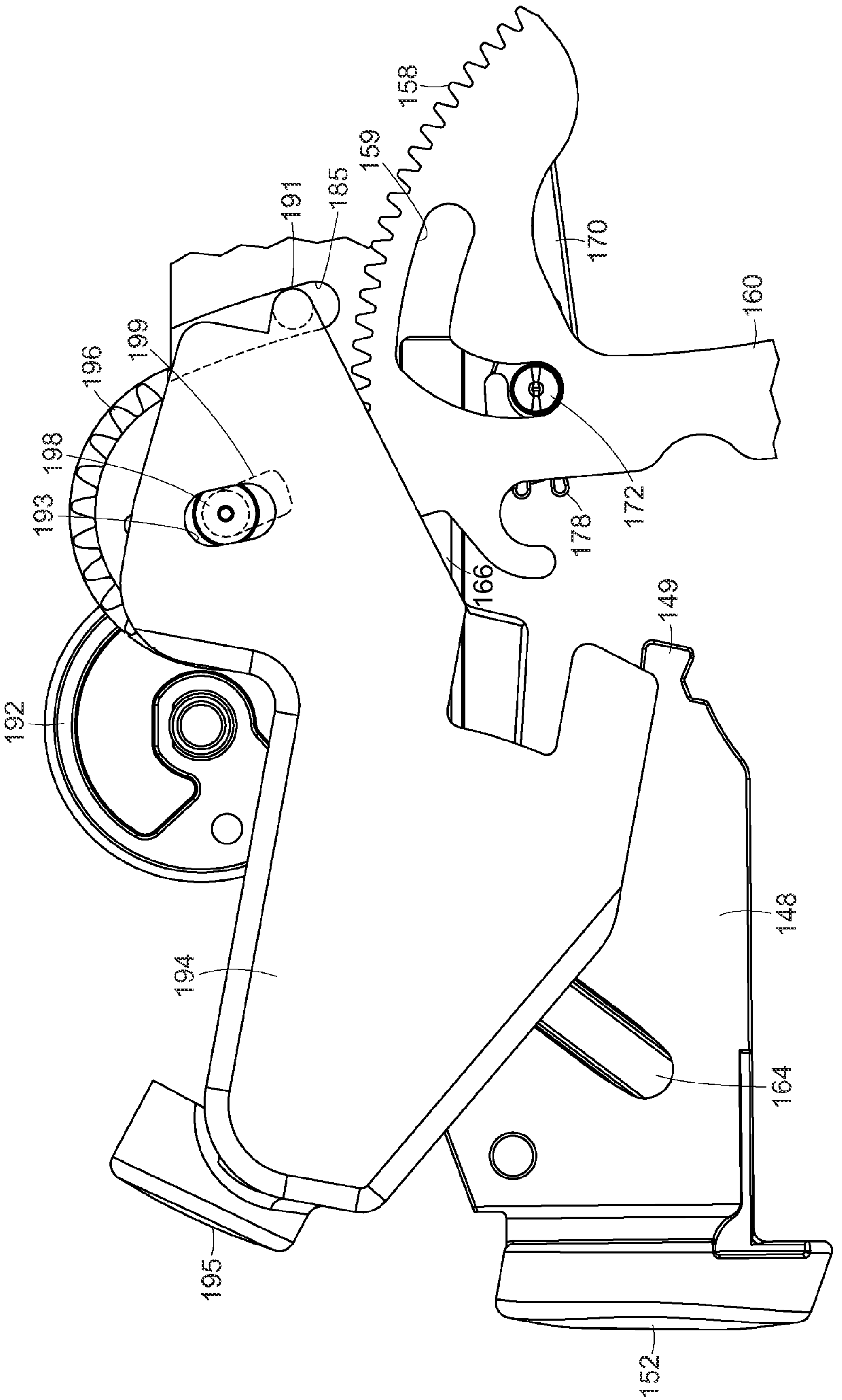
FIG. 32 is an elevational view of the return mechanism of FIG. 29 illustrating a return carriage of the return mechanism in an actuated position.
Figure 33:
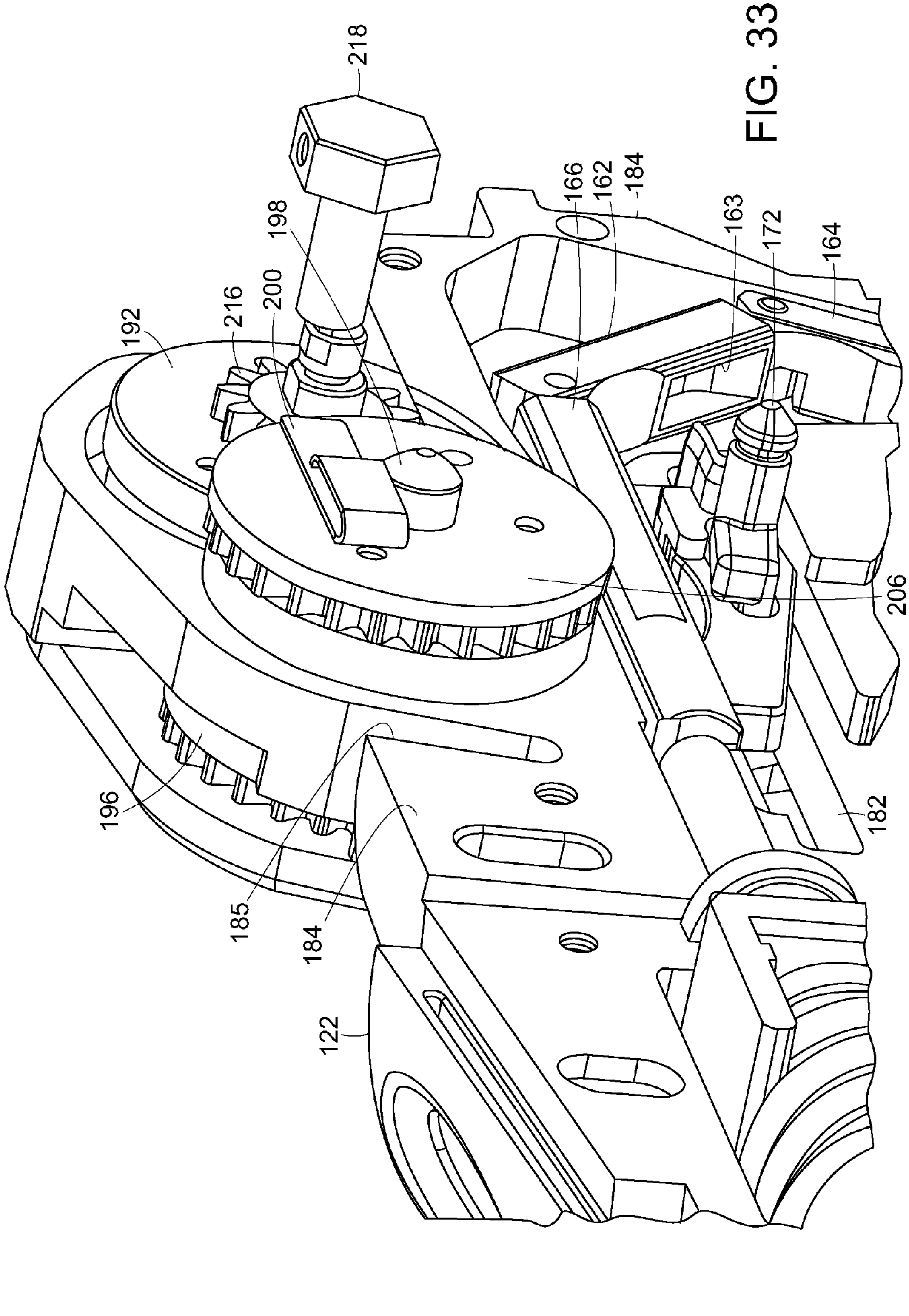
FIG. 33 is a partial perspective view of the return mechanism of FIG. 29 with some components of the return mechanism removed.
Figure 34:
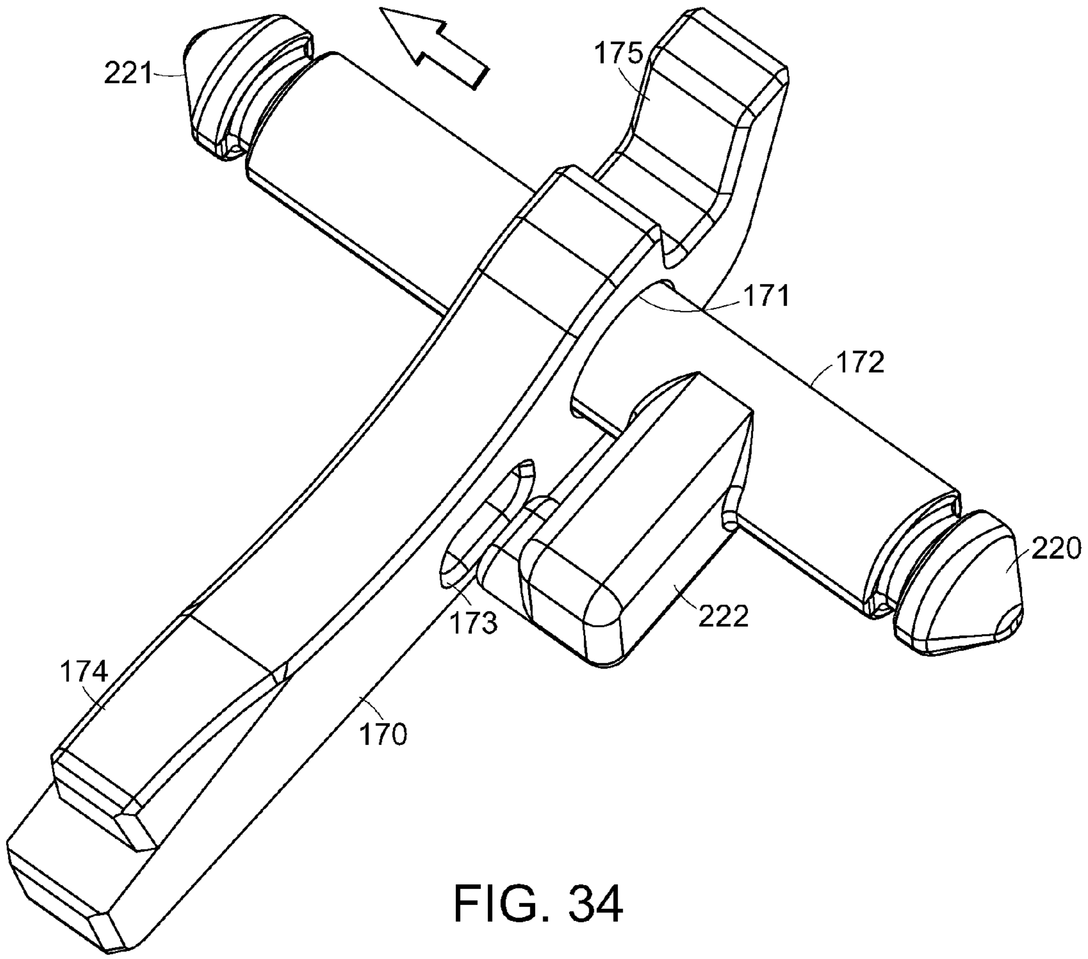
FIG. 34 is a perspective view of the pawl and firing pin of the firing drive of FIG. 19.
Figure 35:
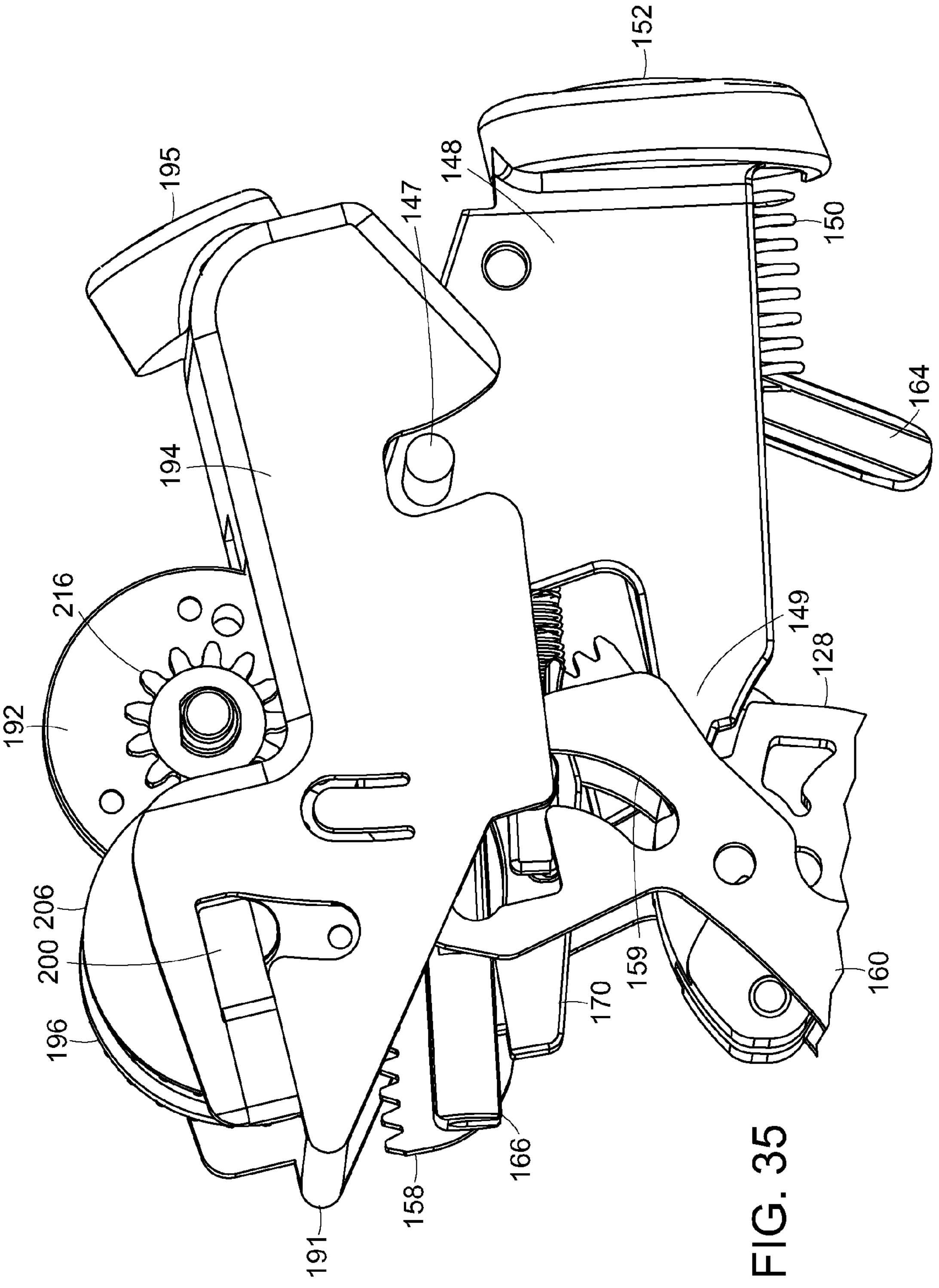
FIG. 35 is a perspective view of the return mechanism of FIG. 29 illustrating the return carriage in an actuated position and the firing trigger returned to its unactuated position.

When return carriage 194 is positioned in its unactuated position illustrated in FIGS. 29-31, firing trigger 160 can be configured to advance firing member 166 as described above and gear portion 158 of trigger 160 can be operatively engaged with trigger gear 196. In various embodiments, gear portion 158 and trigger gear 196 can be operably engaged such that a rotation of trigger 160 about pin 161 can drive trigger gear 196 about an axis defined by return pin 198. In at least one embodiment, when return carriage 194 is in its unactuated position, trigger gear 196 can be configured to rotate freely about return pin 198 such that the rotation of trigger gear 196 is not transmitted, or at least not substantially transmitted, to return pin 198. More particularly, referring to FIG. 30, key 199 of return pin 198 can be biased out of engagement with trigger gear 196 such that the rotation of trigger gear 196 is not transmitted to key gear 206 and reel 192. As a result, an actuation of trigger gear 196 does not rotate, or at least substantially rotate, reel 192 when return carriage 194 is in its unactuated position.

After the cutting member and the staple driver have been advanced within end effector 106, return carriage 194 can be moved into its actuated position. In various embodiments, referring to FIG. 30, reel 192 can include cam member 202 extending therefrom which can contact return carriage 194 and rotate return carriage 194 downwardly. In at least one embodiment, cam member 202 can contact return carriage 194 during the final actuation of trigger 160 which advances the cutting member and staple driver within end effector 106. In at least one such embodiment, cam member 202 can contact return carriage 194 after the third actuation of firing trigger 160. In various embodiments, referring to FIGS. 32-35, when gear carriage 194 is moved into its actuated position, return carriage 194 can be configured to operably engage trigger gear 196 with reel 192. In at least one embodiment, referring to FIGS. 33 and 35, return carriage 194 can include biasing spring 200 where, when return carriage 194 is in its unactuated position, spring 200 can be located in the position illustrated in FIG. 33 and, when return carriage 194 is moved into its actuated position illustrated in FIG. 35, spring 200 can contact return pin 198 and bias return pin 198 toward trigger gear 196. In at least one embodiment, referring to FIG. 31, trigger gear 196 can include D-shaped cavity 197 therein which can, under certain circumstances explained below, receive key 199 extending from return pin 198 and operably engage trigger gear 196 with key gear 206 and reel 192. In various embodiments, the movement of return carriage 194 into its actuated position can be accompanied by an audio and/or tactile feedback to inform the surgeon that the return mechanism of the surgical instrument has been engaged with trigger 160.

Figure 36:
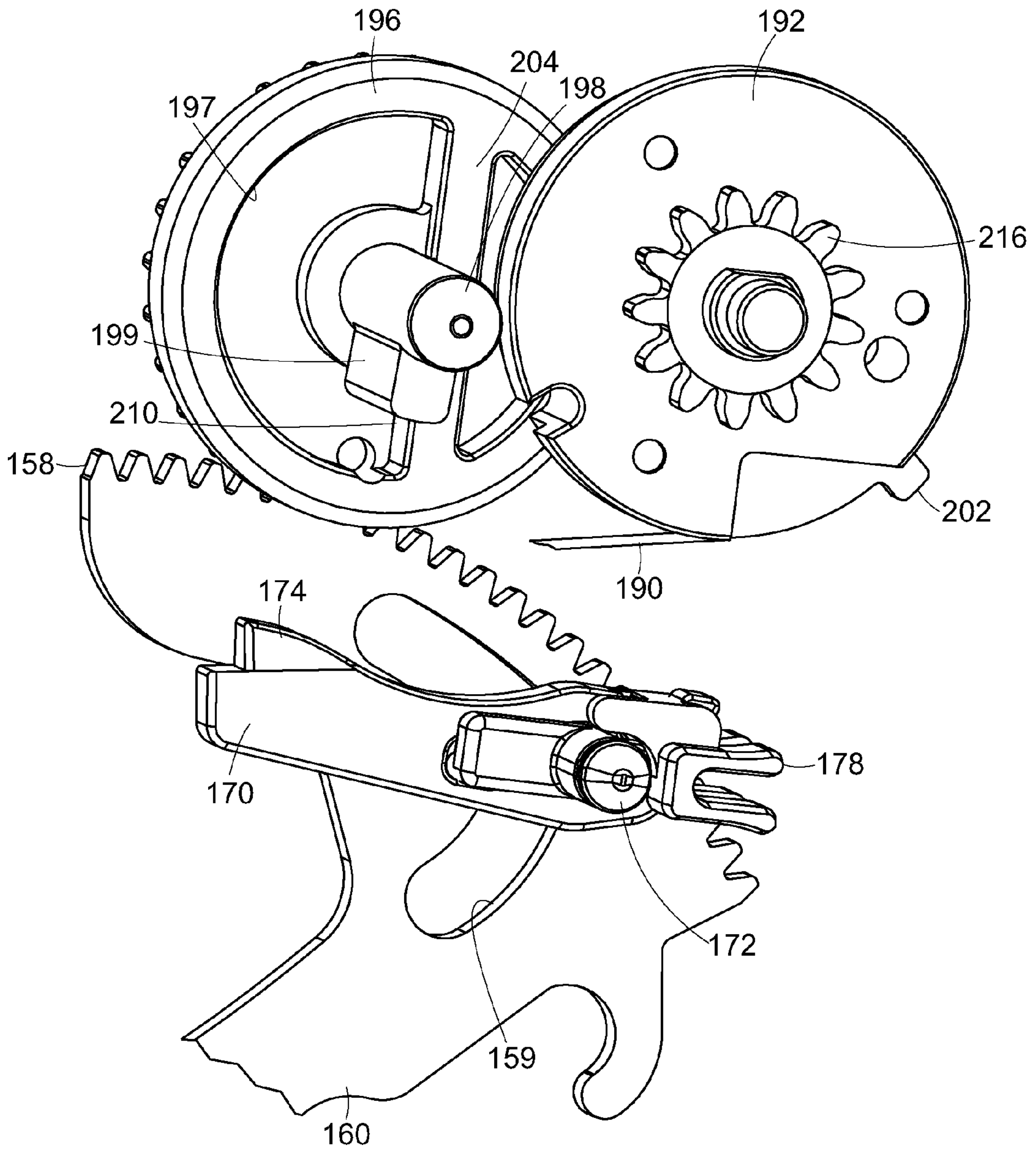
FIG. 36 is a partial perspective view of the return mechanism of FIG. 29 arranged in the configuration illustrated in FIG. 35 illustrating a return pin of the return mechanism operably engaged with the firing trigger.
Figure 37:
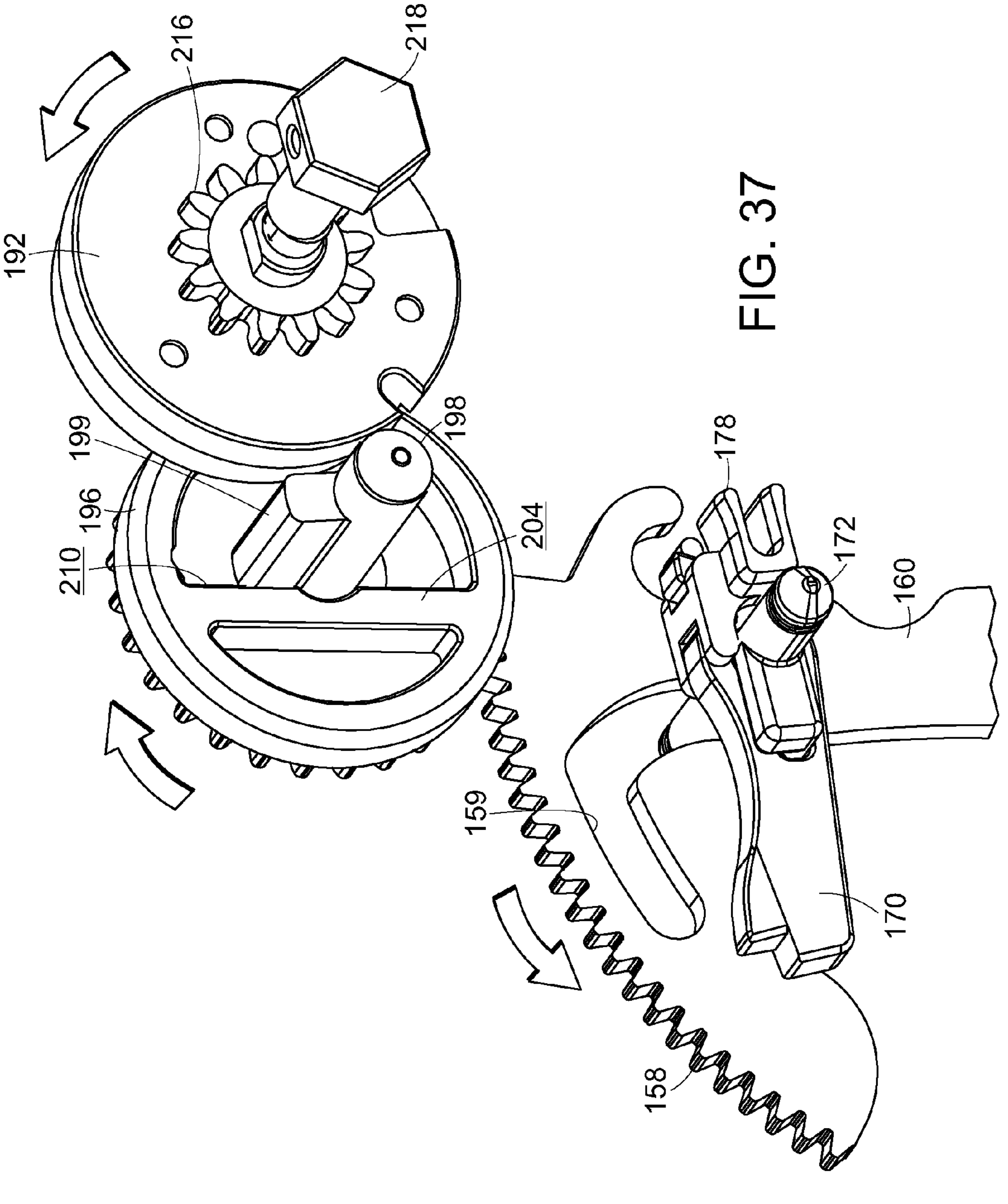
FIG. 37 is a partial perspective view of the return mechanism of FIG. 29 illustrating the firing trigger in an actuated position after rotating the return pin.
Figure 39:
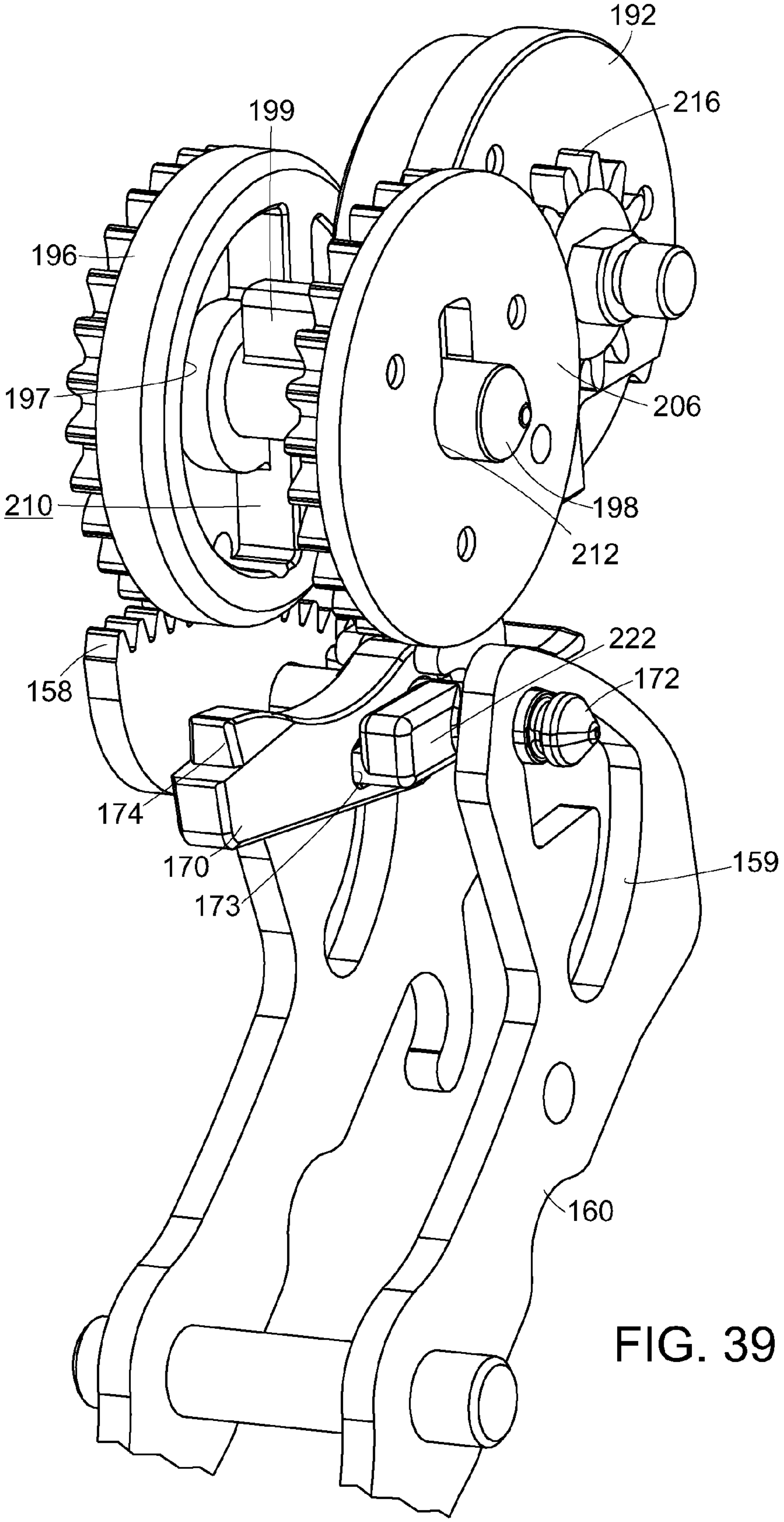
FIG. 39 is a partial perspective view of the return mechanism of FIG. 29 illustrating the firing trigger returned to its unactuated position.
Figure 40:
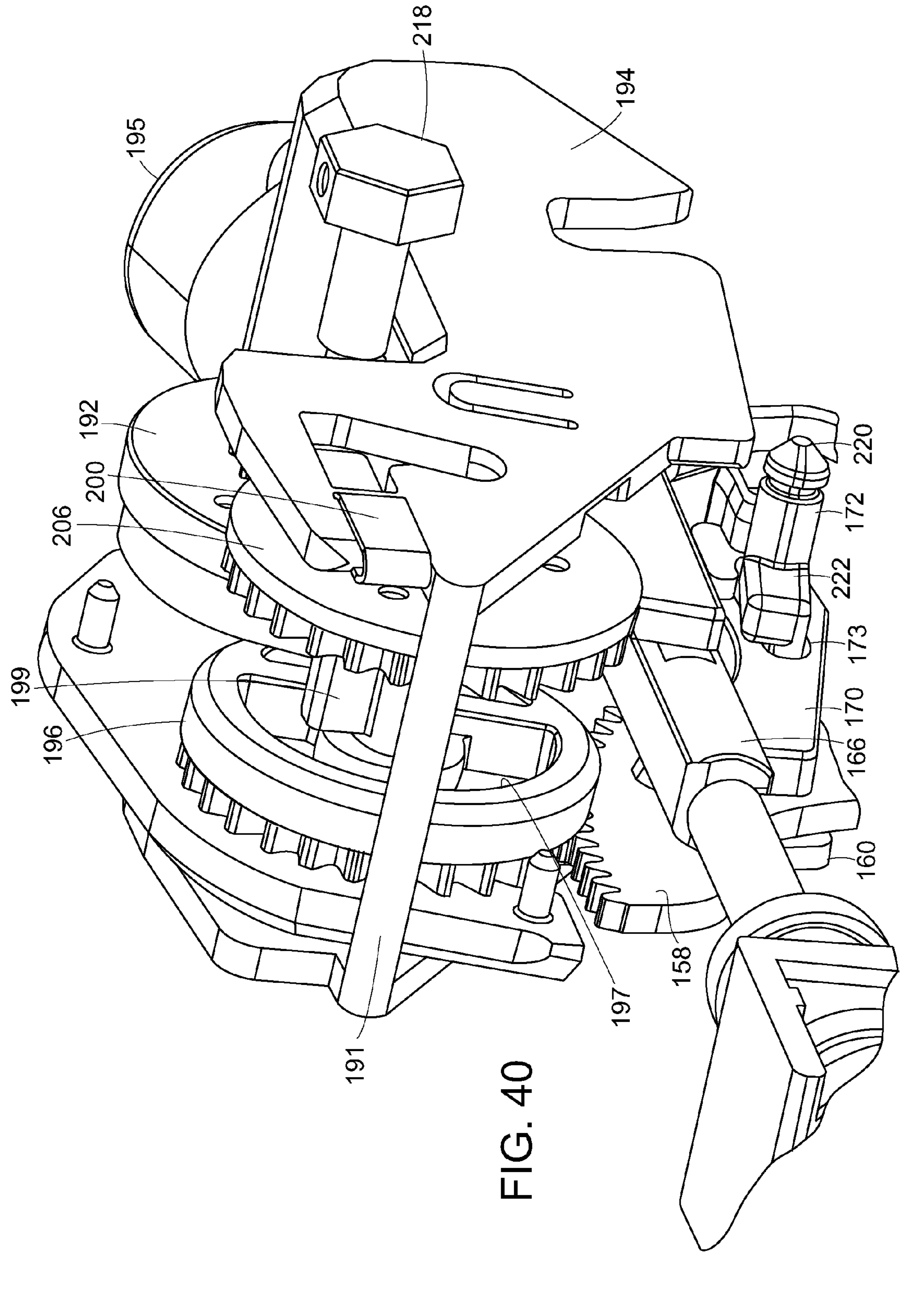
FIG. 40 is a perspective view of the return mechanism of FIG. 29 illustrating the return carriage returned to its unactuated position.
Figure 41:
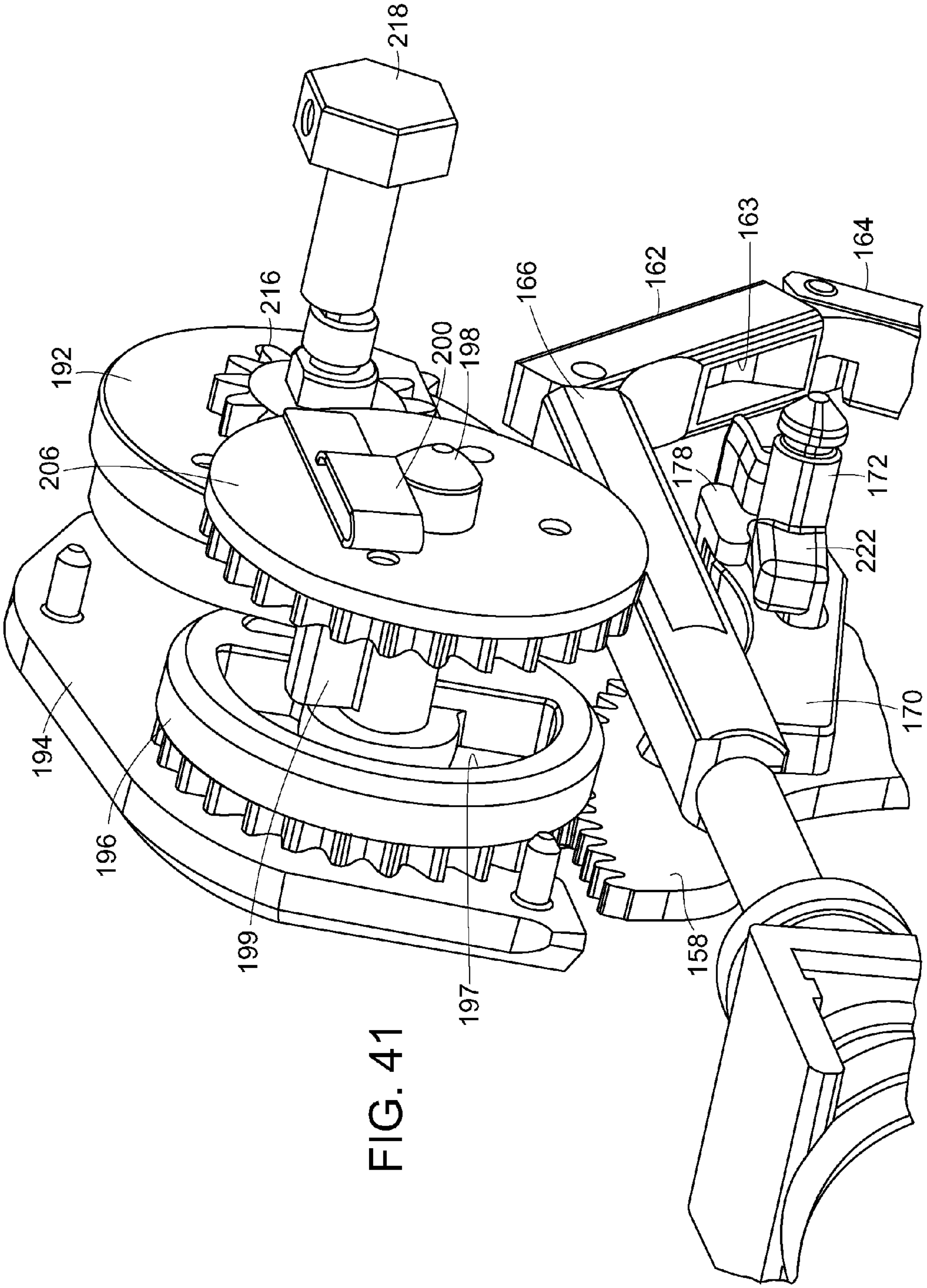
FIG. 41 is a perspective view of the return mechanism of FIG. 29 arranged in the configuration of FIG. 40 illustrating the relative relationship between a biasing spring and the return pin of the return mechanism with some components of the return mechanism removed.
Figure 42:
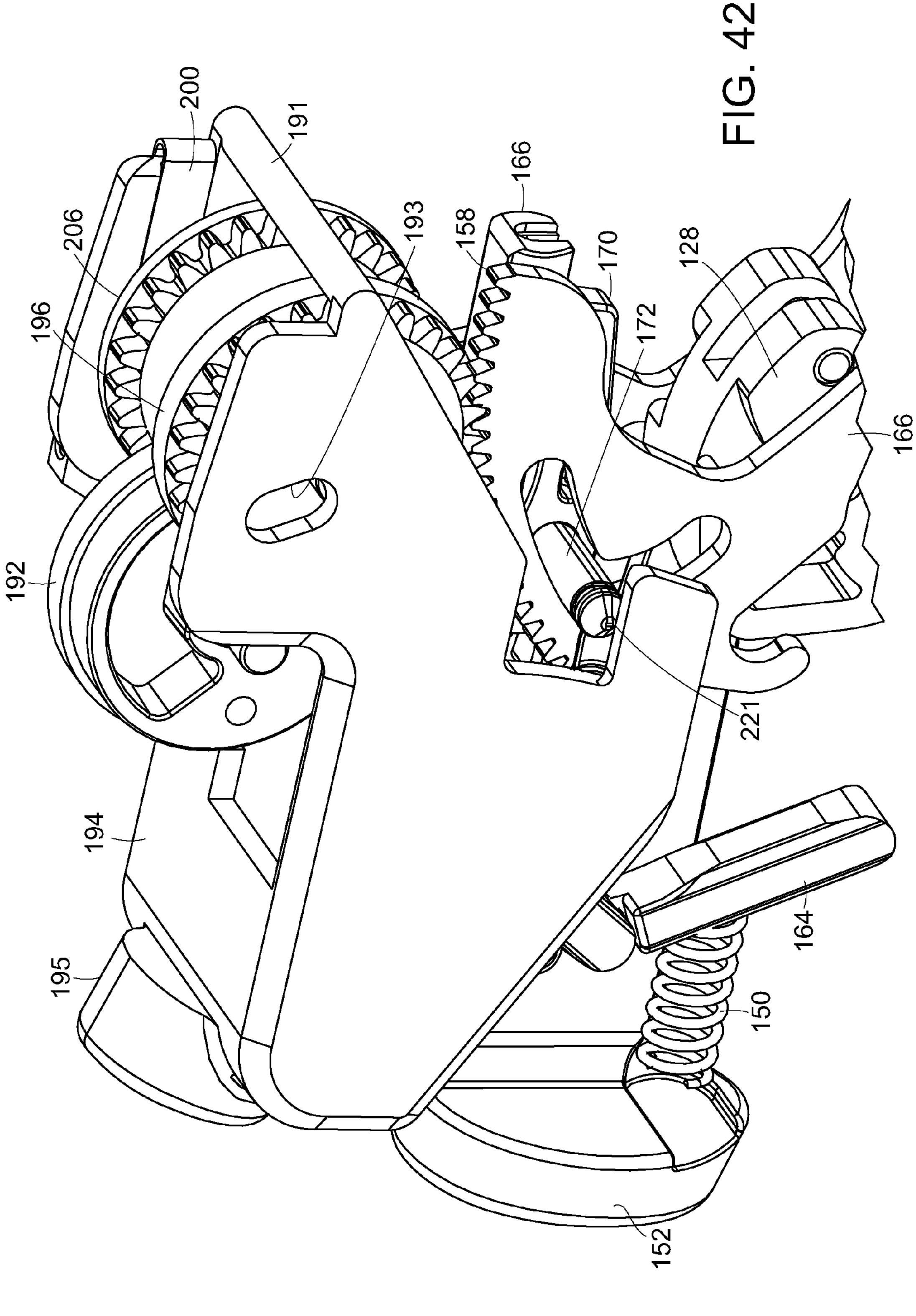
FIG. 42 is a perspective view of the return mechanism of FIG. 29 arranged in the configuration of FIG. 40 illustrating the return carriage operably engaged with the firing pin of the firing drive and the return pin of the return mechanism in order to reset the firing drive and the return mechanism to the their initial configurations.

Further to the above, when return pin 198 is slid toward trigger gear 196, D-shaped cavity 197 can be positioned such that key 199 does not immediately enter cavity 197. On the contrary, referring to FIG. 31, spring 200 can bias return pin 198 such that key 199 initially abuts face 204 of trigger gear 196. After trigger 160 is released and is returned to its unactuated position, however, D-shaped cavity 197 can be rotated and aligned with key 199 such that spring 200 can bias key 199 into cavity 197 as illustrated in FIG. 36. In at least one embodiment, referring to FIG. 31, when return pin 198 is slid toward trigger gear 196, an end of return pin 198 can be received in slot 193 in return carriage 194 as illustrated in FIG. 32. After key 199 has been inserted into cavity 197, a subsequent actuation of trigger 160 can cause drive surface 210 of D-shaped cavity 197 to abut key 199 and rotate return pin 198 to a position illustrated in FIGS. 37 and 38. In effect, an actuation of trigger 160, in at least one embodiment, can rotate key 199 approximately half a revolution such that key 199, which is initially extending substantially downwardly (FIG. 36), can be rotated such that key 199 is extending substantially upwardly (FIG. 37). Thereafter, trigger 160 can be released and trigger gear 194 can be rotated relative to key 199 where key 199 can remain oriented in a substantially upward direction as illustrated in FIGS. 39-41.

Figure 38:
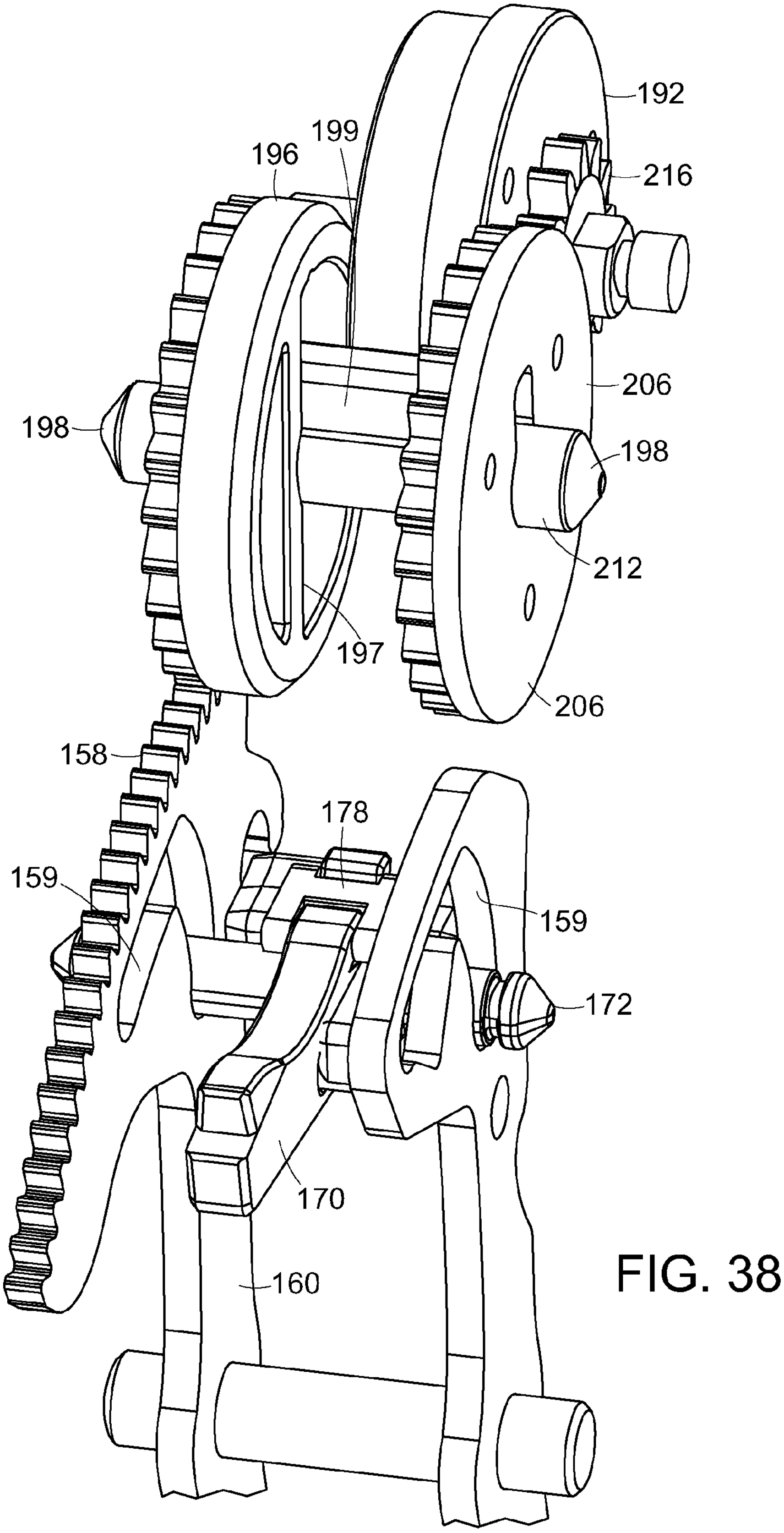
FIG. 38 is an additional perspective view of the return mechanism of FIG. 29 arranged in the configuration illustrated in FIG. 37.

In various embodiments, referring primarily to FIG. 38, key gear 206 can be operably engaged with return pin 198 such that the rotation of return pin 198 can be transmitted to key gear 206. In at least one embodiment, key gear 206 can include key-shaped aperture 212 which can be configured to slidably receive key 199 of return pin 198. In at least one such embodiment, key 199 can be operably engaged with both recess 197 of trigger gear 196 and aperture 212 of key gear 206 when return pin 198 is engaged with trigger gear 196. In various alternative embodiments, key gear 206 can be fixedly mounted to return pin 198. In such embodiments, when return pin 198 is slid relative to trigger gear 196, key gear 206 can also be slid relative to trigger gear 196. In various embodiments, referring generally to FIG. 38, reel 192 can include spur gear 216 mounted thereto, where spur gear 216 can be operatively engaged with key gear 206 such that the rotation of key gear 206 can be transmitted to reel 192. In at least one embodiment, key gear 206, when it is slid toward trigger gear 196 as described above, can be slid into operative engagement with reel 192. In alternative embodiments, spur gear 216 can be configured such that key gear 206 is in operative engagement therewith regardless of whether key gear 206 has been biased toward trigger gear 196.

As a result of the above, when return carriage 194 is positioned in its actuated position illustrated in FIG. 32, an actuation of trigger 160 can rotate reel 192 and wind band 190 around at least a portion thereof. In the event that key 199 cannot be operably engaged with trigger gear 196 when return carriage 194 is actuated, reel 192 can be rotated manually to retract band 190. In at least one such embodiment, referring to FIGS. 33 and 37, bolt, or fastener, 218 can be operatively engaged with reel 192 such that the rotation of bolt 218 can effect rotation of reel 192. In various embodiments, a surgeon can insert bolt 218 through an opening in surgical instrument housing 103 and engage bolt 218 with reel 192. In at least one embodiment, surgical instrument 100 can further include a counting mechanism (not illustrated) which can count the actuations of trigger 160 and, in at least one such embodiment, bolt 218, for example, can be operably engaged with the counting mechanism to rotate reel 192. In various embodiments, as a result, the surgical instrument can include a first, or primary, actuator for winding reel 192 and a second actuator which can be configured to wind reel 192 in lieu of the first actuator.

In various embodiments, as described above, reel 192 can be configured to pull band 190 and retract firing member 166 and firing links 162 and 164 proximally. More particularly, as described above, firing member 166 and firing links 162 and 164 can be retracted relative to pawl 170 in order to reposition firing member 166 and firing links 162 and 164 in their starting positions. In such embodiments, especially in embodiments where pawl 170 is pivotable as described above, the return mechanism of surgical instrument 100 can be further configured to hold pawl 170 out of operative engagement with firing member 166 and firing links 162 and 164 while they are moved relative to pawl 170. More particularly, when return carriage 194 is moved into its actuated position illustrated in FIG. 35, return carriage 194 can be configured to contact an end of firing pin 172 and slide firing pin 172 toward pawl 170 such that firing pin 172 engages pawl 170 and prevents pawl 170 from pivoting upwardly. More particularly, referring to FIG. 34, firing pin 172 can include first end 220 which can include a beveled and/or rounded surface, for example, where, when return carriage 194 contacts first end 220, return carriage 194 can push firing pin 172 toward pawl 170. In at least one embodiment, pawl 170 can include recess 173 which can be configured to receive key 222 extending from firing pin 172 when firing pin 172 is moved toward pawl 170. When key 222 and recess 173 are operatively engaged, firing pin 172 can prevent pawl 170 from pivoting upwardly into engagement with firing member 166 and firing links 162 and 164.

After firing member 166 and firing links 162 and 164 have been retracted, a new staple cartridge 110 can be secured in end effector 106 and surgical instrument 100 can be reset such that it can be used to incise and staple soft tissue once again. In various embodiments, referring to FIGS. 39-42, return carriage 194 can be moved from its actuated position illustrated in FIG. 32 to its unactuated position illustrated in FIG. 40. In at least one embodiment, return carriage 194 can be rotated, or pivoted, upwardly when a force is applied to button portion 195. Alternatively, return carriage 194 can be moved upwardly when, referring to FIG. 29, trigger lock 148 is rotated upwardly to disengage follower portion 149 from closure trigger 128 in order to reopen end effector 106 as described above. More particularly, when a force is applied to button portion 152 of trigger lock 148, trigger lock 148 can be rotated upwardly such that projection 147 extending therefrom can contact return carriage 194 and move return carriage 194 upwardly as well. In either event, referring to FIG. 42, when return carriage 194 is moved upwardly into is unactuated position, return carriage 194 can disengage firing pin 172 from pawl 170 and, in addition, disengage return pin 198 from trigger gear 196. More particularly, return carriage 194 can be configured to abut beveled, or rounded, end 221 of firing pin 172 such that, when return carriage 194 is rotated upwardly, return carriage 194 can slide return pin 172 away from pawl 170 and disengage key 222 from recess 173. Similarly, when return carriage 194 is moved upwardly, a side wall of slot 193 can be configured to contact an end of return pin 198 and slide return pin 198 away from trigger gear 196 to disengage key 199 from D-shaped recess 197. In short, in at least the illustrated embodiment, when button portion 152 of lock member 148 is depressed and return carriage 194 is moved upwardly, the surgical instrument can be reset and can be reused once again.

Although the surgical instruments described above can be reset after the cutting member and staple driver have been completely advanced within end effector 106, button portion 195 of return carriage 194, for example, can be depressed after the cutting member and staple driver have been only partially advanced within end effector 106. In various embodiments, return carriage 194 can further include guide pin 191 extending between opposite sides of return carriage 194. In at least one such embodiment, guide pin 191 can be slidably received within guide slot 185 (FIG. 31) in frame 184 such that slot 185 and pin 191 can define a path for return carriage 194. In various embodiments, guide pin 191 and guide slot 185 can be configured to assure that return carriage 194 engages firing pin 172 and return pin 198 and resets the surgical instrument when return carriage 194 is moved from its actuated position to its unactuated position as described above.

Figure 43:
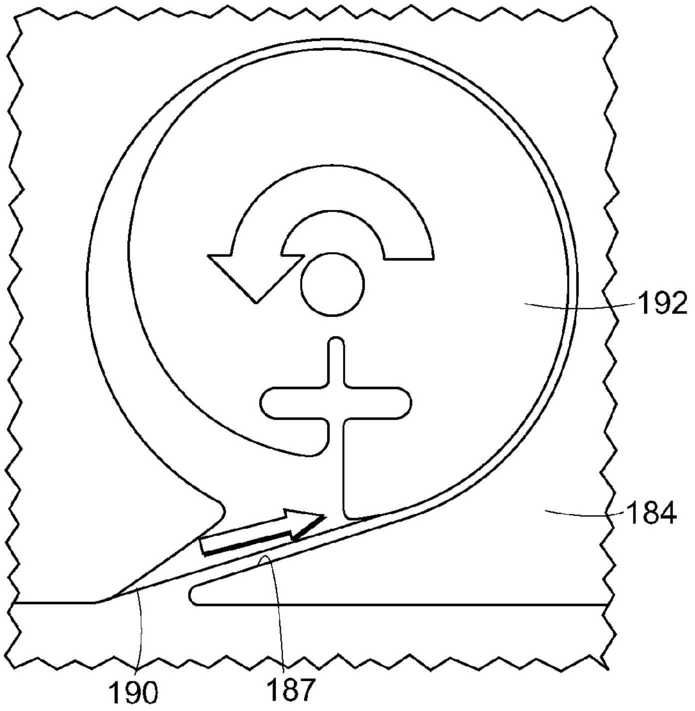
FIG. 43 is a detail view of a reel of the return mechanism of FIG. 29 illustrating the relative relationship between a return band of the return mechanism and the stapler frame of FIG. 26.
Figure 44:
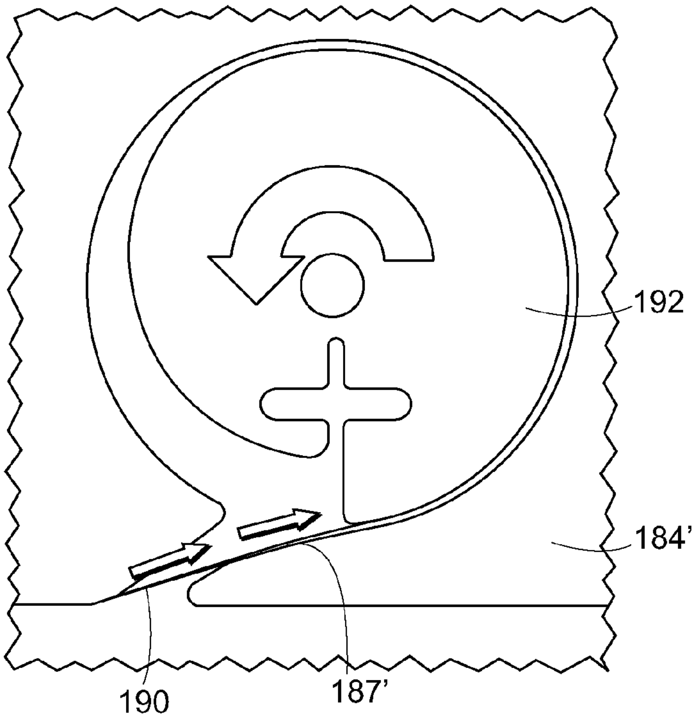
FIG. 44 is a detail view of the reel of FIG. 43 illustrating the relative relationship between the return band and an alternative embodiment of the stapler frame of FIG. 26.
Figure 45:
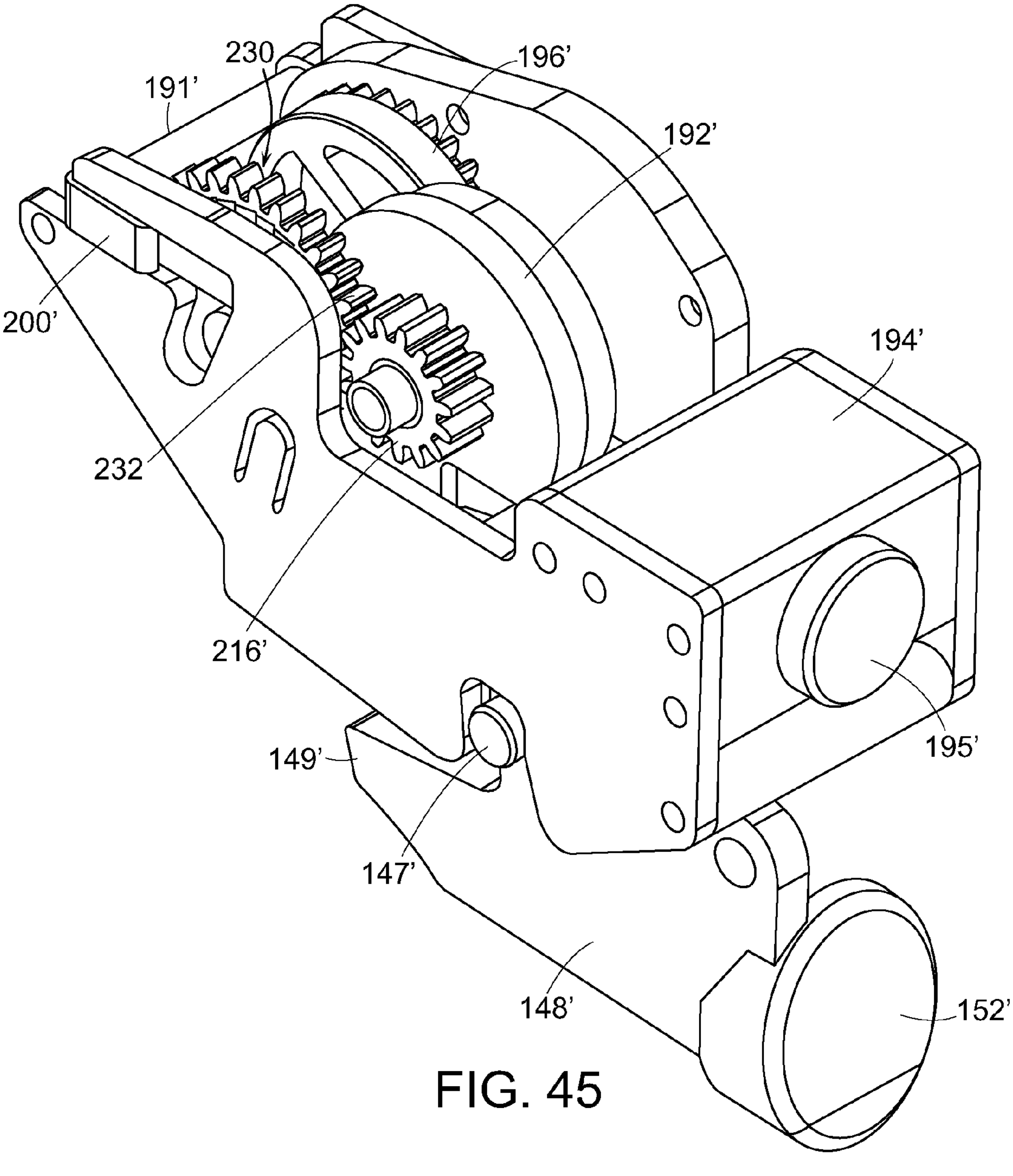
FIG. 45 is a perspective view of a return mechanism of a surgical instrument in accordance with an alternative embodiment of the present invention having an anti-back-up ratchet mechanism.
Figure 46:
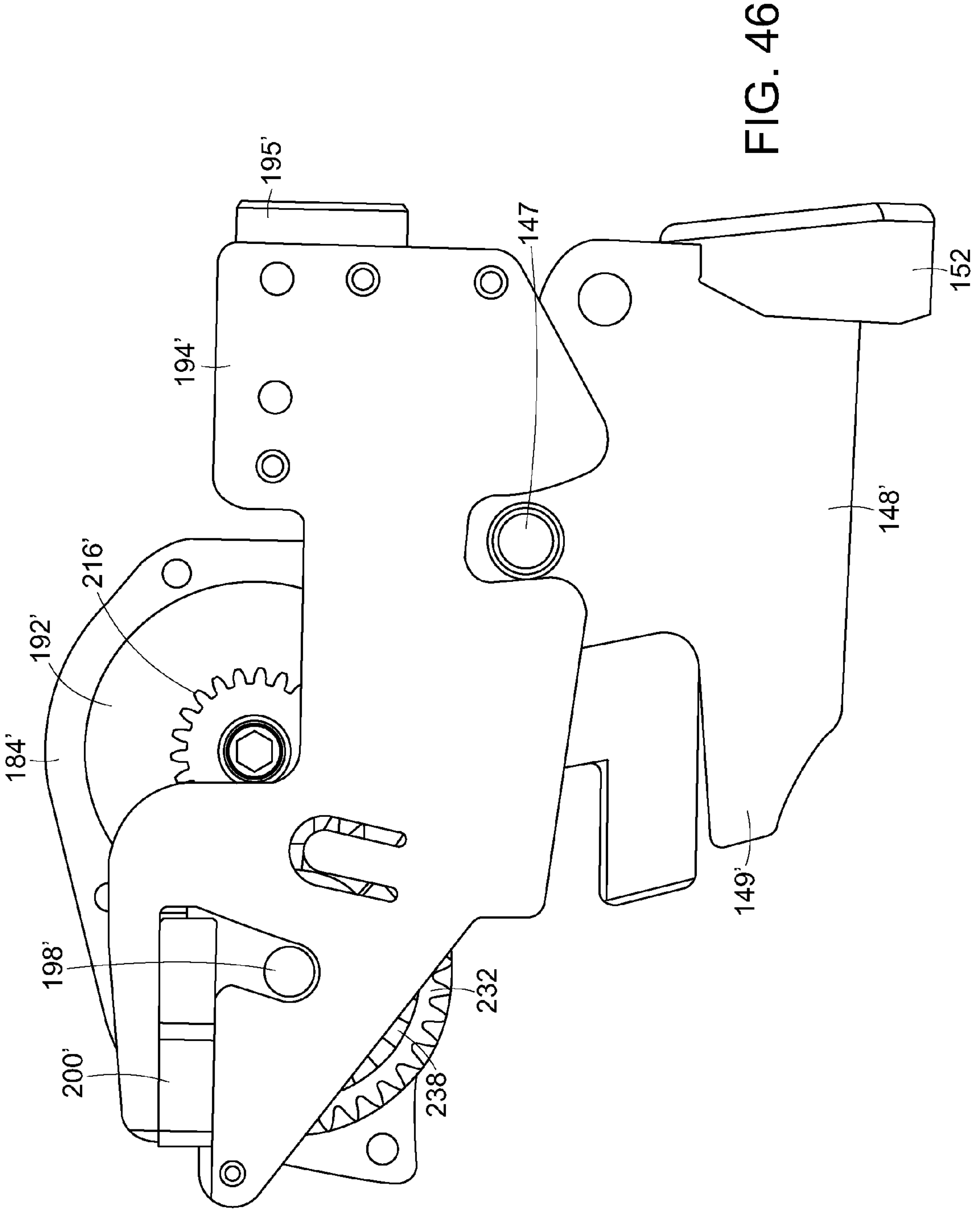
FIG. 46 is an elevational view of the return mechanism of FIG. 45 having a return carriage in an unactuated position.

In various embodiments, surgical instrument 100 can further include a brake for preventing, or at least partially inhibiting, the firing drive from advancing and/or retracting the cutting member and staple driver, for example, within end effector 106. In at least one embodiment, referring to FIG. 43, frame 184 can include brake surface 187 where brake surface 187 can be configured to apply a braking force to band 190. More particularly, when band 190 is pulled proximally and/or distally as described above, frame 184 can be configured such that band 190 slides over brake surface 187 and a friction force is created therebetween. In various embodiments, referring to FIG. 44, brake surface 187' can be configured such that the path of band 190 between firing member 166 and reel 192 is interrupted by brake surface 187' and a significant normal force can be applied to band 190.

In at least one embodiment, band 190 can be engaged with brake surface 187' when band 190 is at rest such that a static friction force between band 190 and brake surface 187' can prevent, at least initially, band 190 from moving relative to brake surface 187' when a pulling force is applied to band 190. When the pulling force applied to band 190 exceeds the static friction force, band 190 can be moved relative to brake surface 187'. Such embodiments may be particularly useful when trigger 160 is actuated more than one time to advance the cutting member and/or staple driver within end effector 106. More particularly, after an actuation of trigger 160, pawl 170 can be retracted relative to firing member 166 as described above and, in various embodiments, the friction force between band 190 and brake surface 187' can prevent, or at least partially inhibit, firing member 166 and/or firing links 162 and 164 from moving proximally, and/or distally, as pawl 170 is retracted. As a result of the above, the alignment between tooth 174 of pawl 170 and the recesses in firing member 166 and firing links 162 and 164 can be maintained when pawl 170 is moved relative thereto.

Similarly, in at least one embodiment, the stiffness of band 190 can also assist in holding firing member 166 and firing links 162 and 164 in position. More particularly, in order for firing member 166 to 'back up', or move proximally, firing member 166 would have to push band 190 proximally and, in effect, wind band 190 around reel 192. In various embodiments, the stiffness of band 190 can be such that a significant force to wind band 190 around reel 192 is required and, as a result, firing member 166 can be held in place. To further increase the force required to wind band 190 around reel 192, referring to FIG. 44, the path of band 190 can be controlled such that is not wound onto reel 192 in a tangential direction. More particularly, if the path of band 190 is such that it is wound onto reel 192 in a non-tangential direction, a portion of the force transmitted through band 190 will be lost thus resulting in a poor mechanical advantage for winding reel 192.

In various embodiments, surgical instrument 100 can include a brake which can be engaged with reel 192, or any other suitable component of the firing drive, to prevent firing member 166 and/or firing links 162 and 164 from being retracted unintentionally, for example. In at least one embodiment, although not illustrated, the brake can be moved between a first position and a second position, where, when the brake is in the first position, the brake can apply a first braking force to band 190, for example. In at least one such embodiment, the brake can apply, when it is in the second position, a second braking force to band 190, for example, which can be greater than or less than the first braking force. In various alternative embodiments, the brake may not be engaged with band 190 or any other portion of the firing drive when the brake is in the second position. In various embodiments, although not illustrated, surgical instrument 100 can include a detent mechanism which can apply a braking force to reel 192 and/or band 190. In at least one such embodiment, the detent mechanism can include a ball detent and a spring member for biasingly engaging the ball detent against reel 192 and/or band 190.

Figure 47:
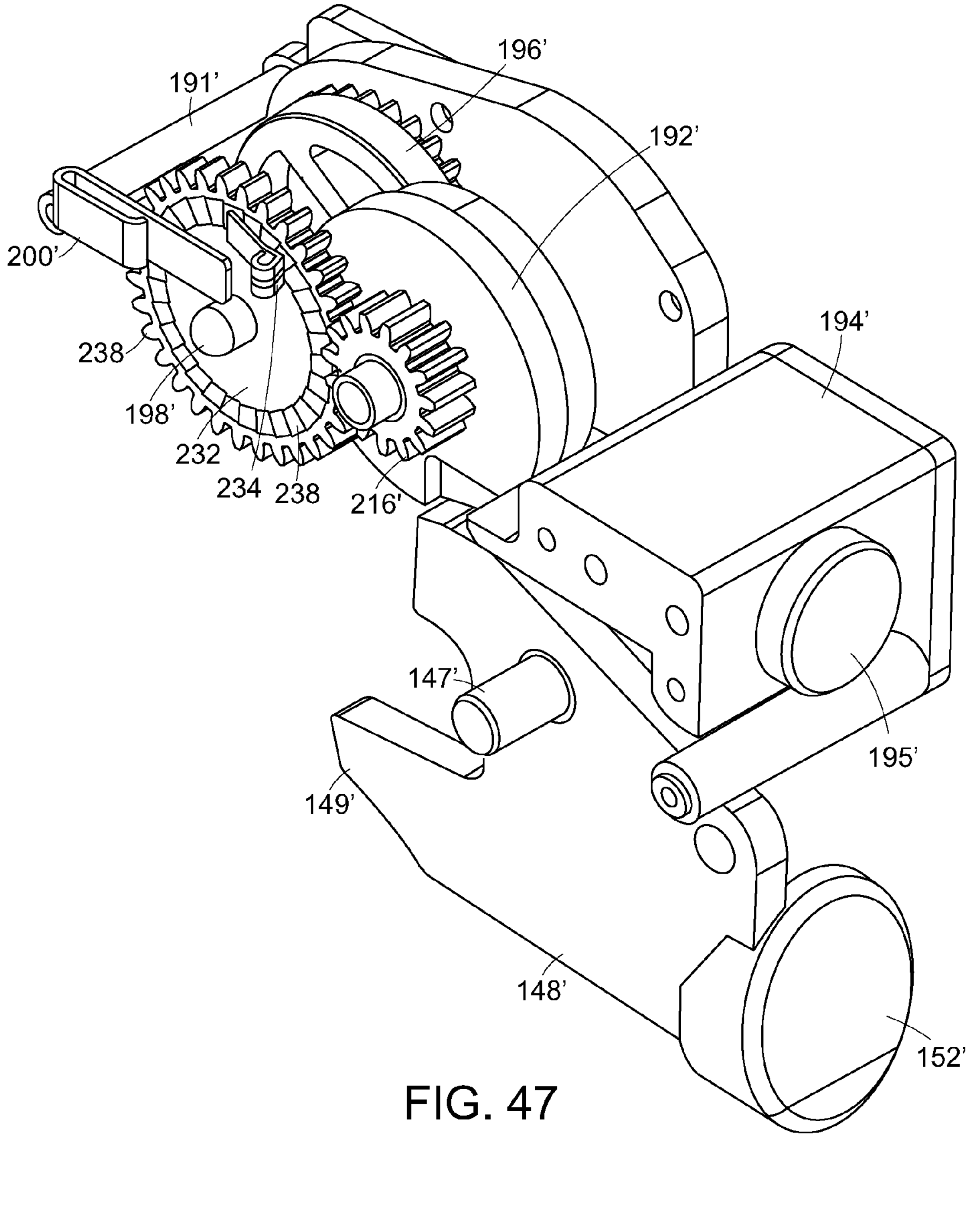
FIG. 47 is a perspective view of the return mechanism of FIG. 45 with some components of the surgical instrument removed.
Figure 48:
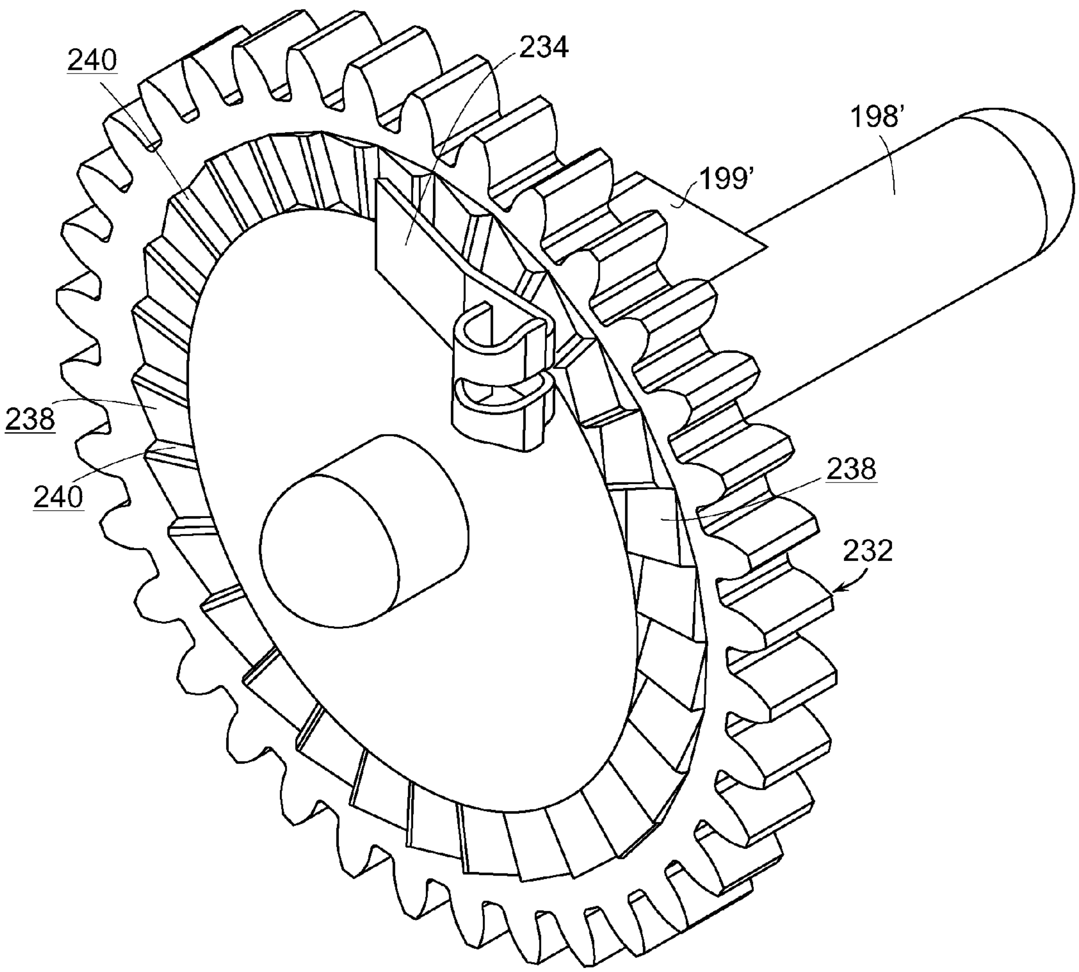
FIG. 48 is a perspective view of a return gear, return pin, and anti-back-up pawl of the ratchet mechanism of FIG. 45.
Figure 49:
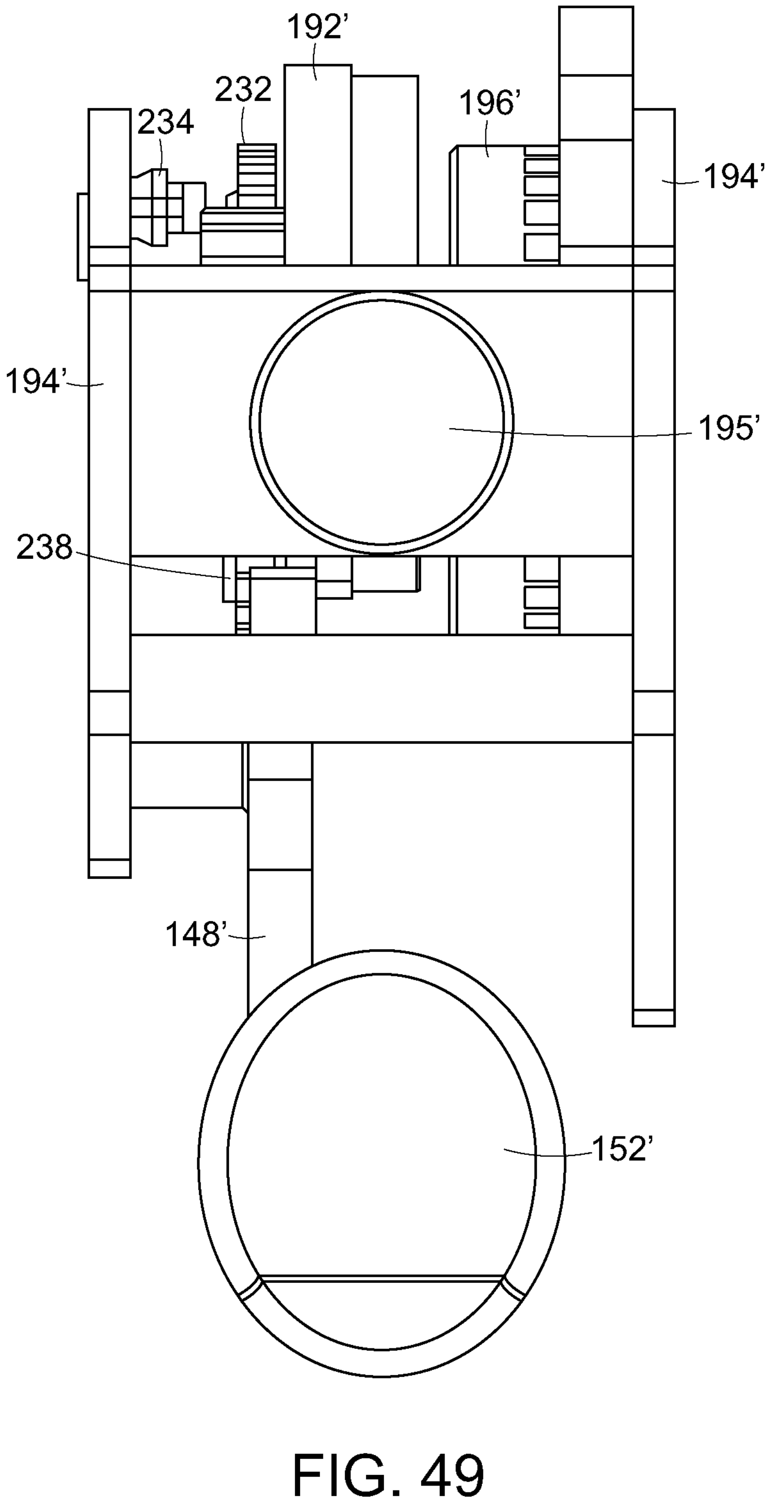
FIG. 49 is another elevational view of the return mechanism of FIG. 45.

In various embodiments, surgical instrument 100 can include a ratchet which can allow reel 192 to turn in a first direction but can, in various circumstances, prevent reel 192 from turning in a direction opposite the first direction. In at least one embodiment, referring to FIGS. 45-49, surgical instrument 100 can include ratchet assembly 230, where ratchet assembly 230 can include ratchet wheel 232 and ratchet pawl 234. In various embodiments, ratchet wheel 232 can operate in substantially the same way as key gear 206 described above except that, referring primarily to FIGS. 47 and 48, ratchet wheel 232 can include ratchet teeth 236 which can, owing to a ratcheting engagement with ratchet pawl 234, prevent ratchet wheel 232 from being turned in a clockwise direction, for example, when return carriage 194' is in its unactuated position (FIG. 47). More particularly, each ratchet tooth 236 can include a flat surface 240 where, referring to FIG. 48, at least one of flat surfaces 240 can abut edge 235 of pawl 234 and thereby prevent ratchet wheel 232 from being rotated in a clockwise direction.

Each ratchet tooth 236 can further include an inclined surface 238, where inclined surfaces 238 can be configured to slide underneath pawl 234 when ratchet wheel 232 is turned in a counter-clockwise direction. As a result of the above, ratchet assembly 230 can allow band 190 to be pulled distally by firing member 166, for example, but prevent, or at least substantially inhibit, band 190 from being moved proximally, at least when return carriage 194' is in its unactuated position. When return carriage 194' is pivoted downwardly into its actuated position, as described above with regard to return carriage 194, ratchet wheel 232 can be slid toward trigger gear 196' and out of operative engagement with ratchet pawl 234. Thereafter, as a result, ratchet wheel 232 can be rotated in either a clockwise or counter-clockwise direction without interference, or at least substantial interference, from ratchet pawl 234. In various alternative embodiments where ratchet wheel 232 is not slid toward trigger gear 196', ratchet pawl 234 can be moved downwardly and out of operative engagement with ratchet teeth 236 when return carriage 194' is moved into its actuated position. In either event, when return carriage 194' is in its actuated position, trigger gear 196' and return pin 198' can rotate ratchet wheel 232 and cam 192' to retract band 190 and firing member 166.

Figure 68:
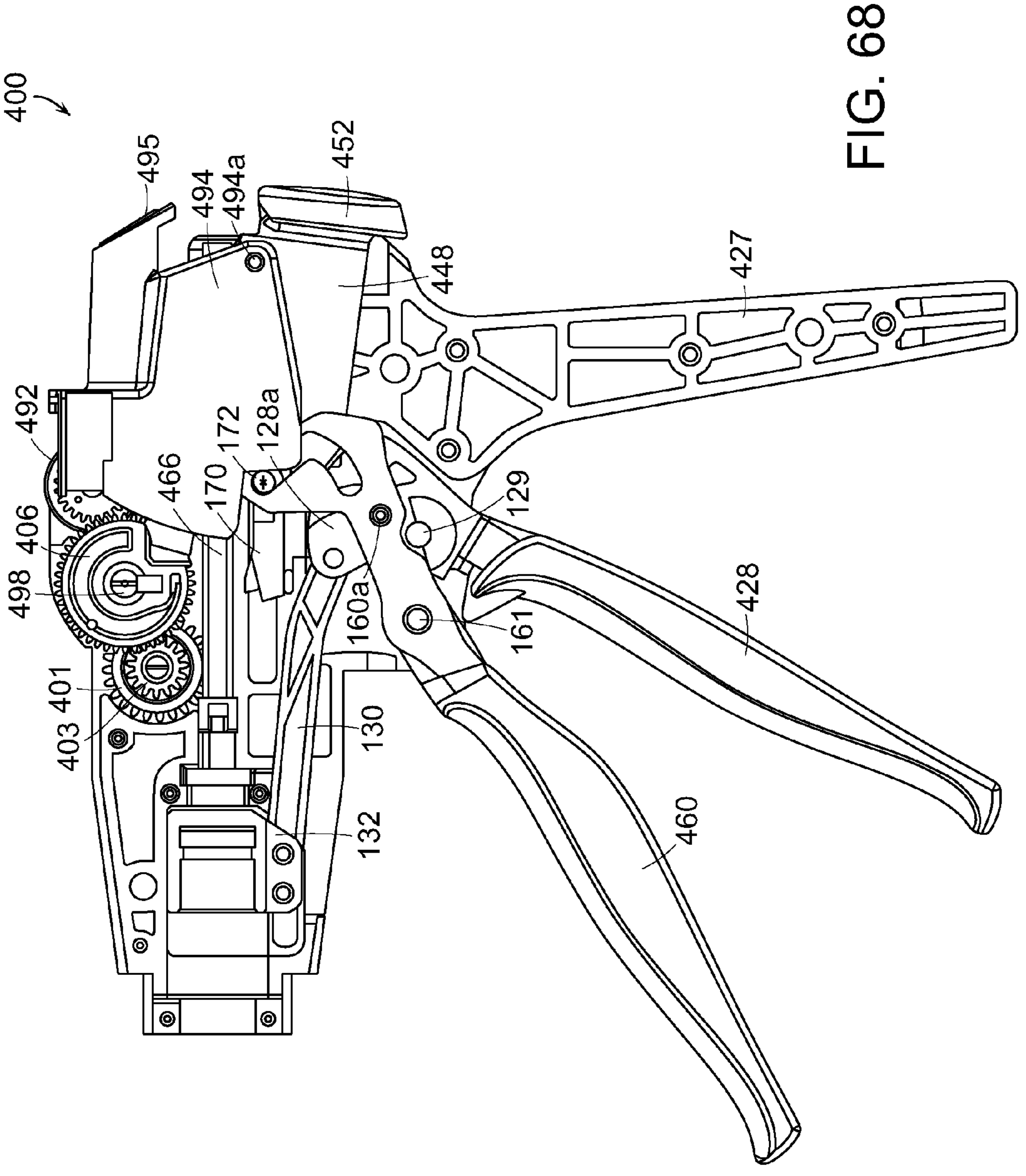
FIG. 68 is an elevational view of a surgical instrument in accordance with an embodiment of the present invention with some components of the surgical instrument removed.
Figure 69:
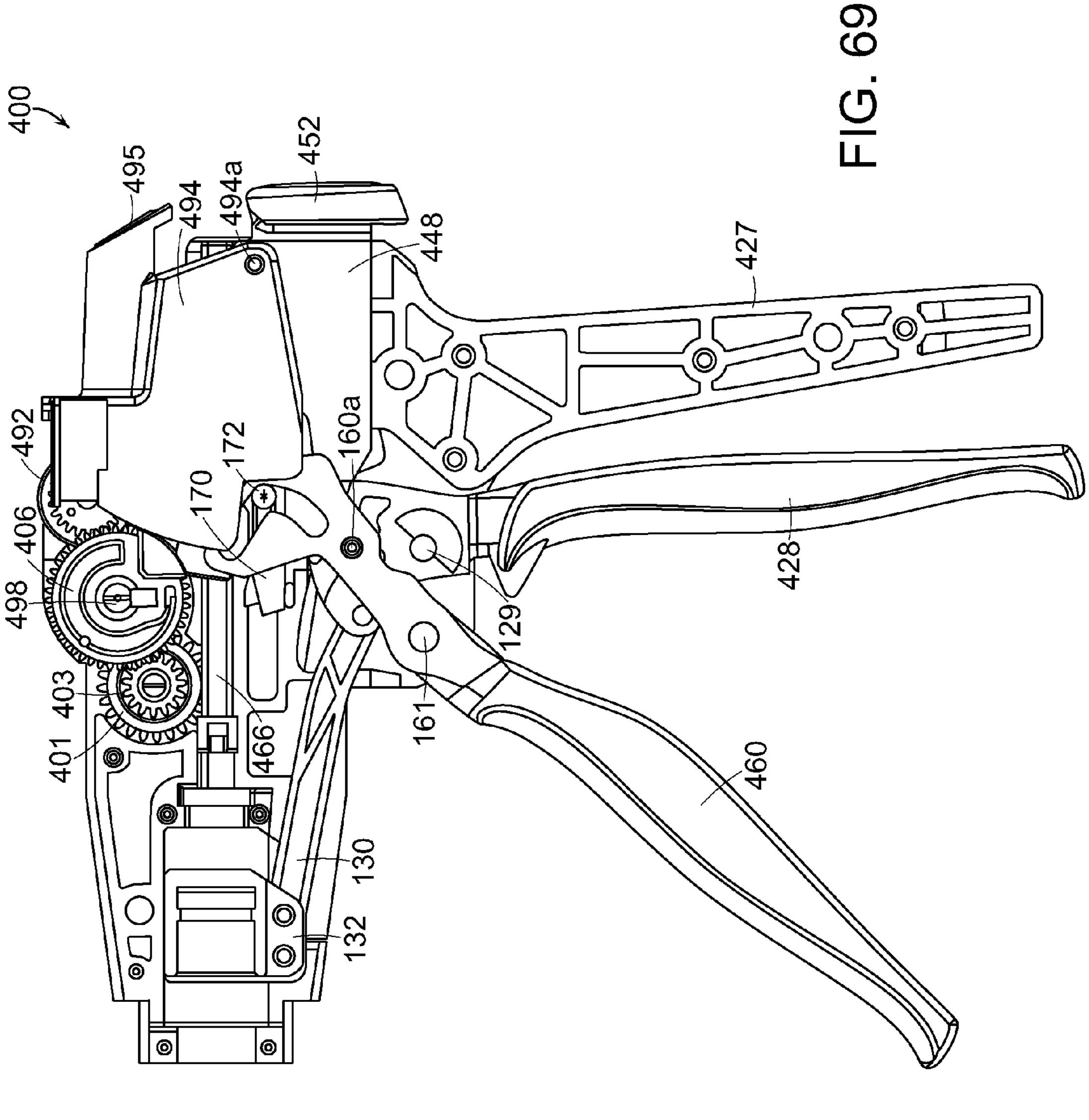
FIG. 69 is an elevational view of the surgical instrument of FIG. 68 illustrating a closure trigger in an actuated position.
Figure 70:
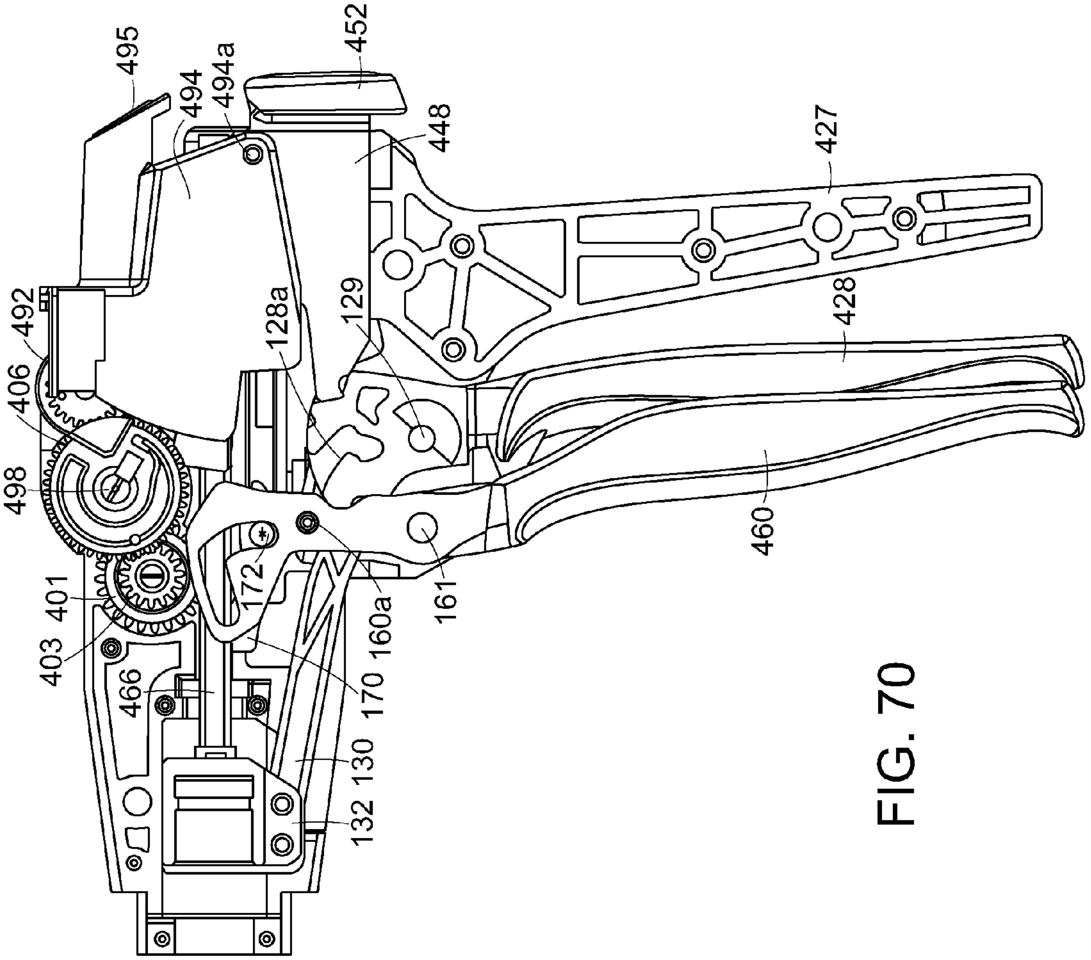
FIG. 70 is an elevational view of the surgical instrument of FIG. 68 illustrating a firing trigger in an actuated position after a first actuation of the firing trigger.

In various embodiments, referring to FIGS. 68-86, surgical instrument 400 can include a closure system for closing the anvil of an end effector, a firing drive for advancing a firing rod, cutting member, and/or staple driver within the end effector, and a gear-driven reversing drive for retracting at least one of the firing rod, cutting member, and/or staple driver relative to the end effector. In at least one embodiment, referring to FIG. 68, the closure system can include closure trigger 428, drive link 130, and driver 132 where, similar to the above, closure trigger 428 can be configured to displace drive link 130 and driver 132 when closure trigger 428 is moved from its unactuated position illustrated in FIG. 68 to its actuated position illustrated in FIG. 69. In various embodiments, the actuation of closure trigger 428 can unlock the firing drive. In at least one embodiment, the firing drive can include firing trigger 460 which, when closure trigger 428 is rotated toward handle 427, can be moved between a locked position illustrated in FIG. 68 and an unlocked position illustrated in FIG. 69. In at least one such embodiment, closure trigger 428 can include slot, or groove, **128*a* which can receive pin, or projection, 160*a* extending from firing trigger 460, wherein a sidewall of slot 128*a* can be configured to prevent pin 160*a*, and firing trigger 460, from moving, or at least substantially moving, relative to closure trigger 428 when closure trigger 428 is in its unactuated position (FIG. 68). When closure trigger 428 is actuated, or closed, the side wall of slot 128*a* can abut pin 160*a* and move firing trigger 460 between its locked position illustrated in FIG. 68 and its unlocked position illustrated in FIG. 69. In such an unlocked position, slot 128*a* can be oriented to permit pin 160*a* to move within slot 128*a* thereby allowing firing trigger 460 to move relative to closure trigger 428** and advance the firing drive as described in greater detail below.

In various embodiments, referring to FIG. 68, the firing drive can comprise firing trigger 460, firing pin 172, and pawl 170, wherein firing trigger 460 can be operably engaged with firing rod, or member, 466 via pawl 170 and firing pin 172 in order to advance the cutting member and the staple driver within the end effector. In at least one such embodiment, similar to the above, pawl 170 can be pivoted upwardly into engagement with firing member 466 such that, when firing trigger 460 is actuated, referring to FIG. 70, firing trigger 460 can advance firing pin 172, pawl 170, and firing member 466 distally. Thereafter, referring to FIG. 101, pawl 170 can be pivoted downwardly out of engagement with firing member 466 such that pawl 170 can be retracted proximally relative to firing member 466 when firing trigger 460 is released or returned to its unactuated, and unlocked, position illustrated in FIG. 72. Upon comparing FIGS. 69 and 72, it is readily apparent that a first cycle of the firing drive has moved firing member 466 distally and has also repositioned pawl 170, firing pin 172, and firing trigger 460 such that firing trigger 460 can be actuated a second time to further advance firing member 466. In such circumstances, referring to FIG. 102, pawl 170 can be pivoted upwardly into operative engagement with firing member 466 and advanced distally by actuating firing trigger 460 once again.

Figure 73:
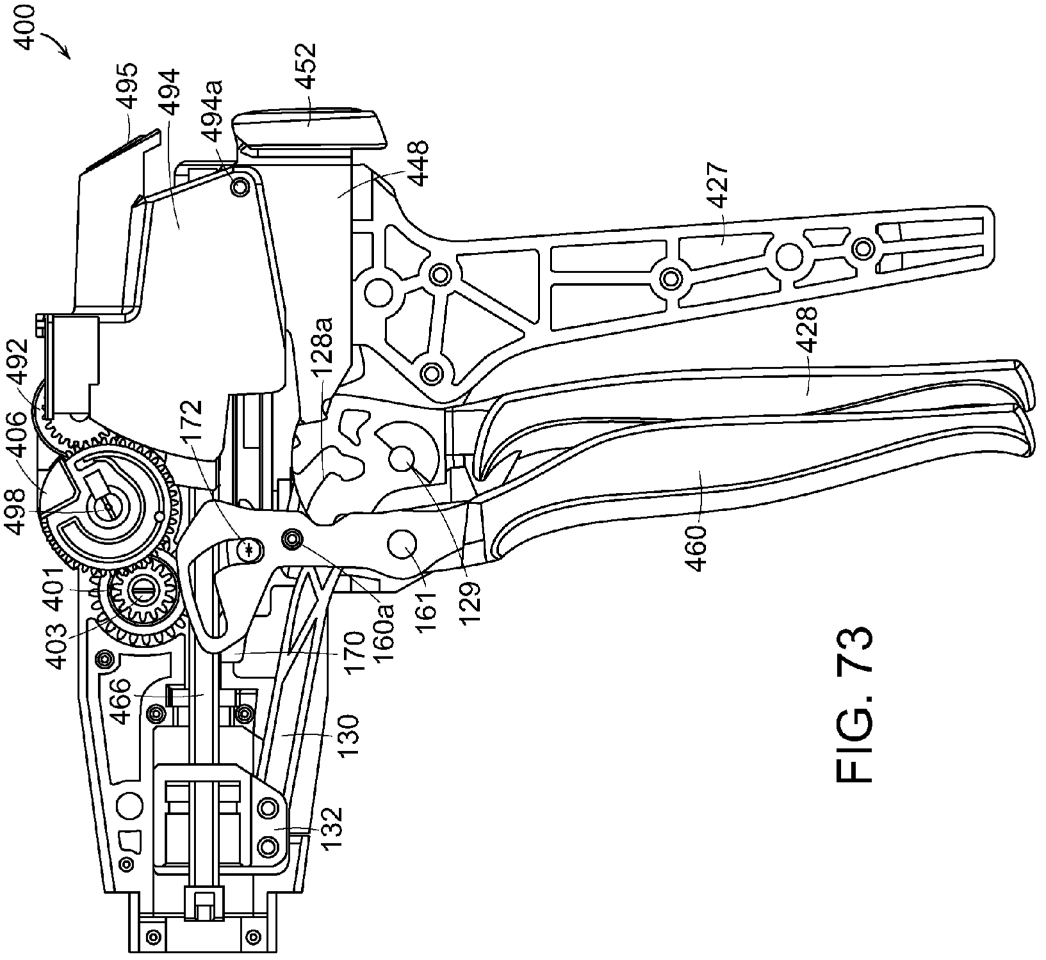
FIG. 73 is an elevational view of the surgical instrument of FIG. 68 illustrating the firing trigger in an actuated position after a second actuation of the firing trigger.
Figure 74:
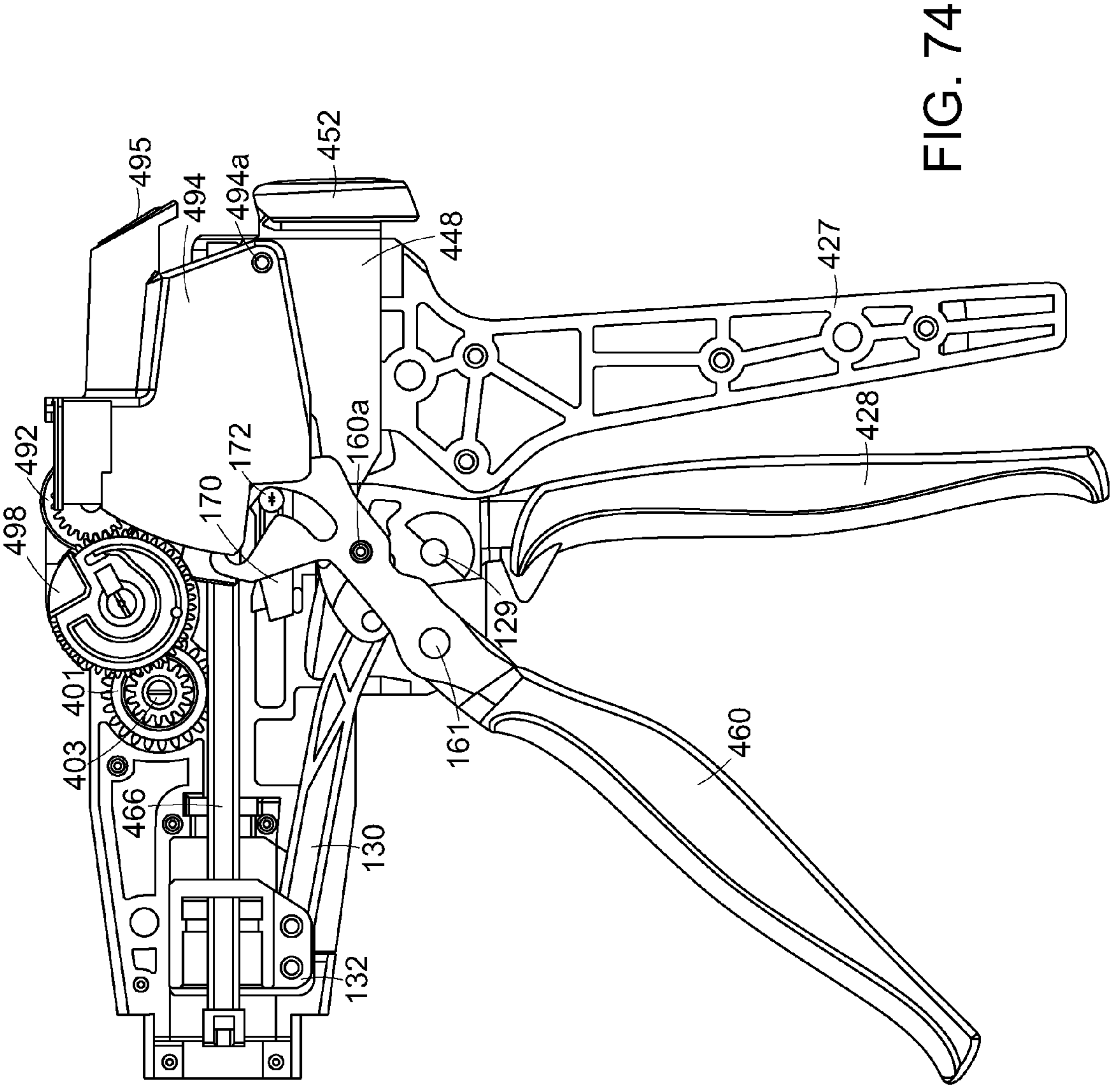
FIG. 74 is an elevational view of the surgical instrument of FIG. 68 illustrating the firing trigger in an unactuated position after it has been released from its second actuation.
Figure 75:
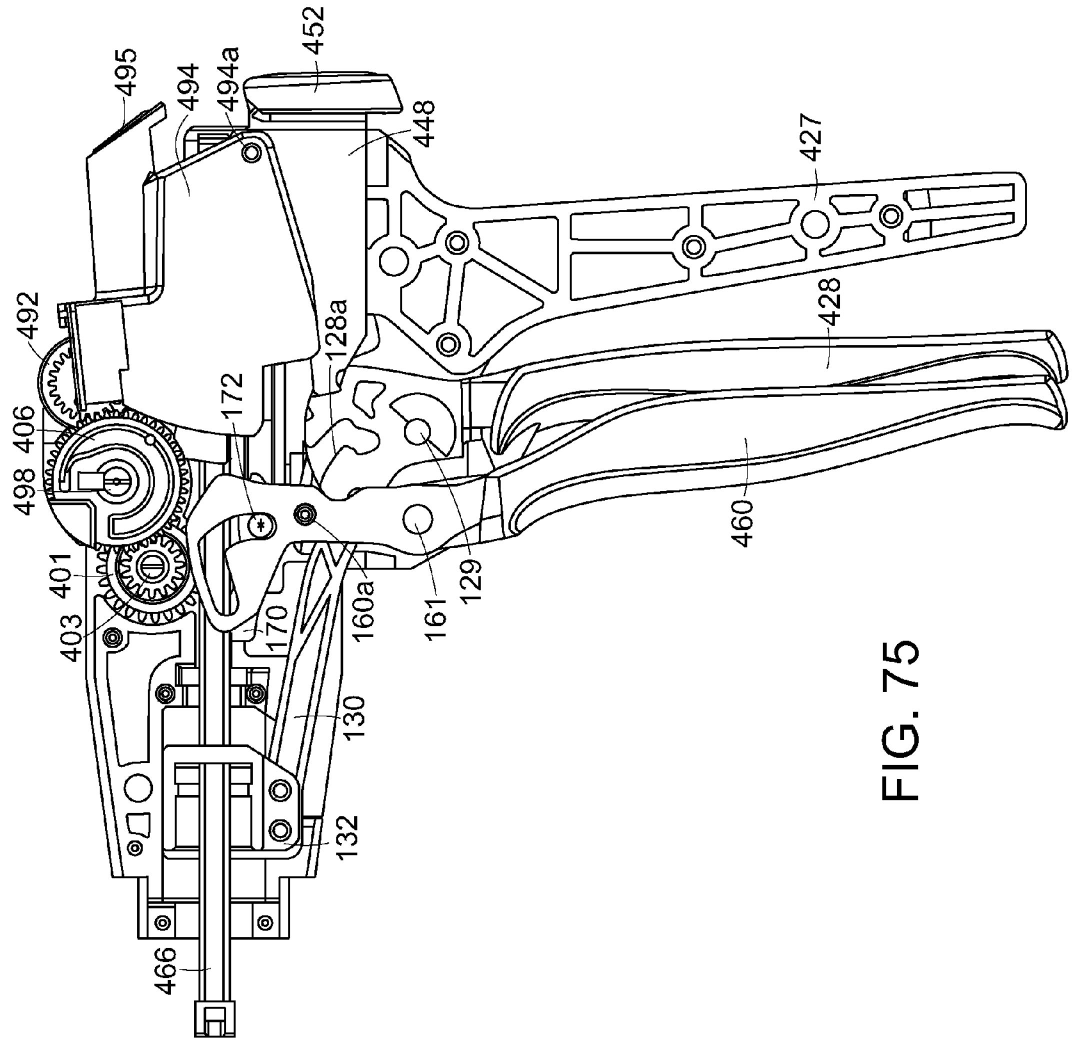
FIG. 75 is an elevational view of the surgical instrument of FIG. 68 illustrating the firing trigger in an actuated position after a third actuation of the firing trigger.
Figure 82:
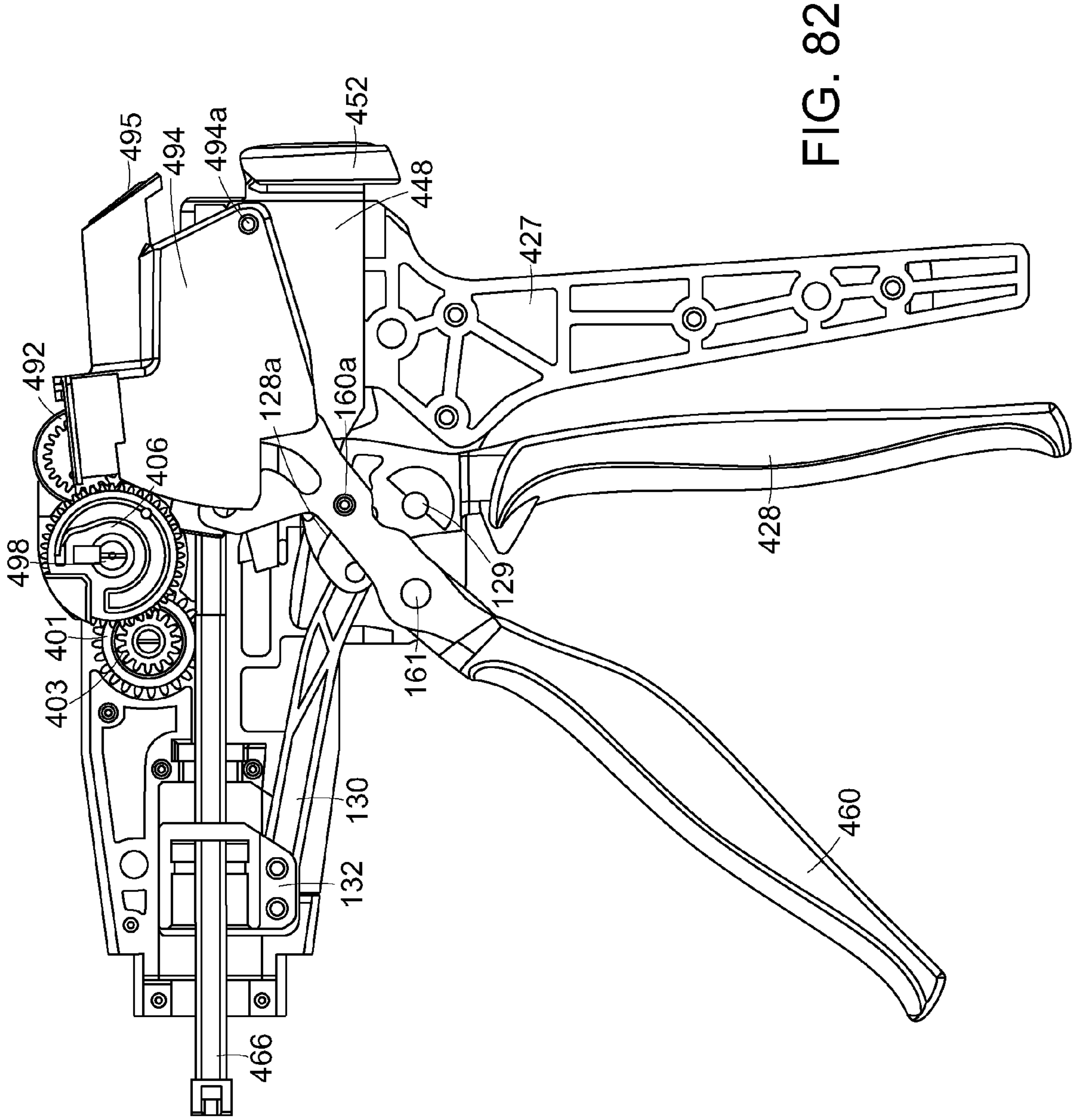
FIG. 82 is an elevational view of the return carriage of the surgical instrument of FIG. 68 in an actuated position and the reversing mechanism operably engaged with the firing member.
Figure 83:
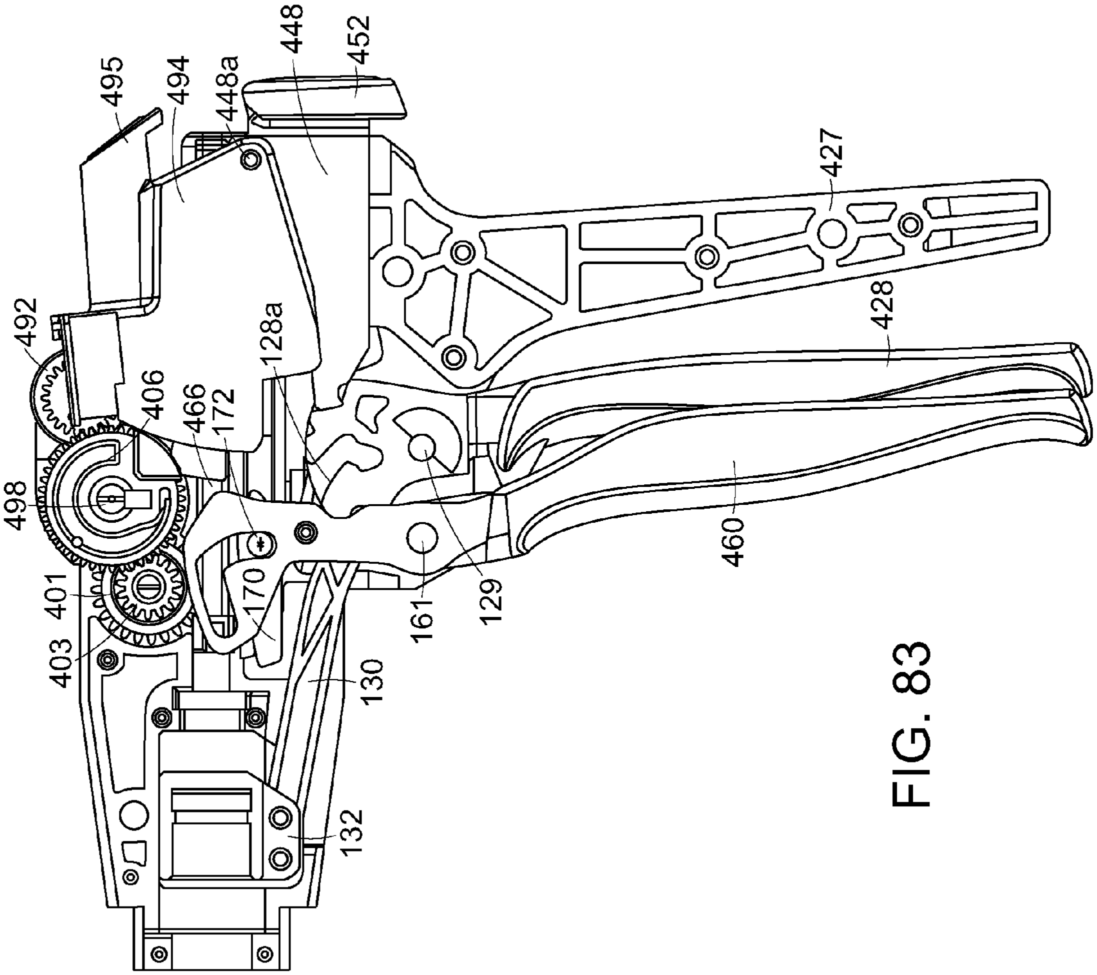
FIG. 83 is an elevational view of the surgical instrument of FIG. 68 illustrating the firing trigger in an actuated position after a fourth actuation which has retracted the firing member.
Figure 101:
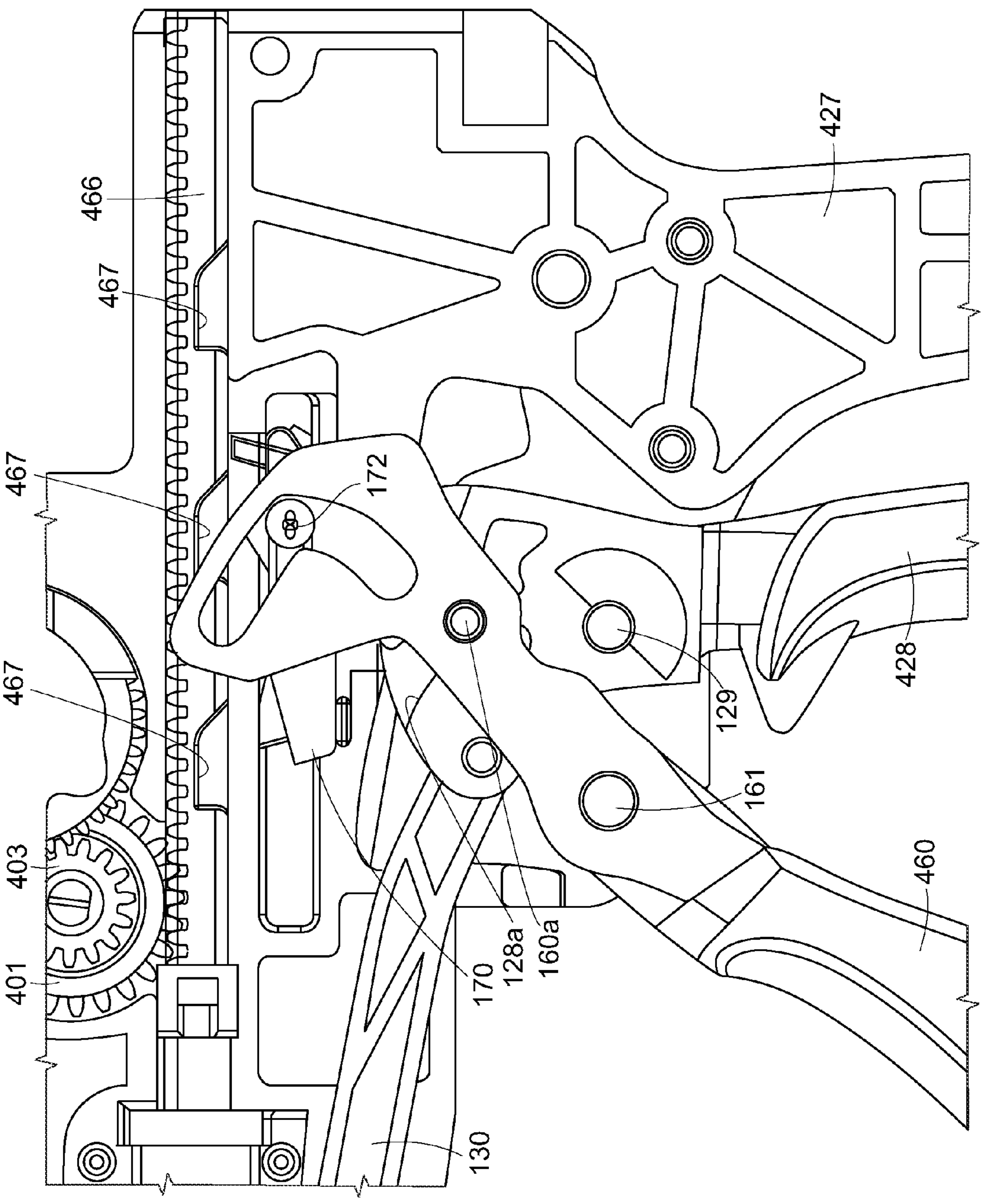
FIG. 101 is an elevational view of a surgical instrument in accordance with an alternative embodiment of the present invention including the firing drive and the reversing drive of the surgical instrument of FIG. 68 with some components of the surgical instrument removed wherein the pawl of the firing drive is illustrated as it would appear when it is withdrawn relative to the firing member.
Figure 102:
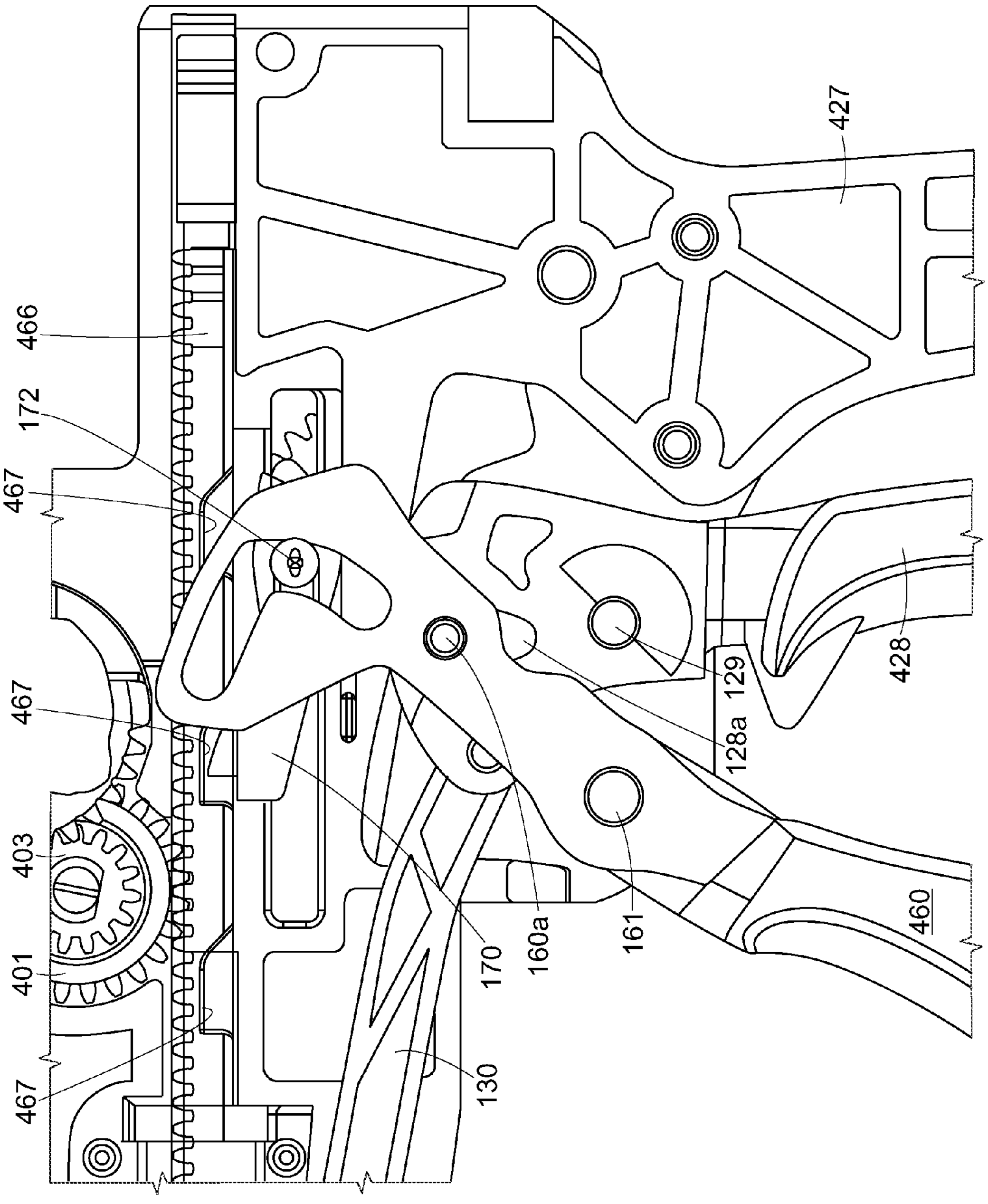
FIG. 102 is an elevational view of the surgical instrument of FIG. 101 illustrating the pawl operably engaged with the firing member.

In various embodiments, referring to FIGS. 101 and 102, firing member 466 can include a plurality of recesses 467 which can each receive at least a portion of pawl 170 such that pawl 170 can serially engage the recesses 467 in order to advance firing member 466 a plurality of times as described above. More particularly, in at least one embodiment, firing member 466 can include three recesses 467 which can allow firing member 466 to be advanced at least three times by trigger 460. By way of example, FIG. 73 illustrates the firing drive upon a second actuation of trigger 460, FIG. 74 illustrates the firing drive after trigger 460 has been returned to its unactuated position after its second actuation, FIG. 75 illustrates the firing drive upon a third actuation of trigger 460, and FIG. 82 illustrates the firing drive after trigger 460 has been returned to its unactuated position after its third actuation. At such point, as described in greater detail below, the firing drive can be disengaged from firing member 466 and the reversing drive can be operably engaged with firing member 466 such that, in various embodiments, firing member 466 can be retracted relative to the end effector and the surgical instrument can be reset. Although firing trigger 460 is actuated three times in order to fully advance firing member 466 in the illustrated exemplary embodiment, other embodiments are envisioned which can utilize more than, or less than, three strokes or actuations of the firing trigger.

In various embodiments, as outlined above, surgical instrument 400 can further include a gear-driven reversing drive, or mechanism, which can be configured to retract firing member 466, the cutting member, and/or the staple driver relative to the end effector of the surgical instrument. In at least one embodiment, the reversing mechanism can be operably engaged with firing member 466, or any other suitable portion of the firing drive, to move firing member 466 proximally. In at least one such embodiment, referring to FIG. 71, the reversing drive can include a gear train comprising trigger gear 496, key gear 406, pinion gear 401, intermediate gear 403, and spur gear 416, for example. In various embodiments, referring to FIG. 84, the reversing drive can further include gear portion 158 extending from firing trigger 460 which can be configured such that, when firing trigger 460 is rotated about pin 161, similar to the above, gear portion 158 can rotate trigger gear 496 about an axis defined by return pin 498. In at least one embodiment, gear portion 158 and trigger gear 496 can include teeth and/or recesses which can be configured to cooperate and transmit rotational motion therebetween.

Figure 77:
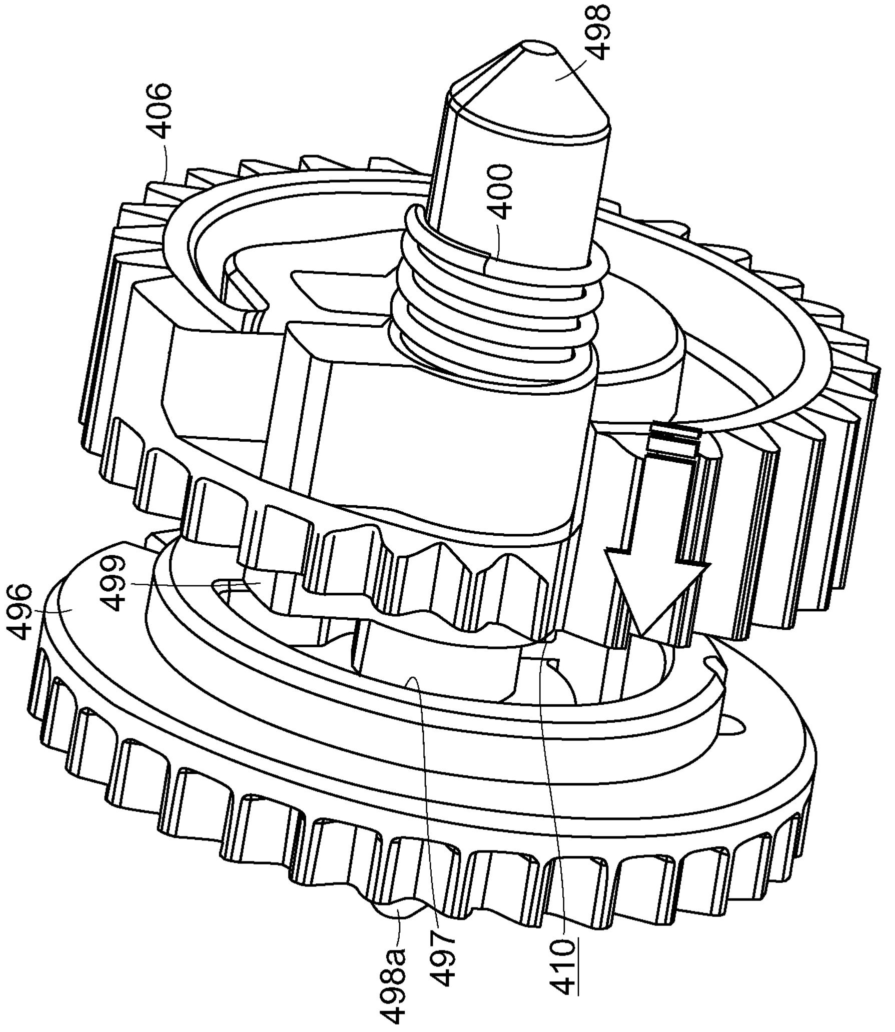
FIG. 77 is a perspective view of a trigger gear, key gear, and a return pin of the gear train of the reversing mechanism of FIG. 71.
Figure 78:
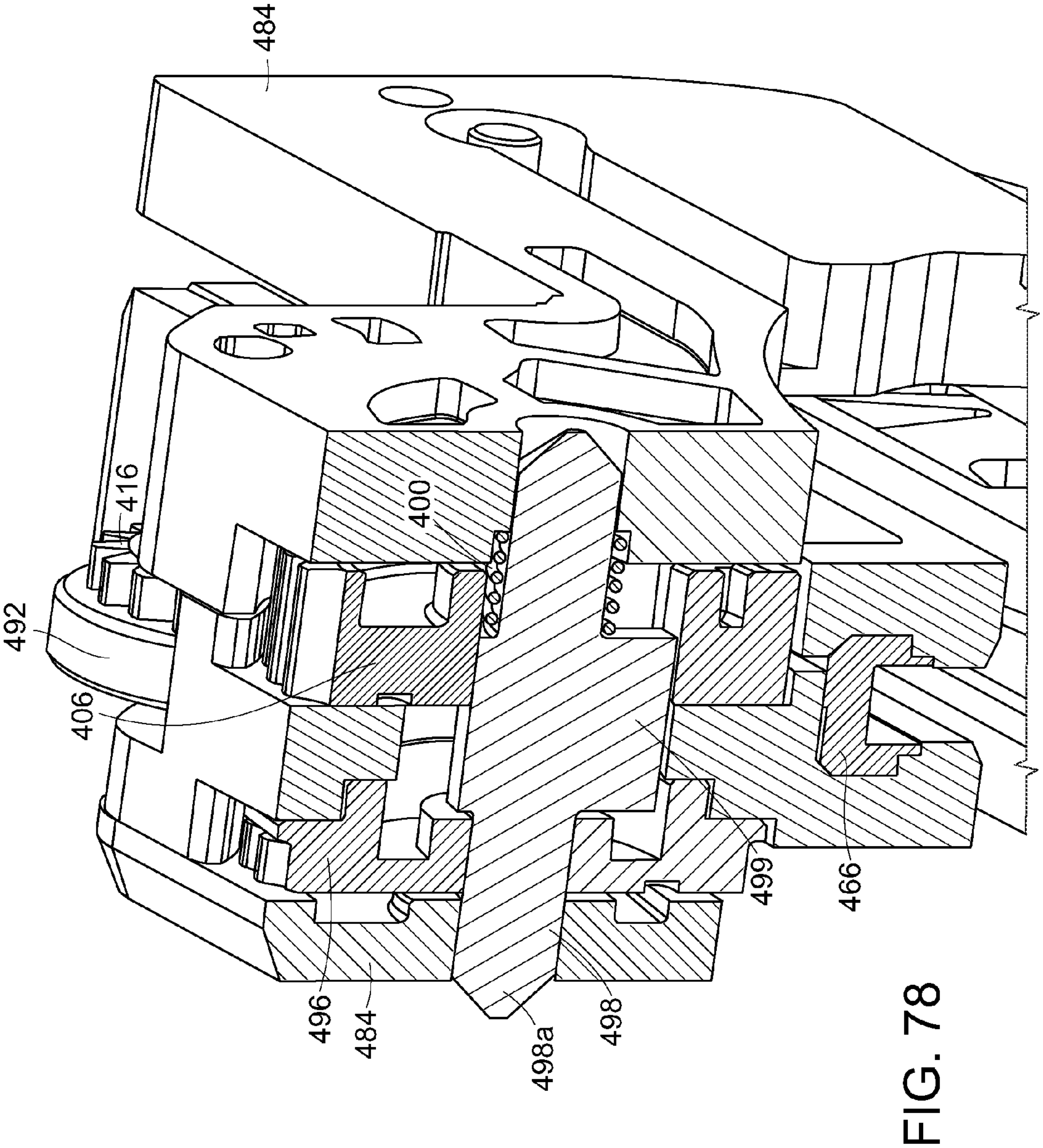
FIG. 78 is a cross-sectional view of the surgical instrument of FIG. 68 illustrating the return pin of FIG. 77 operatively engaged with the trigger gear and the key gear of the reversing mechanism of FIG. 71.
Figure 79:
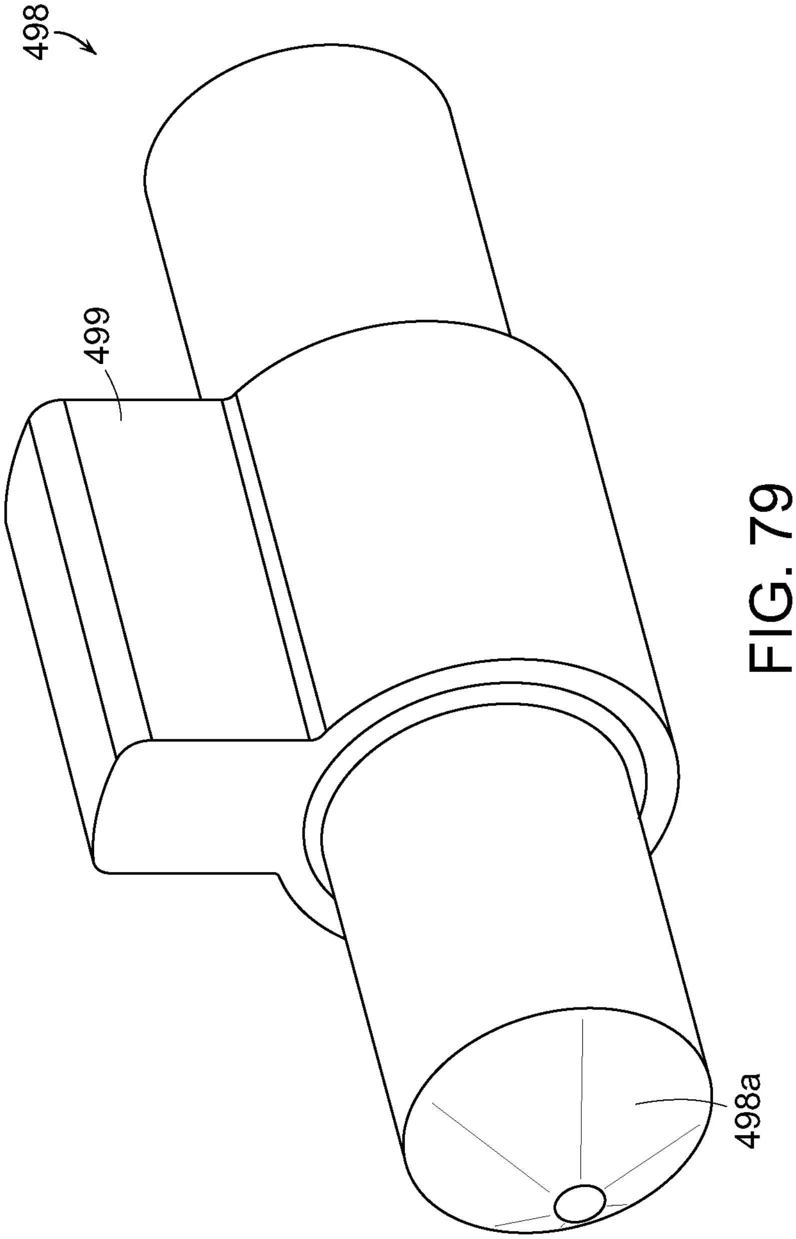
FIG. 79 is a perspective view of the return pin of FIG. 77.
Figure 80:
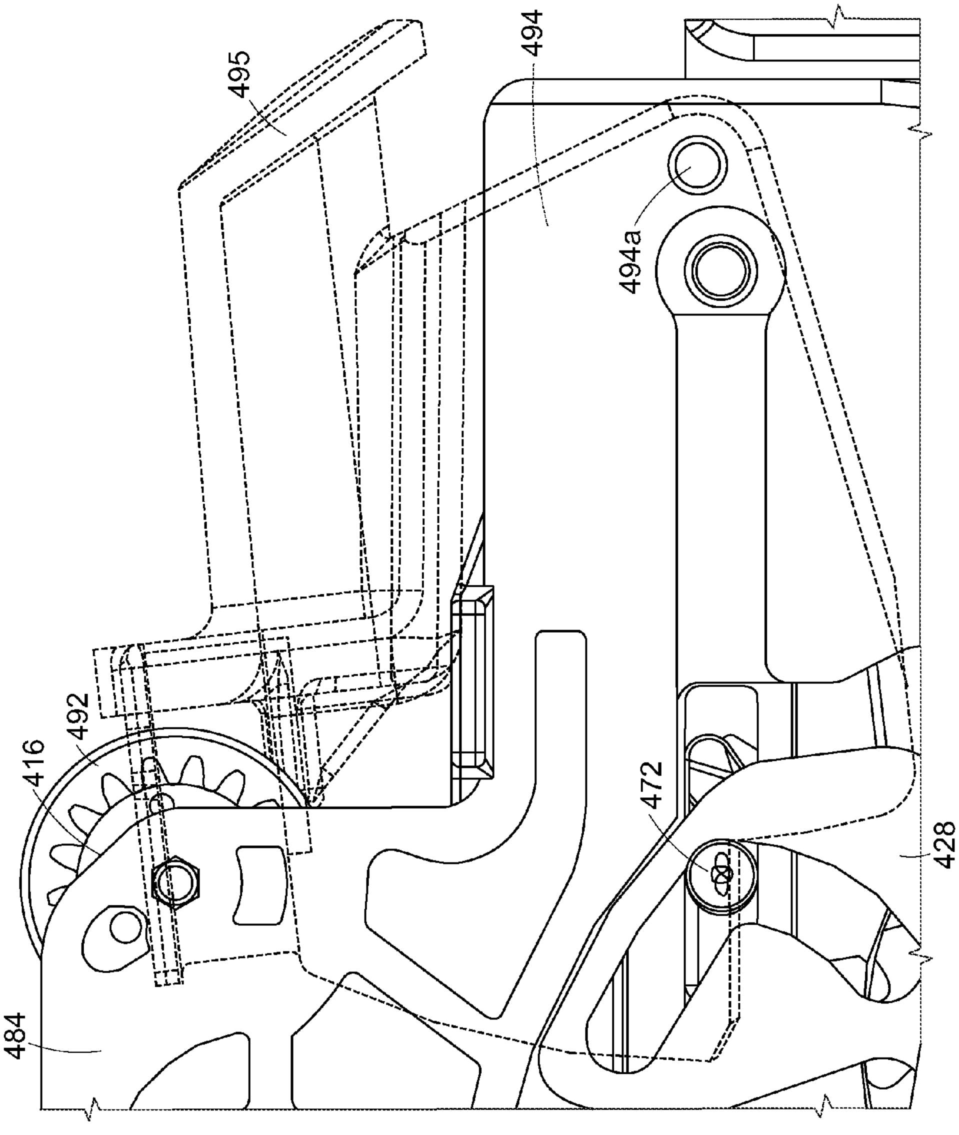
FIG. 80 is another elevational view of the return carriage of FIG. 76 in an actuated position.
Figure 81:
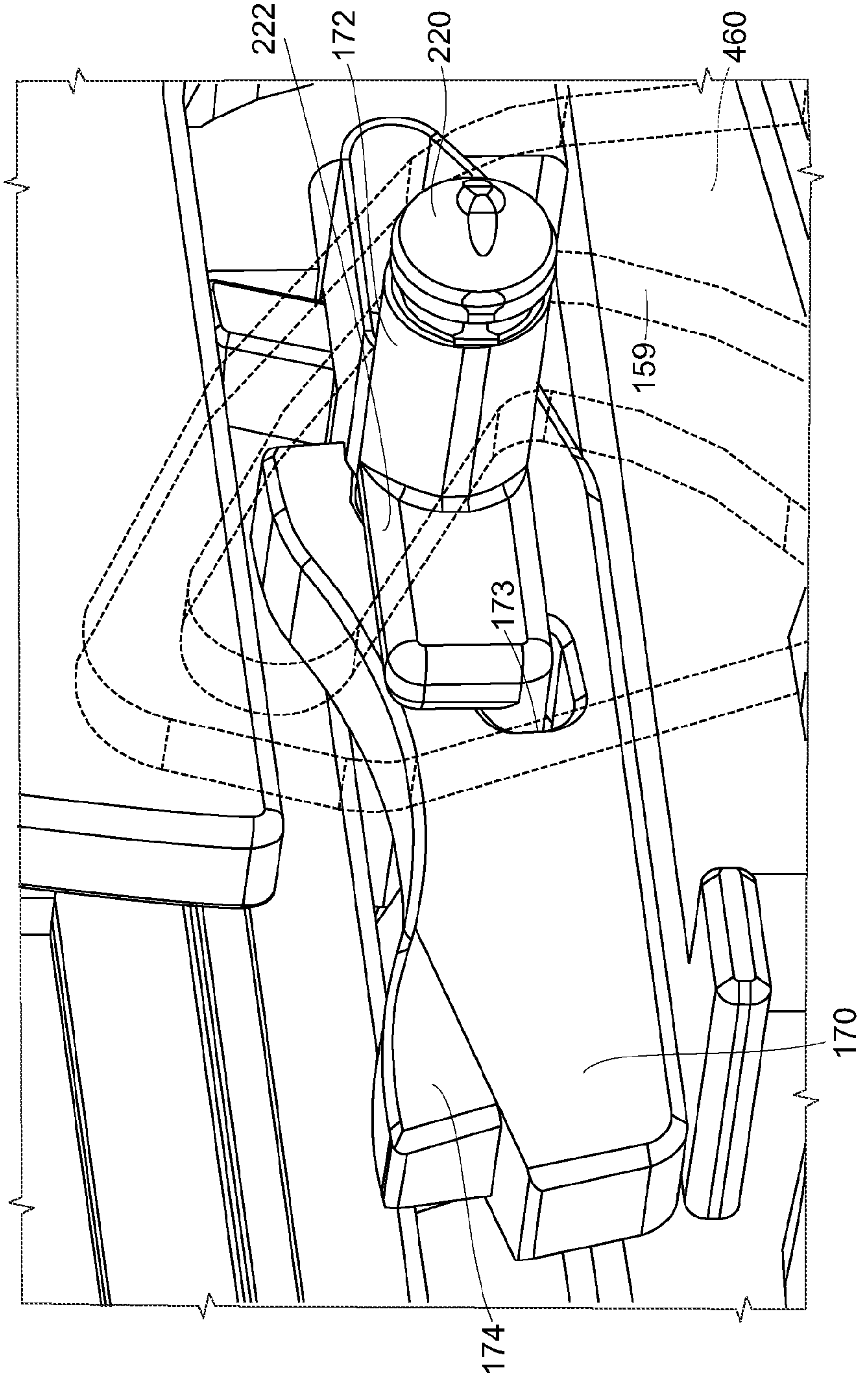
FIG. 81 is a perspective view of a firing pin engaged with a pawl of the firing drive of the surgical instrument of FIG. 68.

Referring to FIG. 77, also similar to the above, trigger gear 496 and return pin 498 can be configured such that they can be selectively engaged and disengaged with one another. In at least one such embodiment, trigger gear 496 can be operably disengaged with return pin 498 when firing member 466 is advanced by the firing drive. Stated another way, trigger gear 496 can be configured such that it does not transmit, or at least substantially transmit, rotational motion to return pin 498 when firing member 466 is being advanced by the firing drive as described above. Furthermore, in at least one such embodiment, referring to FIGS. 77 and 79, return pin 498 can include key 499 extending therefrom wherein key 499 can be held out of operative engagement with D-shaped cavity 497 in trigger gear 496 until the reversing drive is operatively engaged with firing member 466 as described in greater detail below. In order to hold key 499 out of operative engagement with trigger gear 496, referring to FIG. 84, return pin 498 can include end 498*a* which can be displaced, and/or held in position, by return carriage 494 such that key 499 is positioned outside of D-shaped cavity 497.

Figure 71:
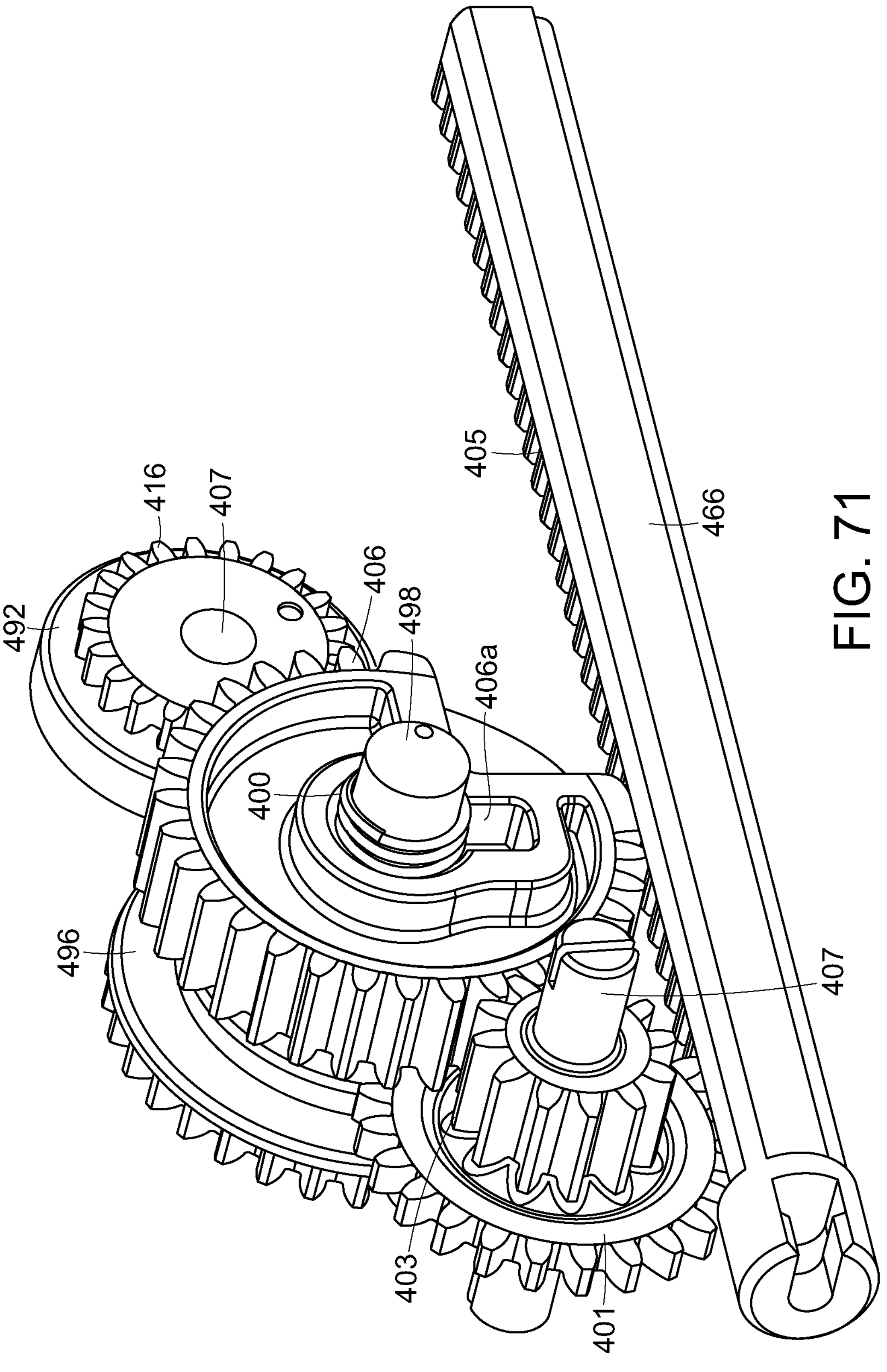
FIG. 71 is a perspective view of a gear train of a reversing mechanism of the surgical instrument of FIG. 68 for retracting a firing member.
Figure 72:
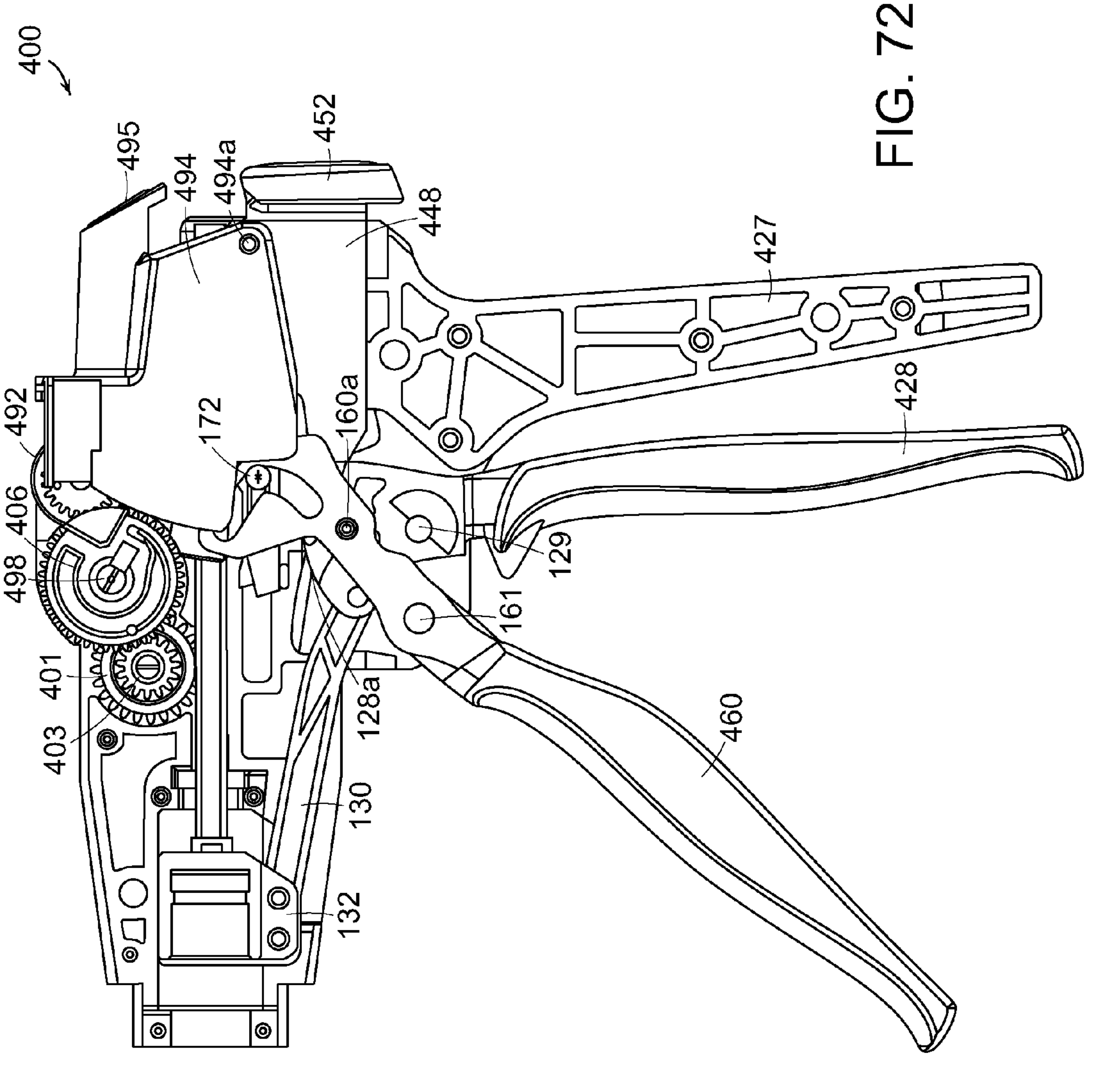
FIG. 72 is an elevational view of the surgical instrument of FIG. 68 illustrating the firing trigger in an unactuated position after it has been released from its first actuation.

Before trigger gear 496 and return pin 498 are operatively engaged as mentioned above, pinion gear 401 of the reversing drive, referring to FIG. 71, can be operatively engaged with rack portion 405 of firing member 466 such that, when firing member 466 is advanced distally by the firing drive as described above, rack portion 405 can rotate pinion gear 401 about an axis defined by axle 407. In various embodiments, rack 405 can include a plurality of teeth and/or grooves which can be configured to convert translational movement of firing member 466 into rotational movement of pinion gear 401. In various embodiments, intermediate gear 403 can be mounted to or integrally formed with pinion gear 401 such that the translation of firing member 466 can rotate intermediate gear 403 as well. In at least one embodiment, intermediate gear 403 and key gear 406 can include teeth and/or recesses which can be configured to cooperate and transmit rotational motion therebetween. Similarly, spur gear 416 can include teeth and/or recesses which can be configured to cooperate with the teeth and/or recesses of key gear 406 and transmit rotational motion therebetween. Thus, in view of the above, the advancement of firing member 466 can rotate gears 401, 403, 406, and 416 of the gear train.

Figure 84:
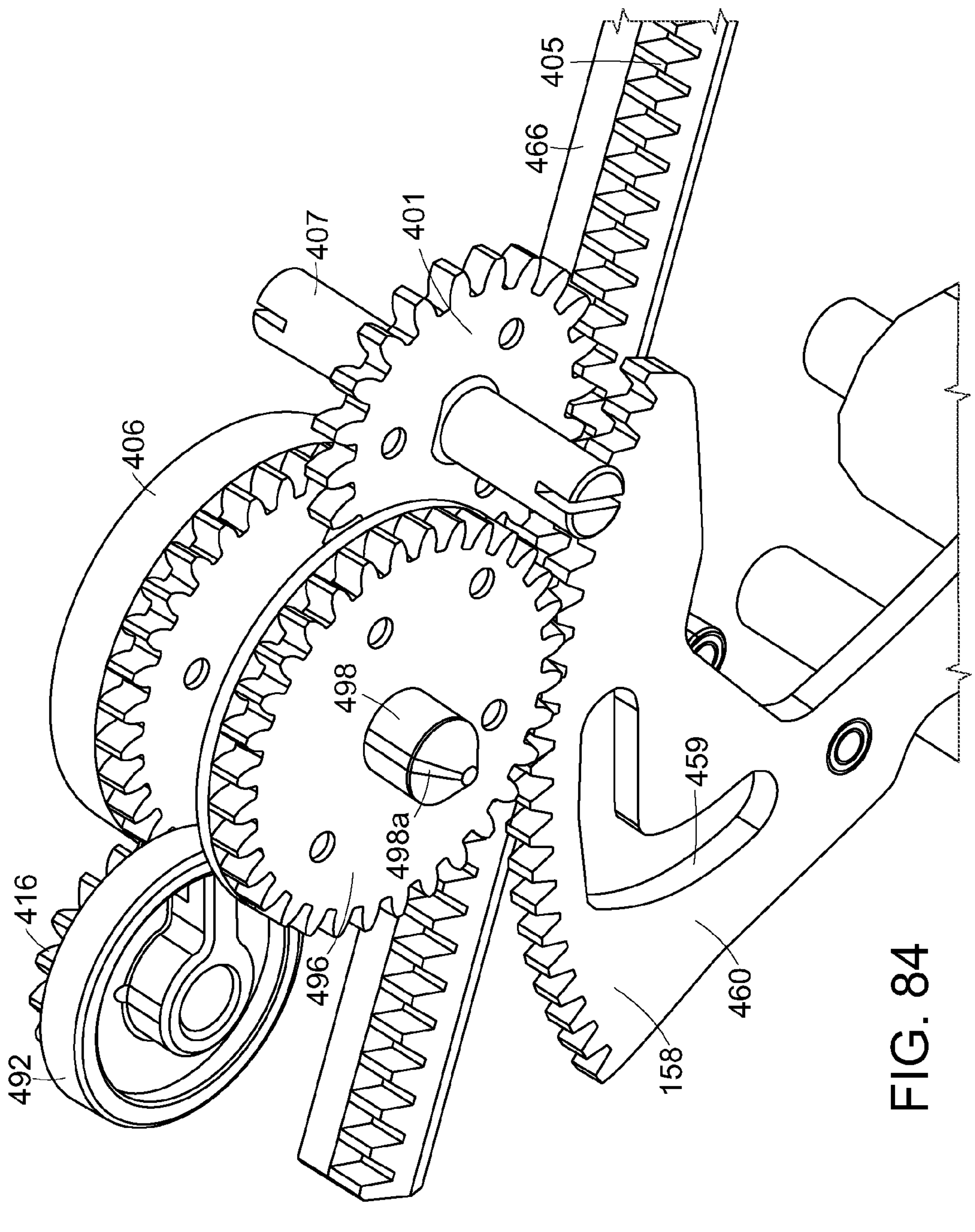
FIG. 84 is a perspective view of the reversing mechanism of FIG. 76 with some components removed.
Figure 85:
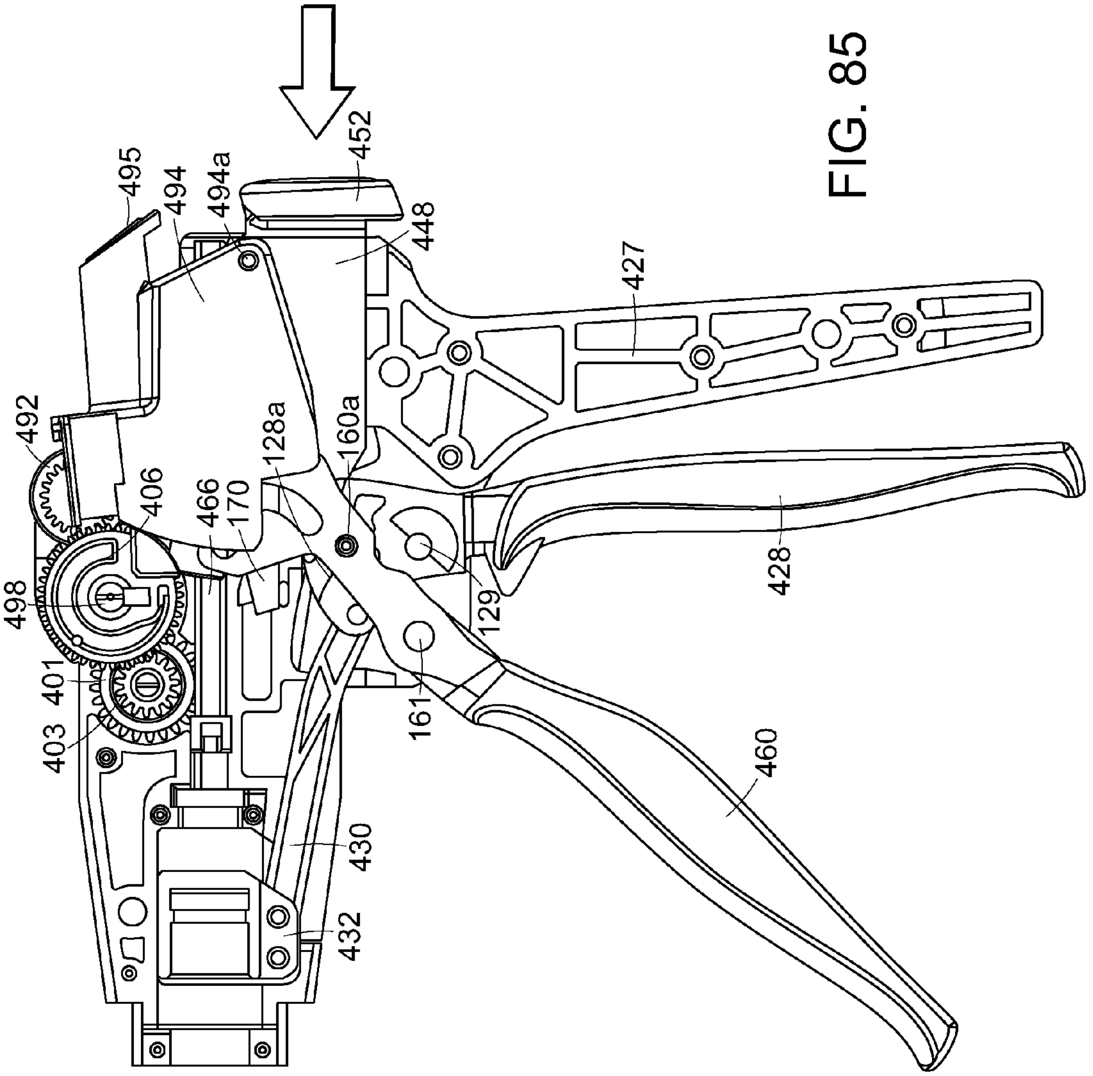
FIG. 85 is an elevational view of the surgical instrument of FIG. 68 illustrating the firing trigger in an unactuated position after it has been released from its fourth actuation.
Figure 86:
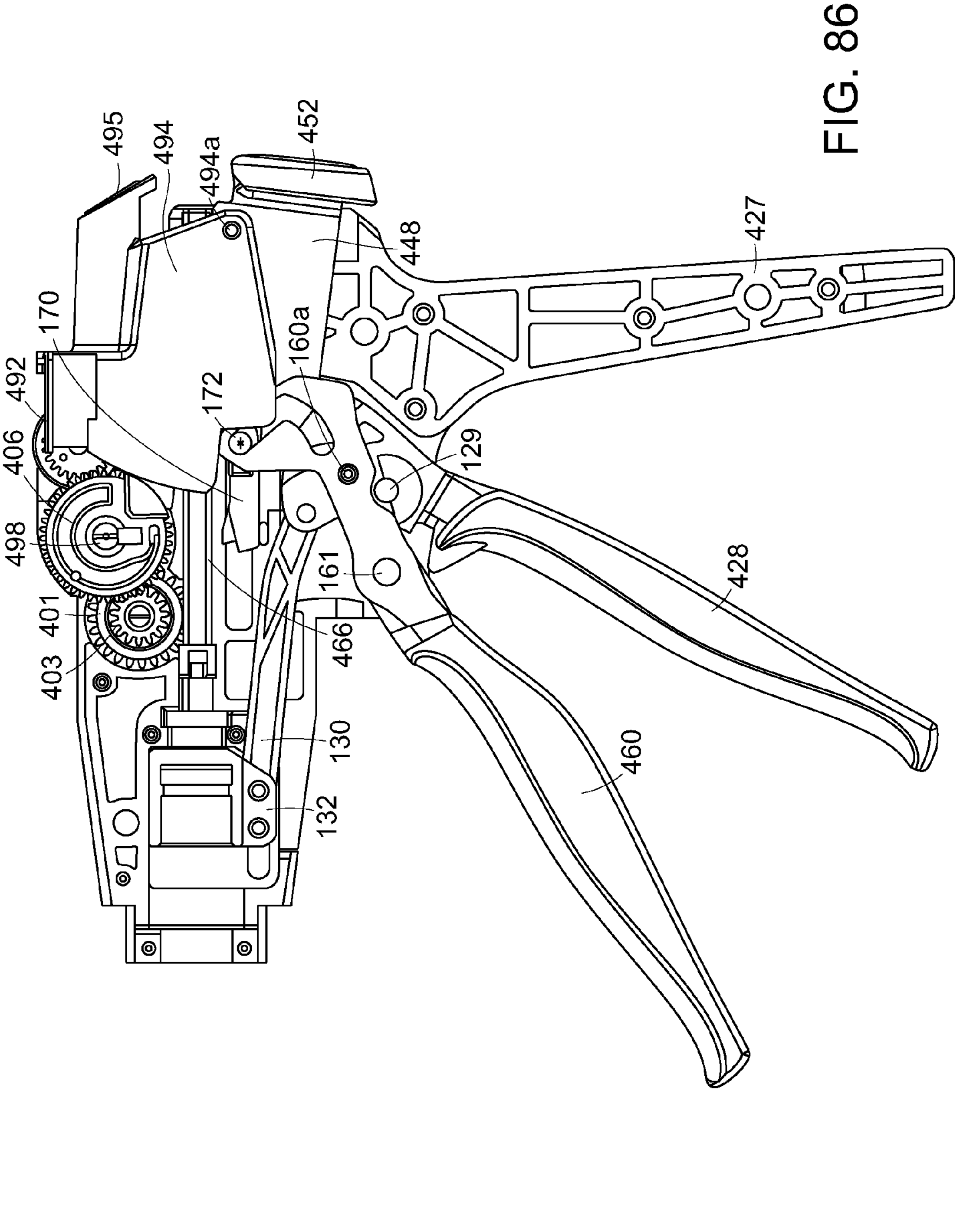
FIG. 86 is an elevational view of the surgical instrument of FIG. 68 illustrating the return carriage of FIG. 76 rotated upwardly into an unactuated position and also illustrating the closure trigger in its unactuated position.
Figure 87:
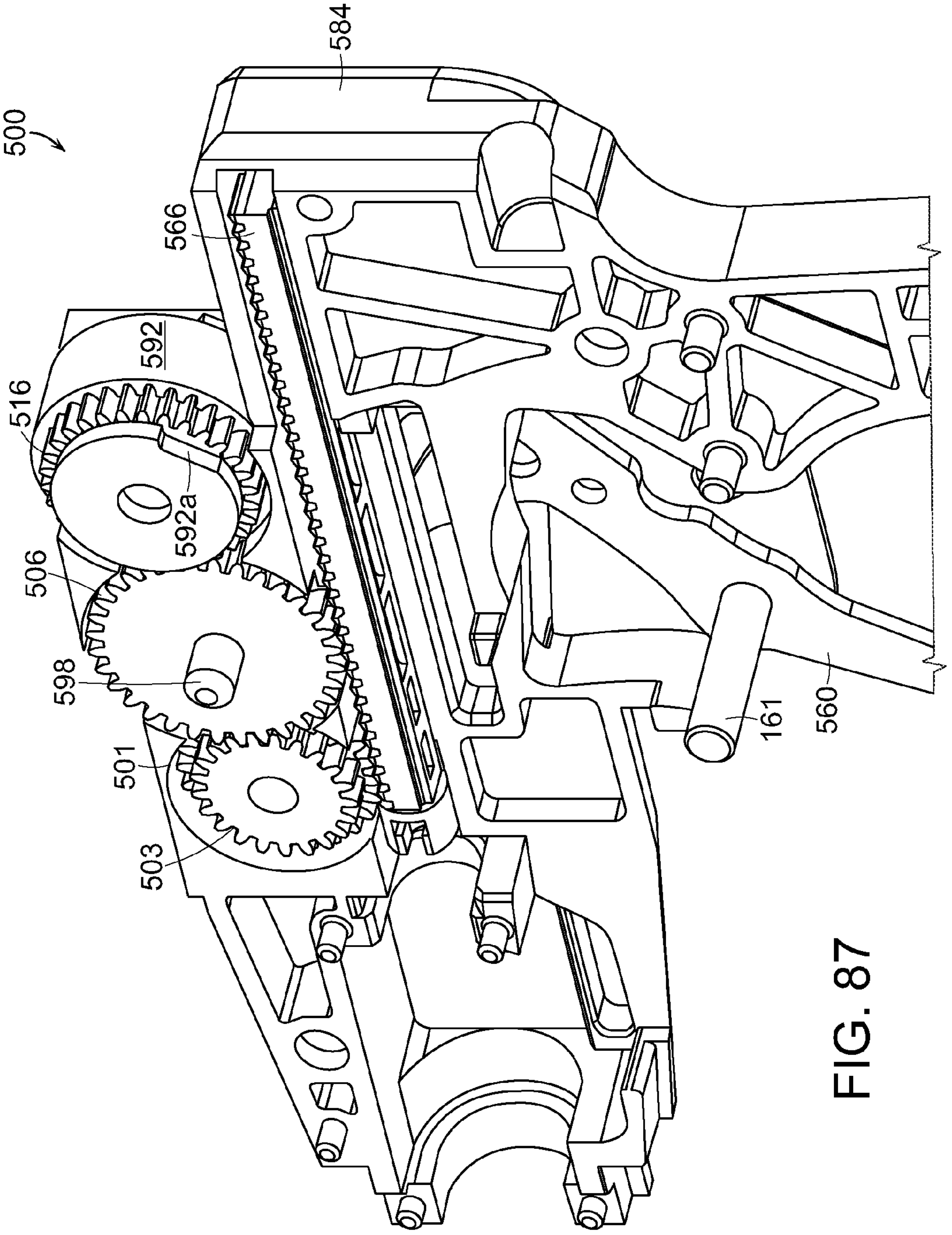
FIG. 87 is a perspective view of a surgical instrument in accordance with an alternative embodiment of the present invention with some components of the surgical instrument removed.

In at least one embodiment, referring to FIGS. 71 and 84, spur gear 416 can be mounted to or integrally-formed with indicator gear 492 such that, when spur gear 416 is rotated by key gear 406 as outlined above, indicator gear 492 can be rotated by spur gear 416. Thus, in at least one such embodiment, the forward advancement of firing member 466 can rotate indicator gear 492 about an axis defined by aperture 407. In various embodiments, indicator gear 492 can include at least one indicium thereon, such as letters, numbers, and/or any other suitable symbols, for example, for displaying the number of times that firing trigger 460 has been actuated, for example. In at least one such embodiment, the housing of the surgical instrument can include a window or aperture therein wherein a numeral "1", for example, on indicator gear 492 can be aligned with the window after a first actuation of firing trigger 460. Similarly, a numeral "2", for example, on indicator gear 492 can be aligned with the window after a second actuation of firing trigger and, correspondingly, a numeral "3", for example, can be aligned with the window after a third actuation. Alternatively, in at least one embodiment, indicator gear 492 can include indicia thereon which can correspond to the number of remaining actuations which are necessary to fully advance firing member 466, the cutting member, and/or the staple driver relative to the end effector.

Figure 76:
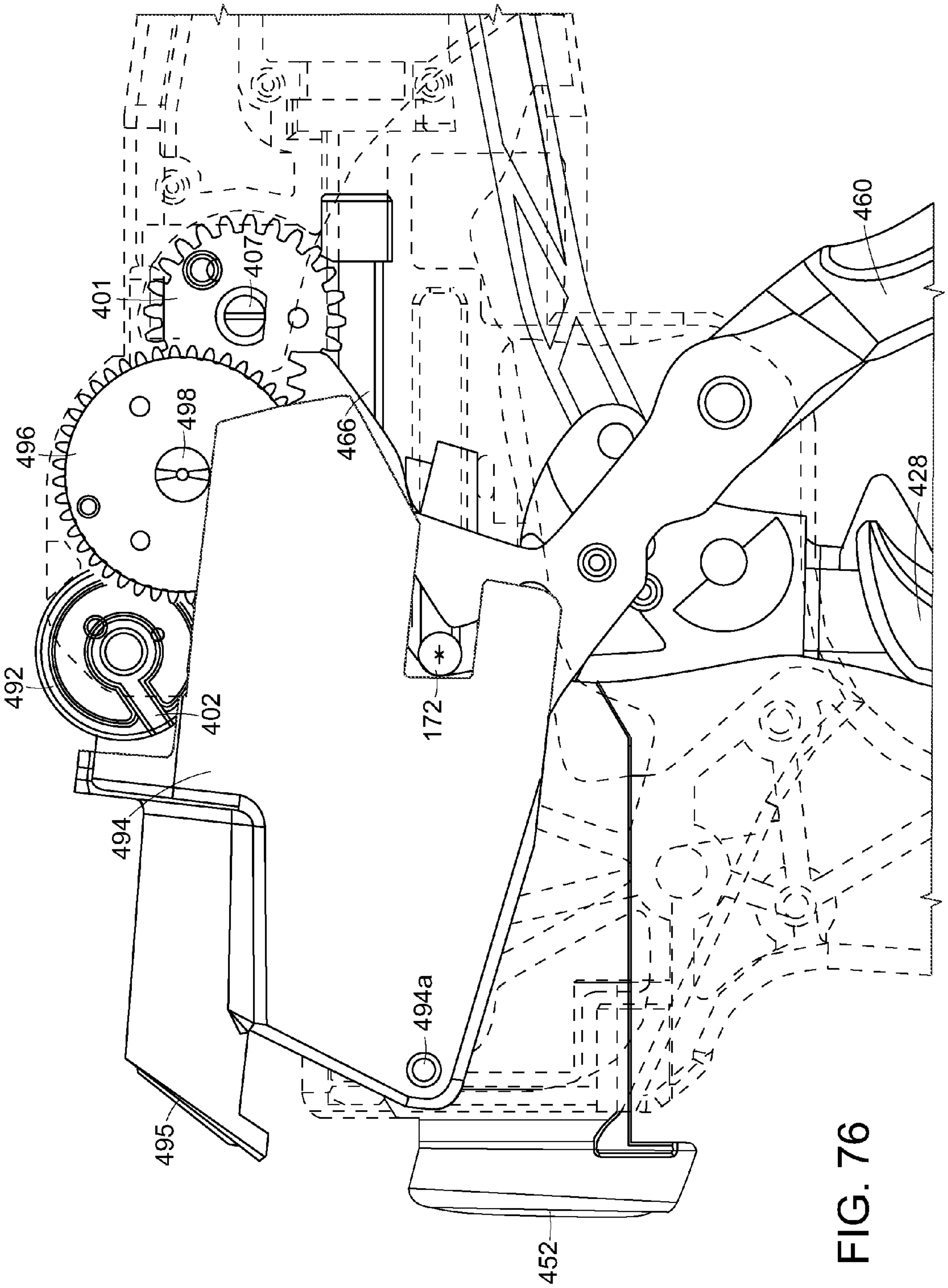
FIG. 76 is another elevational view of the surgical instrument of FIG. 68 illustrating a return carriage of the reversing mechanism after it has been rotated downwardly into an actuated position.

After firing member 466 has been fully advanced relative to the end effector, or at least suitably advanced, return carriage 494 can be rotated downwardly, referring to FIGS. 76 and 82, in order to operably couple the reversing drive, firing trigger 460, and firing member 466. In various embodiments, return carriage 494 can be rotated about pin 494*a* such that return carriage 494 no longer contacts, or at least substantially contacts, return pin 498. Thereafter, referring to FIGS. 77 and 78, spring 400 can slide or displace return pin 498 toward trigger gear 496 and position at least a portion of key 499 within cavity 497. In at least one such embodiment, referring to FIG. 78, spring 400 can be positioned intermediate frame 484 and key 499 of return pin 498 such that, when return carriage 494 no longer contacts end 498*a*, spring 400 can expand and displace key 499 into cavity 497. In various embodiments, referring to FIG. 80, return carriage 494 can also operably disengage the firing drive from firing member 466 when return carriage 494 is rotated downwardly as described above. More particularly, referring to FIG. 81, return carriage 494 can contact end 220 of firing pin 172 such that firing pin 172 can be slid toward pawl 170 and, as also described above, firing pin 172 can include key 222 extending therefrom which can engage recess 173 in pawl 170 to prevent pawl 170 from being pivoted upwardly to engage firing member 466. Thus, when pawl 170 is prevented from operably engaging firing member 466, the firing drive may no longer engage firing member 466 and the reversing drive can retract firing member 466 without interference from the firing drive.

Further to the above, in various embodiments, return carriage 494 can be rotated downwardly manually by a surgeon or by another clinician, for example. In various embodiments, referring generally to FIGS. 68 and 82, the surgeon can apply a force to button portion 495 such that return carriage 494 can be pivoted downwardly about an axis defined by pin 494*a*. Such a force can be applied after a predetermined amount of actuations of the firing trigger although, in various embodiments, such a force can be applied before the predetermined amount of actuations of the firing trigger is reached. In addition to or in lieu of the above, at least one of the gears of the reversing mechanism can be configured to contact return carriage 494 after a predetermined number of actuations of firing trigger 460. In various embodiments, referring to FIG. 76, indicator gear 492 can include cam 402 which can be configured to contact a portion of return carriage 494 and apply a force thereto upon the third actuation of firing trigger 460. In at least one such embodiment, the advancement of firing member 466 can rotate indicator gear 492 a predetermined amount upon each actuation of trigger 460 such that cam 402 can contact carriage 494 upon the third, or final, stroke of trigger 460 which advances firing member 466. In effect, indicator gear 492, or any other suitable gear of the reversing mechanism, can be configured to be rotated a predetermined amount before switching the surgical instrument from an 'advancing' operating mode to a 'reversing' operating mode.

Once return pin 498 has been operably engaged with trigger gear 496 and firing pin 172 has been engaged with pawl 170 in order to prevent pawl 170 from operably engaging firing member 466 as described above, firing trigger 460 can be actuated once again in order to retract firing member 466.

In at least one such embodiment, the subsequent actuation of firing trigger 466 can rotate trigger gear 492 and, owing to the operative engagement between trigger gear 492 and return pin 498, trigger gear 492 can rotate key gear 406. More particularly, referring to FIGS. 71, 77, and 78, return pin key 499 can be operatively engaged with drive surface 410 of trigger gear 492 in addition to a sidewall of cavity 406*a* within key gear 406 such that the rotation of trigger gear 496 is transmitted to key gear 406 via return pin 498. In various embodiments, referring again to FIG. 71, the rotation of key gear 406 can rotate intermediate gear 403 and pinion gear 401 in order to drive, or retract, firing member 466 proximally. In effect, when trigger 460 is operably engaged with the reversing drive, pinion gear 401 can be rotated in a direction which is opposite the direction in which it is rotated when firing trigger 460 is operably engaged with the firing drive. In various embodiments, the size, or pitch radius, of gears 401, 403, 406, 492, 496 and gear portion 158 of trigger gear 460, for example, can be selected such that firing member 466 can be returned by one actuation of trigger 460, although other embodiments are envisioned in which more or less than one actuation of trigger 460 can be utilized.

After firing member 466 has been retracted, return carriage 494 can be pivoted upwardly into it its unactuated position in order to reset the surgical instrument. In various embodiments, referring to FIGS. 85 and 86, the surgeon or clinician can apply a force to button portion 452 of trigger lock 448 such that trigger lock 448 can rotate upwardly and abut return carriage 494. In such circumstances, trigger lock 448 can rotate return carriage 494 upwardly as well and position carriage 494 in its unactuated position. In doing so, return carriage 494 can engage end 221 of firing pin 172 in order to slide firing pin 172 away from pawl 170 and disengage key 222 from recess 173 in pawl 170 thereby allowing pawl 170 to re-engage firing member 466 upon a subsequent actuation of firing trigger 460. Return carriage 494 can also re-engage end 498*a* of return pin 498 when it is rotated upwardly so as to slide key 499 away from trigger gear 496, thereby operably disengaging return pin 498 from trigger gear 496 and, correspondingly, operably disengaging the reversing drive from firing member 466. Thereafter, the spent staple cartridge can be detached from the surgical instrument and replaced with a new staple cartridge such that the surgical instrument can be used once again.

In various alternative embodiments, a surgical instrument can include a clutch configured to operably engage and disengage a reversing drive with a firing member. In at least one embodiment, referring to FIGS. 87-94, surgical instrument 500, similar to surgical instrument 400, can include firing trigger 560 which can be configured to drive a firing pin and a pawl of a firing drive, for example, so as to advance firing member 566, a cutting member, and/or staple driver relative to an end effector. In various embodiments, also similar to the above, the surgical instrument can further include a reversing drive comprising pinion gear 501, intermediate gear 503, key gear 506, and spur gear 516. In at least one such embodiment, owing to the operative engagement between rack portion 505 of firing member 496 and pinion gear 501, the advancement of firing member 466 can rotate gears 501, 503, 506 and 516 as described in greater detail below. In various embodiments, return, or key, pin 598 can be mounted to or integrally formed with key gear 506 such that rotational motion is transmitted therebetween. In at least one such embodiment, referring to FIG. 89, at least a portion of return pin 598 can include a non-circular cross-section including flat portion 598*b*, for example, which can, referring to FIG. 92, be slidingly received within a correspondingly-shaped aperture 506*b* in key gear 506. Also similar to the above, firing trigger 560 can include gear portion 558 which can be operatively engaged with trigger gear 596 such that gear portion 558 can rotate trigger gear 596 about an axis defined by key pin 598, as described in greater detail below.

Figure 88:
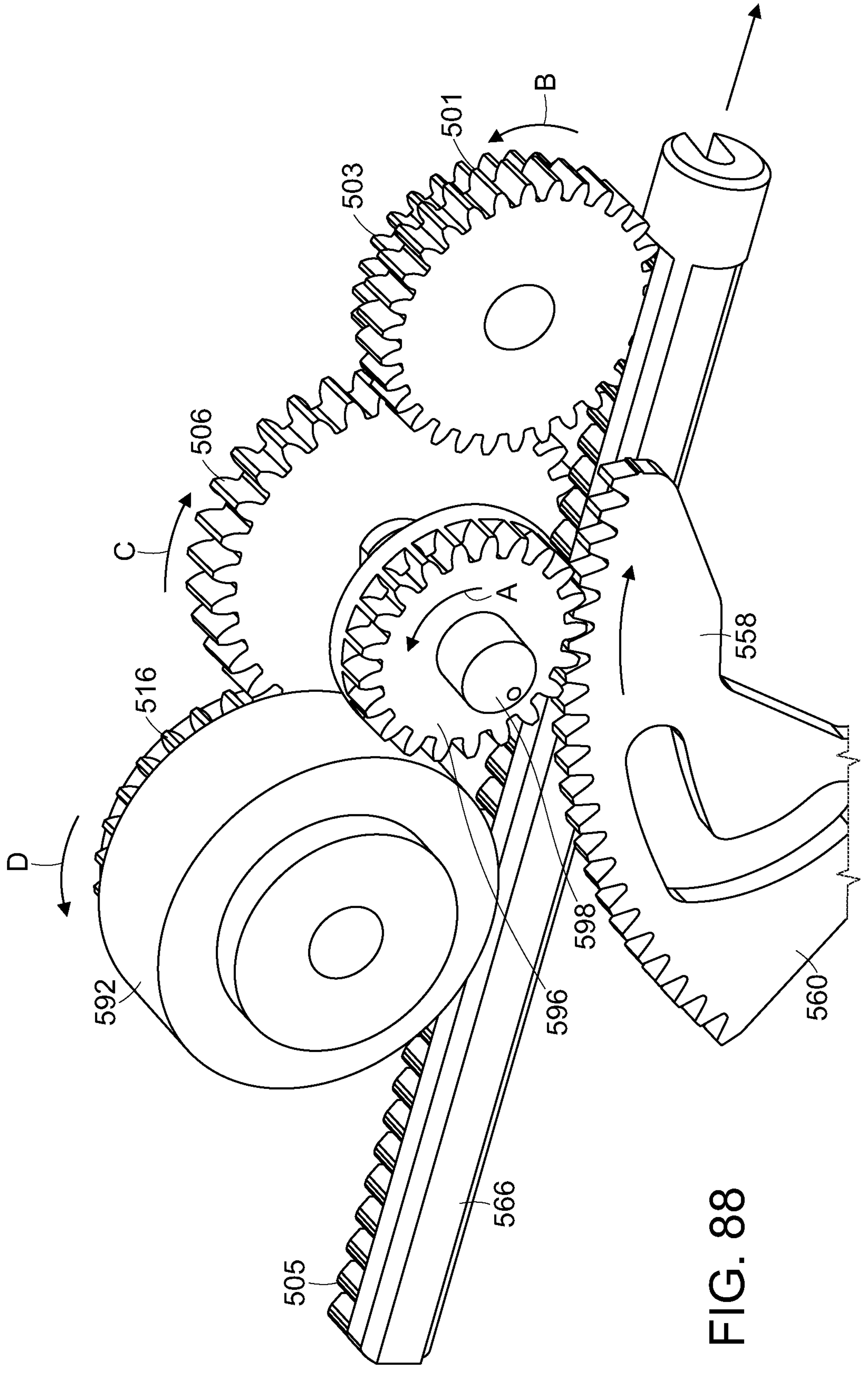
FIG. 88 is a perspective view of a reversing mechanism of the surgical instrument of FIG. 87 including a gear train illustrating the directions in which the gears of the gear train can rotate when a firing member of the surgical instrument is advanced.
Figure 89:
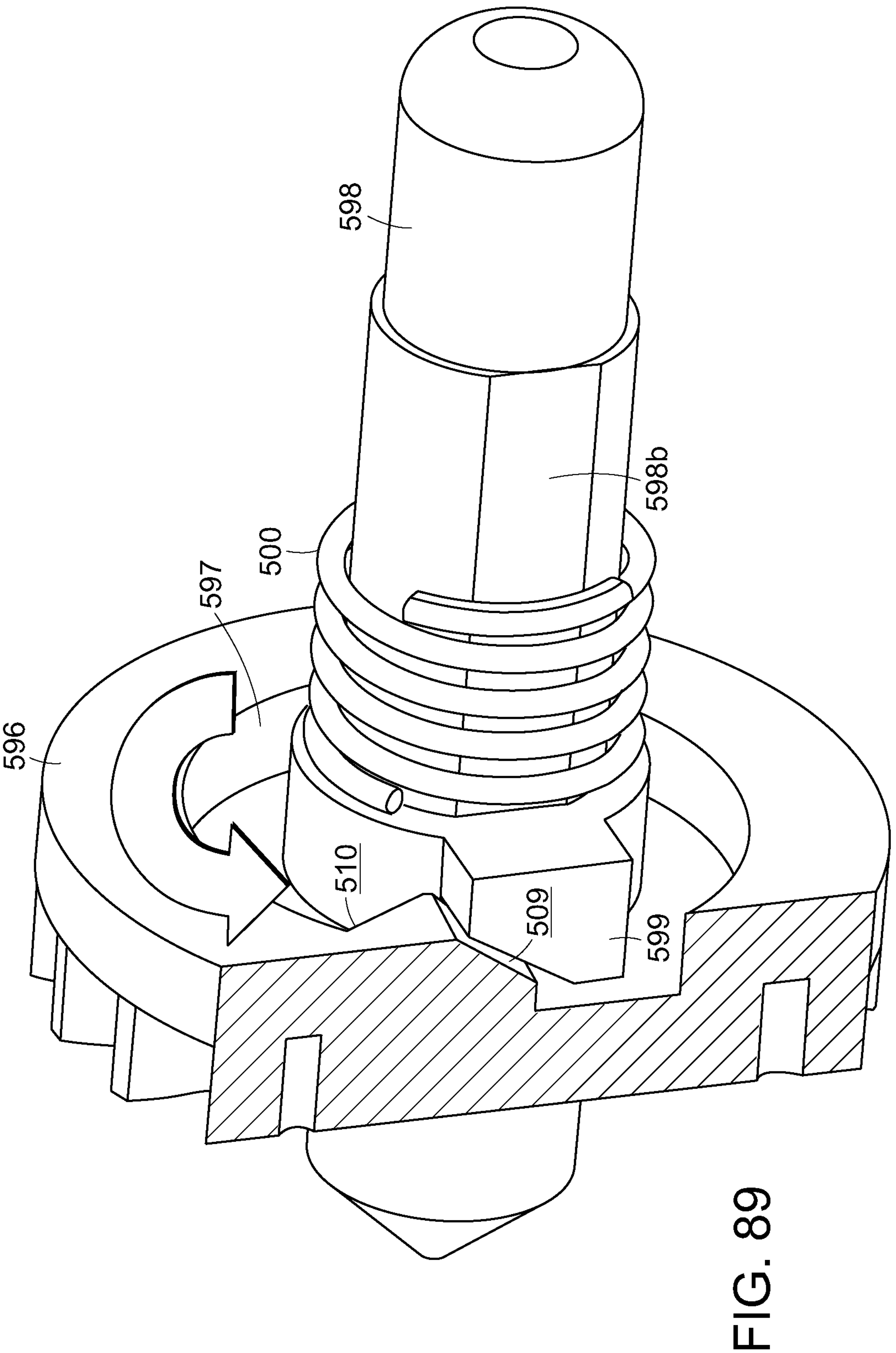
FIG. 89 is a perspective view of a trigger gear and a return pin of the reversing mechanism of FIG. 88 illustrating the trigger gear in cross-section.
Figure 90:
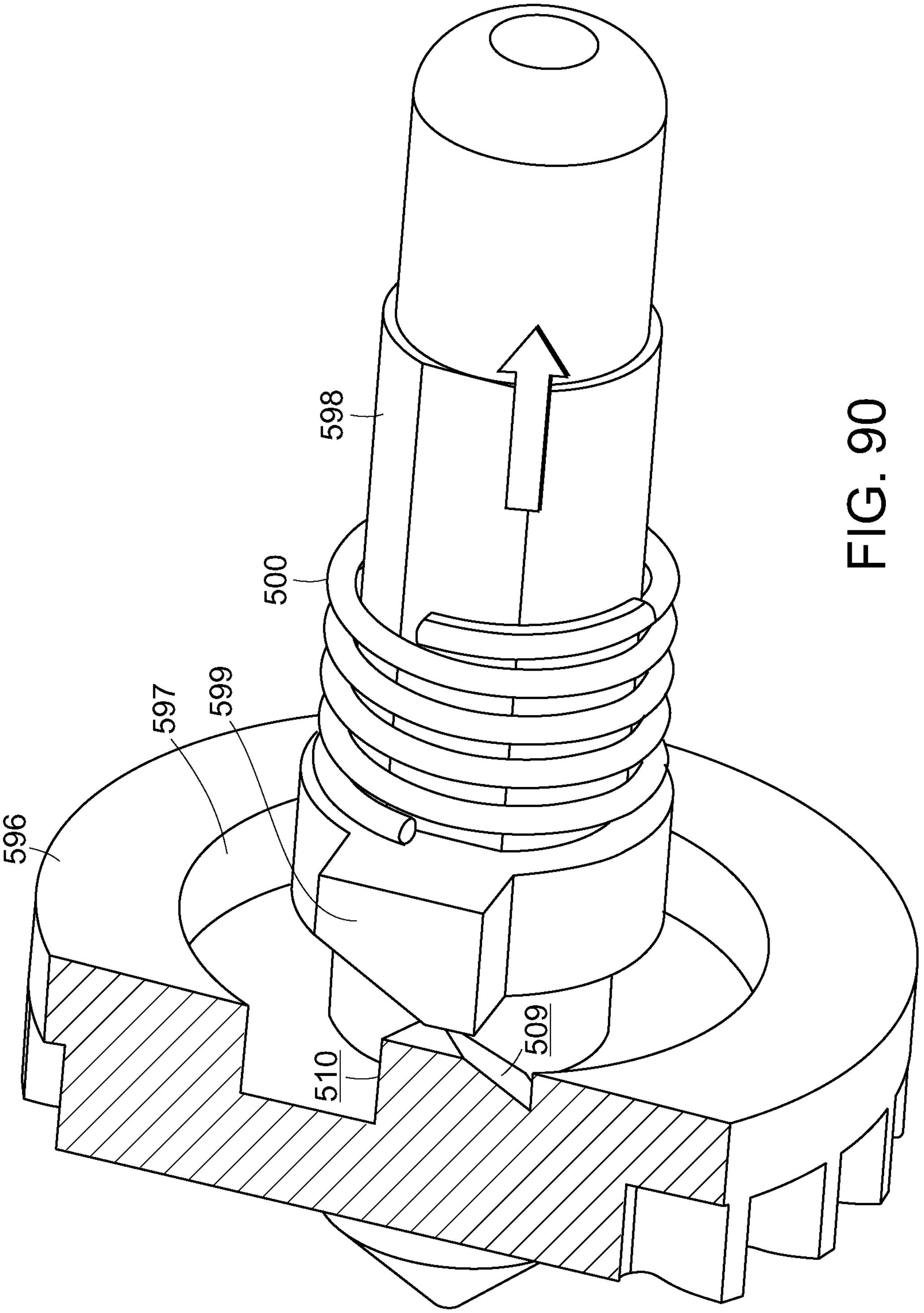
FIG. 90 is another perspective view of the trigger gear and return pin of FIG. 89 illustrating the return pin out of operative engagement with the trigger gear.
Figure 91:
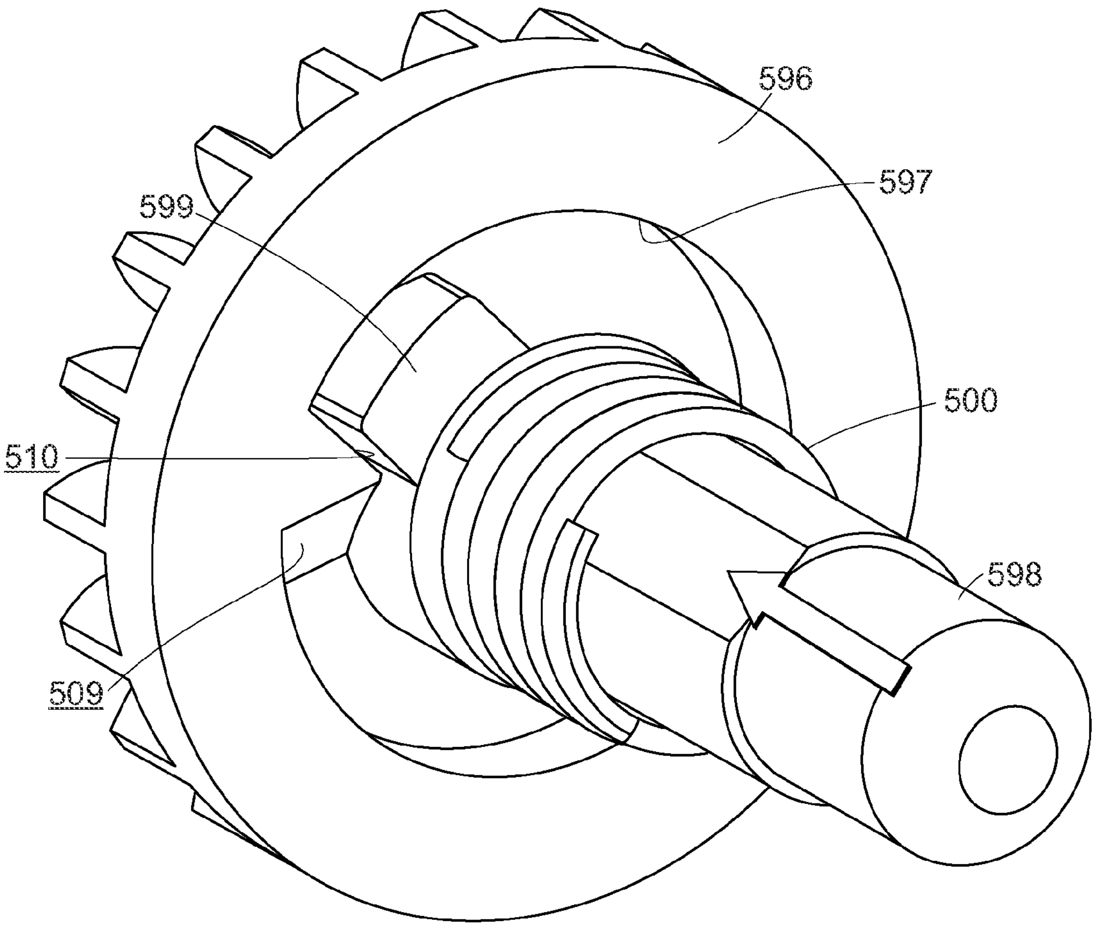
FIG. 91 is a perspective view of the trigger gear and return pin of FIG. 89 illustrating the return pin re-engaged with the trigger gear.

In use, upon the first actuation of firing trigger 560, firing trigger 560 can, similar to the above, rotate trigger gear 596 about key pin 598 without directly transmitting rotational movement to key pin 598 via trigger gear 596. Referring to FIG. 88, the first actuation of firing trigger 560 can rotate trigger gear 596 in a direction indicated by arrow "A", i.e., clockwise for the purposes of this discussion. Also upon the first actuation of firing trigger 560, firing member 566 can rotate pinion gear 501 and intermediate gear 503 in a direction indicated by arrow "B", key gear 506 in a direction indicated by arrow "C", and spur gear 516 and indicator gear 592 in a direction indicated by arrow "D". In various embodiments, as illustrated in FIG. 88, trigger gear 596 and key gear 506 can be rotated in opposite directions during the first actuation of trigger 560 and may not operably engaged with each other until after the first actuation of trigger 560 as described further below. When trigger 560 is released or returned to its unactuated position after its first actuation, the pawl of the firing drive, for example, can be disengaged from the firing member 566 such that pinion gear 501 and key gear 506, for example, are not rotated, or at least substantially rotated, when trigger 560 is returned to its starting, or unactuated, position. Trigger gear 596, however, can be rotated by firing trigger 560 when trigger 560 is returned to its unactuated position and, as a result, trigger gear 596 can be rotated relative to key gear 506 as illustrated in FIG. 89. As trigger 560 is returned to its unactuated position, as described above, inclined surface 509 of trigger gear 596 can contact clutch dog 599 of key pin 598 and displace key pin 598 away from trigger gear 596 as illustrated in FIG. 90. Thereafter, trigger gear 596 can be further rotated by firing trigger 560 until inclined surface 509 has entirely passed by clutch dog 599 and spring 500 can bias clutch dog 599 into a position behind drive surface 510 as illustrated in FIG. 91. At such point, firing trigger 560 may be in its unactuated position.

Figure 92:
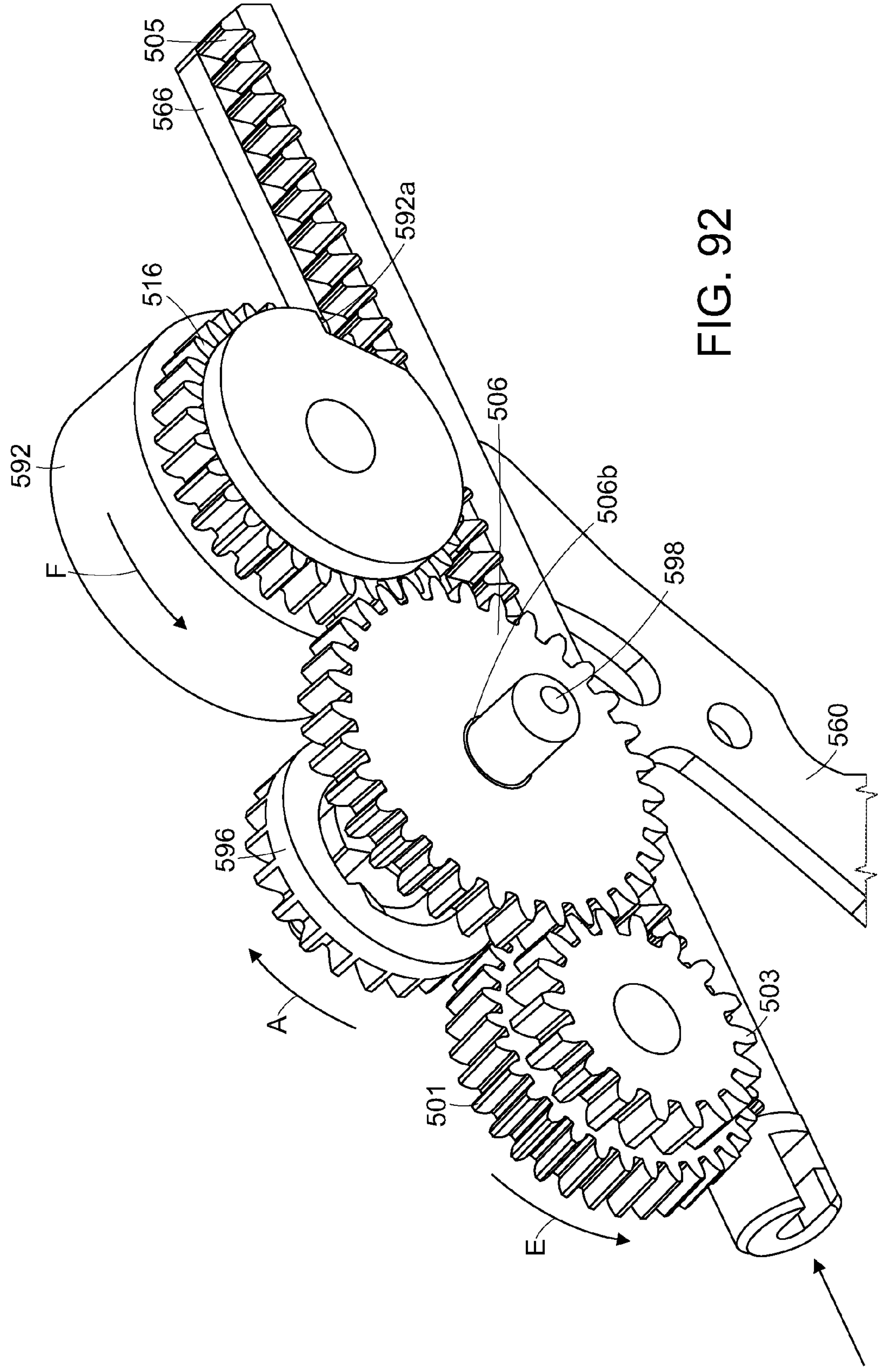
FIG. 92 is a perspective view of the reversing mechanism of FIG. 88 illustrating the directions in which the gears of the gear train rotate when the firing member is retracted.
Figure 93:
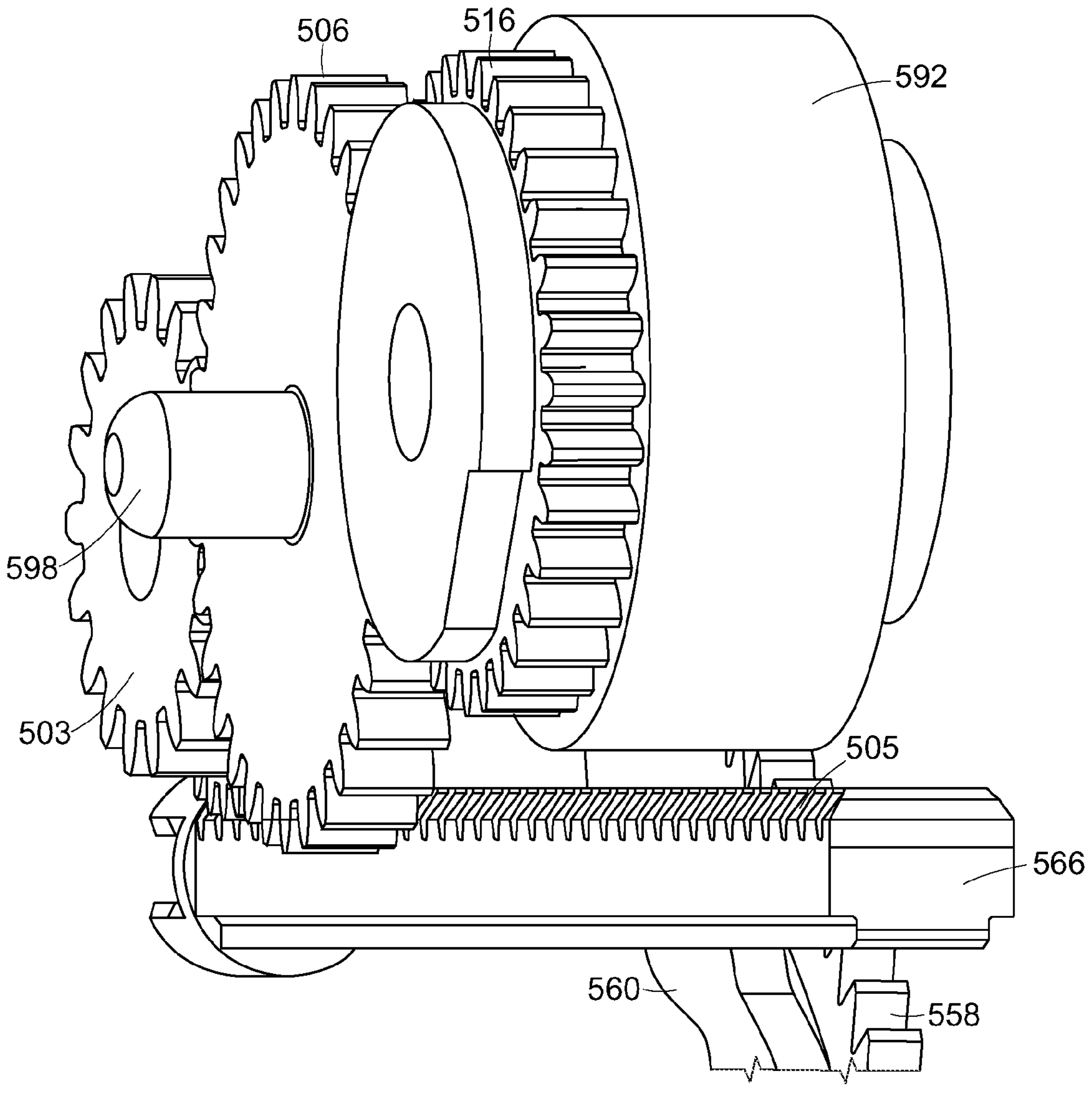
FIG. 93 is a further perspective view of the reversing mechanism of FIG. 88.

Upon a second actuation of firing trigger 560, the pawl of the firing drive can remain disengaged from firing member 566 although the second actuation of firing trigger 560 can once again rotate trigger gear 596 in a direction indicated by arrow A, referring to FIG. 92. Owing to the position of dog 599 behind drive surface 510 of trigger gear 596, the rotation of trigger gear 596 can cause key pin 598 and key gear 506 to rotate in a clockwise direction indicated by arrow A as well, i.e., in a direction opposite of arrow C. Correspondingly, key gear 506 can rotate pinion gear 501 and intermediate gear 503 in a direction indicated by arrow E, i.e., a direction opposite of arrow B, and also rotate indicator gear 592 in a direction indicted by arrow F, i.e., a direction opposite of arrow D. Owing to the rotation of pinion gear 501 in an opposite direction during the second actuation of trigger 560, pinion gear 501 can retract firing member 566 relative to the end effector and reposition, or at least substantially reposition, firing member 566 in its starting, or unactuated, position. Thereafter, firing trigger 566 can be released and returned to its unactuated position. In such circumstances, drive surface 510 of trigger gear 596 can be rotated away from clutch dog 599 and, whereas the pawl of the firing drive can still be operatively disengaged from firing member 566, key pin 598 and key gear 596 can remain in position. In order to reset the surgical instrument, the pawl of the firing drive can be released such that it can re-engage firing member 566 upon the next actuation of trigger 560. In such embodiments, the spent staple cartridge can be replaced such that the surgical instrument can be used once again.

Figure 94:
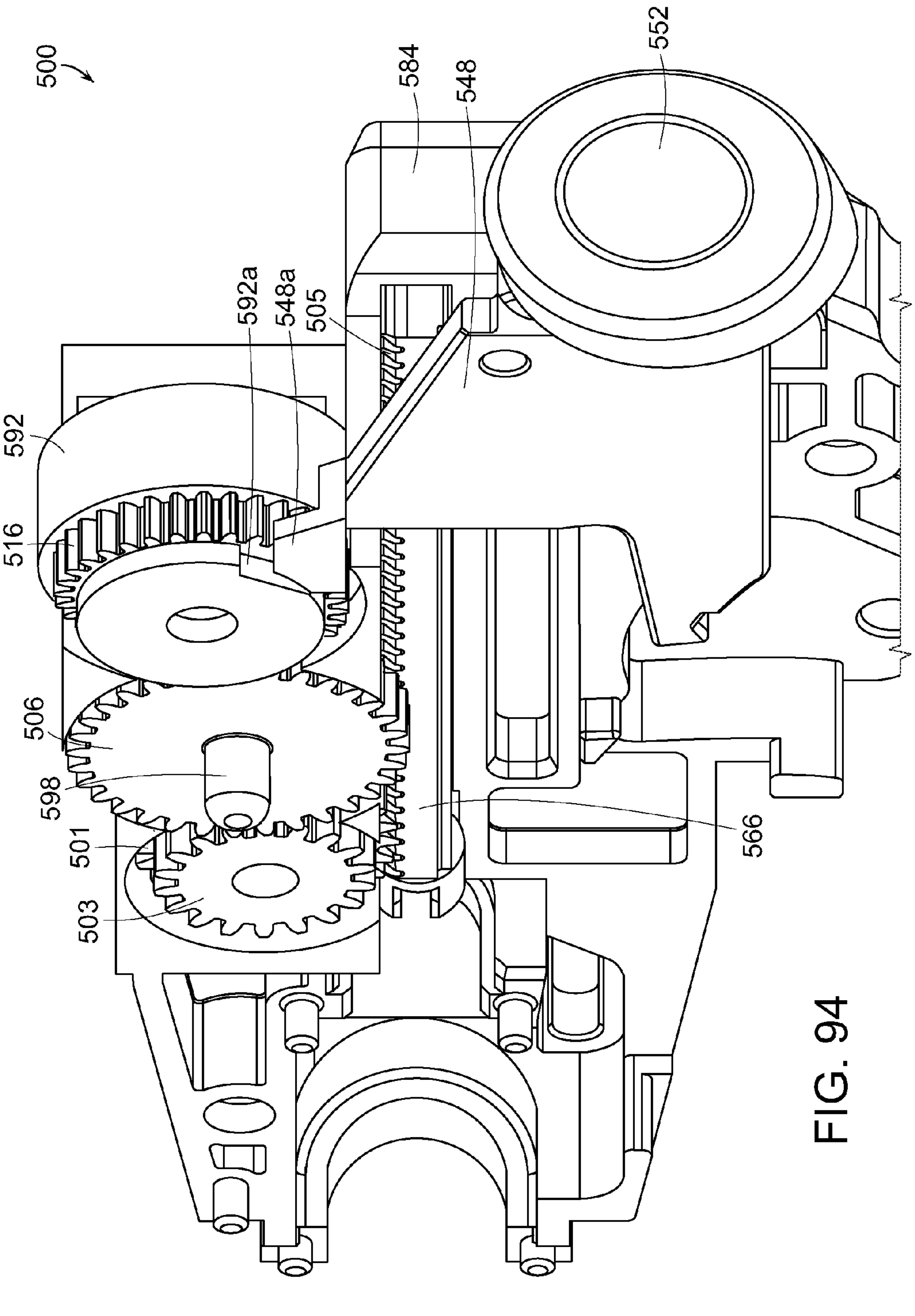
FIG. 94 is a perspective view of the surgical instrument of FIG. 87 illustrating a trigger lock which is configured to engage a gear of the reversing mechanism of FIG. 88 in addition to the trigger.

In various embodiments, referring to FIG. 94, surgical instrument 500 can further include trigger lock 548 which, similar to trigger lock 148 described above, can be utilized to hold a closure trigger in position. In at least one embodiment, trigger lock 548 can be rotated between actuated and unactuated positions to lock and unlock, respectively, a closure trigger such as closure trigger 428 (FIG. 68), for example. In at least one such embodiment, when trigger lock 548 is in its unactuated position, portion 548*a* of trigger lock 548 can be positioned within recess 592*a* of indicator 592 to prevent, or at least substantially prevent, the gear train and firing member 566 from being unintentionally motivated. Stated another way, when portion 548*a* is positioned within recess 592*a*, the firing and reversing drives described above can be rendered substantially inoperative and, as a result, firing member 566 cannot be substantially moved. When trigger lock 548 is moved into its actuated position to hold or lock the closure trigger in place, portion 548*a* of trigger lock 548 can be moved, or rotated, out of recess 592*a* such that the firing and reversing drives described above can be operated.

In various alternative embodiments, a surgical instrument can include a ratchet configured to operably engage and disengage a reversing drive with a firing member. In at least one embodiment, referring to FIGS. 95-100, surgical instrument 600 can include firing trigger 660 which can be configured to drive a firing pin and a pawl of a firing drive, for example, so as to advance firing member 666, a cutting member, and/or staple driver relative to an end effector, similar to the above. In various embodiments, also similar to the above, the surgical instrument can further include a reversing mechanism comprising pinion gear 601, key gear 606, and spur gear 616 where the advancement of firing member 666 can rotate gears 601, 606 and 616 owing to the operative engagement between rack portion 605 of firing member 696 and pinion gear 601. In various embodiments, return, or key, pin 698 can be mounted to or integrally formed with key gear 606 such that rotational motion can be transmitted therebetween. Also similar to the above, firing trigger 660 can include gear portion 658 which can be operatively engaged with trigger gear 696 such that gear portion 658 can rotate trigger gear 696 about an axis defined by key pin 698.

In use, upon the first actuation of firing trigger 660, firing trigger 660 can rotate trigger gear 696 about key pin 698 without directly transmitting rotational movement to key pin 698 and key gear 606. More particularly, referring to FIG. 97, trigger gear 696 can include aperture 696*a* which can be configured such that there is a clearance fit between key pin 698 and the sidewalls of aperture 696*a* and, as a result, key pin 698 can rotate therein. Furthermore, referring to FIG. 96, key gear 606 can include ratchet face 606*c* and trigger gear 696 can include ratchet face 696*c* which, when firing member 666 is being advanced by the firing drive, can be operably disengaged, or separated, from one another such that rotational movement is also not transmitted therebetween. After firing member 666 has been sufficiently advanced, similar to the above, return carriage 694 can be rotated downwardly about pin 694*a*, for example, such that return carriage 694, referring to FIG. 99, can be disengaged from end 698*a* of return pin 698. In such circumstances, as described in greater detail below, return pin 698 can be operatively engaged with trigger gear 696 and firing member 666 can be retracted.

Figure 95:
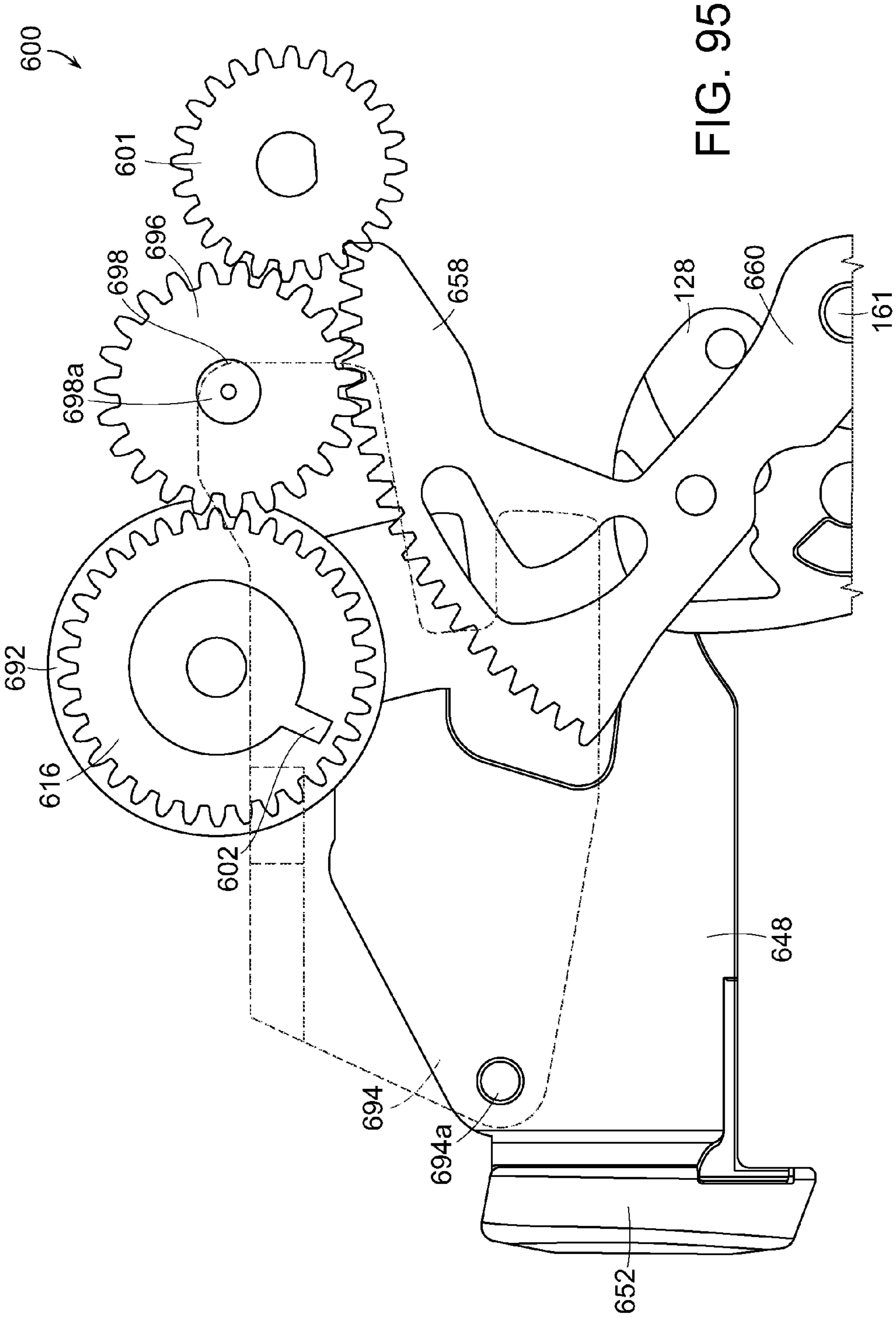
FIG. 95 is an elevational view of a reversing mechanism of a surgical instrument in accordance with an alternative embodiment of the present invention illustrating a return carriage in an unactuated position with some components of the surgical instrument removed.
Figure 96:
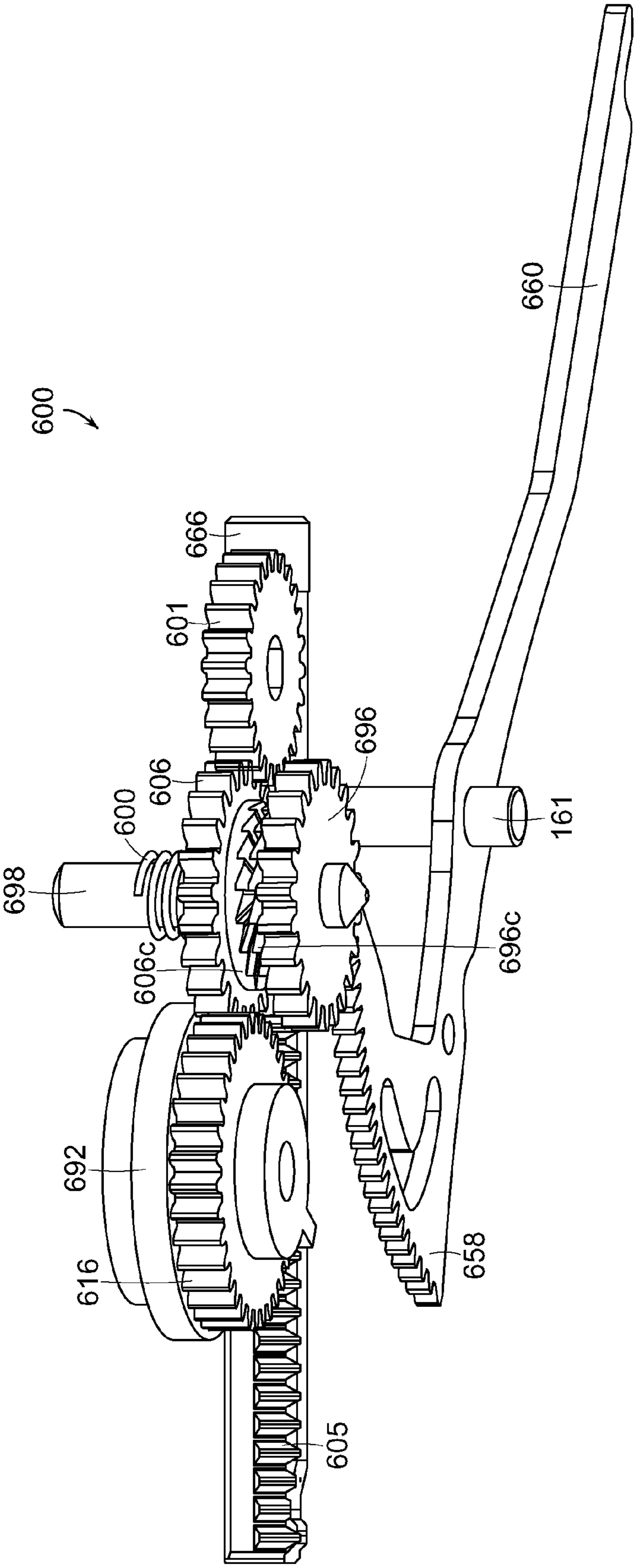
FIG. 96 is a perspective view of the reversing mechanism of FIG. 95 illustrating a trigger gear having a ratchet face and, in addition, a key gear having a ratchet face with some additional components of the surgical instrument removed.
Figure 98:
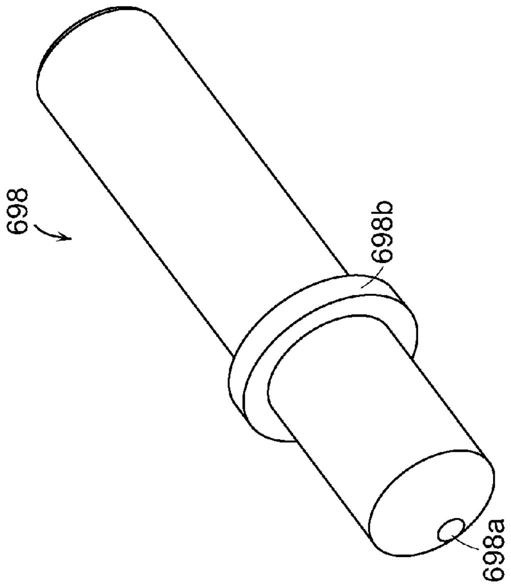
FIG. 98 is a perspective view of a return pin of the reversing mechanism of FIG. 95.
Figure 97:
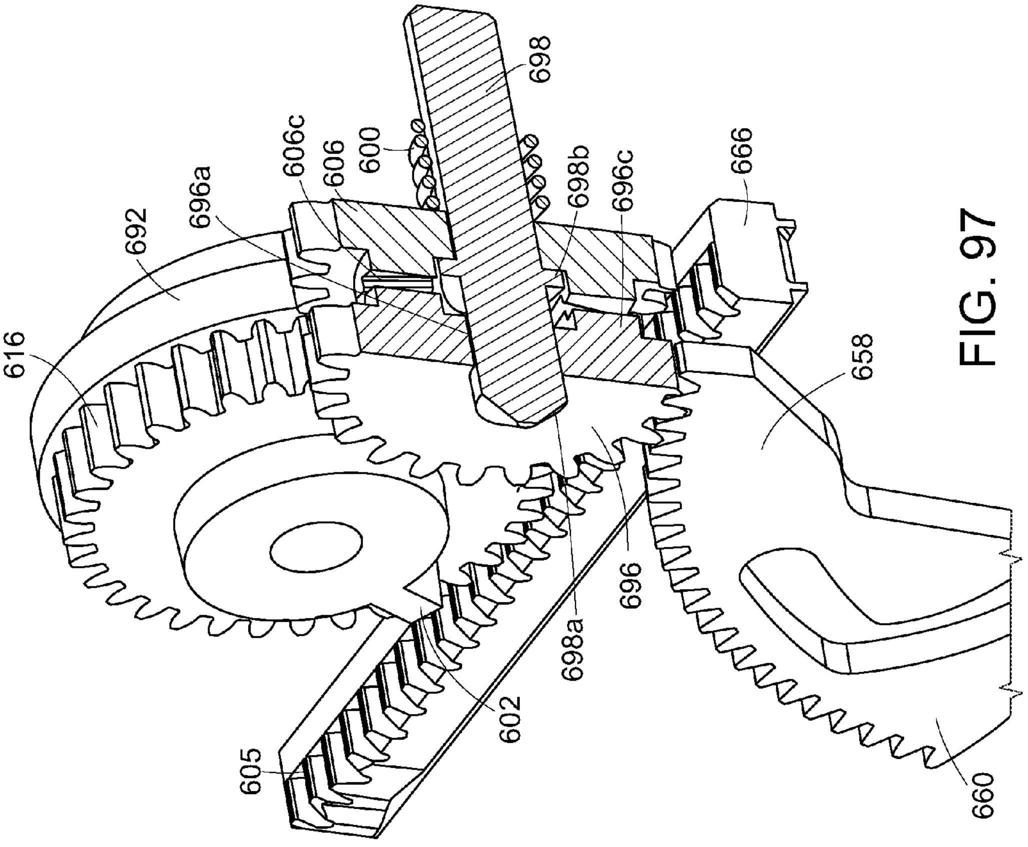
FIG. 97 is a cross-sectional view of the reversing mechanism of FIG. 95 illustrated in the configuration of FIG. 96.
Figure 99:
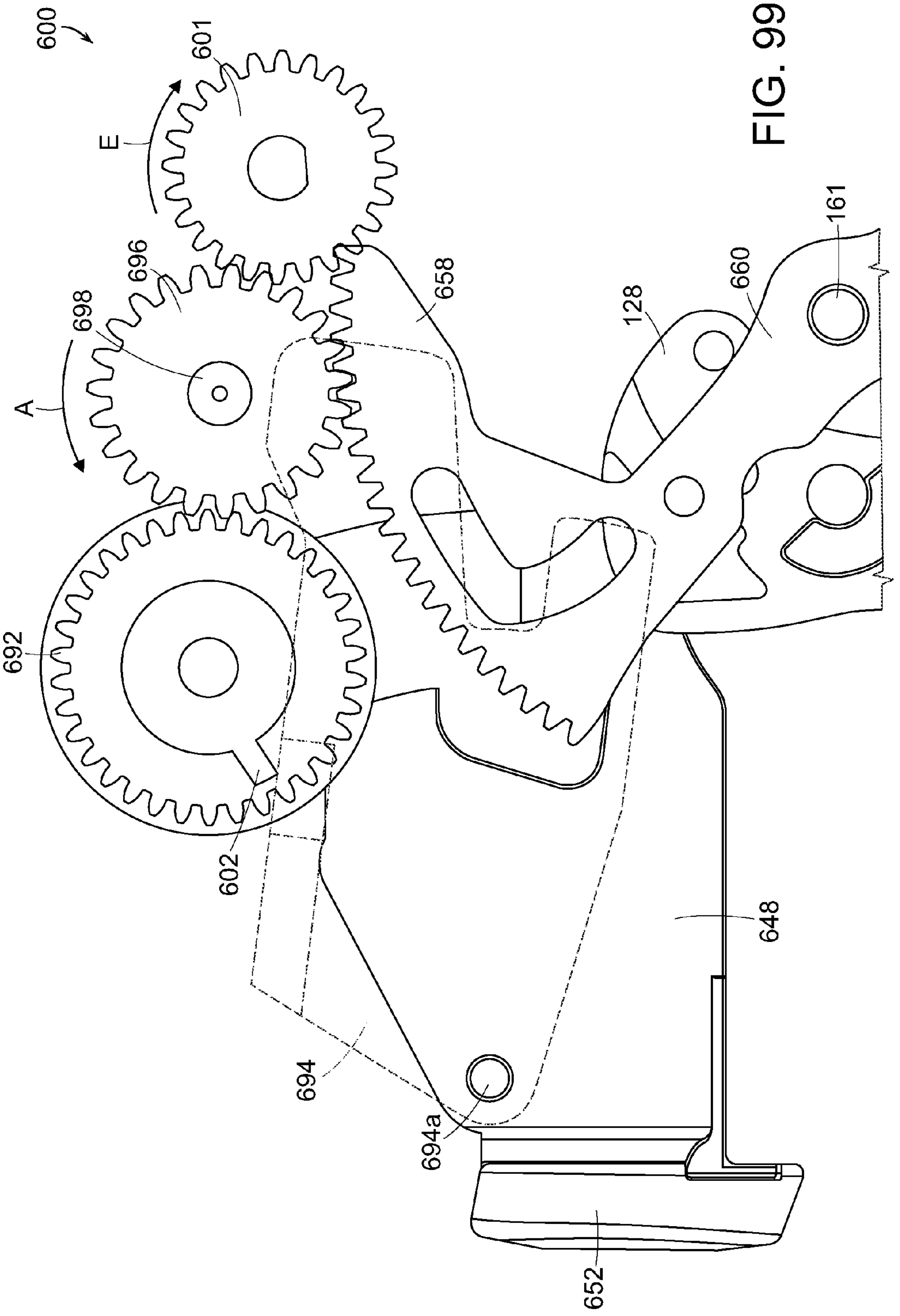
FIG. 99 is an elevational view of the reversing mechanism of FIG. 95 illustrating the return carriage in an actuated position.

In various embodiments, further to the above, return carriage 694 can be manually moved between its unactuated position illustrated in FIG. 95 to its actuated position illustrated in FIG. 99, similar to return carriage 494. In addition to or in lieu of the above, at least one of the gears in the gear train, such as indicator gear 692, for example, can include a cam, such as cam 602, for example, which can contact return carriage 694 and rotate it downwardly after a predetermined amount of actuations of firing trigger 660. Thereafter, in either event, key gear 606 can be slid toward trigger gear 696 by spring 600. More particularly, referring to FIG. 100, spring 600, which can be positioned, or compressed, intermediate key gear 606 and a frame of the surgical instrument, for example, such that, once return carriage 694 has been disengaged from end 698*a* of return pin 698, spring 600 can expand to slide key gear 606 toward trigger gear 696. Furthermore, in at least one embodiment, return pin 698 can be mounted to or integrally formed with key gear 606 such that return pin 698 can be slid toward trigger gear 696 with key gear 606. In at least one embodiment, referring to FIG. 97, return pin 698 can include collar 698*b* in which key gear 606 can abut and push return pin 698 toward trigger gear 696.

Figure 100:
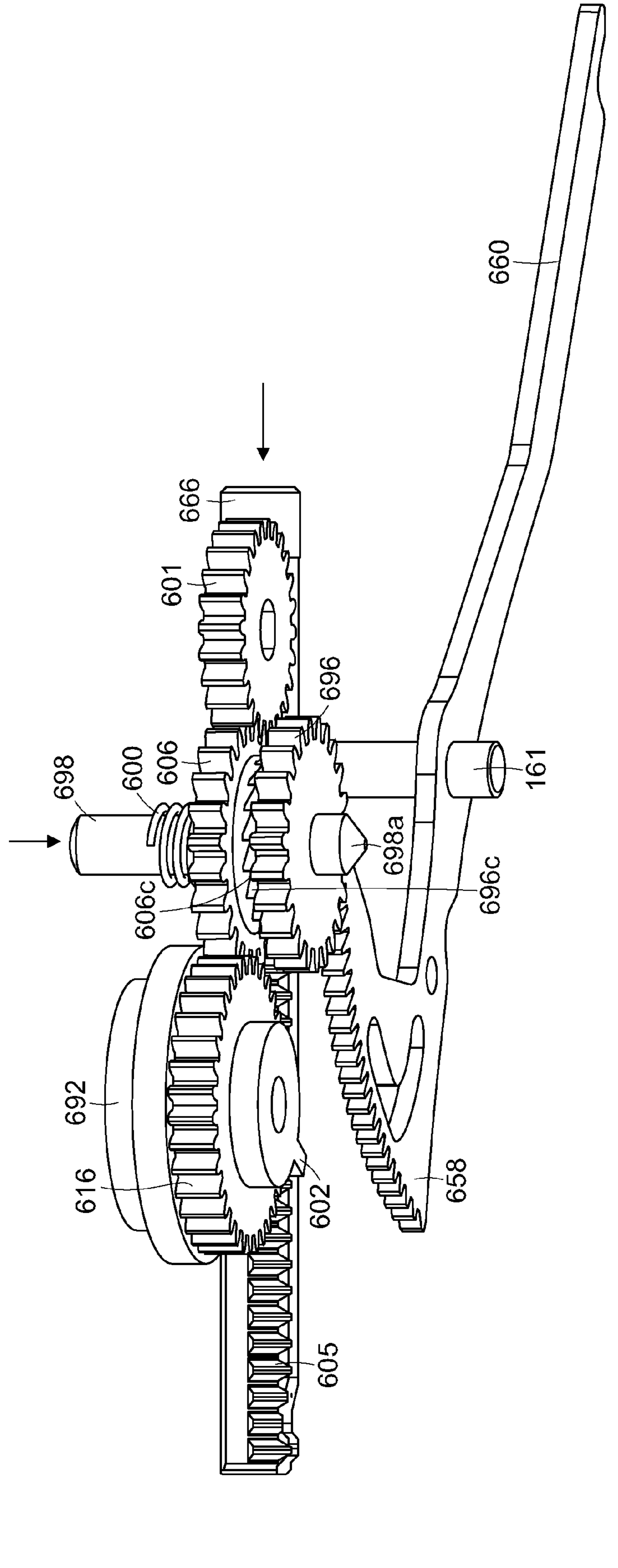
FIG. 100 is a perspective view of the reversing mechanism of FIG. 95 wherein the ratchet faces of the trigger and key gears are engaged with one another.

In various embodiments, as a result of the above, ratchet faces 606*c* and 696*c* can be positioned against one another by spring 600 when return carriage 694 is rotated downwardly into its actuated position as illustrated in FIG. 100. In at least one embodiment, referring to FIG. 97, ratchet faces 606*c* and 696*c* can each include teeth extending therefrom which can cooperate to transmit rotational movement therebetween. In use, upon a subsequent actuation of firing trigger 660, firing trigger 660 can rotate trigger gear 696, and key gear 606, in a clockwise direction indicated by arrow A, referring to FIG. 99, wherein key gear 606 can rotate pinion gear 601 in a direction indicated by arrow E. As a result of the operative engagement between pinion gear 601 and rack portion 605 of firing member 666, for example, pinion gear 601 can retract firing member 666, the cutting member, and/or the staple driver relative to the end effector, similar to the above. In at least one embodiment, gears 601, 606, and 696 and gear portion 658 can be configured such that firing member 666 can be fully retracted with one actuation of trigger 460.

Thereafter, firing trigger 460 can be released and/or returned to its unactuated position. In at least one such embodiment, ratchet faces 606*c* and 696*c* can include beveled surfaces which can allow ratchet faces 606*c* and 696*c* to rotate relative thereto when trigger 660 is returned to its unactuated position. In such circumstances, trigger gear 696 can be rotated in a counterclockwise direction, i.e., in a direction opposite of that indicated by arrow A. In at least one embodiment, ratchet faces 606*c* and 696*c* can rotate relative to each other eventhough the ratchet faces are in contact with one another. Thereafter, return carriage 694 can be rotated upwardly such that it can contact end 698*a* of return pin 698 and slide return pin 698 and key gear 606 away from trigger gear 696. In such circumstances, as a result, ratchet face 606*c* can be disengaged from ratchet face 696*c* such that they are no longer operably engaged with one another. In at least one such embodiment, return carriage 694 can apply a force to end 698*a* of return pin 698, wherein the force can be transmitted to key gear 606 via collar 698*b* in order to displace key gear 606 away from trigger gear 696.

Figure 103:
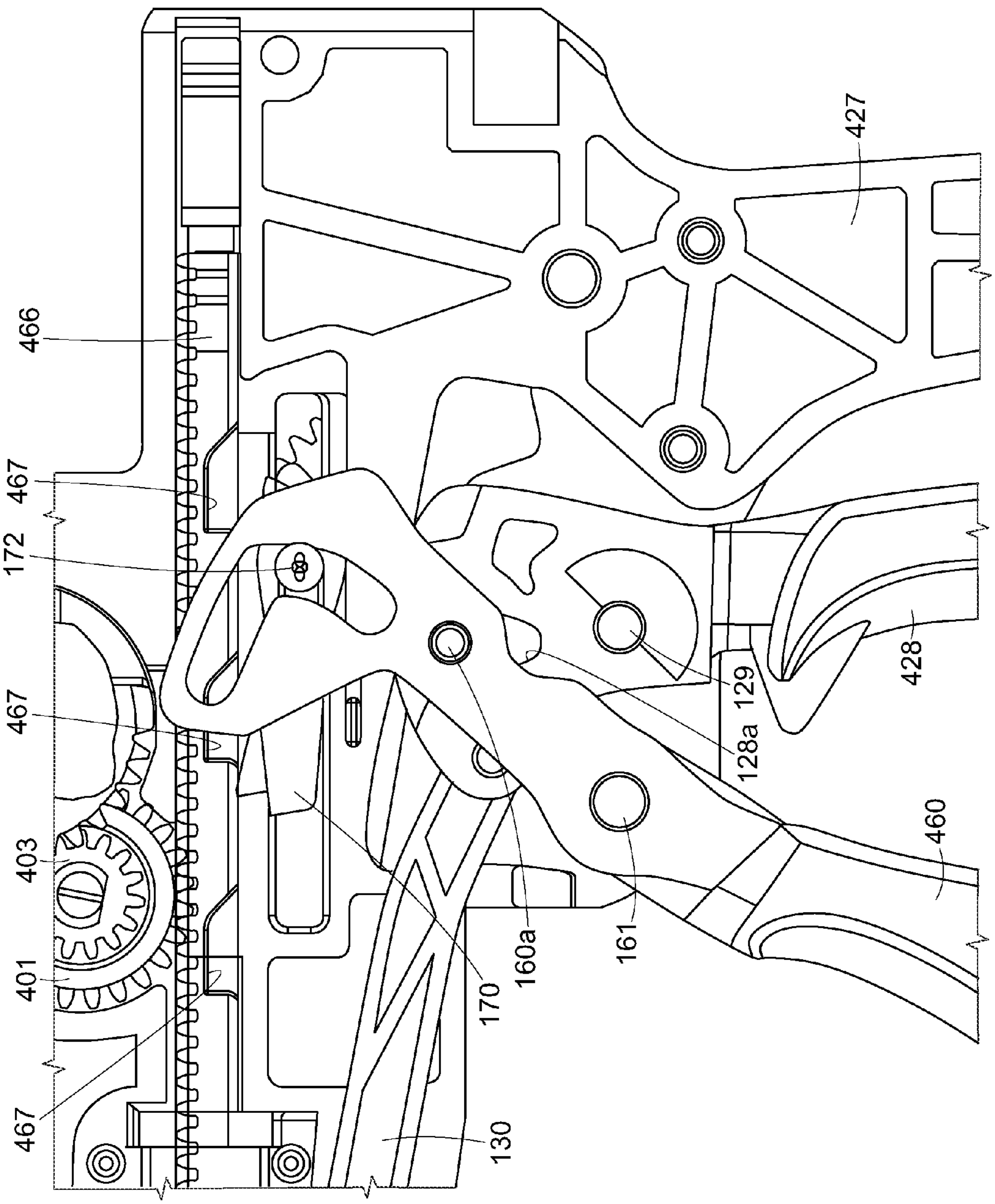
FIG. 103 is an elevational view of the surgical instrument of FIG. 101 illustrating misalignment between the pawl and a recess in the firing member when the firing member unintentionally backs-up relative to its intended position.

As described above, surgical instruments in accordance with the present invention can include a firing drive having a pawl which can be configured to advance a firing member relative to an end effector. In various embodiments, as described above, pawl 170 can be pivoted upwardly to engage a recess 467 in firing member 466, for example, and advance firing member 466 distally. Thereafter, referring once again to FIGS. 101 and 102, pawl 170 can be pivoted downwardly and retracted proximally relative to firing member 466 so as to reposition pawl 170 such that pawl 170 can be pivoted upwardly once again to engage another recess 467 and further advance firing member 466. In various circumstances, though, pawl 170 may not be able to engage a recess 467 when it is pivoted upwardly as illustrated in FIG. 103. Such circumstances may arise when firing member 466, for example, is unintentionally moved by forces or energy transmitted through and/or stored within the various mechanisms of the surgical instrument. If the pawl is unable to re-engage the firing member, the surgical instrument may be rendered inoperable and, as a result, the surgical instrument may have to be manually reset. In order to ameliorate this condition, surgical instruments in accordance with various embodiments of the present invention can include an anti-backup mechanism which can retain, or at least substantially retain, the firing member in position.

Figure 104:
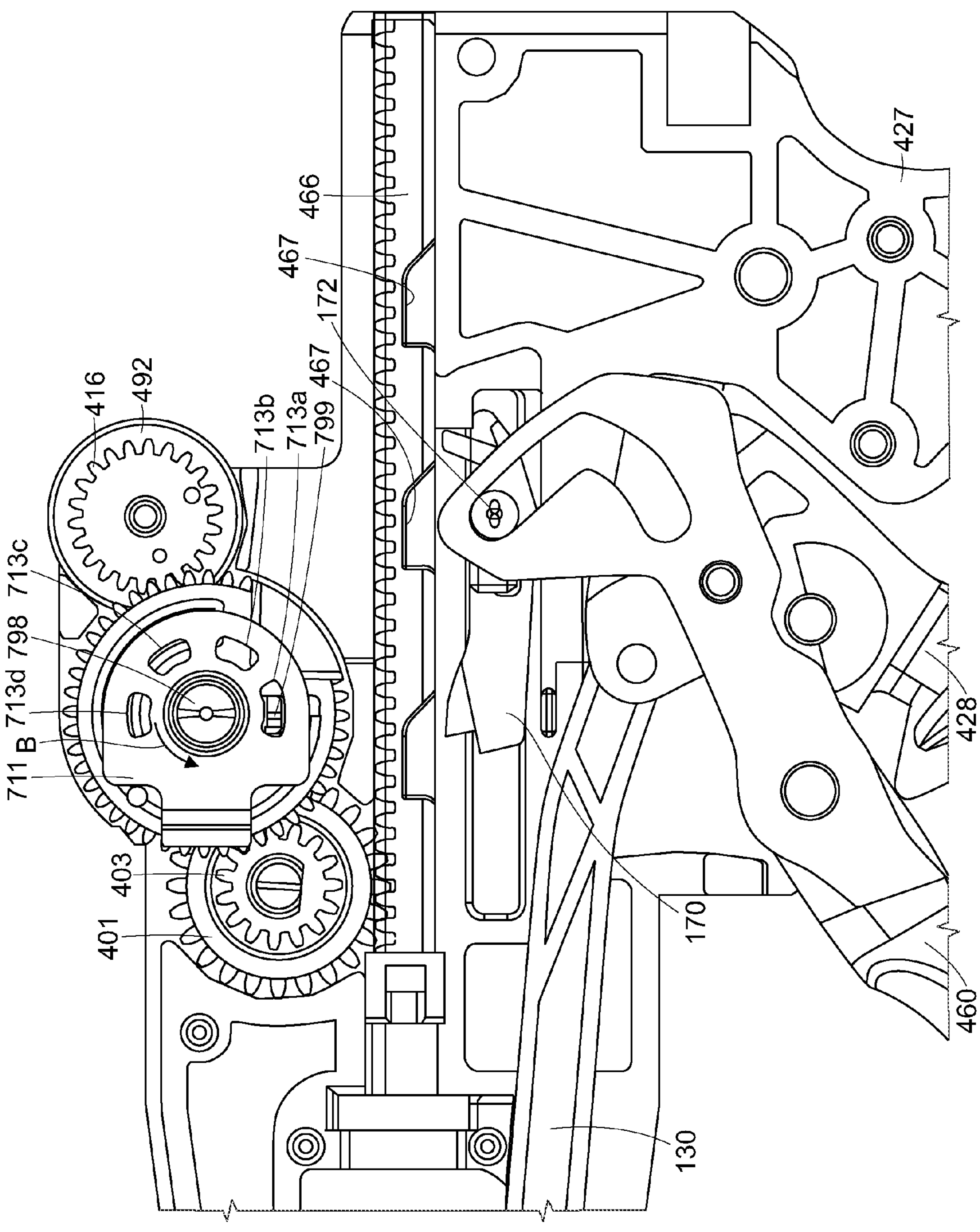
FIG. 104 is an elevational view of a surgical instrument in accordance with an alternative embodiment of the present invention including an anti-backup mechanism with some components of the surgical instrument removed.

In various embodiments, referring to FIG. 104, an anti-backup mechanism can be configured to hold at least a portion of a firing drive and/or reversing drive in position while pawl 170 is retracted relative to firing member 466, for example. In at least one embodiment, an anti-backup mechanism can include indexing mechanism, or plate, 711 which can be configured to permit return pin 798 to rotate in a counter-clockwise direction indicated by arrow B when firing member 466 is advanced, as described above, yet prohibit, or at least substantially prohibit, return pin 798 from rotating in a clockwise direction, i.e., in a direction opposite of arrow B. In effect, as return pin 798 is rotatably engaged with key gear 406, and key gear 406 is operably engaged with firing member 466 via intermediate gear 403 and pinion gear 401, indexing mechanism 711 can also prevent, or at least substantially prevent, firing member 466 from being retracted proximally. Furthermore, as described in greater detail below, indexing mechanism 711 can also inhibit firing member 466 from being unintentionally advanced distally as well.

Figure 106:
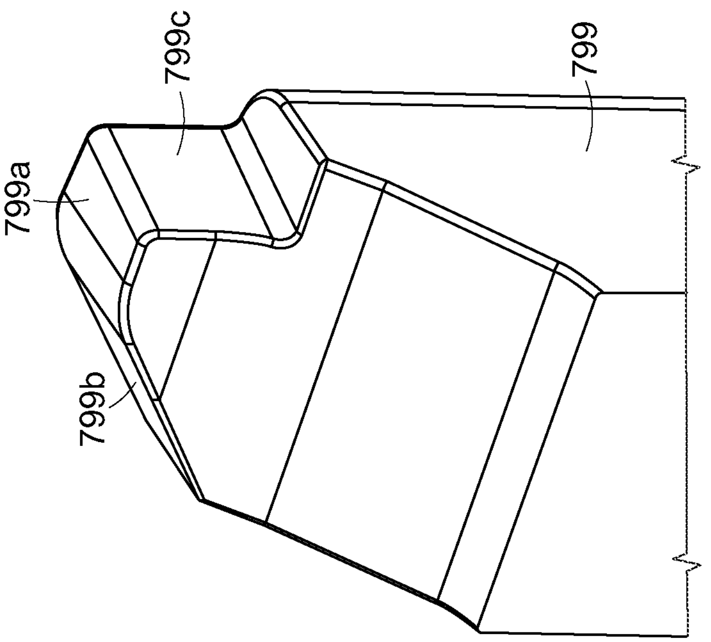
FIG. 106 is a detail view of a key extending from the return pin of FIG. 105.
Figure 105:
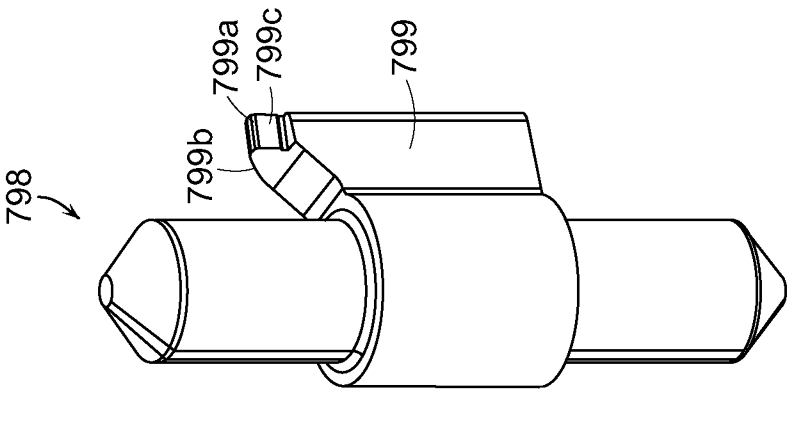
FIG. 105 is a perspective view of a return pin of the anti-backup mechanism of FIG. 104.
Figure 107:
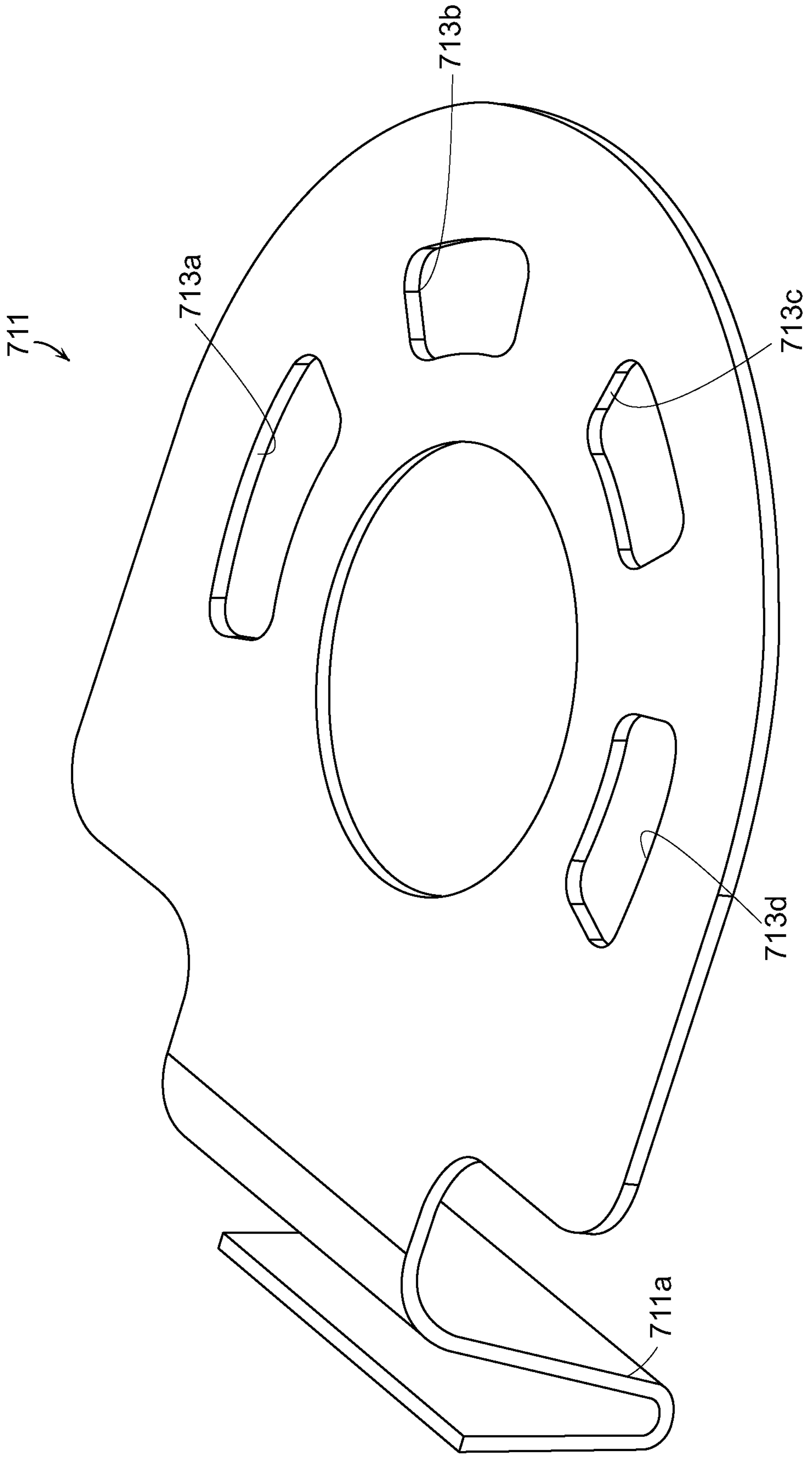
FIG. 107 is a perspective view of an indexing element of the anti-backup mechanism of FIG. 104.
Figure 108:
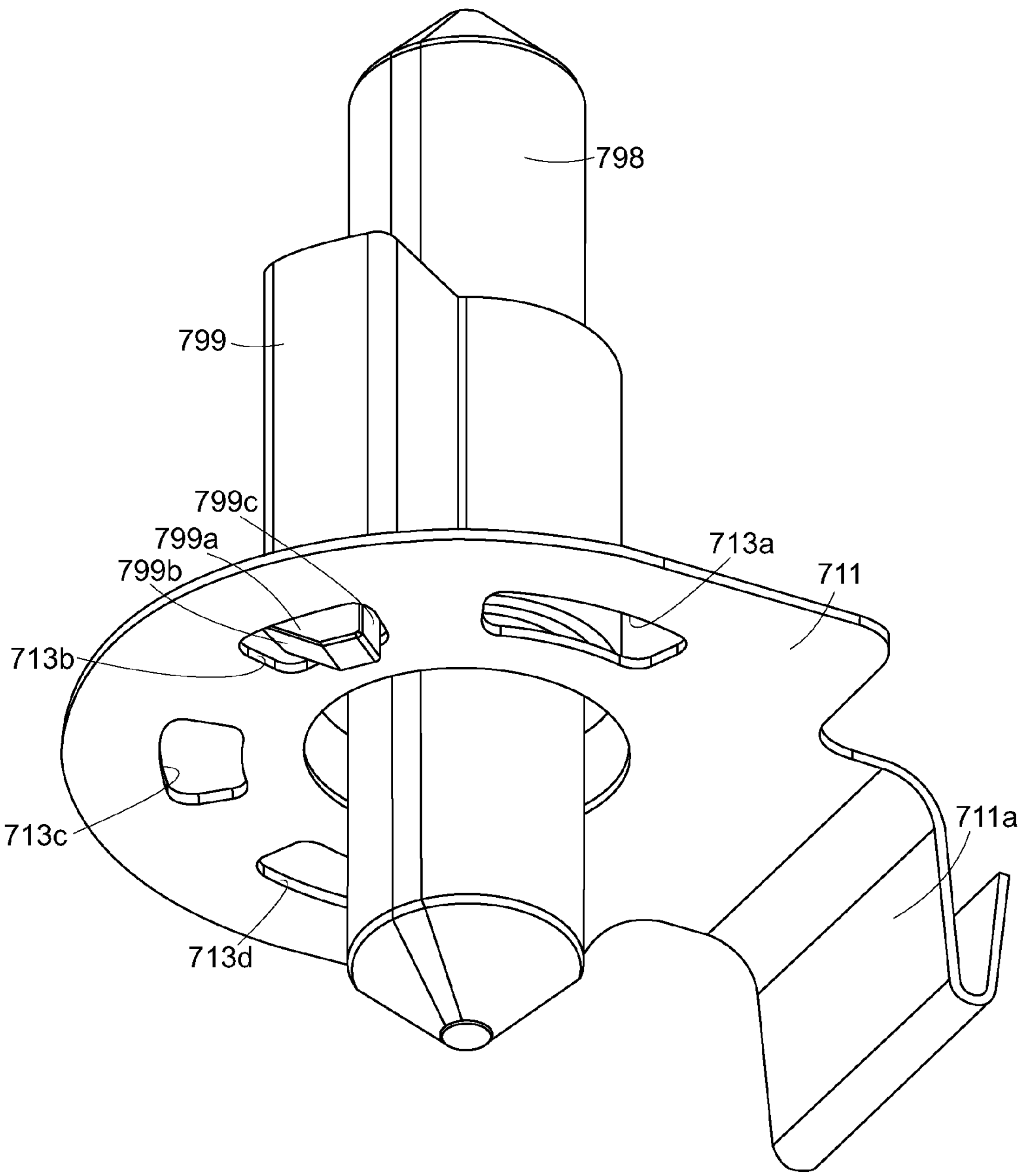
FIG. 108 is a perspective view of the return pin of FIG. 105 operably engaged with the indexing element of FIG. 107.
Figure 111:
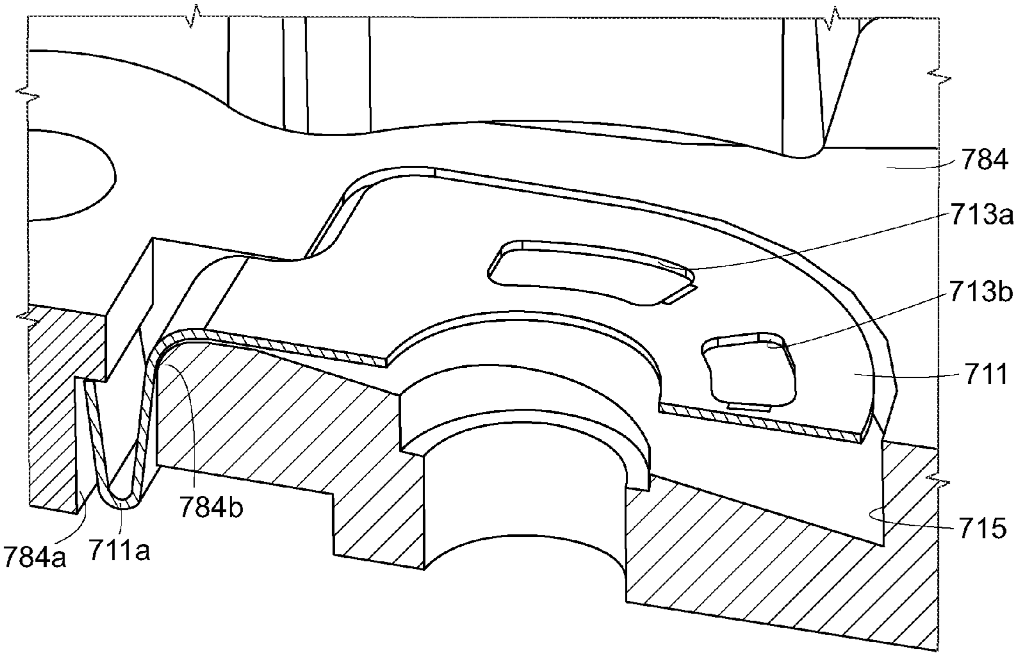
FIG. 111 is a cross-sectional view of the indexing element of FIG. 107.

In order to prevent return pin 798 from unintentionally rotating as outlined above, indexing element 711 can include one or more recesses and/or apertures therein for holding or retaining return pin 798 in position. In various embodiments, referring to FIGS. 104, 107, and 111, indexing mechanism 711 can comprise a leaf spring including clip end **711*a* which can be retained within recess 784*a* of frame 784 such that indexing mechanism 711 can flex and/or rotate relative to fulcrum 784*b* of frame 784. In at least one embodiment, referring to FIGS. 105 and 106, return pin 798 can include key 799 extending therefrom wherein key 799 can be configured to engage indexing mechanism 711. More particularly, in at least one such embodiment, indexing mechanism 711 can include a plurality of recesses, or apertures, 713*a-d*, referring to FIGS. 107 and 108, which can each be configured to retain projection 799*a* extending from key 799 therein and thereby hold return pin 798** in position as described in greater detail below.

Figure 109:
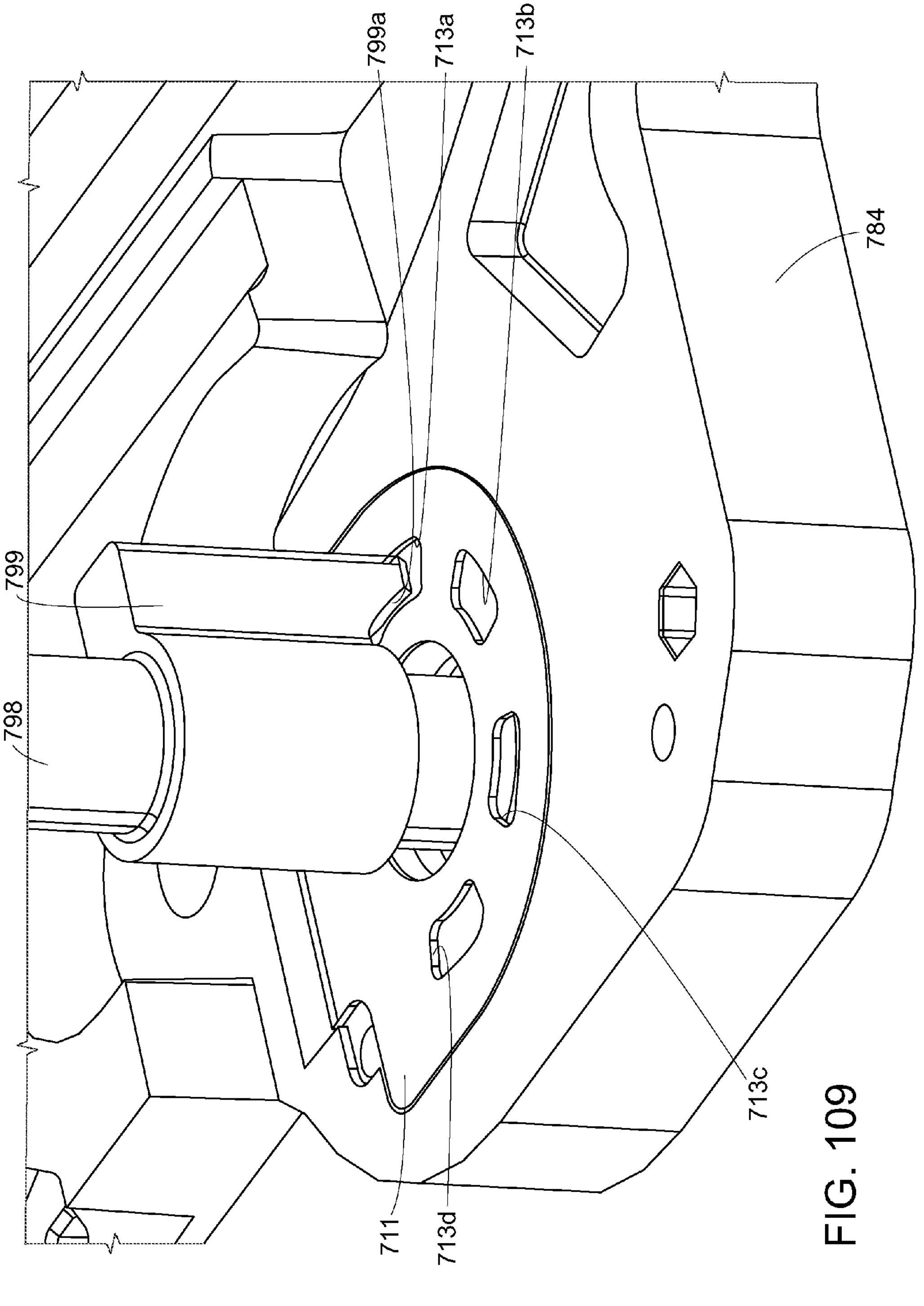
FIG. 109 is a perspective view of the return pin and the indexing element illustrating the key of the return pin positioned within a first aperture in the indexing element.
Figure 110A:
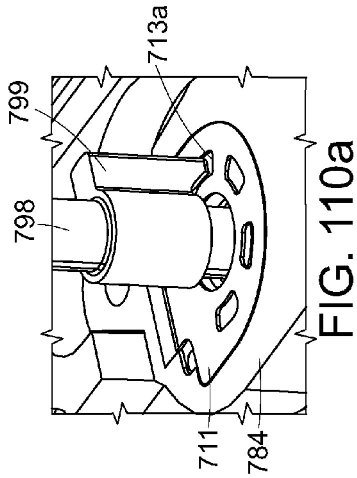
FIG. 110*a* is another perspective view of the return pin key and the indexing element of FIG. 109.
Figure 110B:
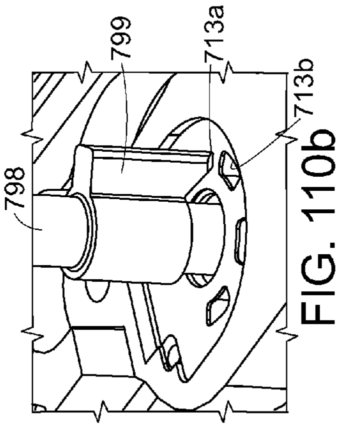
FIG. 110*b* is a perspective view of the return pin key depressing the indexing element when the return pin key is moved from the first aperture to a second aperture of the indexing element.

In use, an end effector of the surgical instrument can be closed onto the soft tissue of a patient, for example and, thereafter, as outlined above, a firing member of the surgical instrument can be advanced by a firing drive. Prior to the advancement of the firing member, projection **799*a* of return pin 798 can be received within first aperture 713*a* of indexing element 711 as illustrated in FIG. 110*a*. In various embodiments, referring to FIGS. 106 and 109, key 799 can further include inclined or beveled surface 799*b* which can be configured such that, when return pin 798 is rotated in a direction indicated by arrow B by firing member 466, pinion gear 401, intermediate gear 403, and key gear 406 upon the first actuation of trigger 460, beveled surface 799*b* can contact the edge of aperture 713*a* and deflect and/or rotate indexing mechanism 711 downwardly as illustrated in FIG. 110*b*. Notably, a certain amount of force may be required to deflect and/or rotate indexing mechanism 711 and, as a result, the possibility of return pin 798 being unintentionally displaced from recesses 713 can be reduced. More particularly, absent a large pulling force applied to firing member 766, for example, the recesses in the indexing element may be able to hold key 799 of return pin 798 therein and, correspondingly, the possibility that firing member 466** may be unintentionally advanced can also be reduced.

Figure 110C:
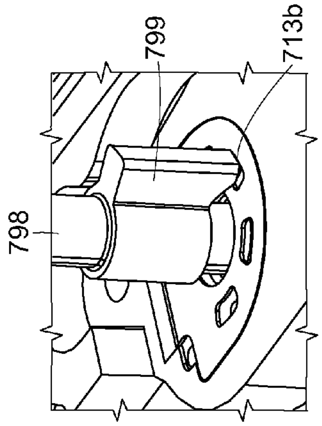
FIG. 110*c* is a perspective view of the key portion of the return pin positioned within the second aperture of the indexing element.

By the end of the first actuation of firing trigger 460, key 799 can be positioned within second aperture **713*b* of indexing mechanism 711 as illustrated in FIG. 110*c*. In such a position, key 799 can be prevented from moving backward into aperture 713*a* owing to stop surface 799*c*. More particularly, referring to FIG. 108, key 799 can further include stop surface 799*c* which can be configured to abut the perimeter of aperture 713*b*, for example, and, owing to the configuration of stop surface 799*c*, aperture 713*b* and stop surface 799*c* can be configured to prevent key 799 from deflecting or rotating indexing mechanism 711 downwardly within recess 715 (FIG. 111) and allowing return pin 798 to be rotated in a direction opposite of arrow B. In at least one such embodiment, stop surface 799*c* and the perimeter of aperture 713*b* can include surfaces which are parallel to one another. In other various embodiments, the abutting surfaces can include at least partially beveled portions which can be configured such that, when stop surface 799*c* is forced against the edge of aperture 713*b*, key 799 can be further drawn into aperture 713*b* as opposed to being lifted out of the same. In either event, owing to the operative relationship between return pin 798, the gears of the gear train, and firing member 466 as described above, firing member 466 can be prevented, or at least substantially prevented, from unintentionally retracting proximally by indexing member 711. In such embodiments, as a result, the possibility that pawl 170 may be misaligned relative to the recesses 467 within firing member 466 when pawl 170 is retracted relative to firing member 466**, for example, can be reduced.

Figure 110D:
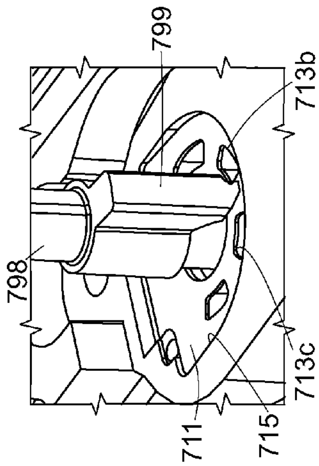
FIG. 110*d* is a perspective view of the return pin key depressing the indexing element when the return pin key is moved from the second aperture to a third aperture of the indexing element.
Figure 110E:
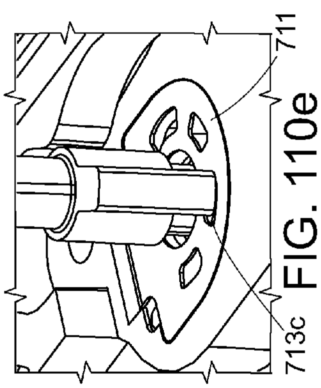
FIG. 110*e* is a perspective view of the key portion of the return pin positioned within the third aperture of the indexing element.
Figure 110F:
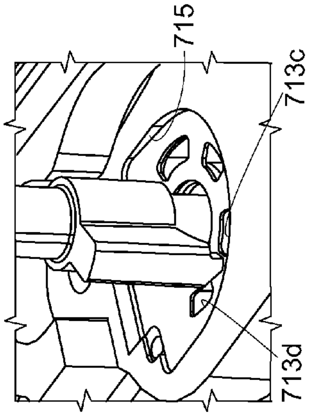
FIG. 110*f* is a perspective view of the return pin key depressing the indexing element when the return pin key is moved from the third aperture to a fourth aperture of the indexing element.
Figure 110G:
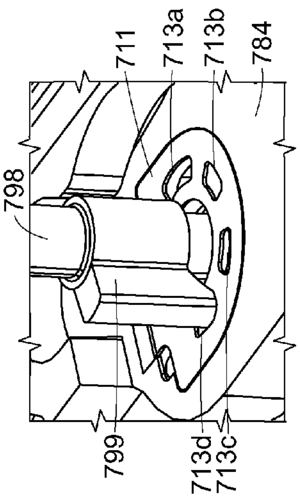
FIG. 110*g* is a perspective view of the key portion of the return pin positioned within the fourth aperture of the indexing element.

Upon a second actuation of firing trigger 460, firing member 466 can once again rotate gears 401, 403, and 406 such that return pin 798 is rotated in a direction indicated by arrow B. In various embodiments, as a result, beveled surface **799*b* can contact the edge of second aperture 713*b* and deflect and/or rotate indexing mechanism 711 downwardly as illustrated in FIG. 110*d*. By the end of the second actuation of firing trigger 460, key 799 can be positioned within third aperture 713*c* of indexing mechanism 711 as illustrated in FIG. 110*e*. In such a position, key 799 can be prevented from moving backward into second aperture 713*b* owing to stop surface 799*c*, similar to the above. Furthermore, upon a third actuation of firing trigger 460, firing member 466 can once again rotate return pin 798 in a direction indicated by arrow B and, as a result, beveled surface 799*b* can contact the edge of third aperture 713*c* and deflect and/or rotate indexing mechanism 711 downwardly as illustrated in FIG. 110*f*. By the end of the third actuation of firing trigger 460, key 799 can be positioned within fourth aperture 713*d* of indexing mechanism 711 as illustrated in FIG. 110*g*. In such a position, similar to the above, key 799 can be prevented from moving backward into third aperture 713*c* owing to stop surface 799*c***.

At such point, in order to operably engage the reversing drive with the firing member, similar to the above, return pin 798 and key 799 can be moved toward trigger gear 496 in order to operably engage key gear 406 with trigger gear 496. In various embodiments, as a result, projection **799*a* can be moved away from indexing member 711 and out of fourth aperture 713*d*. Thereafter, upon the return stroke of firing trigger 460, firing member 466 can be retracted and return pin 798 can be rotated in a clockwise direction, i.e., in a direction opposite arrow B. At such point, firing member 466 and pawl 170 will have both been returned to their staring positions, return pin 798 will have been rotated such that it is realigned with first aperture 713***a*, and return pin 798 can be disengaged from trigger gear 496 such that key 499 is slid into engagement with first aperture 713*a*. Thereafter, as a result, the surgical instrument can be used once again.

Figure 112:
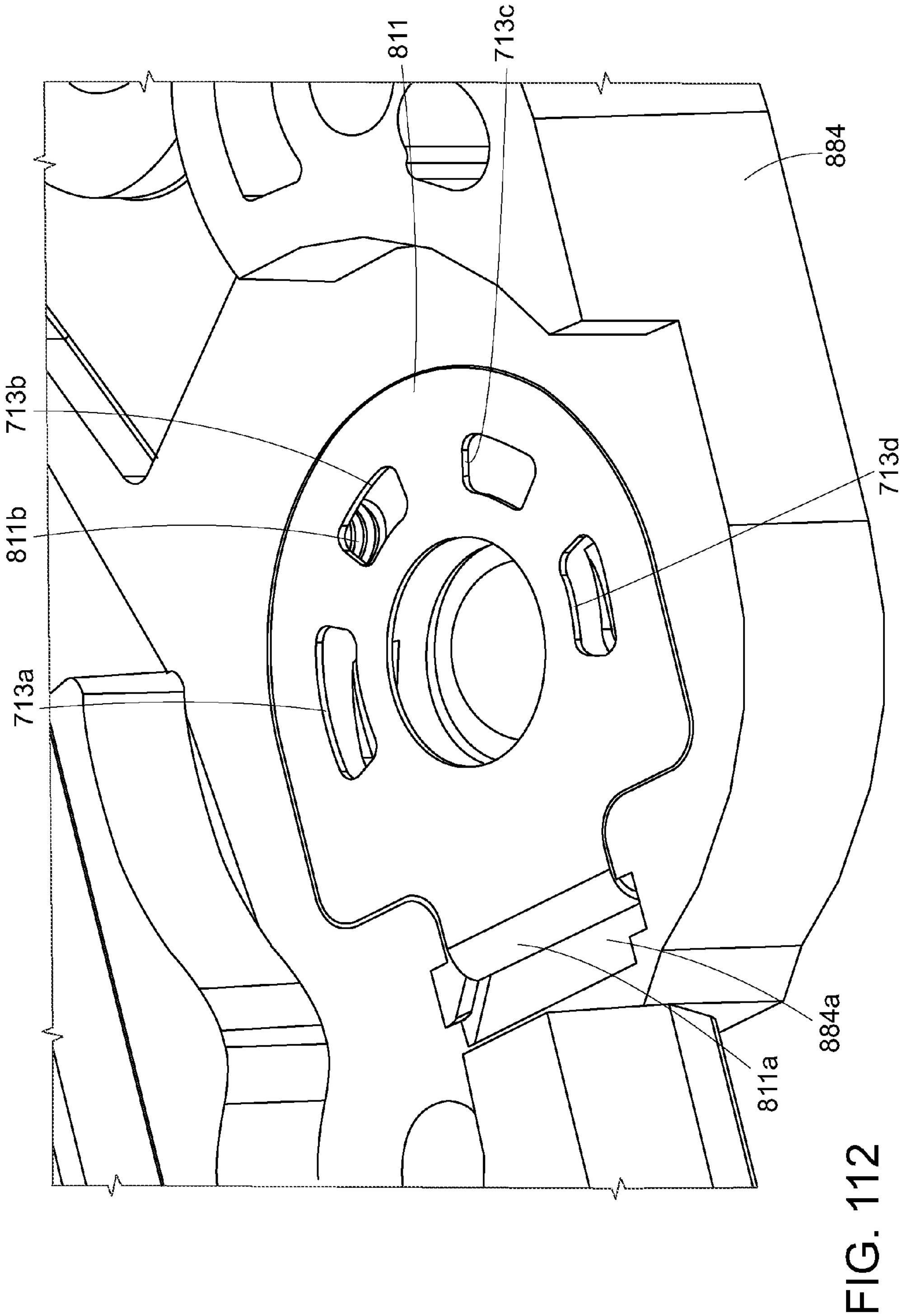
FIG. 112 is a perspective view of an indexing element in accordance with an alternative embodiment of the present invention and a return spring operatively engaged with the indexing element.
Figure 113:
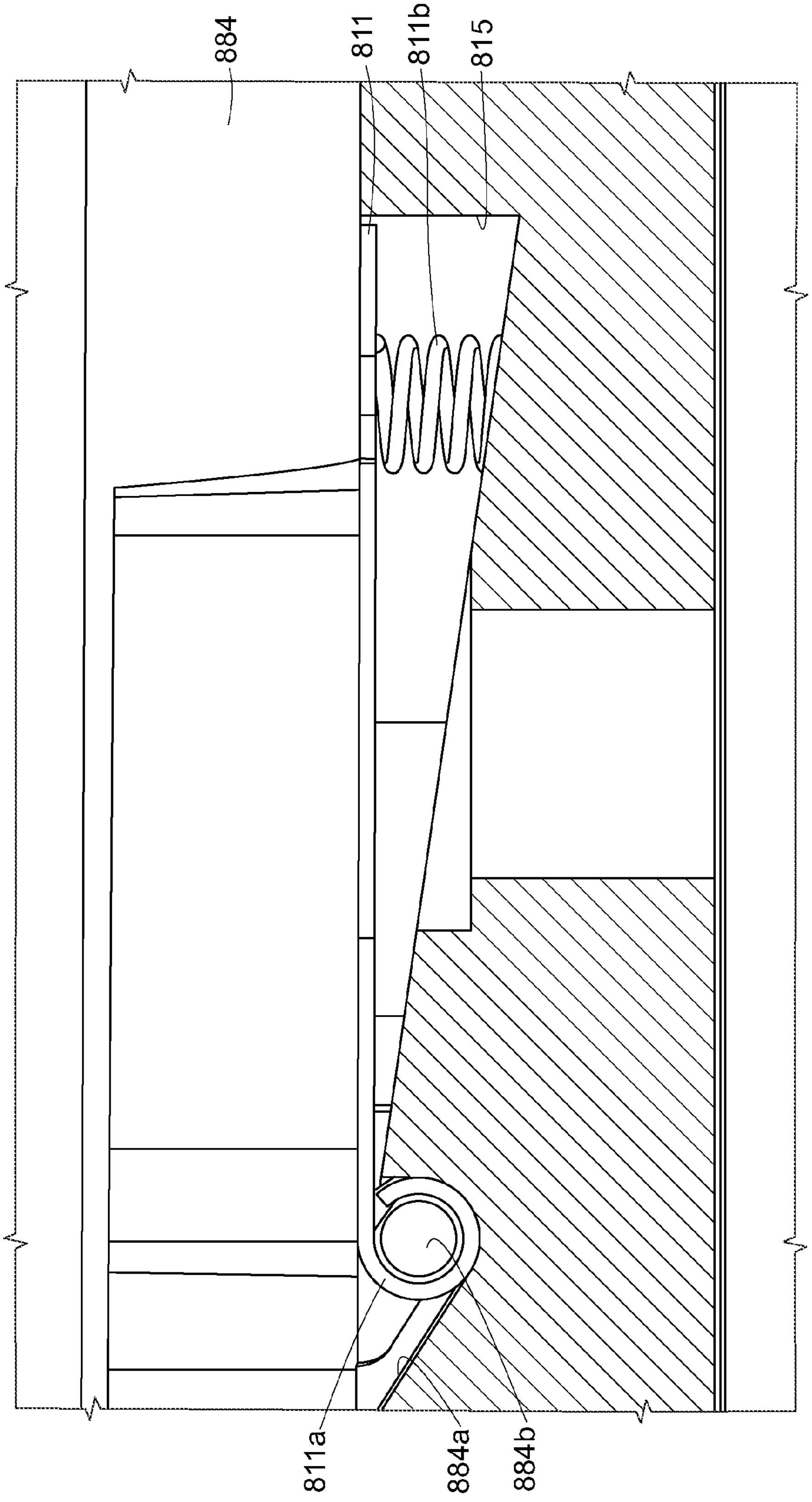
Figure 114:
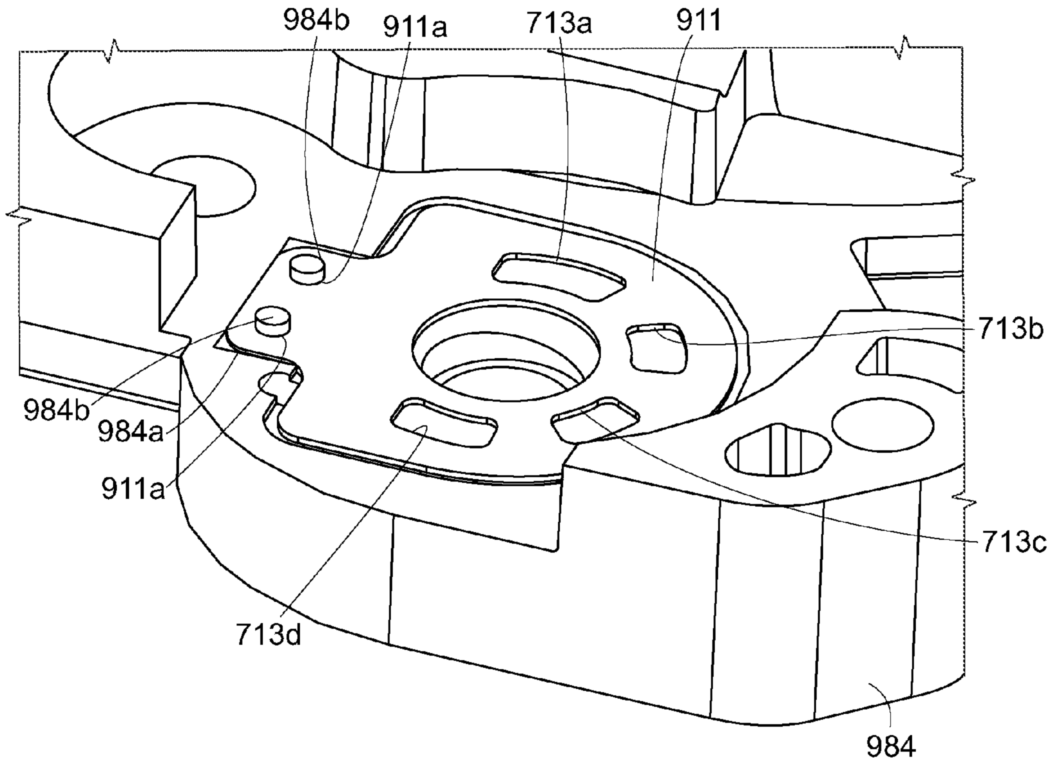

In various alternative embodiments, referring to FIGS. 112 and 113, an anti-backup mechanism can include indexing element, or plate, 811 which can be rotatably mounted within recess 884*a* of frame 884 such that hinge end 811*a* can be rotatably mounted to pin portion 884*b*. In at least one embodiment, similar to the above, indexing element 811 can be rotated and/or deflected relative to pin 811*b*. In various embodiments, the anti-backup mechanism can further include at least one spring element, or return spring, 811*b* within recess 815 which can be configured to bias indexing member 811 into the position illustrated in FIGS. 112 and 113. Similarly, return spring 811*b* can be further configured to restore indexing element to such a position after it has been deflected by key 799 as outlined above. In various embodiments, the at least one return spring can be positioned intermediate indexing element 811 and a sidewall of recess 815, for example. In various alternative embodiments, referring to FIG. 114, an anti-backup mechanism can include indexing element 911 which, similar to the above, can be mounted within recess 984*a* of frame 984. In at least one such embodiment, frame 984 can further include mounting projections 984*b* which can be configured to be press-fit within apertures 911*a* in indexing element 911 such that indexing element 911 can be flexed and/or rotated relative to frame 984.

In various alternative embodiments, an anti-backup mechanism in accordance with at least one embodiment of the present invention can include a ratchet mechanism for preventing, or at least limiting, undesirable movement of the firing member and/or gear train. In various embodiments, referring to FIGS. 115-118, the ratchet mechanism can include a pawl which can be configured to allow the gears of the gear train, such as indicator gear 492 and spur gear 416, for example, to rotate in a first direction when they are driven by the firing member, such as firing member 466, for example, yet prohibit, or at least limit, the gears from rotating in an opposite direction when the pawl of the firing drive, such as pawl 170, for example, is retracted relative to the firing member. In at least one embodiment, referring to FIG. 116, the ratchet mechanism can include leaf spring, or pawl, 1011 which can limit the rotation of spur gear 416 as described in greater detail below.

Further to the above, when firing member 466, for example, is advanced by firing trigger 460, for example, firing member 466 can rotate spur gear 416 in a direction indicated by arrow D (FIG. 116) owing to the operative engagement of pinion gear 401, intermediate gear 403, key gear 406, and spur gear 416 as described above. When spur gear 416 is rotated in direction D, in at least one embodiment, gear teeth 416*a* of gear 416 can be configured to contact and deflect pawl 1011 such that gear teeth 416*a* can pass thereby. However, in the event that firing member 466 is unintentionally retracted and/or spur gear 416 is rotated in a direction indicated by arrow H, pawl 1011 can be configured such that at least a portion thereof can be positioned intermediate two adjacent gear teeth 416*a* and prevent, or at least limit, spur gear 416 from rotating in direction H. In various embodiments, referring to FIG. 116, at least a portion of pawl 1011 can be wedged between gear teeth 416*a* or 'bite' into gear 416 such that gear 416 cannot substantially rotate in direction H, at least not until the reversing drive of the surgical instrument is operably engaged with the firing member as described in greater detail below.

Figure 115:
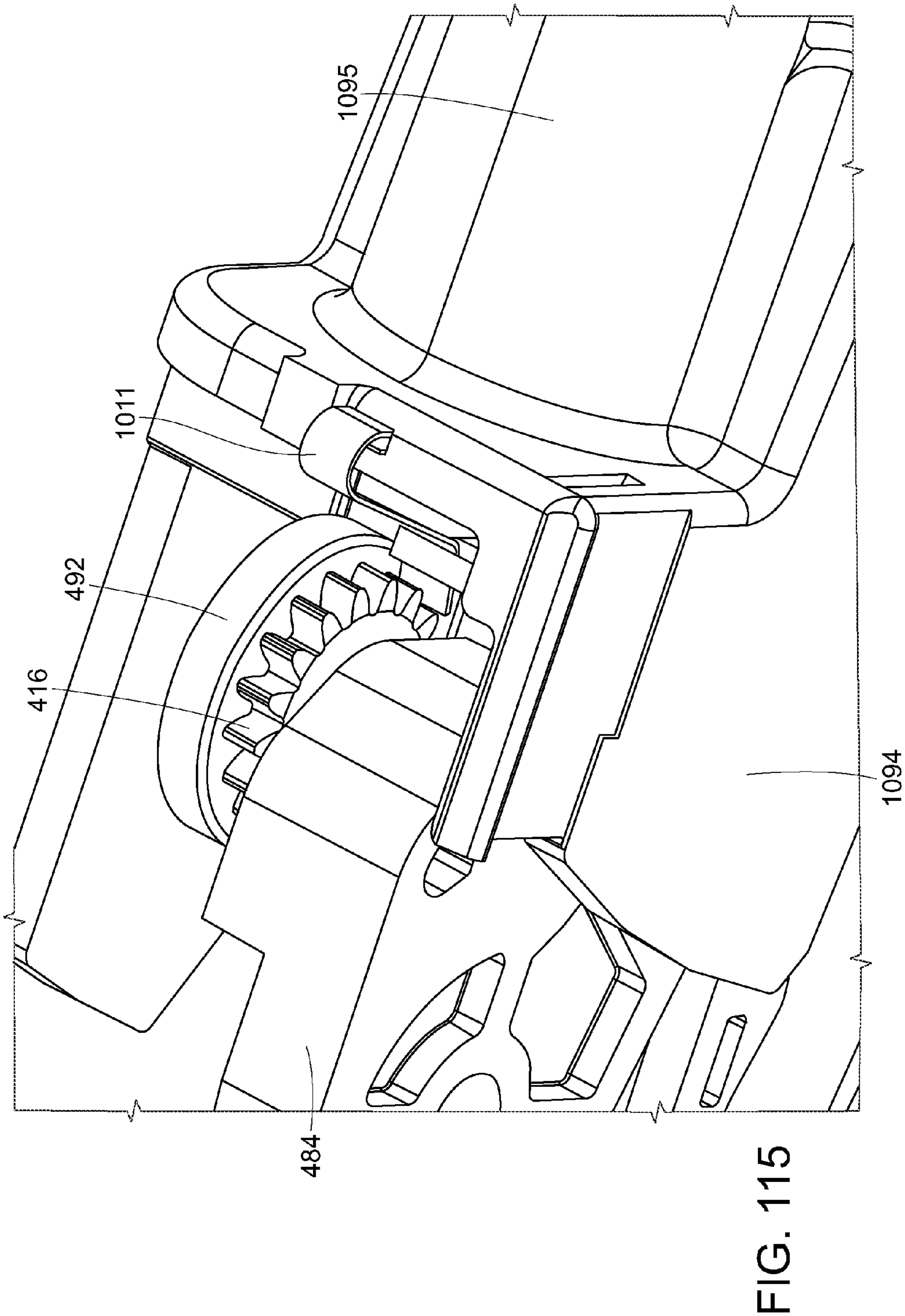
Figure 116:
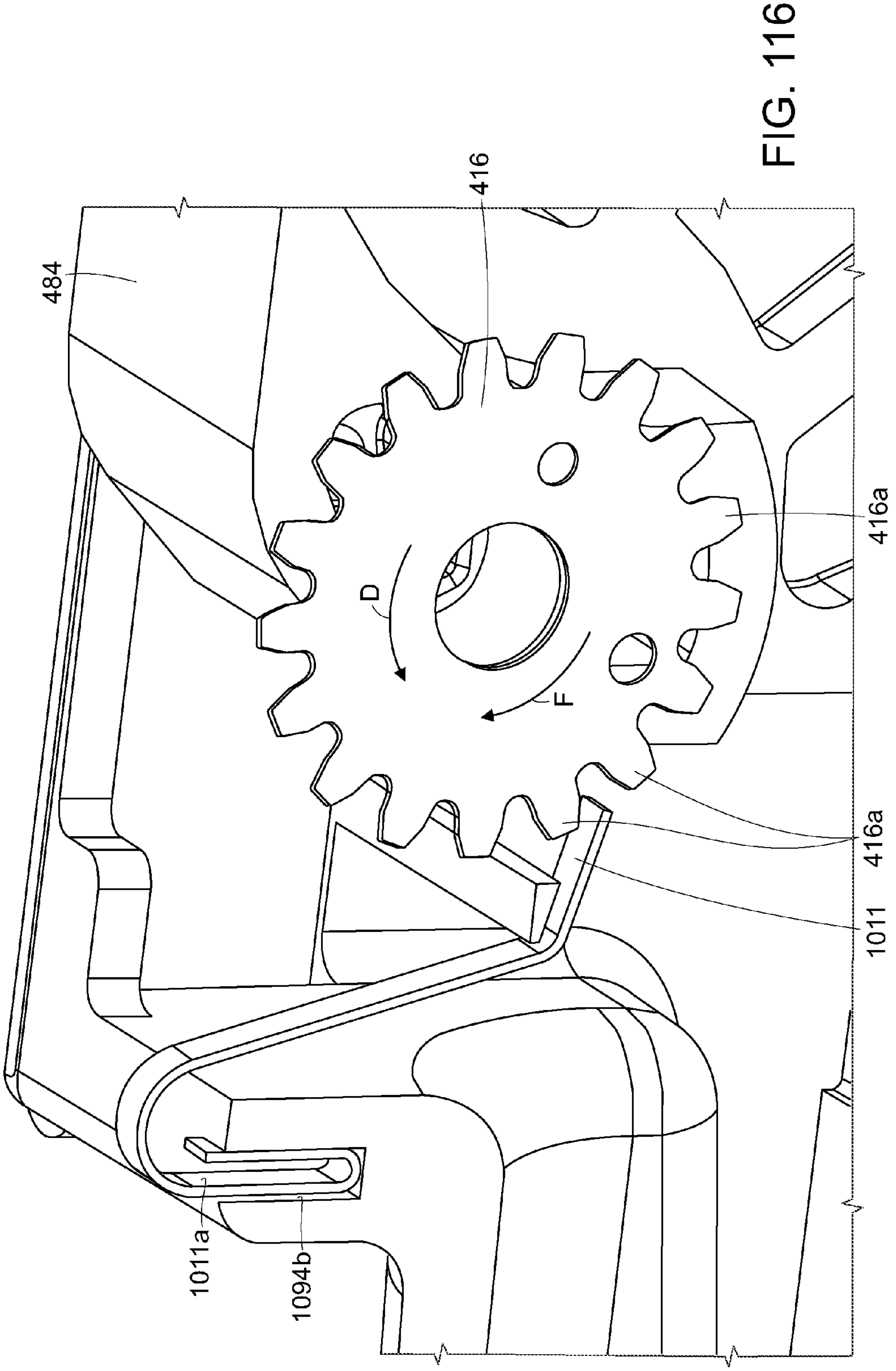
Figure 117:
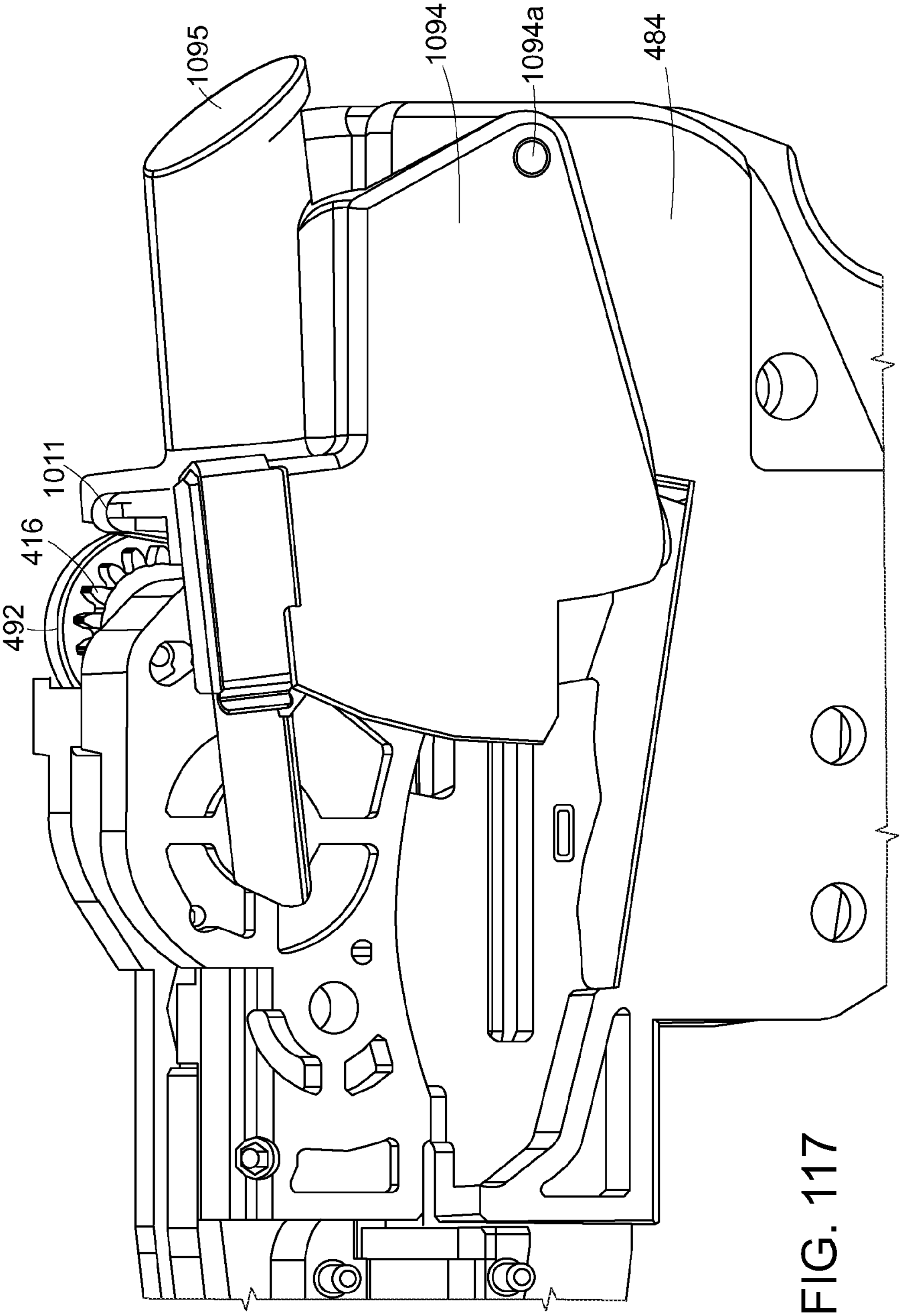
Figure 118:
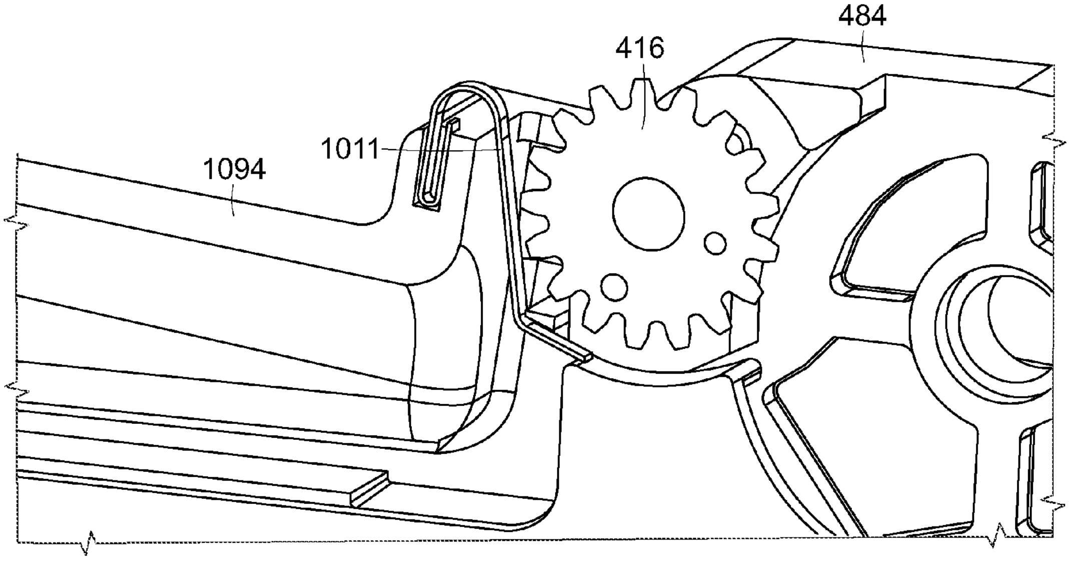

In various embodiments, the surgical instrument can include a return carriage which can be moved between an unactuated position as illustrated in FIGS. 115 and 116 and an actuated position as illustrated in FIGS. 117 and 118 to place the surgical instrument in its reversing or retracting mode of operation. Similar to return carriage 494, in at least one embodiment, return carriage 1094 can be rotated relative to frame 484 about pin 1094*a*. In various embodiments, referring to FIG. 118, pawl 1011 can be mounted to return carriage 1094 such that, when return carriage 1094 is rotated downwardly into its actuated position, pawl 1011 can be moved out of operative engagement with spur gear 416. In such circumstances, spur gear 416 can be permitted to rotate in a direction indicated by arrow H when the surgical instrument is placed in its reversing mode. When spur gear 416 is permitted to rotate in direction H, the gear train can be permitted to rotate without interference, or at least substantial interference, from the anti-backup mechanism such that the firing member can be retracted as outlined above. After the firing member has been sufficiently retracted, return carriage 1094 can be rotated upwardly into its unactuated position and pawl 1011 can be operably re-engaged with spur gear 416.

In various circumstances, a reversing drive of a surgical instrument may be prevented from being properly engaged with a firing member of the surgical instrument. In at least one embodiment, the return carriage of a reversing drive, such as return carriages 494 and 1094, for example, may not be able to properly contact and motivate firing pin 172 and/or return pin 498, for example. More particularly, the return carriage may fail to properly displace firing pin 172 and/or return pin 498 such that key gear 406 is operably engaged with trigger 496 and, furthermore, such that pawl 170 is prevented from operably engaging firing member 466. In various embodiments, as outlined above, a return carriage can include a button portion which can be configured to manually rotate the return carriage downwardly when a force is applied thereto. In various circumstances, however, this force may have insufficient leverage to move the return carriage, especially if the return carriage and/or one of pins 172 and 498 is stuck in position, for example.

In various embodiments of the present invention, a surgical instrument can include a switch which can be better configured to manually engage the reversing drive of the surgical instrument with the firing member. In at least one embodiment, referring to FIG. 119, the switch can include first and second portions, wherein first portion 1194 can be movably connected relative to frame 1184, for example, and wherein second portion 1118 can also be movably connected relative to frame 1184 as well. In various embodiments, first switch portion 1194 can be pivotably connected to frame 1184 such that, when first switch portion 1194 is pivoted downwardly by a cam, similar to cam 402, for example, first portion 1194 can be configured to disengage return pin 498 and allow key portion 499 of return pin 498 to engage trigger gear 496 as described above. In various embodiments, although not illustrated in FIG. 119, return carriage 1194 can include arm 1194*d* extending therefrom which can be moved away from end 498*a* of return pin 498 such that a spring, for example, can bias return pin 498 into operative engagement with trigger gear 496.

In addition to the above, first switch portion 1194, when pivoted downwardly, can be configured to contact return pin 172 and operably engage key 222 of return pin 172 with pawl 170 such that pawl 170 cannot be pivoted upwardly, as also described above. In effect, in at least one such embodiment, first switch portion 1194 can comprise a cam which can be actuated to operably disengage the firing drive from, and operably engage the reversing drive with, the firing member. In various circumstances, only the operation of first portion 1194 may be needed in order to switch the surgical instrument between its advancing and reversing operating modes. In the event, however, that the cam of the reversing drive, such as cam 402, for example, cannot properly position, or actuate, first switch portion 1194, second portion 1118 of the switch may be utilized to actuate first switch portion 1194 as described in greater detail below.

Further to the above, second switch portion 1118 can be actuated in order to actuate first switch portion 1194. In various embodiments, referring again to FIG. 119, second switch portion 1118 can include handle 1118*b* which can be configured to be grasped by a surgeon, for example, such that the surgeon can apply a force thereto and rotate switch portion 1118 about pivot 1118*a*. In at least one embodiment, second switch portion 1118 can be configured to contact first switch portion 1184 and move first portion 1184 between its unactuated position illustrated in FIG. 119 and its actuated position as described above. In various embodiments, in effect, second switch portion 1118 can comprise a cam which can contact first portion 1194 and drive first portion 1194 downwardly such that first portion 1194 contacts firing pin 172 and return pin 498. In at least one such embodiment, referring to FIG. 119, second switch portion 1118 can include contact surface 1118*c* which can be configured to contact surface 1194*c* of first switch portion 1194. In various embodiments, contact surface 1118*c* can be positioned directly above contact surface 1194*c* such that surfaces 1118*c* and 1194*c* can be aligned and the possibility of second switch portion 1118 not contacting first switch portion 1194 can be reduced.

Figure 119:
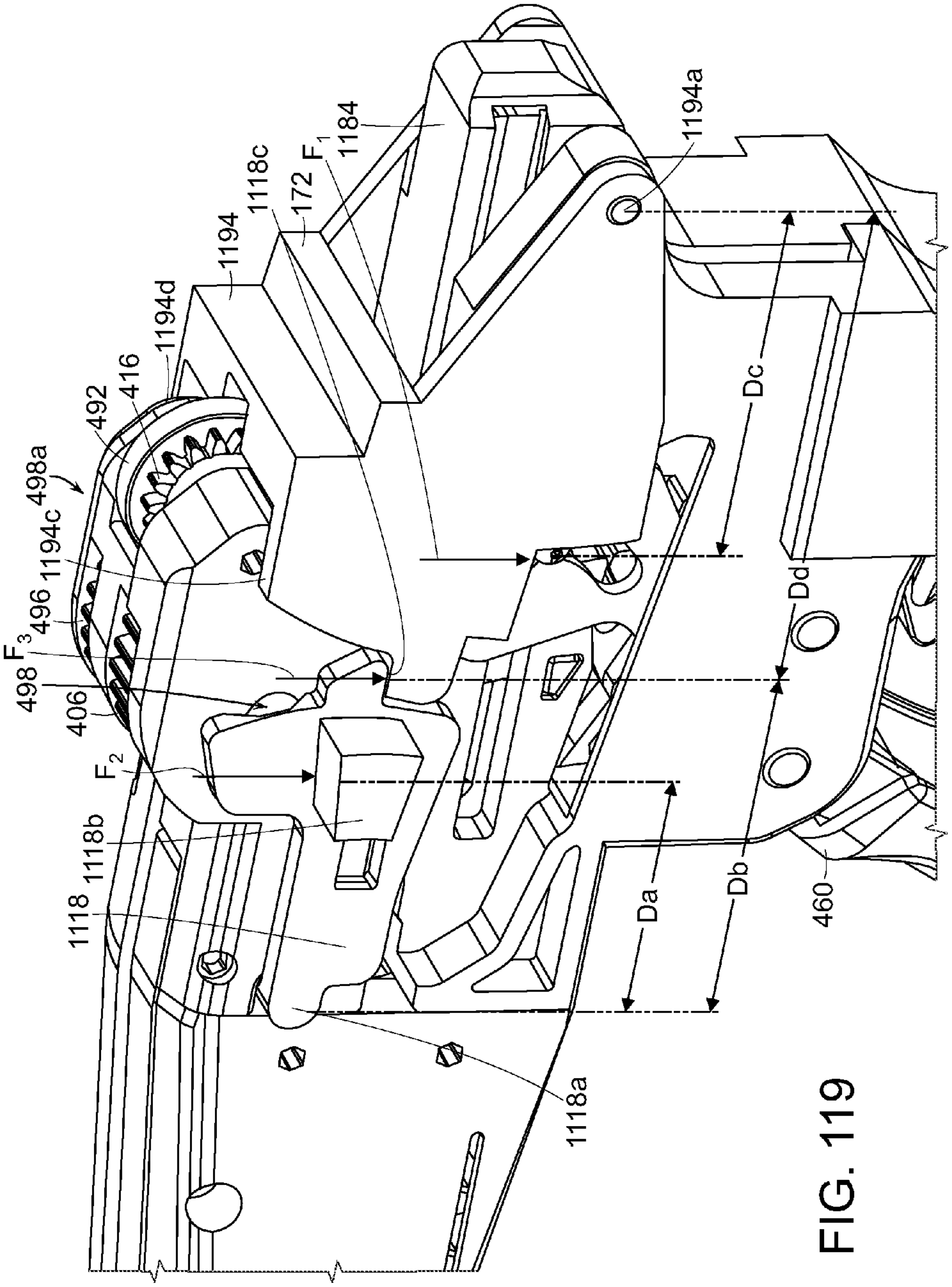

In various embodiments, further to the above, contact surfaces 1118*c* and 1194*c* can be positioned and arranged such that a force, $F_2$, applied to handle 1198*b* has sufficient mechanical advantage to move first switch portion 1194 into its actuated position. In at least one embodiment, handle force $F_2$ can be transmitted through the body of second switch portion 1118 and to first switch portion 1194 via contact surfaces 1118*c* and 1194*c* as transmission force $F_3$. Notably, in various embodiments, transmission force $F_3$ can be different than handle force $F_2$ Further to this point, referring to FIG. 119, the torques associated with handle force $F_2$ and transmission force $F_3$ in order to initially move first switch portion 1194 can be substantially the same, i.e., the product of distance Da and force $F_2$ can substantially equal the product of distance Db and force $F_3$, wherein distance Da can represent the distance between pivot 1118*a* and the application of force $F_2$, and wherein distance Db can represent the distance between pivot 1118*a* and the transmission of force $F_3$. Thus, when distance Da is smaller than distance Db, as illustrated in FIG. 119, force $F_2$ can be larger than force $F_3$. Accordingly, in order for force $F_3$ to be substantially equal to force $F_2$, handle 1118*b* would have to be positioned substantially above surfaces 1118*c* and 1194*c* when force $F_2$ is applied to handle 1118*b*.

In various embodiments, further to the above, transmission force $F_3$ can be transmitted through the body of first switch portion 1194 to firing pin 172 as displacement force $F_1$. Similar to the above, displacement force $F_1$ can be different than transmission force $F_3$. Further to this point, referring again to FIG. 119, the torques associated with displacement force $F_1$ and transmission force $F_3$ in order to initially displace firing pin 172 toward pawl 170, as outlined above, can be substantially the same, i.e., the product of distance Dc and force $F_1$ can substantially equal the product of distance Dd and force $F_3$, wherein distance Dc can represent the distance between pivot 1194*a* and the application of force $F_3$, and wherein distance Dd can represent the distance between pivot 1194*a* and the transmission of force $F_3$. Thus, when distance Dc is smaller than distance Dd, as illustrated in FIG. 119, force $F_1$ can be larger than force $F_3$. In effect, the smaller transmission force $F_3$ can be utilized to apply a larger displacement force $F_1$ to firing pin 172, depending on the selection of distances Da, Db, Dc, and Dd. In various embodiments, as a result, the first and second portions of the switch can be configured such that force $F_2$ supplied by the surgeon, for example, can be sufficient to manually position the first portion of the switch in its actuated position via the second portion of the switch and thereby manipulate the surgical instrument from an advancing operating mode to a reversing operating mode, as outlined further above. In order to return the surgical instrument to its advancing operating mode, first switch portion 1194, for example can be rotated upwardly such that second switch portion 1118 can also rotated upwardly, thereby resetting the switch assembly.

Figure 120:
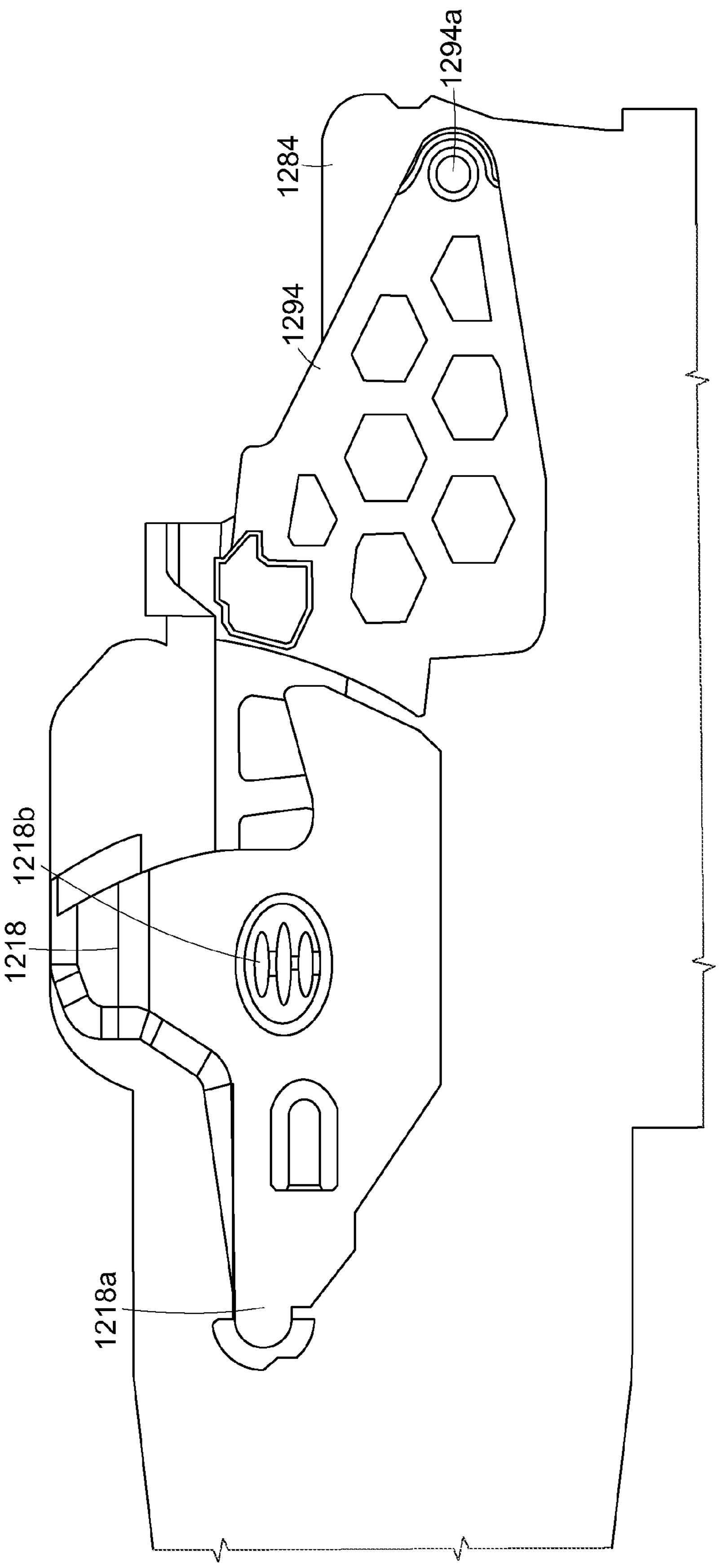
Figure 121:
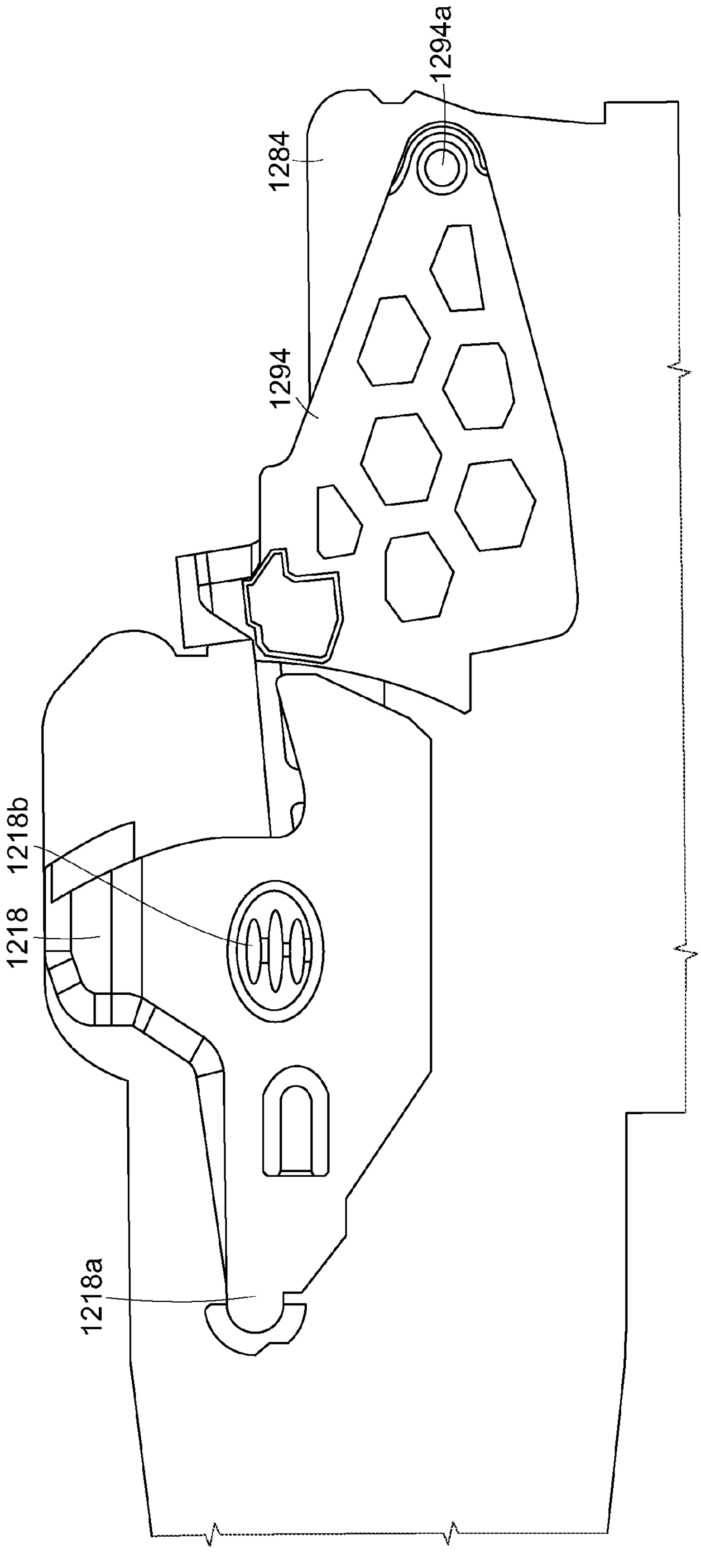
Figure 122:
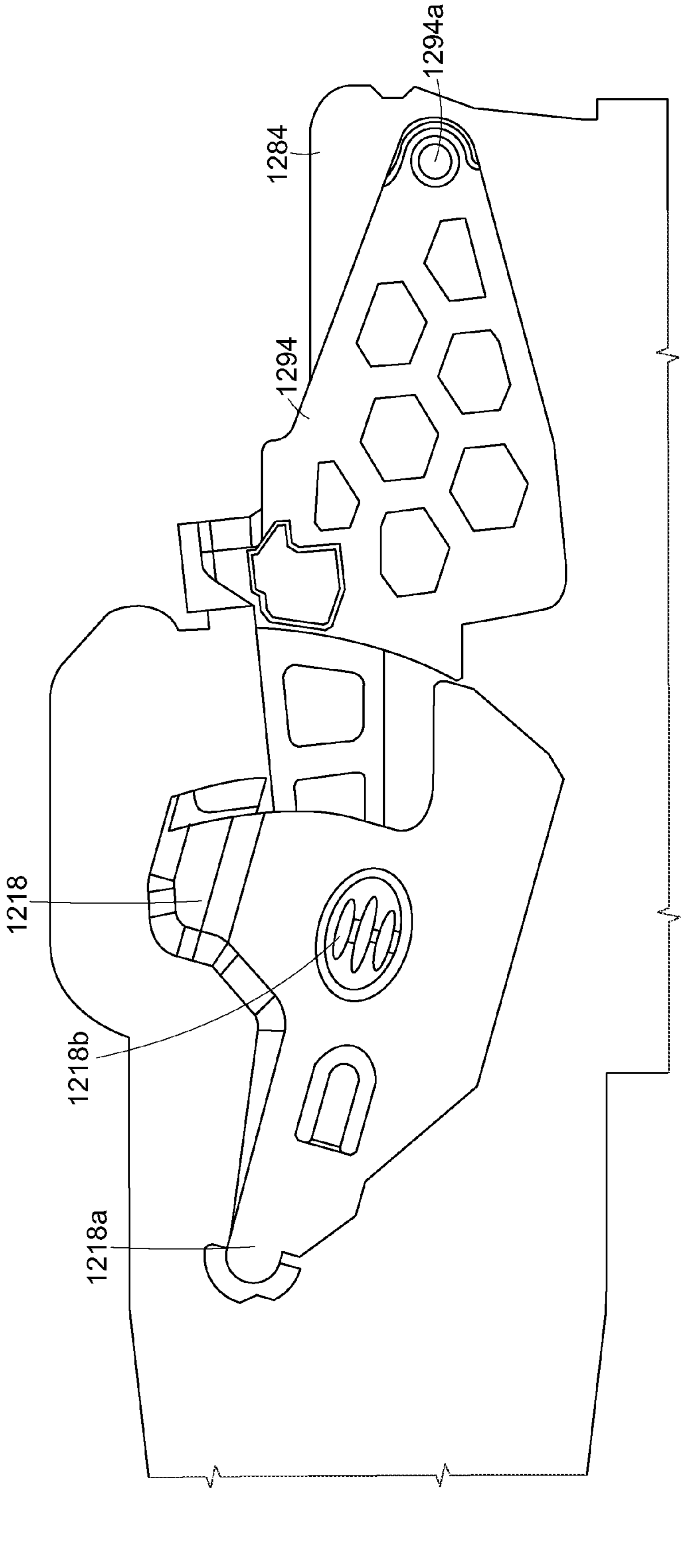

In a further exemplary embodiment, referring to FIGS. 120-122, a surgical instrument can include a switch assembly comprising first portion 1294 which can be pivotably mounted to frame 1284 about pin 1294*a* and, in addition, a second portion 1218 which can be pivotably mounted to frame 1284 about pivot 1218*a*. Although the first and second switch portions can be pivotably mounted to frame 1284, the switch portions can be pivotably mounted to any other suitable portion of the surgical instrument. In various embodiments, similar to the above, first switch portion 1294 can be operated to switch the surgical instrument between advancing and reversing operated modes. In at least one embodiment, first switch portion 1294 can be rotated between its unactuated position illustrated in FIG. 120 and its actuated position illustrated in FIG. 121. Similar to the above, second switch portion 1218 can be moved downwardly by a force applied to handle 1218*b* in order to move first portion 1294 downwardly into its actuated position.

In various embodiments, second switch portion 1218, for example, and the firing trigger of the surgical instrument, such as firing trigger 460, for example, can be configured such that second portion 1218 can be prevented, or at least substantially prevented, from being rotated downwardly unless the firing trigger is in its unactuated position. By requiring that the firing trigger be in its unactuated position before allowing the switch to be operated, first switch portion 1294 of the reversing mechanism may be properly aligned with the firing pin of the firing drive, such as firing pin 172, for example, when first portion 1294 is rotated downwardly. In various embodiments, the surgical instrument can be configured such that the firing pin is positioned within a predetermined range such that the firing pin can be contacted by first switch portion 1294 and slid into engagement with the pawl of the firing drive, such as pawl 170, for example.

Figure 50:
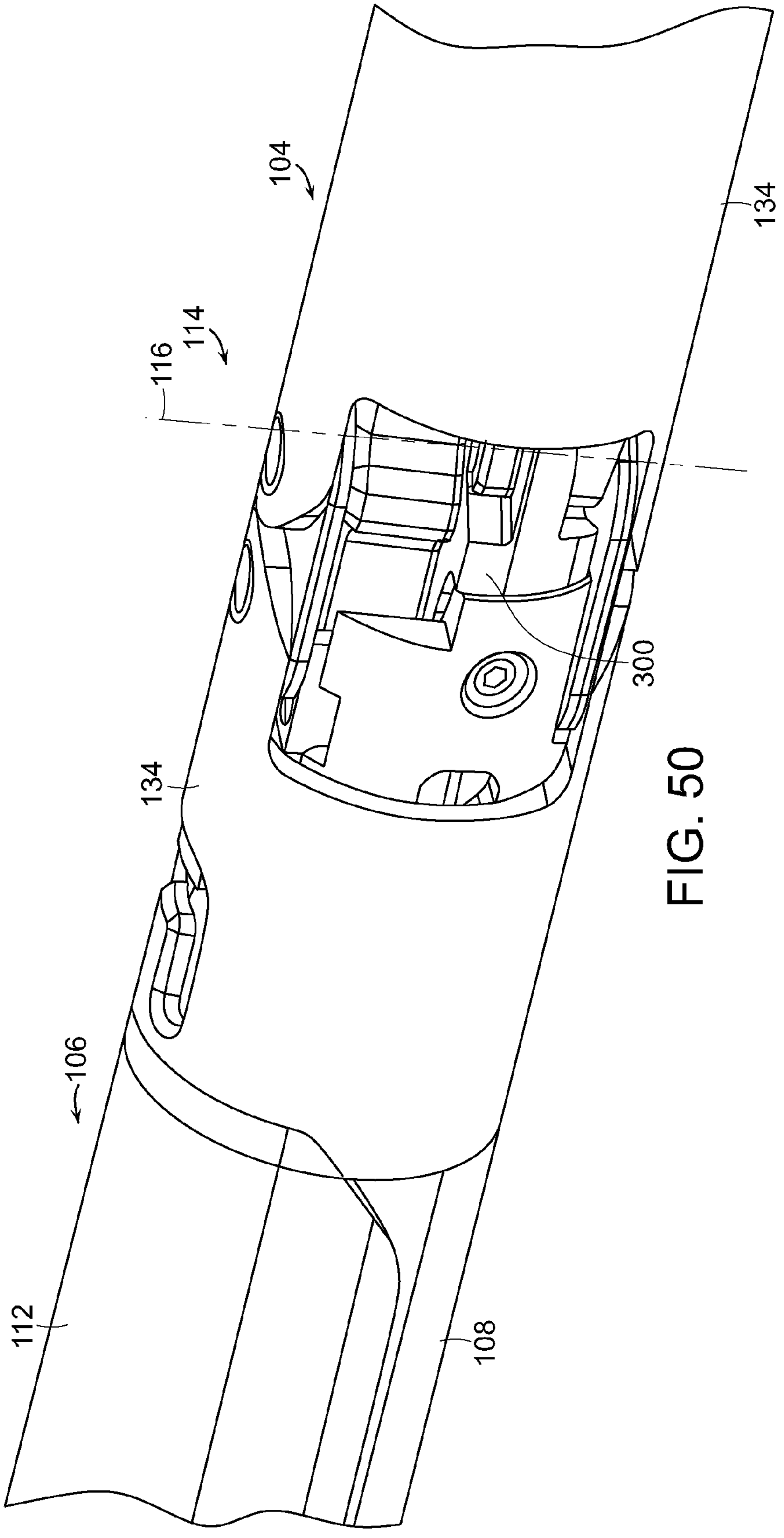
FIG. 50 is a perspective view of the articulation joint of FIG. 5.

In various embodiments, referring to FIG. 50, surgical instrument 100 can include end effector 106 and elongate shaft assembly 104, where end effector 106 and shaft assembly 104 can be pivotably connected by articulation joint 114. As outlined above, articulation joint 114 can allow end effector 106 to be moved, or articulated, relative to shaft assembly 106 about axis 116. In various circumstances, a surgeon can articulate end effector 106 to more easily access a surgical site within a patient's body. More particularly, a surgeon may insert end effector 106 and shaft assembly 104 through a cannula at least partially inserted into the patient's body and, once end effector 106 has passed through the cannula, end effector 106 can be pivoted, or articulated, in order to position end effector 106 relative to soft tissue, for example, in the surgical site that is to be stapled and/or incised. Once end effector 106 has been positioned, the relative relationship between end effector 106 and shaft assembly 104 can be fixed, or locked, by a locking mechanism as described in greater detail further below.

Figure 51:
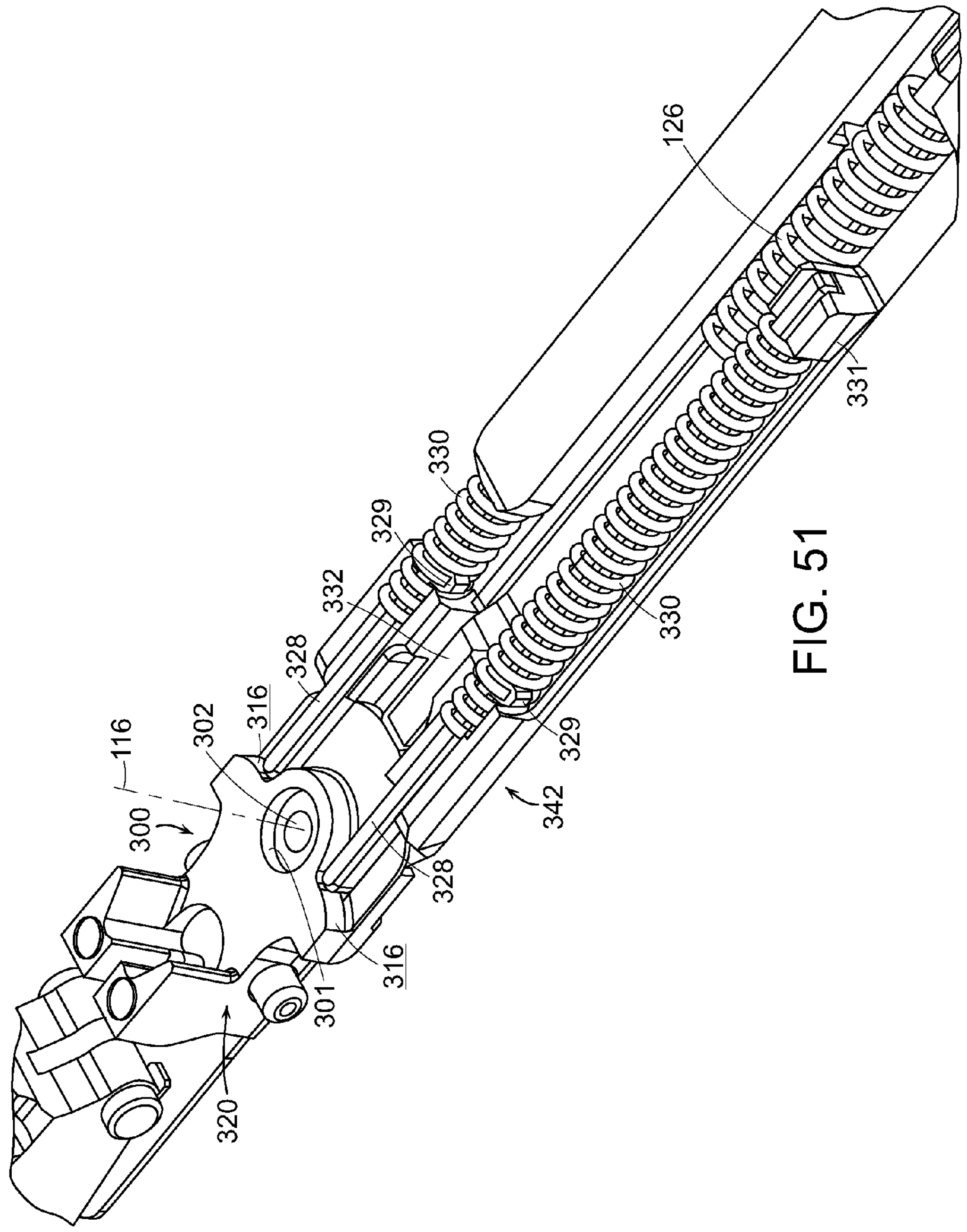
FIG. 51 is a perspective view of the articulation joint of FIG. 5 with some components of the surgical instrument removed.
Figure 52:
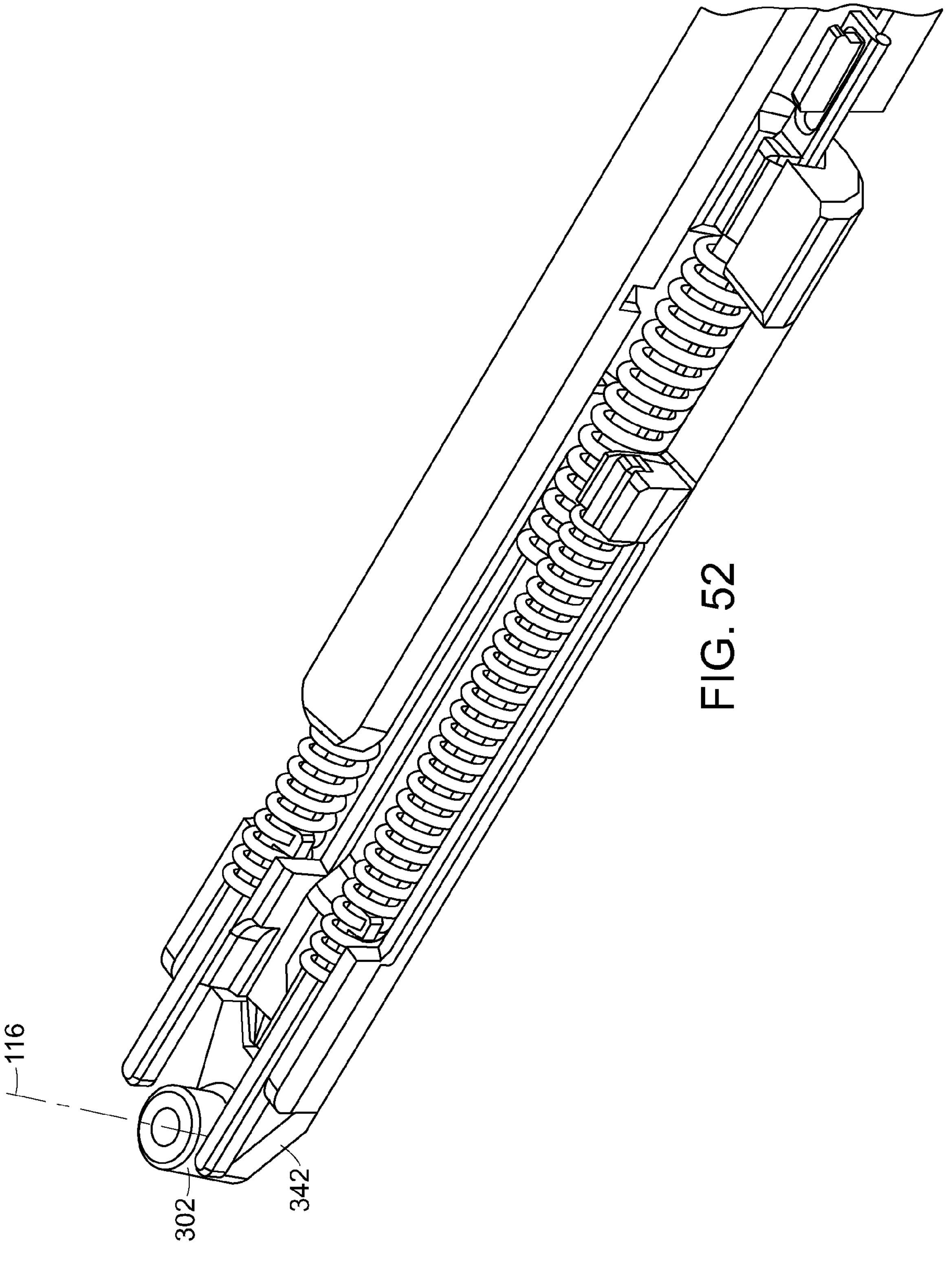
FIG. 52 is a perspective view of the articulation joint of FIG. 5 with additional components of the surgical instrument removed.
Figure 53:
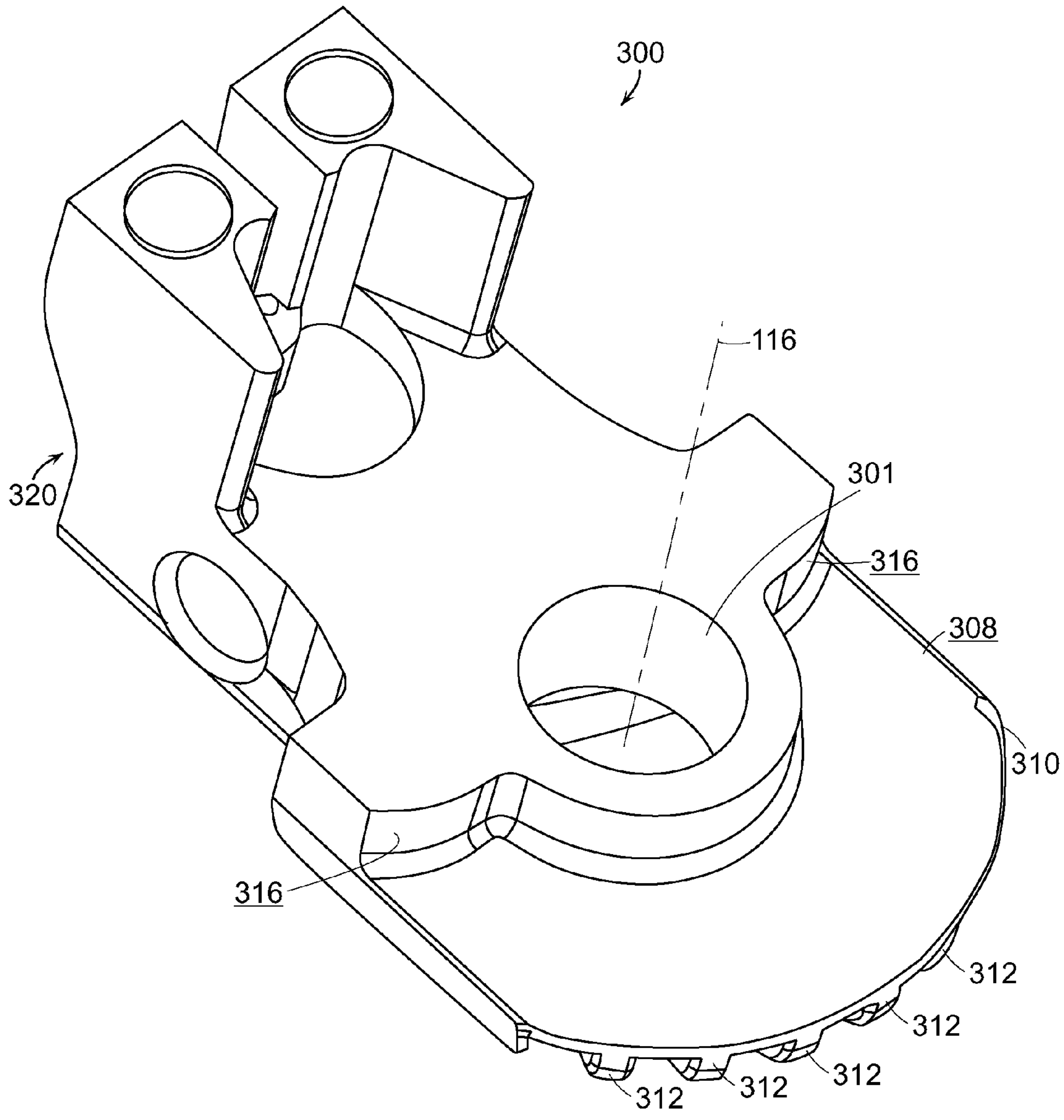
FIG. 53 is a perspective view of a lock member of the end effector of FIG. 3.
Figure 54:
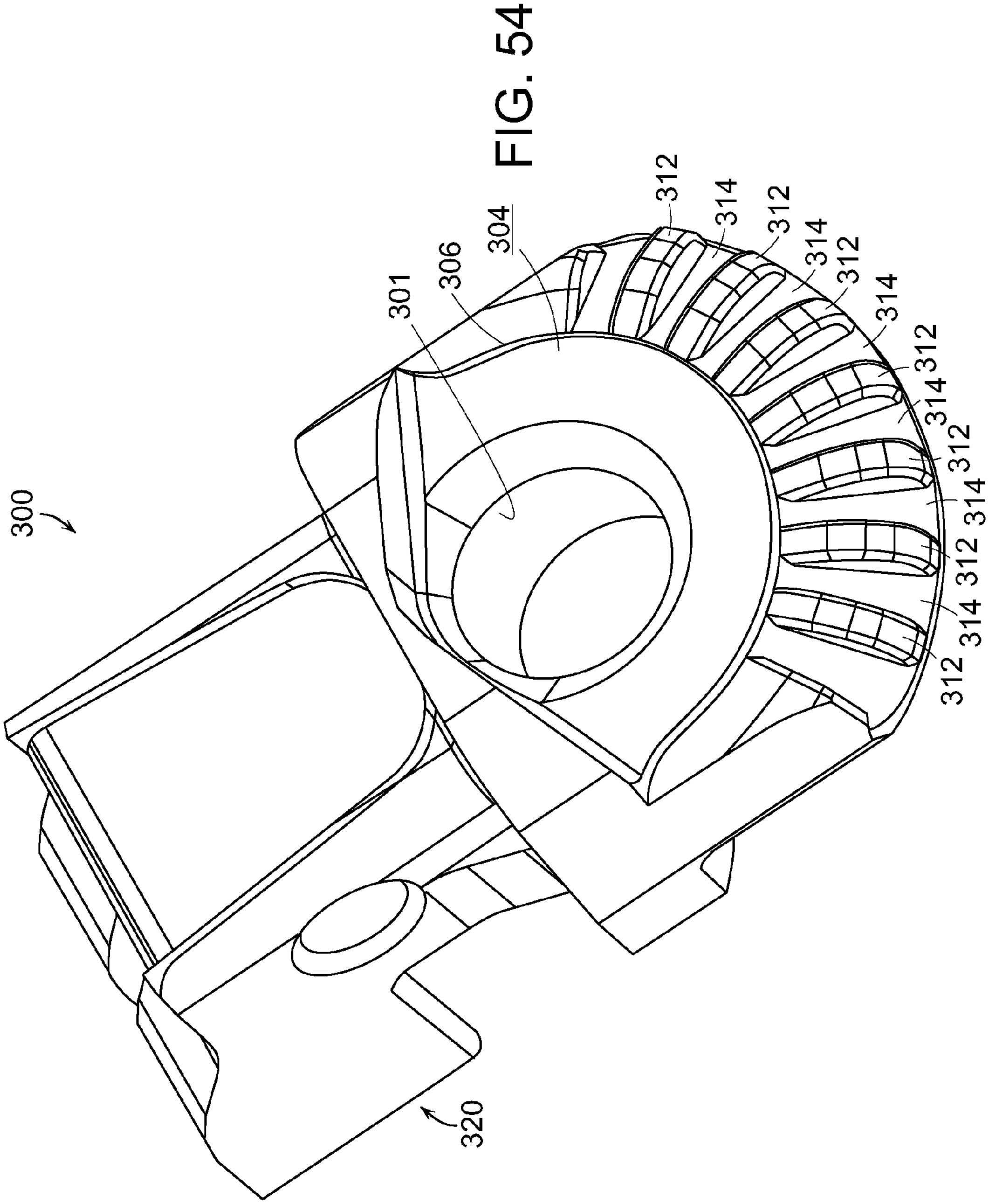
FIG. 54 is another perspective view of the end effector lock member of FIG. 53.
Figure 55:
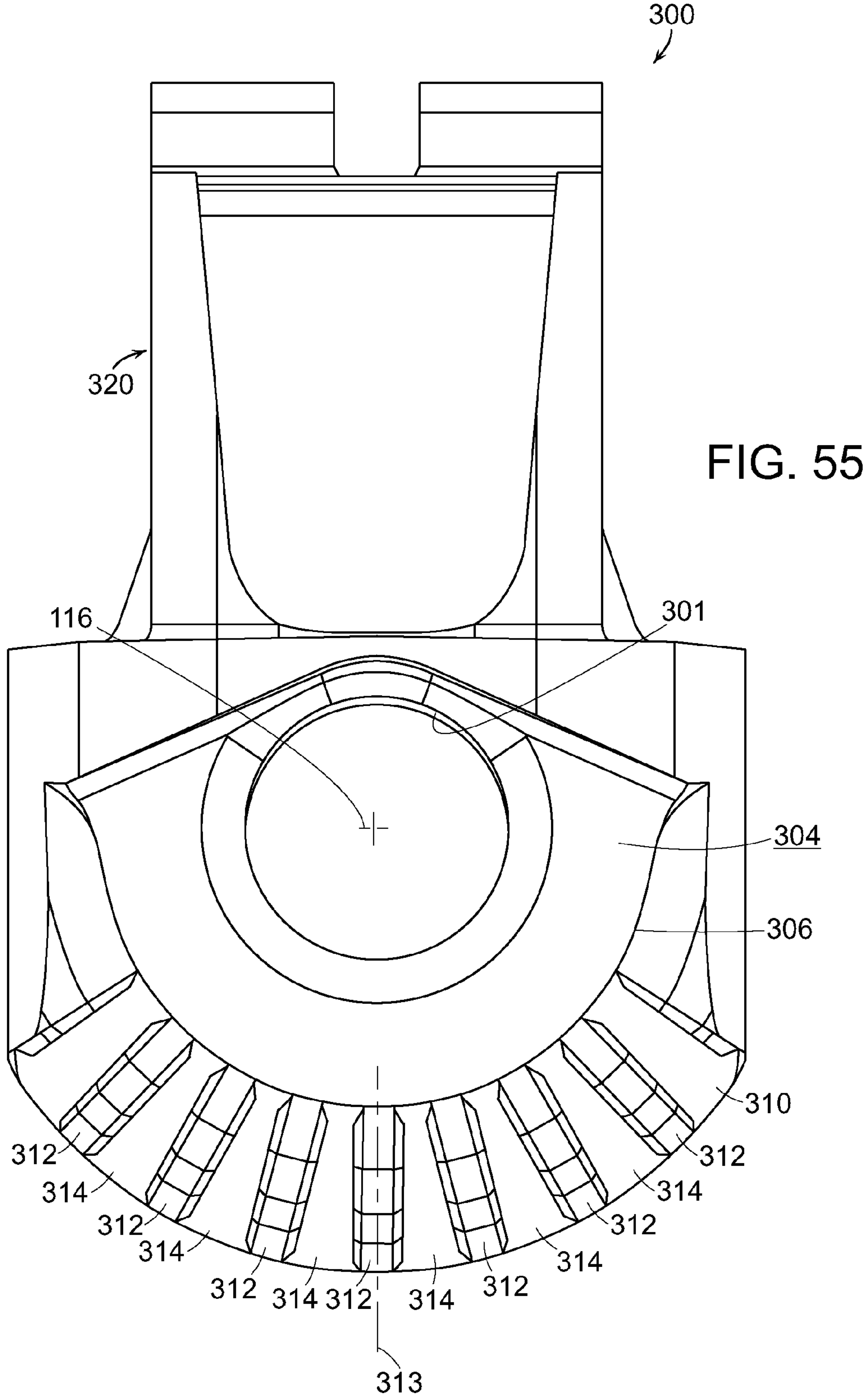
FIG. 55 is a bottom view of the end effector lock member of FIG. 53.
Figure 56:
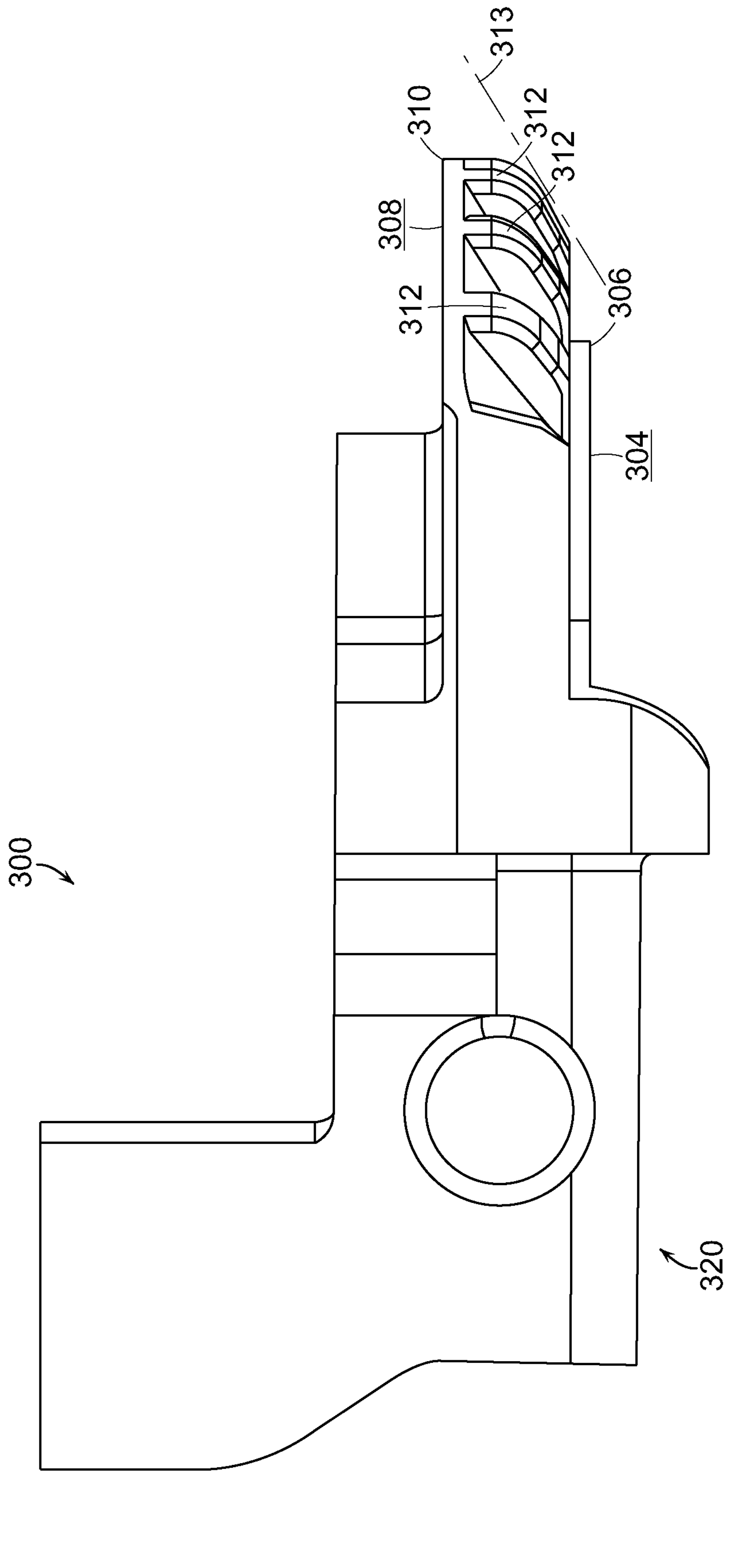
FIG. 56 is an elevational view of the end effector lock member of FIG. 53.

In at least one embodiment, referring to FIGS. 51 and 52, articulation joint 114 can include end effector lock member 300 and pivot 302. In various embodiments, referring to FIGS. 53-56, end effector lock member 300 can include connector portion 320 which can secure lock member 300 to end effector 106 and, referring to FIG. 52, shaft assembly 104 can include pivot connector 342, where pivot connector 342 can include pivot 302 extending therefrom. In various embodiments, lock member 300 can include aperture 301 which can be sized and configured to receive at least a portion of pivot 302 therein. In at least one embodiment, pivot 302 and aperture 301 can be configured such that end effector 106 can rotate freely about axis 116. In other various embodiments, pivot 302 and aperture 301 can be configured such that friction between pivot 302 and aperture 301 can resist, although permit, relative movement between end effector 106 and shaft assembly 104. Although not illustrated, articulation joint 114 can include more than one axis, or pivot, about which end effector 106 can be rotated.

In various embodiments, a surgeon can articulate end effector 106 relative to shaft assembly 104 by pushing end effector 106 against a cavity side wall surrounding a surgical site, for example, and applying a force to shaft assembly 104 such that end effector 106 pivots about axis 116. Thereafter, if the surgeon desires to re-center end effector 106, i.e., orient end effector 106 and shaft assembly 104 along a line, the surgeon can place end effector 106 against a cavity side wall once again, for example, and a apply a force to shaft assembly 104 as described above. In various embodiments, referring to FIGS. 51 and 52, surgical instrument 100 can include a re-centering mechanism which can automatically re-center, or at least substantially re-center, end effector 106 relative to shaft assembly 104. In various embodiments, end effector lock member 300 can include centering surfaces 316 and elongate shaft assembly 104 can include centering shafts 328 and biasing members 330, where biasing members 330 can be configured to bias centering shafts 328 against centering surfaces 316. In at least one such embodiment, centering surfaces 316 can be disposed on substantially opposite sides of axis 116 such that centering shafts 328 can apply a substantially equal torque, or moment, to lock member 300 and, absent an additional motivating force, hold end effector 106 in a substantially centered position. When end effector 106 is articulated by such a motivating force, as described above, lock member 300 can be configured to displace one of centering shafts 328 proximally and compress the biasing member 330 operably engaged therewith. More particularly, the biasing member 330 can be positioned between a guide 331 and at least one projection 329 extending from centering shaft 328 such that, when projection 329 is moved proximally by shaft 328, biasing member 330 is compressed therebetween. After the motivating force is removed, the compressed biasing member 330 can expand and rotate lock member 300 to its center position via centering shaft 328, or to a position where the torque applied by biasing members 330 is substantially balanced. Although biasing member 330 is illustrated as a coil spring, biasing member 330 can include any suitable elastic member.

In various embodiments, a locking mechanism can be used to hold end effector 106 in its articulated position even after the motivating force has been removed. In at least one embodiment, referring to FIGS. 53-56, end effector lock member 300 can include a first portion having first surface 308, a second portion having second surface 304, teeth 312, and recesses 314 defined between teeth 312 where, as described in greater detail further below, teeth 312 and recesses 314 can be configured to be operably engaged with a shaft assembly locking member in order to fix, or lock, the relative relationship between end effector 106 and shaft assembly 104. In various embodiments, teeth 312 and recesses 314 can be positioned intermediate first surface 308 and second surface 304. In at least one embodiment, first surface 308 can extend from aperture 301 to first perimeter 310, and second surface 304 can extend from aperture 301 to second perimeter 306. In various embodiments, first perimeter 310 can define a first plane and second perimeter 306 can define a second plane where teeth 312 and recesses 314 can be positioned intermediate the first and second planes. In embodiments where first perimeter 310 is different than second perimeter 306, teeth 312 can extend at an angle, or bevel, therebetween. In various embodiments, a tooth 312 can intersect first perimeter 310 at a point further away from axis 116 than a point at which the tooth 312 intersects second perimeter 306. In at least one embodiment, at least one of the teeth 312 can define a first axis 313 which can extend between first surface 308 and second surface 304 in a direction which is not perpendicular to first surface 308 and/or axis of rotation 116. In such embodiments, teeth 312 can slide over soft tissue, for example, which is positioned adjacent to articulation joint 114. Stated another way, owing to the angled, or beveled, surfaces of teeth 112, the probability of teeth 112 catching on, or impinging upon, the soft tissue surrounding articulation joint 114 when end effector 106 is articulated can be reduced. In at least one embodiment, teeth 312 may not extend beyond first perimeter 310 such that, in the event that at least a portion of first perimeter 310 is in contact with soft tissue, for example, first perimeter 310 and teeth 312 can, as above, easily slide relative to the soft tissue.

Figure 57:
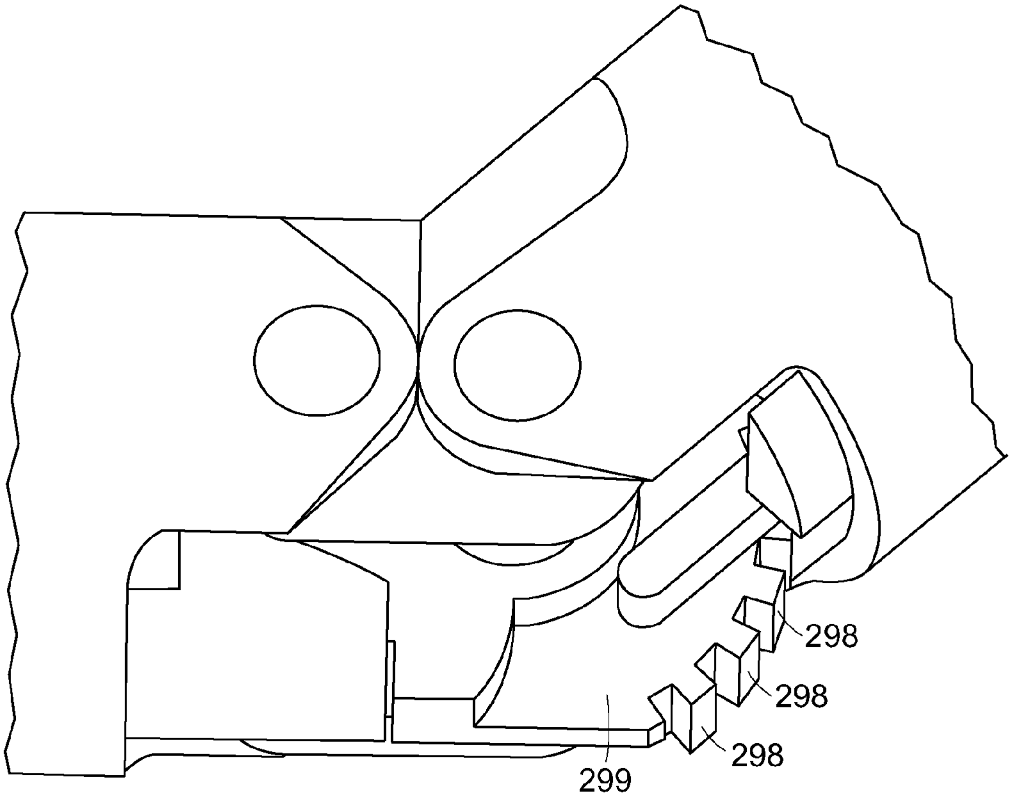
FIG. 57 is a partial perspective view of an articulation joint of a previous surgical instrument.
Figure 58:
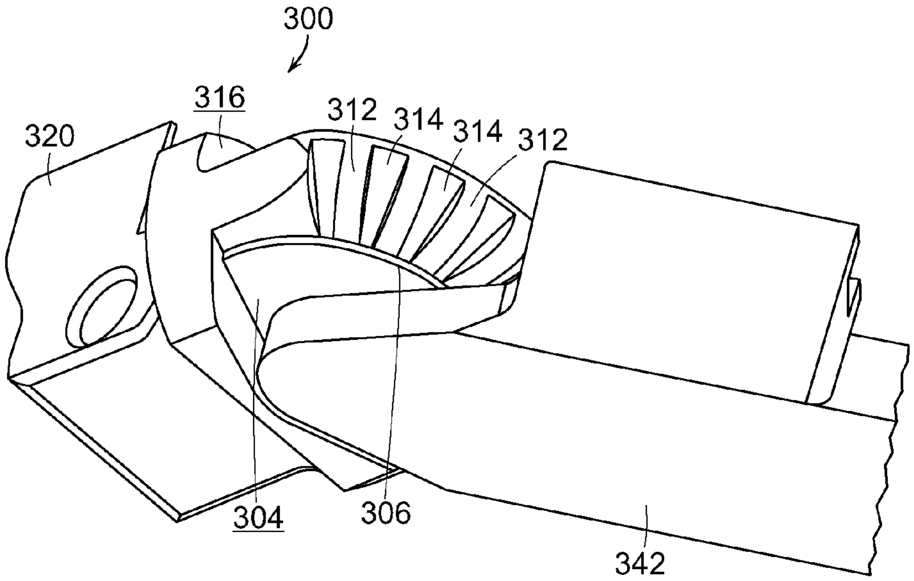
FIG. 58 is a perspective view of the articulation joint of FIG. 5 with some components of the end effector and elongate shaft assembly removed.
Figure 59:
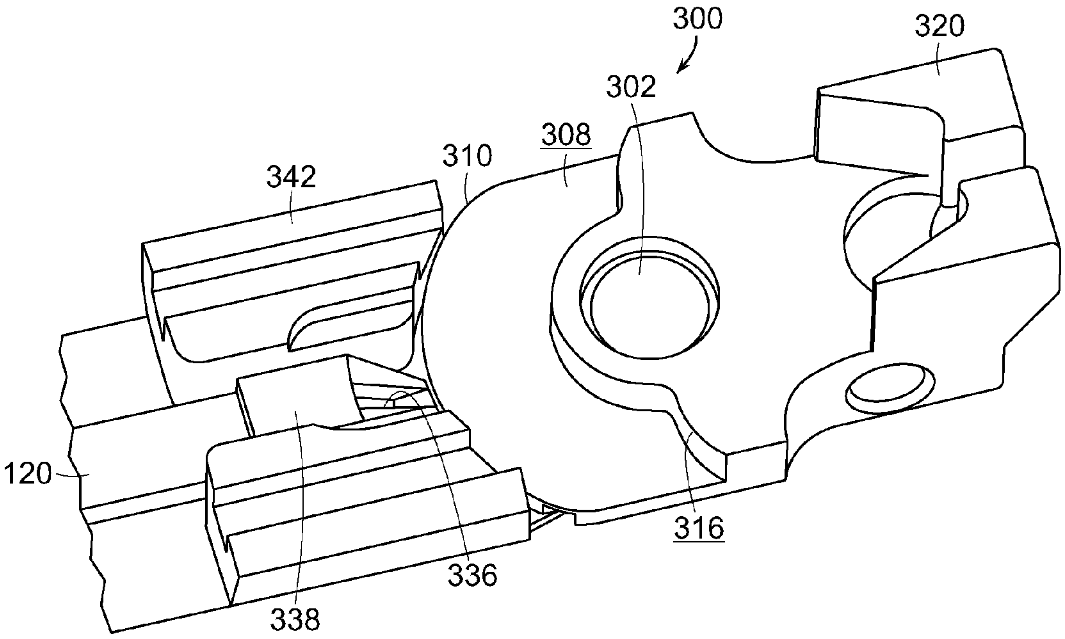
FIG. 59 is another perspective view of the articulation joint of FIG. 5 with some components of the end effector and elongate shaft assembly removed.
Figure 60:
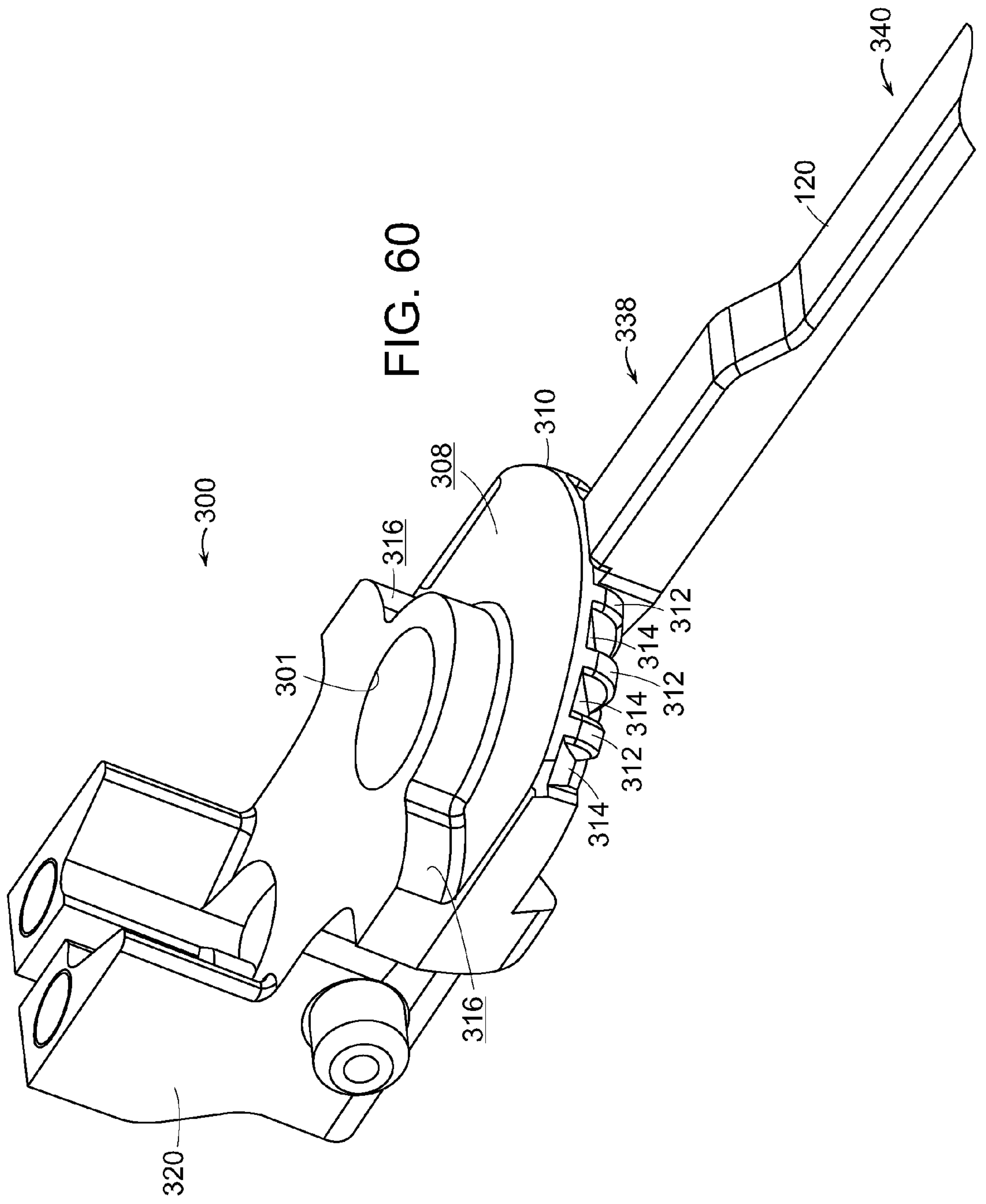
FIG. 60 is a perspective view of the end effector lock member of FIG. 53 operably engaged with a lock member of the elongate shaft assembly.
Figure 61:
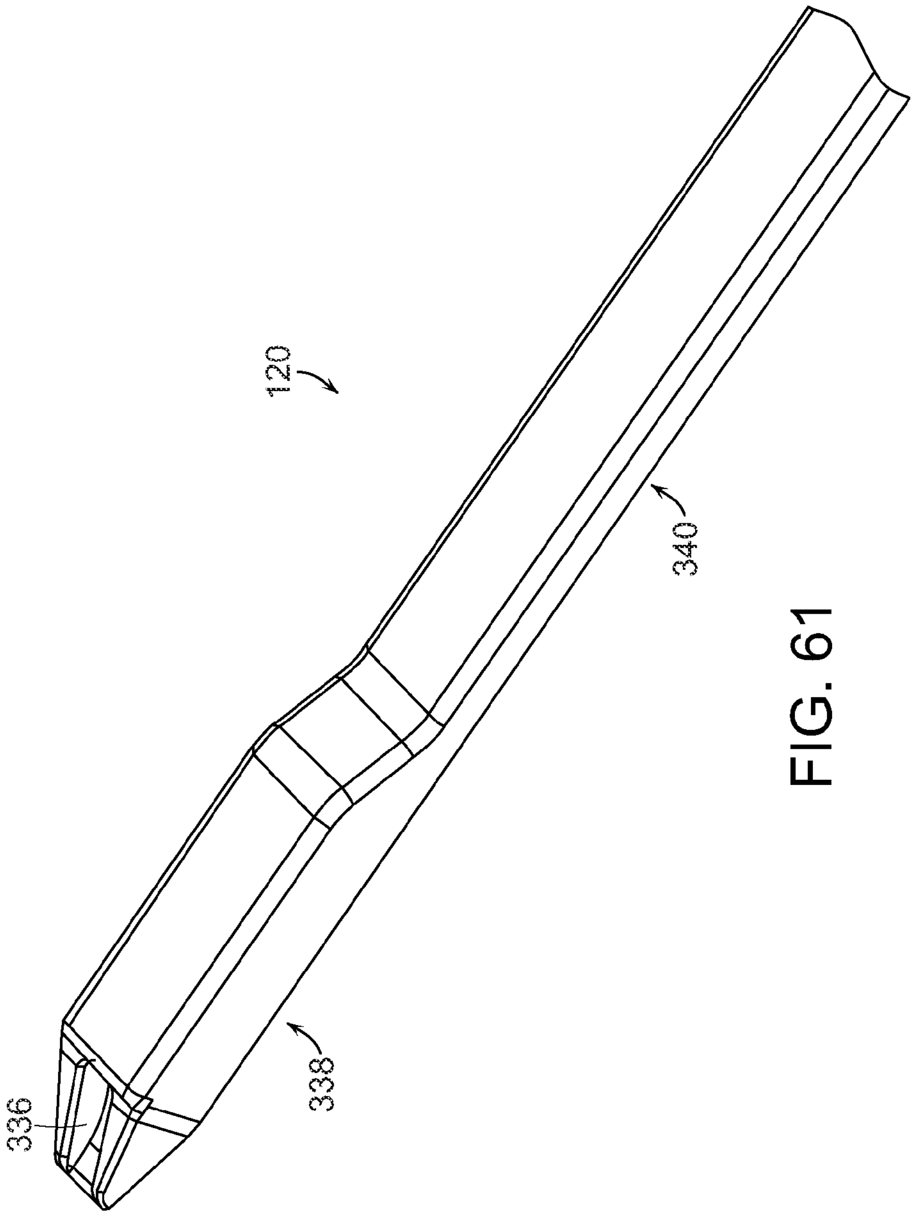
FIG. 61 is a perspective view of the shaft assembly lock member of FIG. 60.
Figure 62:
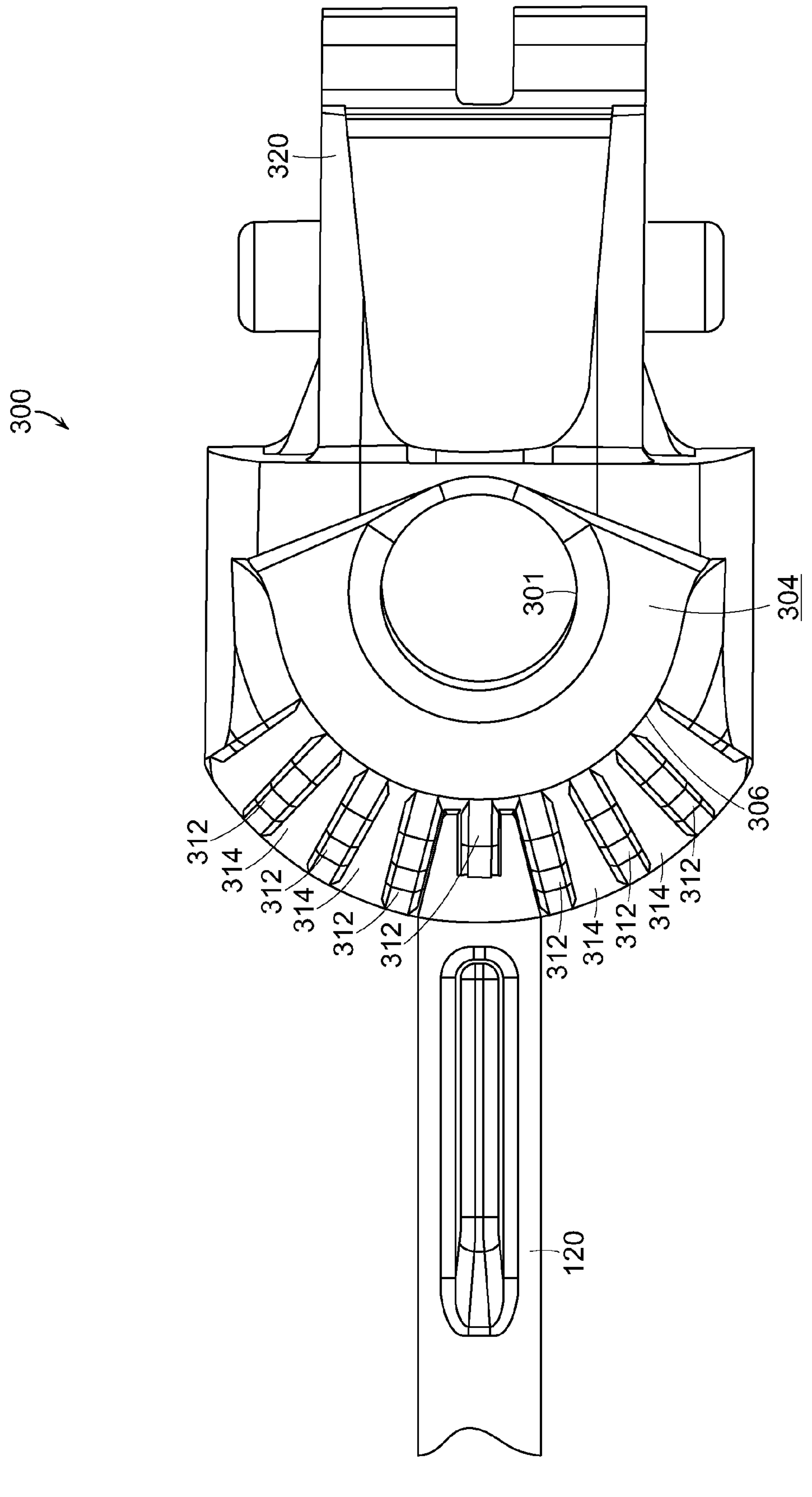
FIG. 62 is a bottom view of end effector lock member of FIG. 53 operably engaged with the shaft assembly lock member of FIG. 60.
Figure 63:
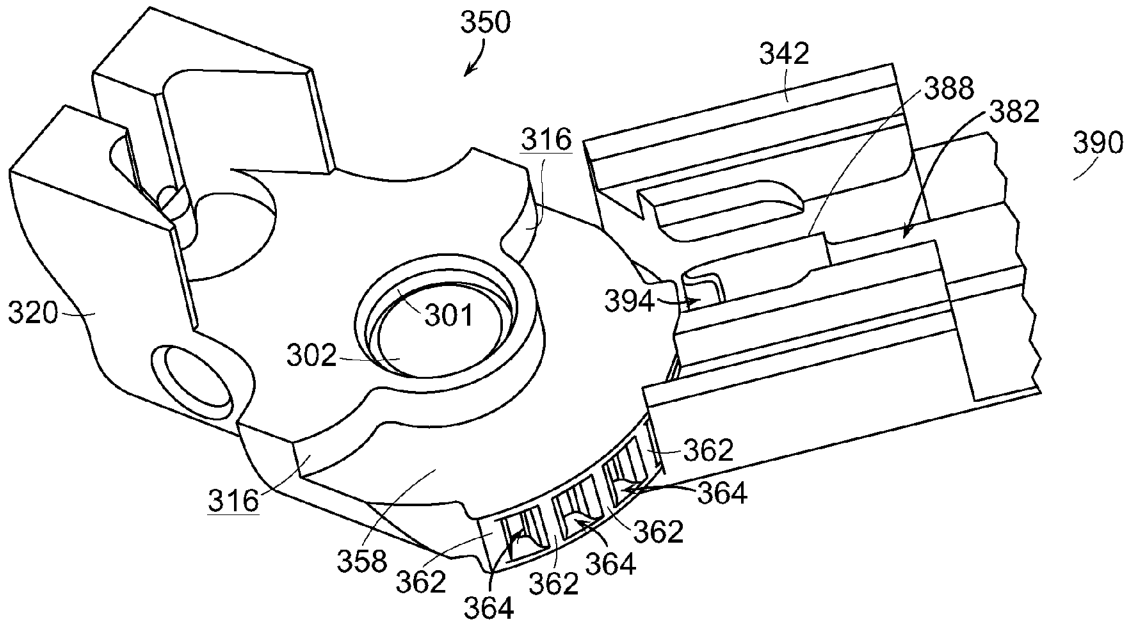
FIG. 63 is a perspective view of an articulation joint of a surgical instrument in accordance with an alternative embodiment of the present invention with some components of the surgical instrument removed.
Figure 64:
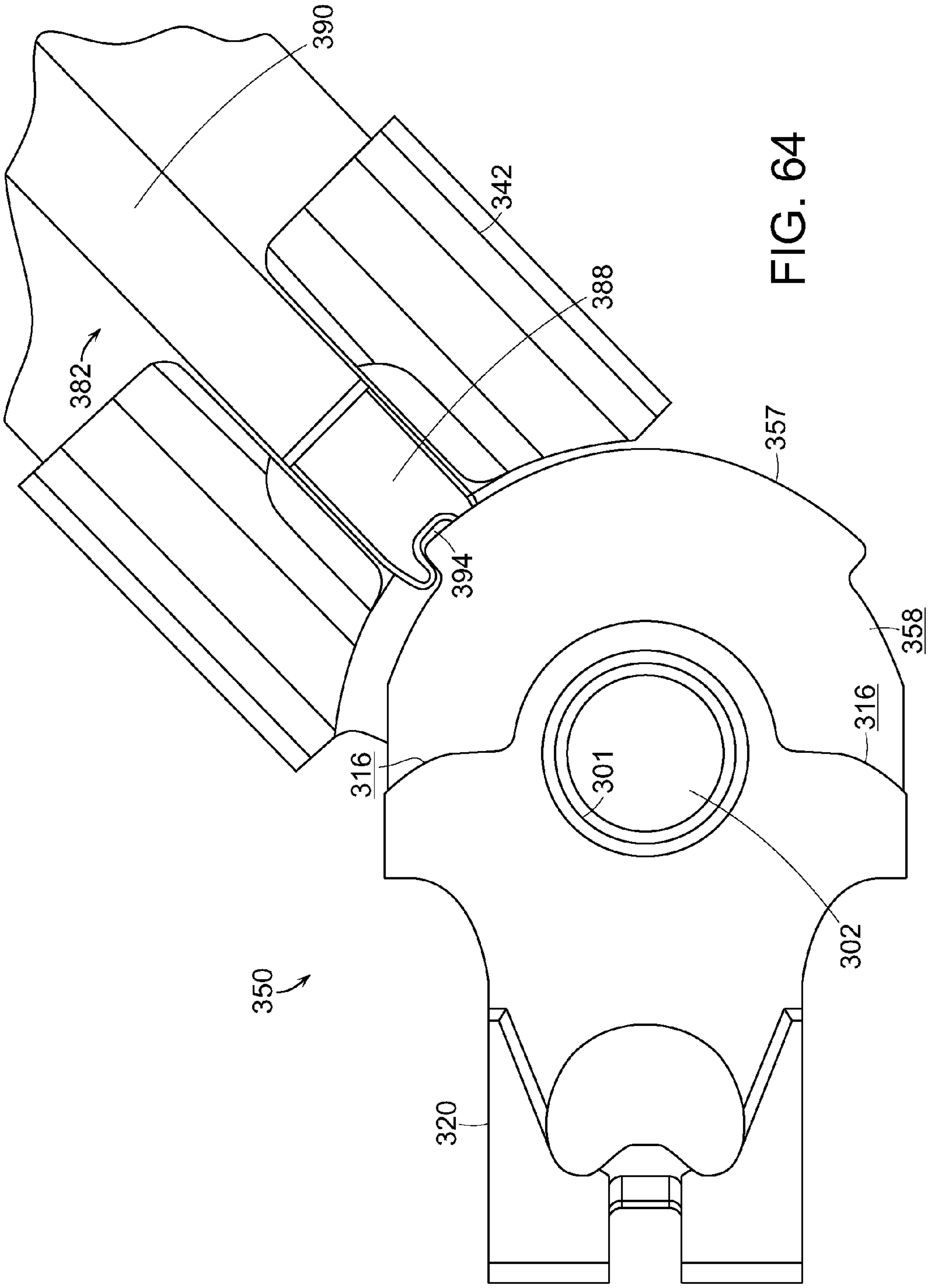
FIG. 64 is a top view of an end effector lock member operably engaged with a shaft assembly lock member of the surgical instrument of FIG. 63.
Figure 65:
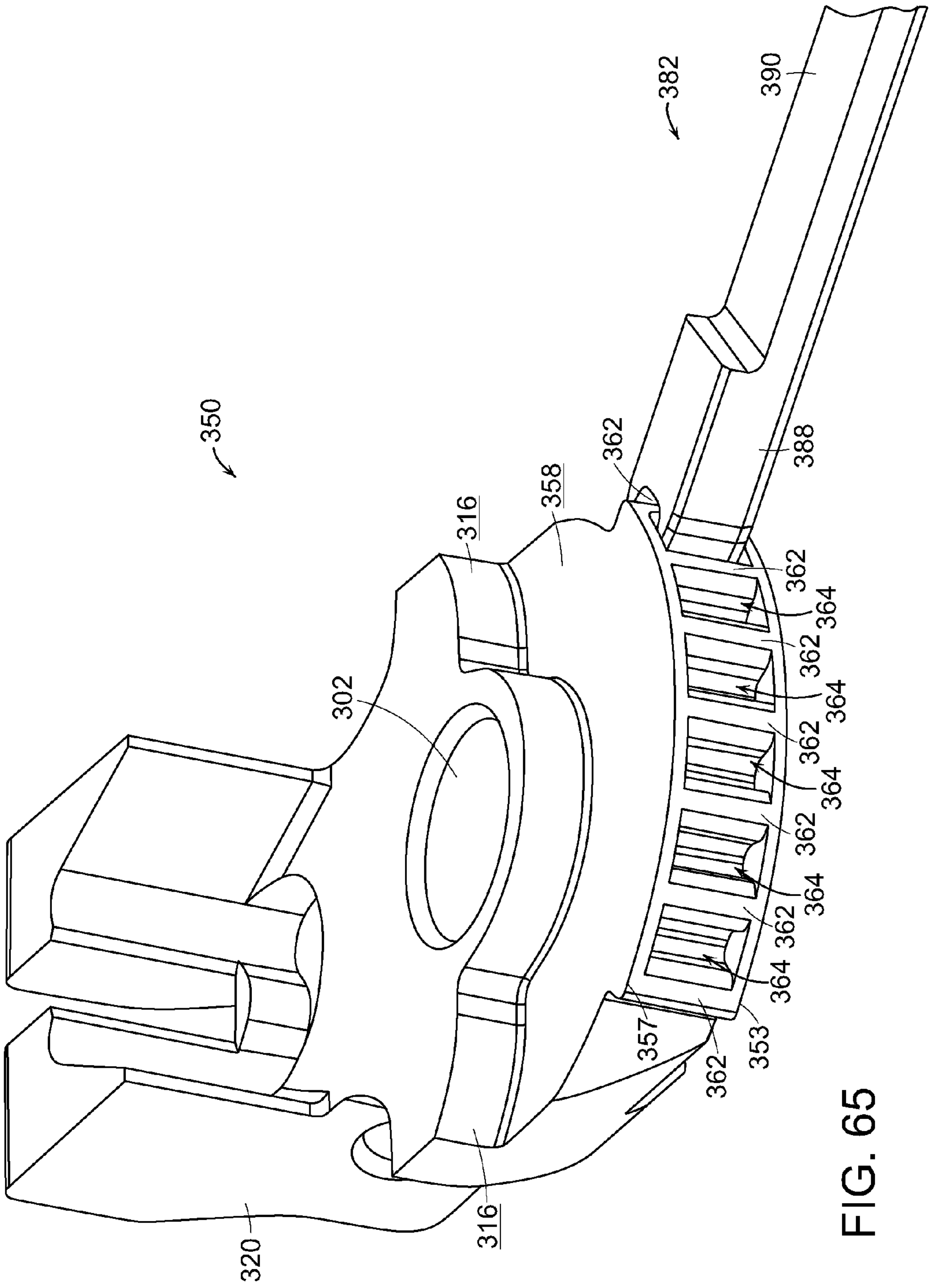
FIG. 65 is a perspective view of the end effector lock member operably engaged with the shaft assembly lock member of FIG. 64.
Figure 66:
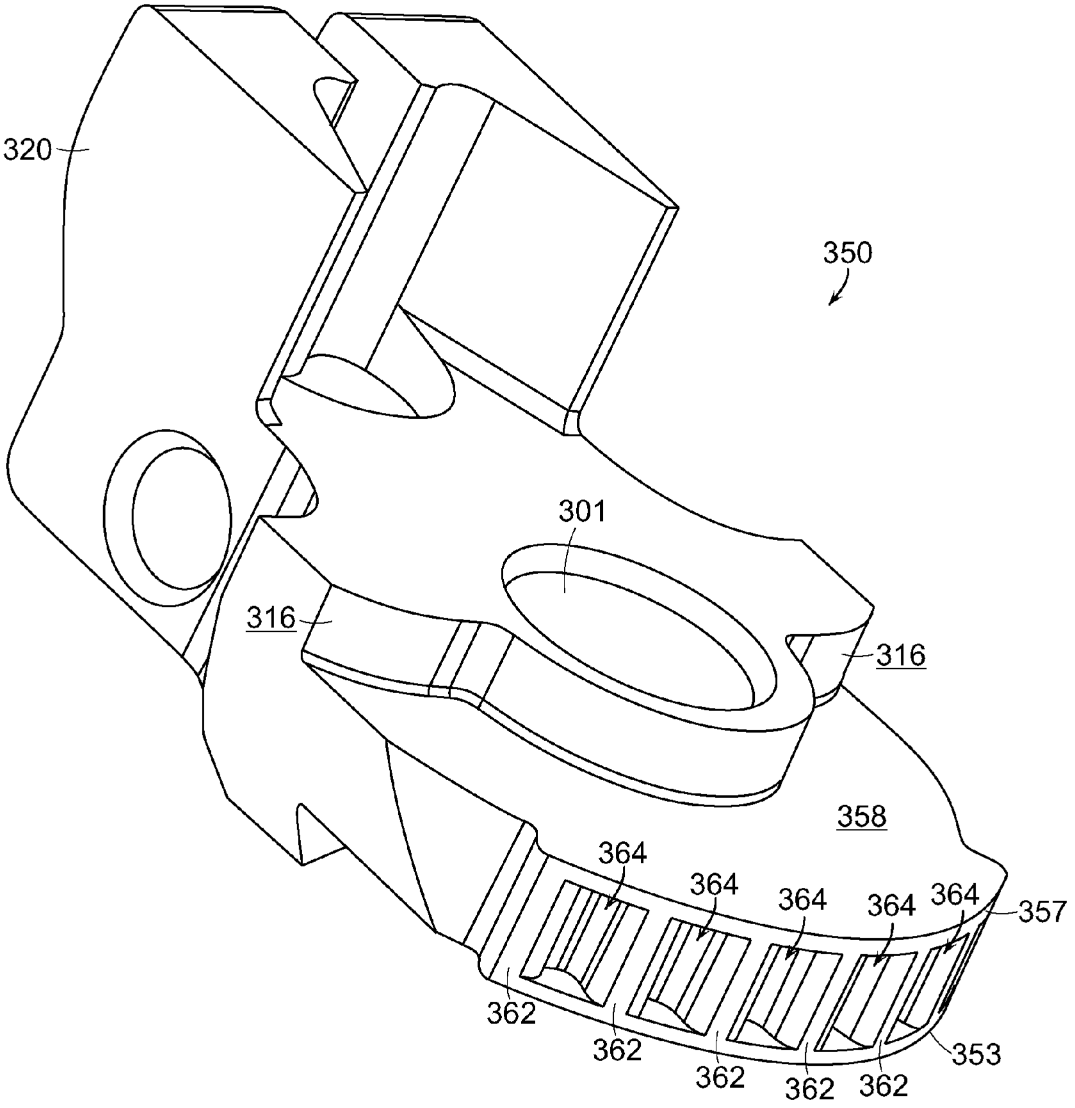
FIG. 66 is a perspective view of the end effector lock member of FIG. 64.
Figure 67:
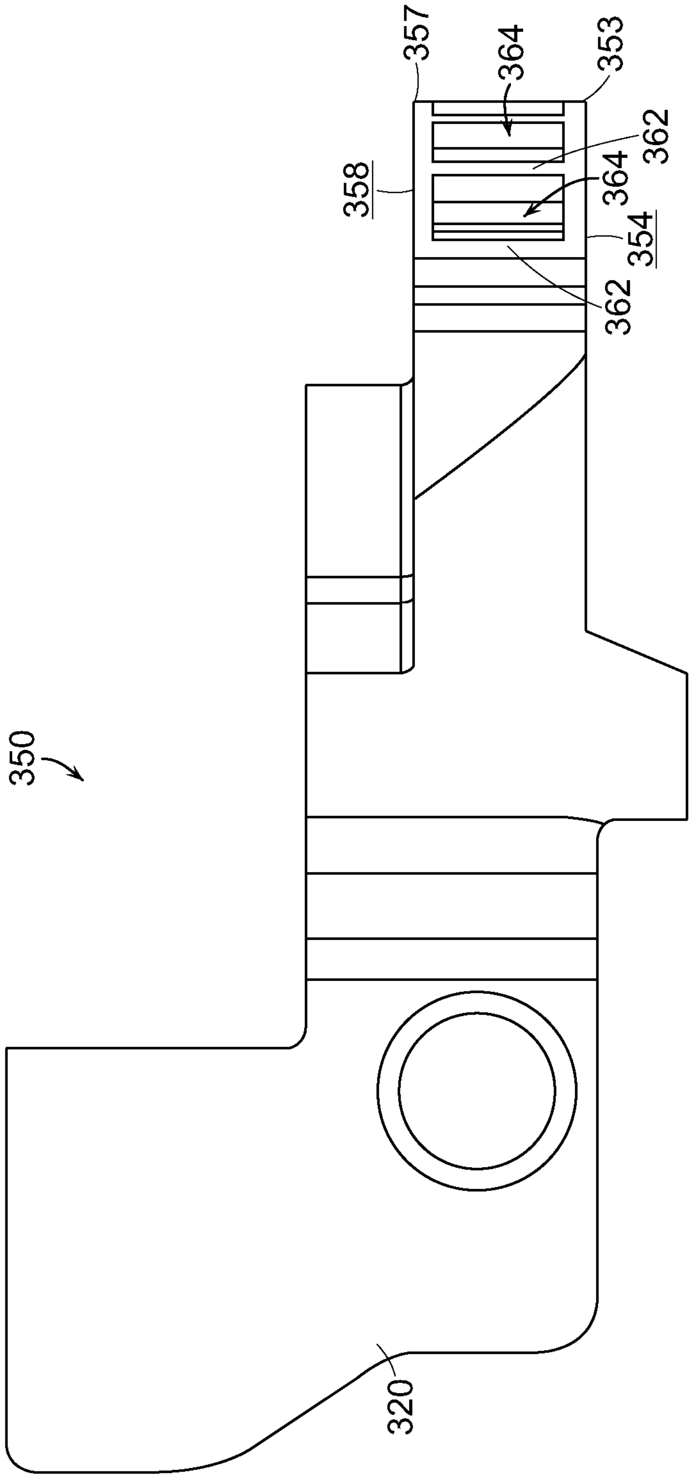
FIG. 67 is an elevational view of the end effector lock member of FIG. 64.

Further to the above, embodiments of the present invention can provide significant advantages over previous surgical instruments. More particularly, referring to FIG. 57, the articulation joints of previous end effectors have included lock members, such as lock member 299, for example, which include teeth 298 that extend outwardly from the perimeter of the lock member. As a result, when the end effector is articulated relative to the shaft assembly of the surgical instrument, teeth 298 can catch on, or impinge upon, the surrounding soft tissue and potentially cause trauma thereto. In various circumstances, tissue can be caught between adjacent teeth 298 such that, when the end effector is articulated, the soft tissue can be pulled into the articulation joint and can be pinched by the relatively moving components of the joint. In embodiments of the present invention in which the teeth of the lock member are angled, or beveled, as outlined above and illustrated in FIG. 58, the soft tissue can more easily flow over the teeth and reduce the possibility that the soft tissue can be pulled into the articulation joint.

As outlined above, referring to FIGS. 59-62, surgical instrument 100 can further include locking member 120 which can be slid relative to end effector 106 and can be operably engaged with end effector 106 to prevent, or at least limit, relative movement between shaft assembly 104 and end effector 106. In at least one embodiment, lock member 120 can be configured to engage at least one of teeth 312 such that end effector 106 is prevented from moving relative to lock member 120. More particularly, lock member 120 can include end portion 338 and shaft portion 340, where end portion 338 can include recess 336 which can be configured to receive a tooth 312 of lock member 300 in a close-fit, or even interference-fit, relationship. In various alternative embodiments, locking portion 338 can be received within at least one of recesses 314 in a close-fit, or interference-fit, relationship similar to the above. In either event, surgical instrument 100 can further include spring 126 which can be configured to bias lock member 120 into engagement with end effector lock member 300. In the event that recess 336 is not aligned with a tooth 312, in at least one embodiment, the biasing force applied to lock member 120 by spring 126 can cause lock member 120 to contact and rotate end effector lock member 300 about axis 116 until one of teeth 312 is aligned with recess 336. In various embodiments, spring 126 can comprise any suitable biasing member including a helical spring, leaf spring, or other biasing material.

In various alternative embodiments, referring to FIGS. 63-67, a surgical instrument can include end effector lock member 350 comprising aperture 301, a first portion including first surface 358, a second portion including second surface 354 (FIG. 67), and connector portion 320. End effector lock member 350 can also comprise teeth 362 and recesses 364 defined between teeth 362 where, in at least one embodiment, teeth 362 and recesses 364 can be positioned intermediate first surface 358 and second surface 354. In various embodiments, referring to FIGS. 65-67, teeth 362 may not extend beyond first perimeter 357 of first surface 358 and/or second perimeter 353 of second surface 354. In at least one such embodiment, teeth 362 may be completely positioned, or contained, between first surface 358 and second surface 354. In at least one alternative embodiment, teeth 362 may partially extend from first perimeter 357 and/or second perimeter 353. In various embodiments, first perimeter 357 and second perimeter 353 can define an outer surface therebetween where recesses 364 can be defined in the outer surface. As a result of the above-described features, end effector lock member 350 can slide relative to soft tissue positioned adjacent to the articulation joint without impinging on the soft tissue. In various embodiments, teeth 362 may be blunted or rounded to further facilitate the relative sliding described above. In at least one embodiment, referring to FIGS. 63-65, a locking mechanism can be configured to engage at least one of teeth 362 and recesses 364 and can include lock member 382 comprising end portion 388 and shaft portion 390. In at least one embodiment, similar to the above, end portion 388 can include recess 394 which can be configured to engage at least one of teeth 362, for example.

In various embodiments, referring now to FIG. 123, surgical instrument 1300 can comprise, similar to the above, an end effector 1306 rotatably coupled to a shaft 1304 about an articulation joint 1315. Also similar to the above, the surgical instrument 1300 can comprise means for opening and closing anvil 1312 relative to staple cartridge channel 1308 and, in addition, means for permitting end effector 1306 to be articulated about axis 1316 of articulation joint 1315. With regard to the means for opening and closing anvil 1312, the surgical instrument 1300 can comprise a closure tube comprising a distal tube component **1334*a* and a proximal tube component 1334*b* which, when advanced distally, i.e., in a direction indicated by arrow Z, can engage anvil 1312 and cam, or rotate, anvil 1312 downwardly toward staple cartridge channel 1308. Correspondingly, when the closure tube is retracted in a direction opposite of arrow Z, the distal tube component 1334*a* can cam anvil 1312 upwardly away from staple cartridge channel 1308 and/or permit a spring to bias anvil 1312** into an open position.

Figure 125:
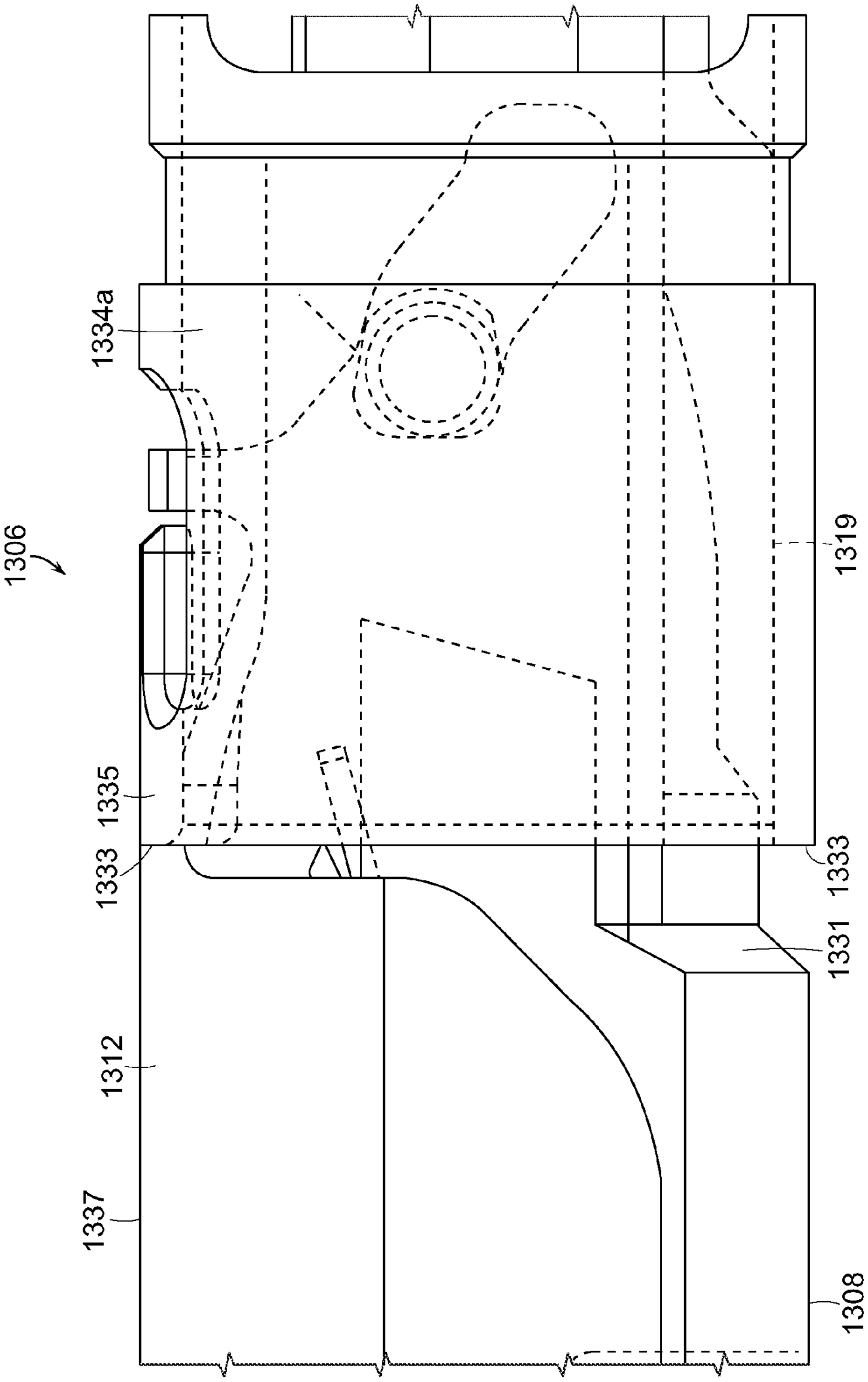

In various embodiments, referring now to FIGS. 124 and 125, distal tube component **1334*a* can be advanced distally such that it at least partially encompasses anvil 1312 and staple cartridge channel 1308. In at least one embodiment, the distal tube portion 1334*a* can comprise a cam portion 1335 which can be configured to contact the anvil 1312 and slide over the outside surface 1337 of anvil 1312. In addition, the cam portion 1335 can be configured to slide over the outside surface 1319 of staple cartridge channel 1318 such that the distal tube portion 1334*a* can encompass the entire perimeter, or an least substantial portion of the perimeter, of anvil 1312. In at least one embodiment, the cam portion 1335 can comprise a continuous circular, or at least substantially circular, ring of material defining an aperture configured to control the position of anvil 1312 relative to staple cartridge channel 1318 and gap, if any, between the anvil 1312 and a staple cartridge positioned within the staple cartridge channel 1318. In certain embodiments, at least one spring, or biasing member, can be positioned intermediate the anvil 1312 and the staple cartridge channel 1318, wherein the spring can be configured to bias the anvil 1312 and/or staple cartridge channel 1318 against an inner perimeter of the distal tube portion 1334*a*** aperture.

In various embodiments, referring again to FIG. 125, the distal tube portion **1334*a* can comprise a distal edge 1333 which can define the distal-most portion of cam portion 1335 in contact with anvil 1312 and staple cartridge channel 1318. In certain embodiments, the staple cartridge channel 1318, for example, can comprise a forward stop, such as stop 1331, for example, configured to limit the distal movement of distal tube portion 1334*a*. In at least one such embodiment, the distal edge 1333 can contact stop 1331 and, as a result, limit the distance in which cam portion 1335 can slide over anvil 1312. In certain circumstances, however, the limitation of the distance in which cam portion 1335 can slide over anvil 1312 can limit the amount of clamping force, or leverage, that the anvil 1312 can apply to tissue positioned intermediate the anvil 1312 and a staple cartridge positioned within staple cartridge channel 1318**.

In various alternative embodiments, referring now to FIGS. 126-128, a distal tube portion **1334*a*' can comprise a first cam portion 1335*a*' configured to engage the anvil 1312 and, in addition, a second cam portion 1335*b*' configured to engage the staple cartridge channel 1318. Much like distal tube portion 1334*a*, distal tube portion 1334*a*' can encompass, or at least substantially encompass, a portion, or perimeter, of end effector 1306 defined by anvil 1312 and staple cartridge channel 1318. In various embodiments, however, the cam portion 1335*a*' can extend distally a greater distance than cam portion 1335*b*'. In at least one such embodiment, as a result, the cam portion 1335*a*' can extend a greater distance over, or around, anvil 1312 than cam portion 1335*b*' can extend under, or around, staple cartridge channel 1308. As illustrated in FIG. 127, the distal tube portion 1334*a*' can comprise a distal edge 1333*a*' which is positioned distally with respect a distal edge 1333*b*' such that, referring to FIG. 128, the cam portion 1335*a*' can extend over a longer distance of anvil 1312 and provide a larger clamping force, or leverage, as compared to the cam portion 1335 of distal tube portion 1334*a*. In various circumstances, as a result, the cam portion 1335*a*' can extend a greater distance over anvil 1312 before the cam portion 1335*b*' comes into contact with stop 1331**.

In various embodiments, referring again to FIG. 126, the inner perimeter of cam portion **1335*a*' can comprise an arcuate or an least partially circular inner profile which matches, or at least substantially matches, an arcuate or an least partially circular outer profile of anvil 1312. In at least one such embodiment, the inner profile of cam portion 1335***a*' can be configured to provide a close fit with the outer profile of anvil 1312 such that there is little, if any, relative transverse, or radial, movement therebetween yet configured to permit the cam portion 1335*a*' to slide relative to anvil 1312 as distal tube portion 1334*a*' is moved distally in the direction of arrow Z. Similar to the above, the inner perimeter of cam portion 1335*b*' can comprise an arcuate or an least partially circular inner profile which matches, or at least substantially matches, an arcuate or an least partially circular outer profile of staple cartridge channel 1308. In at least one such embodiment, the inner profile of cam portion 1335*b*' can be configured to provide a close fit with the outer profile of staple cartridge channel 1308 such that there is little, if any, relative transverse, or radial, movement therebetween yet configured to permit the cam portion 1335*b*' to slide relative to anvil 1312 as distal tube portion 1334*a*' is moved distally in the direction of arrow Z.

As outlined above, referring again to FIG. 123, the end effector 1306 can be rotated relative to the shaft 1304 about articulation joint 1315. In various embodiments, the closure tube comprising distal tube portion 1334*a* and proximal tube portion 1334*b* can comprise one or more articulation links, such as links 1301*a* and 1301*b*, for example, which can permit distal tube portion 1334*a* to rotate relative to proximal tube portion 1334*b* when end effector 1306 is rotated relative to shaft 1304. In at least one embodiment, link 1301*a* and/or link 1301*b* can comprise projections 1303, for example, which can be positioned within apertures in tube portions 1334*a* and 1334*b*, for example, such that links 1301*a* and 1301*b* can pivot relative to proximal tube portion 1334*b* and such that distal tube portion 1334*a* can rotate relative to links 1301*a* and 1301*b*. In various other embodiments, the links 1301*a*, 1301*b* and closure tube portions 1334*a*, 1334*b* can comprise any suitable combination of projections and apertures to permit articulation therebetween. In any event, the links 1301*a* and 1301*b* can provide more than degree of freedom between distal tube portion 1334*a* and proximal tube portion 1334*b*. More particularly, the links 1301*a* and 1301*b* can provide at least two degrees of freedom, i.e., a first degree of freedom between proximal tube portion 1334*b* and links 1301*a*, 1301*b* and a second degree of freedom between links 1301*a*, 1301*b* and distal tube portion 1334*a*.

In use, as outlined above, the end effector 1306 can be articulated relative to shaft 1304 about axis 1316 and then locked into position by a lock. Referring now to FIG. 129, the pivot axis 1316 of articulation joint 1315 can be defined by a pivot 1302 extending from shaft channel portion 1342 wherein the pivot 1302 can be positioned within an aperture in lock portion 1305 of staple cartridge channel 1308. When the lock is disengaged from lock portion 1305, the end effector 1306 can be rotated or pivoted about axis 1316 into a desired position and then locked into place by re-engaging the lock with lock portion 1305. In various embodiments, the end effector 1306 in first and second, or left and right, directions about pivot 1302. Similar to the embodiments described above, the lock can engage at least one of lock teeth 1312 and/or at least one of recesses 1314 positioned intermediate lock teeth 1312. Regardless of whether the end effector 1306 is in a centered position or an articulated position, the closure tube 1334 of shaft 1304 can be advanced distally in order to close anvil 1312, as described above. When closure tube 1334 is advanced distally, the links 1301*a* and 1301*b* can slide relative to axis 1316 and articulation joint 1315 owing, in various circumstances, to the multiple degrees of freedom afforded by links 1301*a* and 1301*b* as described above eventhough the end effector 1306 may be articulated relative to shaft 1304, for example.

Once the closure tube 1334 has been advanced and the anvil 1312 has been closed, a drive bar, such as drive bar 1390 (FIG. 136), for example, can be advanced within the shaft 1304 and the end effector 1306. In various embodiments, referring to FIGS. 136 and 137, drive bar 1390 can comprise a bar portion 1391 configured to transmit a force from a trigger of the surgical instrument handle (FIG. 1), for example, to a cutting member 1392 and/or a staple driver 1393 such that the cutting member 1392 can incise tissue positioned within end effector 1306 and/or such that staple driver 1393 can eject staples, such as staple 1381 (illustrated in phantom in FIG. 136), for example, from a staple cartridge, such as staple cartridge 1380 (FIG. 138), for example, positioned in staple cartridge channel 1308. Turning now to FIG. 129, the lock portion 1305 of end effector 1306 can comprise a guide slot 1321 configured to receive and guide bar portion 1391 of drive bar 1390. In addition, the shaft 1304 can further comprise a frame, or spine 1345 (FIGS. 131 and 132) including a guide slot 1341 also configured to receive guide bar portion 1391 of drive bar 1390, wherein the drive bar 1390 can slide within guide slots 1321 and 1341 when the drive 1390 is advanced distally and/or retracted proximally.

In various embodiments, referring now to FIGS. 129 and 130, the surgical instrument 1300 can further comprise a guide member 1370 which can comprise a guide slot configured to receive at least a portion of drive bar 1390. In at least one embodiment, the guide slot within guide member 1370 can comprise a first sidewall 1371 and a second sidewall 1372 which can be configured to support the bar portion 1391 (illustrated with phantom lines in FIG. 129) when the drive bar 1390 is moved relative to articulation joint 1315. More particularly, when end effector 1306 is articulated in a first, or left, direction, as illustrated in FIG. 129, the first sidewall 1371 can be configured to support the bar portion 1391 of drive bar 1390 as bar portion 1391 is slid relative thereto. In various embodiments, the bar portion 1391 may be sufficiently flexible in order to adopt a change in geometry so as to fit and move within guide slot 1341 and guide slot 1321. In certain circumstances, the guide member 1970 can be configured to assist in preventing the bar 1391 from buckling under the load applied thereto. Similar to the above, the second sidewall 1372 can be configured to support the bar portion 1391 when the end effector 1306 is articulated in a second, or right, direction.

In various embodiments, referring again to FIGS. 129-130, the guide member 1370 can move independently of shaft 1304 and/or end effector 1306. More particularly, in at least one embodiment, the guide member 1370 can be configured to float, or adopt its own position, relative to lock portion 1305 of end effector 1306 and frame 1341 (FIGS. 131 and 132) of shaft 1304, including when end effector 1306 is articulated relative to shaft 1304. In certain embodiments, the guide member 1370 can comprise means for permitting, although limiting, the relative movement between guide member 1370. In at least one such embodiment, the guide member 1370 can comprise a first projection, or boss, 1376 extending therefrom which can be positioned within a first boss slot 1343 in shaft channel portion 1342, wherein the sidewalls of boss slot 1343 are sufficiently spaced from one another to permit end 1378 of guide member 1370 to move relative to shaft 1304 yet limit the range of movement therebetween. Similarly, the guide member 1370 can further comprise a second projection, or boss, 1377 extending therefrom which can be positioned within a second boss slot 1322 of lock portion 1305, wherein the sidewalls of boss slot 1345 are sufficiently spaced from one another to permit end 1379 of guide member 1370 to move relative to shaft 1304 yet limit the range of movement therebetween. In various alternative embodiments, the guide member 1370 could comprise first and second boss slots and the shaft channel portion 1342 and lock portion 1305 could comprise bosses extending therefrom.

In various embodiments, further to the above, the first boss slot 1343 of shaft channel portion 1342 and the first boss 1376 of guide member 1370 can be configured to keep the proximal end 1378 of the slot of guide member 1370 aligned, or at least substantially aligned, with the guide slot 1341 in shaft 1304. Similarly, the second boss 1377 of guide member 1370 and the second boss slot 1322 of lock portion 1305 can be configured to keep the distal end 1379 of the guide slot in guide member 1370 aligned, or at least substantially aligned, with the guide slot 1321 in end effector 1306. In various embodiments, further to the above, the lock portion 1305, for example, can comprise recesses 1323*a* and 1323*b* configured to receive and accommodate the distal corners, or end, of guide member 1370 when end effector 1306 and lock portion 1305 are articulated with respect to shaft 1304, for example. In at least one embodiment, referring primarily to FIG. 130, the recesses 1323*a* and 1323*b* can be configured to provide clearance between the sidewalls of recesses 1323*a* and 1323*b* and the end of guide member 1370.

In various alternative embodiments, referring now to FIGS. 133 and 134, the end effector 1306 can comprise an alternative embodiment of the lock portion 1305, i.e., lock portion 1305'. The lock portion 1305' can comprise recesses 1323*a'* and 1323*b'* which can be configured to receive and support the distal end of guide member 1370, as described in greater detail below. Referring to FIG. 133, the end effector 1306 is illustrated in a straight, or at least substantially straight, alignment with shaft 1304, wherein a gap 1329 is present intermediate guide member 1370 and lock portion 1305 and, in addition, a gap 1349 is present intermediate guide member 1370 and frame, or spine, 1345. In such a position, the guide slot 1341, the guide slot in guide member 1370, and the guide slot 1321 in lock portion 1305 can be aligned, or at least substantially aligned, with one another along a common axis. In such circumstances, the knife bar 1390 may be subjected to an axial load along the axis 1394 during use, although it may be subjected to little, if any, transverse loads which are transverse to axis 1394 and, as a result, the sidewalls of the guide slots may be required to provide little, if any, transverse support to the sides of driver bar 191.

Referring now to FIG. 134, the end effector 1306 is illustrated in an articulated alignment with shaft 1304, as illustrated by the rotation of lock portion 1305'. As also illustrated in FIG. 134, the guide member 1370 has also moved in response to the articulation of end effector 1306. In various embodiments, the movement of end effector 1306 and lock portion 1305' can cause lock portion 1305' to contact guide member 1370 and at least one of, one, rotate guide member 1370 in the same direction as end effector 1306 is being rotated and, two, push guide member 1370 proximally toward frame 1345 of shaft 1304. As illustrated in FIG. 134, the gap 1329 between the distal end of guide member 1370 and lock portion 1305 has been one of eliminated or substantially reduced. As also illustrated in FIG. 134, at least a portion of guide member 1370 can be positioned within first recess 1323*a'* such that relative movement between the distal end of guide member 1370 and lock portion 1305 can be prevented, or at least substantially inhibited. More particularly, in at least one embodiment, a catch 1373*a* extending from guide member 1370 can be positioned within first recess 1323 such that relative movement between catch 1373*a* and lock portion 1305 is prevented, or at least limited, and such that a desired alignment between first sidewall 1371 and a first sidewall 1321*a* of guide slot 1321 can be substantially maintained. Owing to the elimination, or reduction, of gap 1329 and the alignment, or at least substantial alignment, of first sidewall 1371 and first sidewall 1321*a*, the drive bar 1391 can be supported so as to eliminate, or at least reduce, the possibility of drive bar 1391 buckling in a transverse direction, for example.

In various circumstances, further to the above, the end effector 1306 can be rotated in a second direction, or direction opposite the first direction, for example. In such circumstances, similar to the above, the guide member 1370 can move in response to the articulation of end effector 1306. In various embodiments, the movement of end effector 1306 and lock portion 1305' can cause lock portion 1305' to contact guide member 1370 and at least one of, one, rotate guide member 1370 in the same direction as end effector 1306 is being rotated and, two, push guide member 1370 proximally toward frame 1345 of shaft 1304. In such circumstances, also similar to the above, the gap 1329 between the distal end of guide member 1370 and lock portion 1305 can be one of eliminated or substantially reduced and at least a portion of guide member 1370 can be positioned within second recess 1323*b'* such that relative movement between the distal end of guide member 1370 and lock portion 1305 can be prevented, or at least substantially inhibited. More particularly, in at least one embodiment, a catch 1373*b* extending from guide member 1370 can be positioned within second recess 1323*b'* such that relative movement between catch 1373*a* and lock portion 1305 is prevented, or at least limited, and such that a desired alignment between second sidewall 1372 and a second sidewall 1321*a* of guide slot 1321 can be substantially maintained. Owing to the elimination, or reduction, of gap 1329 and the alignment, or at least substantial alignment, of second sidewall 1372 and second sidewall 1321*b*, the drive bar 1391 can be supported so as to eliminate, or at least reduce, the possibility of drive bar 1391 buckling in a transverse direction, for example.

In various embodiments, further to the above, the second boss 1377 extending from guide member 1370 can be configured to work in concert with catches 1373*a* or 1373*b* to prevent, or at least substantially inhibit, relative movement between the distal end of guide member 1370 and lock portion 1305'. More particularly, in at least one embodiment, the second boss 1377 and the second boss slot 1322 can be configured such that second boss 1377 is in contact with a sidewall of the second boss slot 1322 when first catch 1373*a* is positioned within first recess 1323*a'*. Owing to the above, the distal end of guide member 1370 can be prevented, or at least inhibited, from translating and/or rotating relative to lock portion 1305'. In various circumstances, the first catch 1373*a* can be positioned within the first recess 1323*a'* without the second boss 1377 being in contact with a sidewall of second boss slot 1322. In at least one such circumstance, the displacement of drive bar 1390 can cause guide member 1370 to rotate relative to lock portion 1305' and cause second boss 1377 to be positioned against a sidewall of second boss slot 1322.

When the end effector 1306 is rotated in its second direction, similar to the above, the second boss 1377 and the second boss slot 1322 can be configured such that the second boss 1377 is in contact with a sidewall of second boss slot 1322 when second catch 1373*b* is positioned within second recess 1323*b*'. Owing to the above, the distal end of guide member 1370 can be prevented, or at least inhibited, from translating and/or rotating relative to lock portion 1305'. In various circumstances, the second catch 1373*b* can be positioned within the second recess 1323*b*' without the second boss 1377 being in contact with a sidewall of second boss slot 1322. In at least one such circumstance, the displacement of drive bar 1390 can cause guide member 1370 to rotate relative to lock portion 1305' and cause second boss 1377 to be positioned against a sidewall of second boss slot 1322.

As discussed above, the end effector 1306 can be rotated through a range of articulation angles relative to shaft 1304. For example, the end effector 1306 can be rotated between a straight, or center, alignment, as illustrated in FIG. 133, and an articulated alignment, as illustrated in FIG. 134. In the articulated alignment of FIG. 134, the end effector 1306 can be rotated approximately 45 degrees, for example, from the straight, or center, alignment. In other circumstances, referring now to FIGS. 131 and 132, the end effector 1306 can be rotated approximately 75 degrees, for example, from the straight, or center, alignment. When end effector 1306 is rotated, as outlined above, the lock portion 1305' can, in various embodiments, rotate guide member 1370 owing to the operative engagement between first catch 1373*a* of guide member 1370 and first recess 1323*a*' of lock portion 1305', for example. Furthermore, as also outlined above, the rotation of lock portion 1305' can push guide member 1370 proximally toward frame 1345. In various embodiments, the guide member 1370 can comprise a proximal projection, or catch, 1375 which can be configured to slide within a recess in shaft 1304 when the guide member 1370 is pushed proximally. In at least one such embodiment, the proximal catch 1375 can be slid into a recess 1349 defined intermediate the frame 1345 and the proximal shaft portion 1341. In such circumstances, the proximal end 1375 of the guide member 1370 can be prevented, or at least inhibited, from lifting upwardly relative to frame 1345. In addition, in at least one embodiment, the first boss 1376 and the first boss slot 1343 can work in concert with proximal catch 1375 and the catch recess 1349 in shaft 1304 in order to prevent, or at least limit, relative translation and/or rotation between the proximal end of guide member 1370 relative to shaft 1304.

As discussed above, the end effector 1306 can be articulated relative to shaft 1304 about axis 1316 through a range of positions, or orientations. When end effector 1306 is in a straight, or centered, orientation as illustrated in FIG. 133, the distance between the distal end of guide slot 1341, i.e., datum 1330, and the proximal end of guide slot 1321, i.e., datum 1331, can be defined by a first distance 1332*a*. When end effector 1306 is in an articulated orientation as illustrated in FIG. 134, the distance between datum 1330 and datum 1331 can be defined by a second distance 1332*b*. Owing to the articulation of end effector 1306 and the movement of datum 1331 toward datum 1330, the second distance 1332*b* is shorter than the first distance 1332*a*. Similarly, when end effector 1306 is further articulated into the orientation illustrated in FIG. 131, the distance between datum 1330 and datum 1331 can be defined by a third distance 1332*c* which is shorter than the first distance 1332*a* and the second distance 1332*b*. In any event, the reader will understand that the particular degrees of articulation of the end effector 1306 depicted in FIGS. 131, 133, and 134 are exemplary and that the end effector 1306 can be articulated into any other suitable orientation wherein, in such other orientations, the distance between datums 1330 and 1331 may be different.

In various circumstances, the cutting member 1392 can be positioned within the staple cartridge 1380 (FIG. 138) when the end effector 1306 is in its straight and/or articulated orientations. When the end effector 1306 is in its straight orientation, the cutting member 1392 can be positioned in a first position relative to the distal end 1382 of the staple cartridge 1380 and/or the distal end 1384 of cutting knife slot 1383. When the end effector 1306 is articulated relative to shaft 1304, as discussed above, one of the cutting member 1392 and the staple cartridge 1380 may move relative to the other leaving the cutting member 1392 in a second position relative to the distal end 1382 of staple cartridge 1380 and the distal end 1384 of cutting knife slot 1383. In various circumstances, this second position can be closer to the distal end 1382 and distal end 1384 than the first position. In such circumstances, depending on the degree of the articulation, the cutting member 1392 may have a starting position which is closer to the distal end 1382 and the distal end 1384 when the cutting member 1392 is advanced distally by the drive bar 1390. Such different starting positions can result from, one, the cutting member 1392 being held in position, or at least partially held in position, by the stiffness of the drive bar 1390 such that the cutting member 1392 slides within the staple cartridge 1380 when the end effector 1306 is articulated and, two, the distance (1332*a*, 1332*b*, and 1332*c*) between datums 1330 and 1331 changing as the end effector 1306 is articulated, as discussed above.

In some circumstances, further to the above, the distance between the initial position of the cutting member 1392 and the distal ends 1382, 1384 may be the same, or at least the substantially the same, in the minor-image orientations of the end effector 1306. More particularly, the distance between the initial position of the cutting member 1392 and the distal ends 1382, 1384 may be the same when the end effector is articulated in a 45 degree angle to the left of the center orientation as compared to a 45 degree angle to the right of the center orientation, for example. In various embodiments, the initial position of cutting member 1392 may be closest to the distal ends 1382, 1384 when the end effector is at its maximum articulation angle in either direction, left or right. In certain embodiments, the initial position of cutting member 1392 may be furthest away from the ends 1382, 1384 when the end effector 1306 is in its straight, or center, orientation.

In use, as described above, the drive bar 1390 can be advanced distally in order to incise tissue positioned within the end effector 1306 and/or eject staples positioned within the staple cartridge 1380 (FIG. 138). In some embodiments, a surgical stapling instrument can be configured such that the drive bar 1390 is advanced a predetermined, or set, distance by a trigger mechanism, or firing mechanism, of the surgical instrument during use. Stated another way, in various embodiments, such a surgical instrument can be configured to advance the cutting member 1392 a predetermined, or set, distance without regard to whether end effector 1306 is articulated and/or without regard to the degree of articulation of end effector 1306. In various circumstances, however, the cutting member 1392 may stop at different distal positions within the staple cartridge 1380 owing to the different starting positions of the cutting member 1392. More particularly, referring to FIGS. 137 and 138, the cutting edge 1396 of cutting member 1392 can be advanced to a position 1389*a* when the end effector 1306 is in its straight orientation (FIG. 133) and to a different, more distal, position 1389*c* when the end effector is in a fully articulated, or nearly fully articulated, orientation (FIG. 131) eventhough the cutting member 1392 has been advanced the same predetermined, or set, distance.

In various circumstances, the different final positions of cutting member 1392 and cutting edge 1396 can result from the different starting positions of cutting member 1392 within the staple cartridge 1380. As described above, the different starting positions of cutting member 1392 can result from the articulation of end effector 1306, the stiffness of drive bar 1391, and the different distances, such as distances 1332*a* and 1332*c*, for example, between the datums 1330 and 1331 that exist when the end effector 1306 is in its straight orientation (FIG. 133) and articulated orientations (FIG. 131). In various circumstances, as distance 1323*c* is shorter than distance 1323*a*, the cutting member 1392 can be positioned in a more distal initial position in staple cartridge 1380 (as compared to its position when the end effector 1306 is in its straight orientation) before the predetermined or set displacement of the cutting member 1392 is applied thereto and, in various circumstances, the cutting edge 1396 can be advanced to a more distal position within the staple cartridge 1380 to position 1389*c*. Correspondingly, as distance 1323*a* is longer than distance 1323*c*, the cutting member 1392 can be positioned more proximally in the staple cartridge 1380 (as compared to its position when the end effector 1306 is in a fully articulated orientation) before the predetermined, or set, displacement of the cutting member 1392 is applied thereto and, in various circumstances, the cutting edge 1396 may only be advanced to position 1389*a*. Similar to the above, the cutting edge 1396 could be advanced to a position intermediate position 1323*a* and position 1323*c* when the end effector 1306 is only in a partially articulated orientation (FIG. 134).

Referring again to FIG. 138, staple cartridge 1380 can comprise a plurality of staple cavities, such as staple cavities 1385, for example, and staples, such as staples 1381 (FIG. 137), for example, positioned in the staple cavities 1385. In various embodiments, each staple 1381 can comprise one or more staple legs, such as staple legs 1381*p* and 1381*d*, for example, wherein, in at least one embodiment, each staple cavity 1385 can be configured to receive a staple 1381 such that its staple leg 1381*d* is positioned in a distal end 1385*d* of the staple cavity 1385 and such that its staple leg 1381*p* is positioned in the proximal end 1385*p*, of the staple cavity 1385. In various embodiments, it may be desirable for the cutting edge 1396 of cutting member 1392 to be stopped before it crosses an end datum 1386 wherein, in certain embodiments, the end datum 1386 can be defined by and extend through the distal-most staple leg, or legs, 1381*d*, of the distal most staple, or staples, 1381, for example. In other various embodiments, the end datum 1386 could be defined by and extend through any portion of the distal-most staple cavities 1385, for example. In certain embodiments, the end datum 1386 could be defined by and extend through the proximal-most staple legs 1381*p* positioned within the distal-most staple cavities 1385. In any event, when cutting edge 1396 is stopped before the end datum 1386, the cutting edge 1396 may not transect beyond the tissue that has been stapled by staples 1381. In various embodiments, it may be desirable for the cutting edge 1396 to be stopped at least 3 mm short of end datum 1386. In certain embodiments, it may be desirable for the cutting edge 1396 to be stopped in a range between approximately 3 mm and approximately 7 mm short of end datum 1386. In certain other embodiments, a narrower range may be desired. Described herein are means and embodiments for controlling or limiting the advancement of the cutting member 1392 and cutting edge 1396 within the staple cartridge 1380.

As described above, referring again to FIGS. 131, 133, and 134, the guide member 1370 can move relative to lock portion 1305' and shaft 1304, although, in various circumstances, the distal end of guide member 1370 can be captured by and/or positioned against the lock portion 1305'. Referring now to FIG. 140, a drive bar, such as drive bar 1390', for example, can comprise a stop, such as stop 1395', for example, which can be configured to contact guide member 1370 such that the distal advancement of drive bar 1390' and cutting member 1392 can be limited by guide member 1370. More particularly, in various embodiments, the stop 1395' can be configured to contact a stop datum, such as stop datum 1399, for example, on the proximal end of guide member 1370 such that, when stop 1395' contacts stop datum 1399, the drive bar 1390' can no longer be advanced, or at least significantly advanced, in the distal direction into the staple cartridge 1380. When stop 1395' contacts datum 1399, and guide member 1370 is in contact with the lock portion 1305', the final distal-most position of cutting edge 1396 can be largely determined by the predetermined, or set, distance 1397' between the stop surface 1395' and cutting edge 1396, as described in greater detail further below. In various embodiments, the stop 1395' can comprise a downwardly depending tab or projection which can include a perpendicular shoulder, for example, configured to engage a corresponding perpendicular shoulder of stop datum 1399, for example.

Further to the above, in at least one embodiment, with the stop surface 1395' of drive bar 1390' in contact with the guide member 1370 and the guide member 1370 in contact with stop portion 1305' of end effector 1306, the final, distal-most position of the cutting edge 1396 relative to the end 1384 of knife slot 1383 can be dictated by the predetermined distance 1397', the length of the guide slot in guide member 1370, and the distance between datum 1331 and the distal end 1384 of knife slot 1383. In various embodiments, the guide member 1370 can be comprised of a sufficiently rigid material and geometry such that very little, if any, deflection or deformation occurs within the guide slot in guide member 1370 during use. Similarly, the end effector 1306 can be comprised of a sufficiently rigid material and geometry such that very little, if any, deflection or deformation occurs within the knife slot 1383 during use. In certain embodiments, as a result, the guide slot within guide member 1370 and the knife slot 1383 can define a guide path which has little variation in the length thereof regardless of the orientation of the end effector 1306. In at least some embodiments, however, there may be some variation in the length of the guide path. More particularly, although the guide member 1370 can be positioned against the stop portion 1305', the relative alignment between the guide slot in guide member 1370 and the guide slot 1321 in lock portion 1305' may be different in the different orientations of end effector 1306 resulting in different, or at least slightly different, guide path lengths as discussed in greater detail below.

As discussed above, the orientation of end effector 1306 can affect the relative alignment between guide member 1370 and end effector 1306. Referring to FIG. 134 which illustrates the end effector 1306 in an approximately 45 degree orientation, for example, and eventhough the guide member 1370 is in contact with the lock portion 1305', a small gap 1389 can exist between the distal end of guide member 1370 and the lock portion 1305'. When the end effector 1306 is articulated even further, as illustrated in FIG. 131 which illustrates the end effector 1306 in an approximately 75 degree orientation, the gap 1389 between the guide member 1370 and the lock portion 1305' can become larger, albeit slightly, eventhough the guide member 1370 is still in contact with the lock portion 1305'. Such a change in the size of gap 1389 can result in a change in the length of the guide path comprising the guide slot in guide member 1370 and the knife slot 1383. Such changes in the guide path length notwithstanding, the stop datum 1399 may provide a reliable datum against which the distal advancement of drive bar 1390' can be stopped and a reliable means for stopping the cutting edge 1396 at a consistent position, and/or within a narrower range of positions, within the staple cartridge 1380 regardless of the orientation of the end effector 1306. In certain circumstances, the stop 1395' of drive bar 1391 can contact the guide member 1370 and position the guide member 1370 against the lock portion 1305'. Such circumstances can occur, referring to FIG. 133, when the end effector 1306 is in a straight, or at least substantially straight, orientation, for example.

Further to the above, referring now to FIGS. 140 and 141, the stop 1395' of drive bar 1391 can abut the datum surface 1399 of guide member 1370 in order to stop the distal advancement of drive bar 1391 regardless of the orientation of end effector 1306. More particularly, referring to FIG. 140, the stop surface 1395' can abut the datum surface 1399 when the end effector 1306 is in a straight orientation and, similarly, referring now to FIG. 141, the stop surface 1395' of drive bar 1391 can also abut the datum surface 1399 when the end effector 1306 is in an approximately 66 degree orientation, for example. As the reader will note when comparing FIGS. 140 and 141, further to the above, the guide member 1370 has been pushed proximally by the articulation of end effector 1306. When the guide member 1370 has been pushed proximally, the datum surface 1399 may also be pushed proximally which can shorten the distance in which drive bar 1391 can travel distally. Correspondingly, when end effector 1306 is in a straight orientation, the distance in which drive bar 1391 can travel distally can be longer. In various embodiments, as a result of the above, the distance in which the drive bar 1391 can be displaced distally may decrease as the articulation angle of end effector 1306 is increased. In summary, when the end effector 1306 is in an articulated position, the cutting member 1392 may have a more distal starting position; however, such a more distal starting position may be compensated for by the proximally-moved datum surface 1399 which can limit the distal displacement of the cutting member 1392 such that the final distal-most position of cutting member 1392 is the same as, or within a very close range with respect to, the final distal-most position of cutting member 1392 when end effector 1306 is in a straight orientation. Likewise, when end effector 1306 is in a straight orientation, the cutting member 1392 may have a more proximal starting position; however, such a more proximal starting position may be compensated for by the more distal datum surface 1399 which can provide for a longer distal displacement of the cutting member 1392 such that the final distal-most position of cutting member 1392 is the same as, or within a very close range with respect to, the final distal-most position of cutting member 1392 when end effector 1306 is in an articulated orientation.

As discussed above, referring again to FIG. 138, it may be desirable to stop the knife edge 1396 of cutting member 1392 short of end datum 1386. In various embodiments, referring now to FIG. 142, a surgical stapling instrument, such as surgical instrument 1400, for example, can comprise a firing system driven by a motor, such as motor 1410, for example. In use, the motor 1410 can be operated so as to advance a cutting member, such as cutting member 1392, for example, through an end effector, such as end effector 1306, for example, to the same, or at least substantially the same, final distal position within end effector 1306 such that knife edge 1396 is stopped short of end datum 1398 regardless of the angle in which the end effector 1306 has been articulated. In certain embodiments, further to the above, the motor 1410 can be positioned within a handle of the surgical instrument 1400, for example. The surgical instrument 1400 can further comprise a firing switch, or trigger, positioned on and/or operably coupled with the surgical instrument handle, for example, wherein the switch, or trigger, can be operated in order to operably couple motor 1410 with a power source, such as a battery, for example, which can also be positioned within the handle. In use, as described in greater detail below, the firing switch, or trigger, can be operated to supply power from the power source to the motor 1410 in order to advance and/or retract a firing rod 1466, the drive bar 1390, and the cutting member 1392.

In various embodiments, further to the above, the motor 1410 can comprise a drive shaft 1411 operably coupled with a pinion gear 1412, wherein the motor 1410 can be configured to rotate drive shaft 1411 and pinion gear 1412 in a first, or clockwise, direction and/or in a second, counter-clockwise, direction. Referring again to FIG. 142, pinion gear 1412 can be operably coupled with a rack 1413, wherein the rotation of pinion gear 1412 can drive rack 1413 in a distal direction D and/or a proximal direction P depending on the direction in which pinion gear 1412 is rotated. In various embodiments, the pinion gear 1412 and the rack 1413 can each comprise teeth which can co-operate with one another to transmit the rotational motion of gear 1412 to linear, or at least substantially linear, motion of rack 1413. As also illustrated in FIG. 142, the firing drive can further comprise a firing rod 1466 operably coupled with the rack 1413 and, as described in greater detail further below, the drive bar 1390 can be operably coupled with the firing rod 1466 such that the movement of rack 1413 can be transmitted to firing rod 1466 and drive bar 1390. Similar to the above, referring now to FIG. 143, the drive bar 1390 can be operably coupled with cutting member 1392 such that distal movement of rack 1413 can move cutting member 1392 distally and, correspondingly, proximal movement of rack 1413 can move cutting member 1392 proximally.

In use, further to the above, a surgeon can operate the surgical instrument 1400 by manipulating a firing switch, or trigger, on the surgical instrument handle, for example, in order to advance the cutting member 1392 and, ultimately, staple and/or incise tissue positioned within the end effector of the surgical instrument. In various embodiments, the surgical instrument 1400 can further comprise a computer which can comprise one or more inputs, wherein at least one of such inputs can be operably coupled with the firing switch such that the computer can detect the operation of the firing switch. In certain embodiments, the computer can be positioned within the surgical instrument handle, for example. In at least one embodiment, the operation of the switch can close a circuit which, in response thereto, the computer can command the motor 1410 to rotate in a direction which moves the rack 1413 in a proximal direction, i.e., direction P. More particularly, the computer can, in response to the switch input, complete a circuit allowing a voltage potential to be applied to the motor 1410 by the battery which, as a result, can allow the motor 1410 to rotate shaft 1411 and pinion gear 1412. In any event, when cutting member 1392 is pulled proximally by rack 1413, the cutting member 1392 can be brought into contact with a datum, such as datum stop or surface 1398, for example, in the end effector 1306. Once cutting member 1392 is in contact with datum stop 1398, and/or once the computer of the surgical instrument 1400 has detected that cutting member 1392 is in contact with the datum surface 1398, the computer can, in at least one embodiment, open the circuit between the power source and the motor 1410 such that the motor 1410 no longer rotates pinion gear 1412 and such that pinion gear 1412 no longer drives rack 1413 proximally.

In various embodiments, further to the above, the surgical instrument 1400 can further comprise an encoder system which can detect when the cutting member 1392 has contacted the datum surface 1398. In at least one embodiment, the rack 1413 can comprise a plurality of detectable elements 1414 arranged in a linear array positioned thereon and/or therein, wherein the encoder system can further comprise an encoder sensor 1415 configured to detect the detectable elements 1414 as they pass by the encoder sensor 1415. In some embodiments, the detectable elements 1414 can comprise iron which, when the elements 1414 pass in front of sensor 1415, can create disruptions in a magnetic field which are detected by the encoder sensor 1415. In certain embodiments, the detectable elements 1414 can comprise visible demarcations, such as projections, recesses, and/or colored lines, for example, which can be detected by the encoder sensor 1415. In any event, the encoder sensor 1415 can be operably coupled with the computer such that the computer can count the detectable elements 1414 detected by sensor 1415 as rack 1413 is retracted, or moved in a proximal direction P. More particularly, in at least one embodiment, the encoder sensor 1415 can be operably coupled with at least one of the computer inputs such that the computer can receive one or more signals from the encoder sensor 1415. In any event, in various embodiments, the detectable elements 1414 can be positioned at predetermined, or set, distances apart from one another such that the detection of sequential detectable elements 1414 can indicate to the computer that the rack 1413 has been moved a set, or unit, distance. In at least one embodiment, such a set, or unit, distance can comprise 1 mm, for example. In certain embodiments, the motor can comprise an encoder motor including an encoder system integrally incorporated therein wherein the encoder can measure to rotation of motor shaft 1411, for example, and, based on the size and configuration of pinion gear 1412, estimate the proximal and/or distal movement of rack 1413.

In any event, the computer of the surgical instrument 1400 can be configured to compare the output commands sent to the motor 1410 to the input signals received from the encoder sensor 1415 in order to determine whether there is a difference between the expected position and the actual position of the rack 1413 and, correspondingly, the expected and actual positions of cutting member 1392. By way of example, FIG. 145 provides a graphical representation of what the computer may detect, i.e., a first range 1416*a* which indicates that rack 1413 is being retracted toward datum stop 1398 and a second range 1416*b* which indicates that cutting member 1392 is in contact with datum stop 1398 and/or is only moving slightly due to the deformation of datum stop 1398 and/or cutting member 1392, for example. Referring again to FIG. 145, the computer of surgical instrument 1400 can compare the expected movement of rack 1413 based on the commands, or output, being given to motor 1410, as depicted by line 1417, to the detected movement of rack 1413 based on the input of the encoder sensor 1415, as depicted by line 1418, and, when a sufficient difference exists between the expected movement and the actual movement of rack 1413, the computer can operably decouple the power source from the motor 1410 and/or otherwise command the motor 1410 to stop rotating pinion 1412. At such point, the computer of surgical instrument 1400 can record the position of the rack 1413, and cutting member 1392, as being in a 'datum position'. In various embodiments, the computer can comprise memory storage, such as a non-volatile random access memory (NVRAM) chip, for example, which can be configured to store such information, and/or any other information regarding the position of the rack 1413 and cutting member 1392 at any other point during the operation of the surgical instrument.

Once cutting member 1392 is in contact with datum stop 1398, the computer can instruct the motor 1410 to rotate pinion gear 1412 in the opposite direction in order to advance rack 1413 distally, i.e., in direction D. In at least one embodiment, the computer can reverse the polarity of the voltage applied to motor 1410 in order to rotate pinion gear 1412 in the opposite direction. In any event, the computer can instruct motor 1410 to advance cutting member 1392 a predetermined, or set, distance relative to datum stop 1398. In at least one such embodiment, the computer can allow a predetermined, or set, voltage and/or current to be supplied to the motor 1410 from the power source for a predetermined, or set, duration which can, in various circumstances, advance the cutting member 1392 the predetermined distance. In certain embodiments, the magnitude and/or duration, for example, of the voltage and/or current supplied to the motor 1410 can be adjusted based on feedback supplied to the computer. In at least one embodiment, further to the above, the encoder sensor 1415 can be configured to relay the actual, or at least perceived, displacement and position of the rack 1413 to the computer such that the computer can compare the actual position of the rack 1413 to its expected position and, correspondingly, compare the actual and expected positions of the knife edge 1396. In the event that the computer determines that the position of the knife edge 1396, for example, lags its expected position, the computer can increase the duration and/or magnitude of power supplied to the motor 1410 such that the knife edge 1396 arrives at its expected position, or at least substantially close thereto. Alternatively, in the event that the computer determines that the position of the knife edge 1396 leads its expected position, the computer can shorten the duration and/or decrease the magnitude of power being supplied to the motor 1410 such that the knife edge 1396 does not surpass, or at least substantially surpass, its expected position.

In various embodiments, further to the above, the predetermined, or set, distance in which the cutting member 1392 is advanced relative to the datum stop 1398 can be the same, or at least substantially the same, distance regardless of the articulation angle, if any, of end effector 1306. In various circumstances, as a result, the knife edge 1396 can be stopped at the same, or at least substantially the same, position short of end datum 1386. As the reader will note, referring to FIGS. 138 and 143, the datum stop 1398 and end datum 1386 are both positioned distally with respect to the articulation joint of the surgical instrument and, as a result, the potential shifting of the articulation joint components, such as guide member 1370, for example, as discussed above, may not impact the relative arrangement of the datums 1386 and 1398. In at least one exemplary embodiment, the datum stop 1398 can be positioned within the staple cartridge channel of the end effector 1306 and the end datum 1398 can be determined by certain features of the staple cartridge 1380 positioned within the staple cartridge channel, as discussed above. In certain other embodiments, the datum stop 1398 and the end datum 1386 can both be defined by features of a staple cartridge while, in some embodiments, the datums 1398 and 1386 can be defined by features of the staple cartridge channel, for example. In any event, when the cutting member 1392 is positioned against the datum stop 1398 and then advanced distally the predetermined distance, the cutting member 1392, and knife edge 1396, can be positioned reliably, or at least substantially reliably, relative to the end datum 1386.

In various embodiments, referring now to FIG. 144, the interconnection between the distal end of firing rod 1466 and the proximal end of drive bar 1390 can permit relative movement therebetween. In at least one embodiment, the drive bar portion 1391 of drive bar 1390 can comprise a flange, or tab, 1369 depending therefrom which can be positioned within a slot, or groove, 1467 in the firing rod 1466, for example. As illustrated in FIG. 144, the width W2 of the slot 1467 is wider than the width W1 of the tab 1369 such that the tab 1369 can slide proximally and/or distally, for example, within the slot 1467. In certain embodiments, as a result, one or more gaps can be present between the sides 1369*p* and 1369*d* of tab 1369 and the sides 1467*p* and 1467*d* of slot 1467. Such gaps, in various circumstances, may facilitate the articulation of the end effector 1306, for example, by allowing at least some relative movement between the firing rod 1466 and the drive bar 1390 so as to prevent, or at least reduce the possibility of the drive bar 1390 buckling undesirably and/or the possibility of drive bar 1390 undesirably resisting the articulation of end effector 1306. More particularly, in at least some circumstances, the drive bar 1390 may be moved proximally during the articulation of end effector 1306 and, in at least one embodiment, the slot 1467 can be sized and configured to accommodate such proximal movement of drive bar 1390. As discussed further above, the distance in which the drive bar 1390 moves proximally may be directly proportional to the degree of articulation of end effector 1306, i.e., larger articulations of end effector 1306 may result in more proximal movement (FIG. 146*b*) of drive bar 1390 and, correspondingly, smaller articulations of end effector 1306 may result in less proximal movement (FIG. 146*a*). In at least one embodiment, the width W2 of slot 1467 may be such that the proximal side 1369*p* of tab 1369 does not come into contact with the proximal wall 1467*p* of slot 1467. In any event, in various embodiments, the firing drive of the surgical instrument 1400 discussed above may compensate or account for any gaps between the tab 1369 and the slot 1467, for example, in order to position the cutting member 1392 in a desired position relative to end datum 1386.

An exemplary sequence of operating a surgical instrument in accordance with some of the embodiments described above is now provided. In use, a surgeon can unlock the end effector 1306 and articulate the end effector 1306 by positioning it against tissue within the surgical site and applying a force in distal direction along the axis of shaft 1304 such that the end effector 1306 pivots relative to shaft 1304. Once end effector 1306 has been suitably articulated, the end effector 1306 can be locked into position, the end effector 1306 can be positioned such that tissue is positioned intermediate the staple cartridge 1380 and the anvil 1312, and the anvil 1312 can be closed in order to clamp the tissue. As a result of the articulation of end effector 1306, as will be discussed in greater detail below, the drive bar 1390 may move proximally and, as a result, a gap may be created between side 1368*d* of tab 1369 and side 1467*d* of slot 1467. Once the surgeon is satisfied with the positioning of the tissue within the closed end effector 1306, the surgeon can activate a firing switch, or trigger, which can be detected by the computer of the surgical instrument. As described above, the computer can instruct the motor 1410 to retract rack 1413 proximally. In various circumstances, the computer can utilize pulse width modulation in order to limit the power supplied to motor 1410 and pull the rack 1413 slowly. When the rack 1413 is moved proximally, the rack 1413 can pull firing rod 1466 proximally such that side 1467*d* of slot 1467 comes into contact with the side 1368*d* of tab 1369 and, as a result, the gap between side 1467*d* and side 1368*d* can be eliminated. Once side 1467*d* is in contact with side 1368*d*, the rack 1413 and firing rod 1466 can pull cutting member 1392 proximally until cutting member 1392 is in contact with datum stop 1398. In various embodiments, the pulse width modulation applied to motor 1410 can be calibrated such that the force applied to rack 1413 by motor 1410 does not exceed a certain maximum or peak force, such as approximately 30 lbf and/or 40 lbf, for example. By setting such a maximum force, in at least one embodiment, damage to rack 1413, firing rod 1466, driver bar 1390, and cutting member 1392, for example, may be avoided. In any event, the encoder system and the computer of the surgical instrument, described above, can detect when the cutting member 1392 has come into contact with the datum stop 1398 and the power being supplied to the motor 1410 can be disconnected. In certain embodiments, further to the above, the encoder system and the computer can determine whether the cutting member 1392 is moving freely toward the datum stop 1398 or whether the cutting member 1392 has come into contact with the stop datum 1398 and that certain components, such as stop datum 1398 and cutting member 1392, have begun to at least one of elastically or plastically deform. In this reference position, the cutting member 1392 is in contact with the datum stop 1398 (FIG. 143) and there exists a gap 1469 between the side 1467*p* of slot 1467 and the side 1369*p* of the tab 1369. In various embodiments, the computer can instruct the motor 1410 to advance the rack 1413 in the distal direction D such that side 1467*p* of slot 1467 comes into contact with the side 1369*p* of the tab 1369. In at least one such embodiment, the rack 1413 can be advanced distally a predetermined, or set, distance, such as approximately 0.15", for example, in order to eliminate gap 1469 and, possibly, an additional distance, such as approximately 0.025", for example, in order to assure that the gap 1469 has been eliminated and, in at least one embodiment, assure that cutting member 1392 has at least slightly broken contact with the datum stop 1398, for example. This new position can be recorded by the computer as yet another reference position and can be referred to as the "home" position. In various embodiments, the motor 1410 can pause the movement of the cutting member 1392 at the home position and/or continue moving cutting member 1392 distally through its predetermined distance in a continuous manner. As discussed above, the rack 1413, and cutting member 1392, can be moved distally the same distance with respect to the datum stop 1398 and/or home position of the cutting member 1392 regardless of the articulation angle, if any, of the end effector 1306. Accordingly, the cutting member 1392, and knife edge 1396 thereof, may moved into the same final distal position relative to the end datum 1398 and/or distal end 1384 of knife slot 1383, for example. In any event, after the cutting member 1392 has been advanced to its distal-most position, the computer can instruct the motor 1410 to retract the rack 1413 and cutting member 1392 proximally such that the anvil 1312 can be re-opened. In certain embodiments, the firing switch, or trigger, of the surgical instrument, for example, can be manipulated such that the computer instructs the motor 1410 to stop the cutting member 1392 short of its final distal position In various embodiments, as described above, the position of the cutting member 1392 relative to datum stop 1398 in the proximal end of the staple cartridge channel, or staple cartridge 1380, can be determined, or tested, by the methods described above. In certain embodiments, the position of the cutting member 1392 relative to another datum, such as a datum in the distal end of the staple cartridge channel and/or staple cartridge 1380, for example, can be determined, or tested. In at least one such embodiment, the distance between the datum stop 1398 and the distal end of the staple cartridge channel can be determined by advancing the cutting member 1392 distally from the datum stop 1398 and/or home position, for example, until the cutting member 1392 contacts the distal end of the staple cartridge channel. Once in this reference position, the computer can store this position in its memory and, based on such information, calculate the maximum cut length of the cutting member 1392 that is possible and adjust the predetermined, or set, distance that is desired for the cutting member 1392 to travel during use. Such a test can be performed before a staple cartridge is positioned within the staple cartridge channel and before the end effector is positioned within a patient, for example.

As described above, a surgical instrument can comprise an end effector which is articulatable relative to a shaft of the surgical instrument. As also described above, the end effector can be selectively locked into position relative to the shaft. Referring now to FIGS. 147 and 148, a surgical instrument can comprise an end effector including end effector lock member 1500 which can be articulated about pivot 1502. Similar to end effector lock member 300, end effector lock member 1500 can comprise a plurality of teeth 1512 and a plurality of recesses 1514 positioned around a perimeter of lock member 1500 which can be rotated about pivot 1502 when the end effector is articulated. In at least one such embodiment, each recess 1514 can be positioned intermediate two teeth 1512. In various embodiments, the surgical instrument can further comprise a lock member 1538 which can comprise a tooth 1536 configured to be inserted into one of the recesses 1514 in end effector lock member 1500. In use, the tooth 1536 can be disengaged from the recesses 1514 in order to permit the end effector, including lock member 1500, to be rotated into a desired position wherein the lock 1538 can then be advanced distally such that the tooth 1536 is inserted into and engaged with a recess 1514. In certain circumstances, the lock tooth 1536 may not be aligned with a recess 1514 when the lock 1538 is advanced distally. In certain embodiments, the lock tooth 1536 and/or the end effector lock teeth 1512 can comprise one or more beveled or angled surfaces which can be configured to cause the end effector lock member 1500 to rotate slightly, or index, into a position in which a recess 1514 is aligned with the lock tooth 1536.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapler, comprising:
- a channel configured to receive a staple cartridge comprising staples removably stored therein, wherein said channel comprises:
  - a distal end;
  - a proximal portion; and
  - a stop;
- an anvil configured to deform staples ejected from the staple cartridge, wherein said anvil comprises a distal end and a proximal portion, wherein said proximal portion of said anvil is pivotably coupled to said proximal portion of said channel, and wherein said anvil is rotatable between an open position and a closed position; and
- a closure member movable between a first position and a second position, wherein said closure member is configured to move said anvil between said open position and said closed position when said closure member is moved between said first position and said second position, and wherein said closure member comprises:
  - a body;
  - a first camming portion extending from said body a first distance toward said distal end of said channel, wherein said first camming portion is configured to be at least partially positioned around said anvil when said closure member is in said second position; and
  - a second camming portion extending from said body a second distance toward said distal end of said channel, wherein said first distance is larger than said second distance, and wherein said second camming portion is configured to be at least partially positioned around said channel and adjacent to said stop when said closure member is in said second position.

2. The surgical stapler of claim 1, further comprising a handle, a trigger, and a drive member operably coupled with said trigger and said closure member, wherein an actuation of said trigger is configured to move said closure member between said first position and said second position.

3. The surgical stapler of claim 1, further comprising said staple cartridge.

4. The surgical stapler of claim 1, wherein said anvil comprises an arcuate outer surface, and wherein said first camming portion comprises an arcuate inner portion configured to slide over said arcuate outer surface.

5. The surgical stapler of claim 4, wherein said channel comprises an arcuate outer surface, and wherein said second camming portion comprises an arcuate inner portion configured to slide over said arcuate outer surface of said channel.

6. The surgical stapler of claim 5, wherein said arcuate outer surface of said anvil at least substantially matches said arcuate inner portion of said of said first camming portion, and wherein said arcuate outer surface of said channel at least substantially matches said arcuate inner portion of said second camming portion.

7. The surgical stapler of claim 6, wherein said arcuate outer surface of said channel and said arcuate inner surface of said second camming portion form a close fit such that transverse movement between said closure member and said channel is substantially prevented.

8. The surgical stapler of claim 1, wherein said first camming portion is configured to exert a clamping force on said anvil when said closure member is in said second position.

9. A surgical stapler, comprising:

a shaft;

an end effector configured to articulate relative to said shaft at a pivot, wherein said end effector comprises:

an elongate channel configured to receive a staple cartridge, wherein said elongate channel comprises a perimeter that comprises a contact edge; and an anvil pivotably coupled to said elongate channel and rotatable between an open position and a closed position, wherein said anvil comprises a perimeter; and a closure member movable between a proximal position and a distal position, wherein said closure member is configured to move said anvil between said open position and said closed position when said closure member is moved between said proximal position and said distal position, and wherein said closure member comprises:

a first cam comprising a first distal end, wherein a first length is defined between said pivot and said first distal end when said closure member is in said distal position, wherein said first cam is configured to at least partially surround said perimeter of said anvil when said closure member is in said distal position; and a second cam comprising a second distal end, wherein a second length is defined between said pivot and said second distal end when said closure member is in said distal position, wherein said first length is greater than said second length, and wherein said second cam is configured to at least partially surround said perimeter of said channel and to abut said contact edge when said closure member is in said distal position.

10. The surgical stapler of claim 9, further comprising said staple cartridge.

11. The surgical stapler of claim 9, wherein said closure member is tubular.

12. The surgical stapler of claim 11, wherein said closure member is configured to slide around at least a portion of said perimeter of said channel and said perimeter of said anvil when said closure member moves between said proximal position and said distal position.

13. The surgical stapler of claim 12, wherein said perimeter of said anvil comprises an arcuate outer surface, wherein said first cam comprises an arcuate inner portion that substantially matches said arcuate outer surface of said anvil, wherein said perimeter of said channel comprises an arcuate outer surface, and wherein said second cam comprises an arcuate inner portion that substantially matches said arcuate outer surface of said channel.

14. The surgical stapler of claim 9, wherein said first cam exerts a leveraging force on said anvil when said closure member is in said second position.

15. A surgical stapler, comprising:

an end effector comprising:

an elongate channel configured to receive a staple cartridge, wherein said elongate channel comprises a stop; and an anvil pivotably coupled to said elongate channel and rotatable between an open position and a closed position; and a closure member movable between a proximal position and a distal position, wherein said closure member is configured to move said anvil between said open position and said closed position when said closure member is moved between said proximal position and said distal position, and wherein said closure member comprises:

a first portion configured to at least partially surround said perimeter of said anvil and to extend longitudinally past said stop when said closure member is in said distal position; and a second portion configured to at least partially surround said perimeter of said channel and not to extend longitudinally past said stop when said closure member is in said distal position.

16. The surgical stapler of claim 15, further comprising said staple cartridge.

17. The surgical stapler of claim 15, wherein said closure member is tubular.

18. The surgical stapler of claim 15, further comprising a handle, a trigger, and a drive member operably coupled to said trigger and said closure member, wherein an actuation of said trigger is configured to move said closure member between said proximal position and said distal position.

19. The surgical stapler of claim 18, wherein said end effector is configured to articulate relative to said handle.

* * * * *